United States Patent [19]
Zushi et al.

[11] Patent Number: 5,574,007
[45] Date of Patent: Nov. 12, 1996

[54] POLYPEPTIDE CAPABLE OF INTERACTING WITH THROMBIN

[75] Inventors: Michitaka Zushi, Numazu; Komakazu Gomi, Kawasaki; Shuji Yamamoto, Fuji; Koji Suzuki, Tsu; Akio Matsuda, Fuji, all of Japan

[73] Assignee: Asahi Kasei Kogyo Kabushiki Kaisha, Osaka, Japan

[21] Appl. No.: 261,206

[22] Filed: Jun. 15, 1994

Related U.S. Application Data

[63] Continuation of Ser. No. 740,492, Aug. 5, 1991, abandoned.

[30] Foreign Application Priority Data

Aug. 3, 1990 [JP] Japan ............................ 2-204978

[51] Int. Cl.⁶ .................... C07K 14/435; C07K 14/46; A61K 38/17
[52] U.S. Cl. .................... 514/12; 514/2; 530/350; 530/399
[58] Field of Search .................... 530/350, 399; 514/2, 12; 435/69.1, 69.4, 69.6

[56] References Cited

FOREIGN PATENT DOCUMENTS

| 0312598 | 1/1988 | European Pat. Off. . |
| 0445304 | 9/1990 | European Pat. Off. . |
| 8809811 | 6/1988 | WIPO . |
| 88/05053 | 7/1988 | WIPO . |

OTHER PUBLICATIONS

Ryan, J. et al., *J. Biol. Chem.*, 264(3): 20283–87, 1989.
Hayashi et al., J. Biological Chemistry, vol. 265, No. 33, 20156–20159 (1990).
Esmon et al., J. Biol. Chem., 257, 859–864 (1982).
Suzuki et al., Biochemica et Biophysica Acta, 882, 343–352 (1986).
Salem et al., J. Biol. Chem., 259, 12246–12251 (1984).
Kurosawa et al., J. Biol. Chem., 262, 2206–2212 (1987).
Zushi et al., J. Biol. Chem., 264, 10351–10353 (1989).

*Primary Examiner*—Marianne P. Allen
*Attorney, Agent, or Firm*—Birch, Stewart, Kolasch & Birch, LLP

[57] ABSTRACT

Disclosed is a substantially pure polypeptide having a specific amino acid sequence containing (a) an amino acid residue selected from the group consisting of Asp, Glu and Gla wherein Gla represents a γ-carboxyglutamic acid residue or (b) a peptide or polypeptide residue consisting of at least two amino acid residues selected from Asp, Glu and Gla, wherein the above-mentioned at least two amino acid residues are all the same or combinations of the Asp, Glu and Gla. The polypeptide is capable of interacting with thrombin to form a binding therebetween, thereby exhibiting an activity to inhibit the blood coagulation and platelet aggregation by thrombin and/or an activity to promote the thrombin-catalyzed activation of protein C. This novel polypeptide has a low molecular weight so that it is suitable for oral or nasal administration.

12 Claims, 80 Drawing Sheets

FIG.1

285 bp 95 amino acids

5' CACATTGGCACCGACTGTTGAGCGGCCTCC 3'
HisIleGlyThrAspCysSTP
3' ACCGTGGCTGACAACTCGCCGGAGG 5'
(deleter TMd3)

M13mp19TMJ3

FIG. 2

1044 bp
348 amino acids

5' GGCCTGGGGTTCCCCGACCCGTGCTTCAGA 3'
GlyLeuGlyPheProAspProCysPheArg
3' GGACCCCAAGGGGCTGGGCACGAAG 5'
(deleter TMd5)

M13TMD3

FIG. 3

1047 bp
349 amino acids

5' GGCCTGGGGTTCCCCCCGTGCTTCAGAGCC 3'
GlyLeuGlyPheProProCysPheArgAla
3' GGACCCCAAGGGGGGCACGAAGTCT 5'
(deleter TMd6)

M13TMD3

FIG. 4

```
        ┌─────────────┐
        │   177 bp    │
        │59 amino·acids│
        └─────────────┘
               │
   5' GGGCTCGTGCATTCGGGCTGAGCGGCCTCCGTCCAG 3'
      GlyLeuValHisSerGlySTP
   3' GCACGTAAGCCCGACTCGCCGGAGG 5'
              (deleter TMd1)

M13mp19TMJ3
```

FIG. 5

5' TGTGTGGAGCCCGTGGACCCGTGCTTCAGAGCC 3'
CysValGluProValAspProCysPheArgAla
3' ACCTCGGGCACCGAGGCACGAAGTC 5'
Ala
(mutator TMm1)

M13TMD1

FIG.6

```
5' TGTGTGGAGCCCGTGGACCCGTGCTTCAGAGCC 3'
  CysValGluProValAspProCysPheArgAla
3' ACCTCGGGCACCTTGGCACGAAGTC 5'
                Glu
           (mutator TMm2)
```

M13TMD1

FIG. 10

```
5' GGCCTGGGGTTCCCCGACCCGTGCTTCAGA 3'
  GlyLeuGlyPheProAspProCysPheArg
3' GGACCCCAAGGGGCTTGGCACGAAG 5'
                             Glu
        (mutator TMm3)
```

M13TMD7

FIG. 13

```
5' GGCCTGGGGTTCCCC——GACCCGTGCTTCAGA 3'
   GlyLeuGlyPhePro    AspProCysPheArg
3' GGACCCCAAGGGGCTGCTGGGCACGAAG 5'
                  Asp
              (mutator TMm4)
```

M13TMD7

FIG.14

```
       5' GGCCTGGGGTTCCCC————GACCCGTGCTTCAGA 3'
          GlyLeuGlyPhePro      AspProCysPheArg
       3' GGACCCCAAGGGGCTGCTGCTGGGCACGAAG 5'
                       AspAsp
                  (mutator TMm5)
```

M13TMD7

FIG. 15

```
5' GGCCTGGGGTTCCCC——GACCCGTGCTTCAGA 3'
  GlyLeuGlyPhePro   AspProCysPheArg
3' GGACCCCAAGGGGCTTCTGGGCACGAAG 5'
                    Glu
              (mutator TMm6)
```

M13TMD7

FIG. 31(a)

PTTM LINKER

```
                              | Prothrombin leader
                              |←peptide coding region
                              MetAlaHisValArgGlyLeuGln
5'-AGCTTAGCTGACACACTATGGCGCACGTCCGAGGCTTGCAG
3'-ATCGACTGTGTGATACCGCGTGCAGGCTCCGAACGTC
 Hind III
```

---

LeuProGlyCysLeuAlaLeuAlaAlaLeuCysSerLeuValHis
CTGCCTGGCTGCCTGGCCCTGGCTGCCCTGTGTAGCCTTGTGCAC
GACGGACCGACGGACCGGGACCCACGGGACACATCGGAACACGTG

---

SerGlnHisValPheLeuAlaProGlnGlnAlaArgSerLeuLeu
AGCCAGCATGTGTTCCTGGCTCCTCAGCAAGCACGGTCGCTGCTC
TCGGTCGTACACAAGGACCGAGGAGTCGTTCGTGCCAGCGACGAG

---

```
                          | E456Gla
─────────────────────▶|←Coding region
GluArgValArgArgProValGlu
GAGCGGGTCCGGCGACCCGTGGAA-3'
CTCGCCCAGGCCGCTGGGCACCTT-5'
```

FIG. 32(a)

PTTM2linker

Prothrombin leader
◄—peptide coding region
MetAlaHisValArgGlyLeuGln
5'-AGCTTAGCTGACACACTATGGCGCACGTCCGAGGCTTGCAG
3'-ATCGACTGTGTGATACCGCGTGCAGGCTCCGAACGTC LeuProGlyCysLeuAlaLeuAlaAlaLeuCysSerLeuVal
CTGCCTGGCTGCCTGGCCCTGGCTGCCCTGTGTAGCCTTGTG
GACGGACCGACGGACCGGGACCGACGGGACACATCGGAACAC HisSerGlnHisValPheLeuAlaProGlnGlnAlaArgSer
CACAGCCAGCATGTGTTCCTGGCTCCTCAGCAAGCACGGTCG
GTGTCGGTCGTACACAAGGACCGAGGAGTCGTTCGTGCCAGC E456GlaAsp
►◄—coding region
LeuLeuGluArgValArgArgProValGluAsp
CTGCTCGAGCGGGTCCGGCGACCCGTGGAAGAC-3'
GACGAGCTCGCCCAGGCCGCTGGGCACCTTCTG-5'

E456Glu

E456Gla

E456GlaAsp

PURE POLYPEPTIDE OF THE INVENTION/THROMBIN
(mol/mol)

FIG. 54

114bp 38 amino acids

TTCATCTGCACGGACATCTGAGCGGCCTCCGTCCAG
PheIleCysThrAspIleSTP
3'ACGTGCCTGTAGACTCGCCGGAGGC5'
(deleterTMd9)

M13TMD7

FIG. 55(a)

```
1
Met Leu Gly Val Leu Val Leu Gly Ala Leu Ala Leu Ala Gly Leu GlyPhe Pro Ala Pro
                                                                          20
21
Ala Glu Pro Gln Pro Gly Gly Ser Gln Cys Val Glu His Asp Cys Phe Ala Leu Tyr Pro
                                                                          40
41
Gly Pro Ala Thr Phe Leu Asn Ala Ser Gln Ile Cys Asp Gly Leu Arg Gly His Leu Met
                                                                          60
61
Thr Val Arg Ser Ser Val Ala Ala Asp Val Ile Ser Leu Leu Leu Asn Gly Asp Gly Gly
                                                                          80
81
Val Gly Arg Arg Arg Leu Trp Ile Gly Leu Gln Leu Pro Pro Gly Cys Gly Asp Pro Lys
                                                                          100
101
Arg Leu Gly Pro Leu Arg Gly Phe Gln Trp Val Thr Gly Asp Asn Asn Thr Ser Tyr Ser
                                                                          120
```

FIG. 55(b)

```
121
Arg Trp Ala Arg Leu Asp Leu Asn Gly Ala Pro Leu Cys Gly Pro Leu Cys Val Ala Val
                                                                              140
141
Ser Ala Ala Glu Ala Thr Val Pro Ser Glu Pro Ile Trp Glu Gln Gln Cys Glu Val
                                                                              160
161
Lys Ala Asp Gly Phe Leu Cys Glu Phe His Phe Pro Ala Thr Cys Arg Pro Leu Ala Val
                                                                              180
181
Glu Pro Gly Ala Ala Ala Ala Val Ser Ile Thr Tyr Gly Thr Pro Phe Ala Ala Arg
                                                                              200
201
Gly Ala Asp Phe Gln Ala Leu Pro Val Gly Ser Ser Ala Ala Val Ala Pro Leu Gly Leu
                                                                              220
221
Gln Leu Met Cys Thr Ala Pro Pro Gly Ala Val Gln Gly His Trp Ala Arg Glu Ala Pro
                                                                              240
```

FIG. 55(c)

```
241 Gly Ala Trp Asp Cys Ser Val Glu Asn Gly Gly Cys Glu His Ala Cys Asn Ala Ile Pro 260
261 Gly Ala Pro Arg Cys Gln Cys Pro Ala Gly Ala Ala Leu Gln Ala Asp Gly Arg Ser Cys 280
281 Thr Ala Ser Ala Thr Gln Ser Cys Asn Asp Leu Cys Glu His Phe Cys Val Pro Asn Pro 300
301 Asp Gln Pro Gly Ser Tyr Ser Cys Met Cys Glu Thr Gly Tyr Arg Leu Ala Ala Asp Gln 320
321 His Arg Cys Glu Asp Val Asp Asp Cys Ile Leu Glu Pro Ser Pro Cys Pro Gln Arg Cys 340
341 Val Asn Thr Gln Gly Gly Phe Glu Cys His Cys Tyr Pro Asn Tyr Asp Leu Val Asp Gly 360
```

FIG. 55(d)

```
361
Glu Cys Val Glu Pro Val Asp Pro Cys Phe Arg Ala Asn Cys Glu Tyr Gln Cys Gln Pro
                                                                            380

381
Leu Asn Gln Thr Ser Tyr Leu Cys Val Cys Ala Glu Gly Phe Ala Pro Ile Pro His Glu
                                                                            400

401
Pro His Arg Cys Gln Met Phe Cys Asn Gln Thr Ala Cys Pro Ala Asp Cys Asp Pro Asn
                                                                            420

421
Thr Gln Ala Ser Cys Glu Cys Pro Glu Gly Tyr Ile Leu Asp Asp Gly Phe Ile Cys Thr
                                                                            440

441
Asp Ile Asp Glu Cys Glu Cys Glu Asn Gly Gly Phe Cys Ser Gly Val Cys His Asn Leu
                                                                            460

461
Thr Phe Glu Cys Ile Cys Gly Pro Asp Ser Ala Leu Val Arg His Ile Gly Thr Asp Cys
                                                                            480
```

FIG. 55(e)

```
481
Asp Ser Gly Lys Val Asp Gly Gly Asp Ser Gly Ser Gly Glu Pro Pro Pro Ser Pro Thr
                                                                            500

501
Pro Gly Ser Thr Leu Thr Pro Pro Ala Val Gly Leu Val His Ser Gly Leu Leu Ile Gly
                                                                            520

521
Ile Ser Ile Ala Ser Leu Cys Leu Val Val Ala Leu Leu Ala Leu Leu Cys His Leu Arg
                                                                            540

541
Lys Lys Gln Gly Ala Ala Arg Ala Lys Met Glu Tyr Lys Cys Ala Ala Pro Ser Lys Glu
                                                                            560

561
Val Val Leu Gln His Val Arg Thr Glu Arg Thr Pro Gln Arg Leu
```

NUCLEOTIDE SEQUENCE-DETERMINED REGION (A)

1 Kb

NUCLEOTIDE SEQUENCE-DETERMINED REGION (B)

FIG. 61 (a)

```
   1 AGATCTTTCAGGATGGTGCTGATGGGGGCGAGGGCAAAACACCACCGGTGATCCTGA
  61 CGTGGAGGTTGTGATAGAAGGAGAGCAAGGGGACGATGATGTGGACCTTGTGATTGA
 121 GGAGGATCATGGCGATGAGGAGGATGAGGAAGAGATTACCCGATCTGATCCTCCCCC
 181 GAACGAGGGGACCAGGAGCGGGAGGAGCACCAGAGAACCGGAGCAGCACCGGAGCACC
 241 TCAAGAACCAGACCGACGAGCAGCTCCCCGCCACAGAACAACCGAAGTACCGCCCGGC
 301 CGCAGCGGACGAGCAGCTCTGGGCACCGTCCTGTCCAACTTCTCAAACCAGCTCAGCGCCCT
 361 CAACCGCGTCGGTCTGGGAATCTCTCTTCGCCATGGGCGAAGCTCTACGGGTGGCGCTCAG
 421 CATCCTGCCGGGACACAGTCGTCTCGTGGGTGCCTGGGTGCCTACTCCAGCAGCAG
 481 GTGGACACAGTCGTCTCGTGGGTGCCTGGGTGCCTGTACGTGATCAAGGACGTGATCCGGGTCT
 541 TGGGTCGCAGCCTCGTGTGGGTGCCTGTACGTGATCAAGGACGTGATCCGGGTCT
 601 ACGCCAAGCACCGCAAGGTGGCGGCTATGGCAACCGGCGGGTCAGAACGTGACCGGC
 661 CAAGGAGGAACGCGGGGCTCGTCGAGATGAACGGTCATATCCAGTGATACAACGCAGCATGGGAACGG
 721 AGTTTGGGCTGGCCAGGGTAGAGATGACGGTCTACCGCCCAAACGTTGGTATGCGACT
 781 ACTAGTAATTACTACTGGGCAGAGTCTACCGCCCAAACGTTGGTATGGGTTATTGTAAAC
 841 GTTCCACGCCAATCTTTCACCGTCGCTATCAGAATCGGCGTATCATTGACGGCACCAG
 901 AATGATGCGTTGGTACTAATAGTAGGTACGAGGTAACAACAGTAAAGATACTGCCATTAT
 961 AGAAAGAGGAAGTCGCTCCCTGCAATGCCGCGCCACAAGCGCCTTTGCCGAGGACGC
1021 CGGAACCCAAACGCAGATCAGATCGGGGGCAACGGAAGCTTAGGGACGGAAATGGGGTA
1081 ATACGAGTAATAATCCCCACCACCAAGAAGCTCCCAACCAAAACAACCACCATACCACTCCAC
1141 CTTTTCACCCCGCCATCTTCTCCCGACAGAAAAGACAAAACAACCACCATACCACTCCAC
1201 AGAGCATTGTTCTTCCTTCAGGACTACCACGCGTCGATTCACAGTCAAAATGTCT
                                                                  MetSer

1256 CTCTCTAACAAGCTGTCCATTACTGATGTCGACCTCAAGGGCAAGAGG
     LeuSerAsnLysLeuSerIleThrAspValAspLeuLysGlyLysArg

1306 GTCCTGATTCGG/GTACGTCTTCCTCTCCCCAATTGTCCTACCGTCGTCATTG
     ValLeuIleArg
```

FIG. 61(b)

```
1358  TTGCCCCTCCATTGAGGCGGACACCGGGATGGATGGGCTACCCAAAAAAAACACAACCA
1418  CAGCAATGCATTGAGAAAAGCTAATCGAACCCCGCCATCACGCAG/GTCGACTTC
                                                   ValAspPhe

1472  AACGTGCCCCTCGACGAGAACAAGAAGATCACCAACAACCAGCGCATC
      AsnValProLeuAspGluAsnLysLysIleThrAsnAsnGlnArgIle

1520  GTCGGTGCCCTCCCCACCATCAAGTACGCCGTCGAGCATGGCGCCAAG
      ValGlyAlaLeuProThrIleLysTyrAlaValGluHisGlyAlaLys

1568  GCCGTCATCCTCATGTCCCACCTTGGCCGCCCCAACGGCACCCCCAAC
      AlaValIleLeuMetSerHisLeuGlyArgProAsnGlyThrProAsn

1616  CCCAAGTACTCGCTGCAGCCCGTCGTCCCCGAGCTCGAGAAGCTGCTC
      ProLysTyrSerLeuGlnProValValProGluLeuGluLysLeuLeu

1664  GGCAAGAGCGTCACTTTCGCCCCCGACTGCGTCGGCGCCGAGGTCGAG
      GlyLysSerValThrPheAlaProAspCysValGlyAlaGluValGlu

1712  GGCATCGTGCCAAAGCCTGCAAAGGCCGTTGTCCTGCTCGAGAAC
      GlyIleValAlaLysAlaAspGlyAlaValValLeuLeuGluAsn

1760  CTCCGCTTCCACATCGAGGAGGAGCAGCCCAAGGATAAGGATGGA
      LeuArgPheHisIleGluGluGluGlySerAlaLysAspLysAspGly

1808  AACAAGACCAAGGCTGACAAGGCCAAAGTTGACGAGTTCCGCAAGGGG
      AsnLysThrLysAlaAspLysAlaLysValAspGluPheArgLysGly
```

FIG. 61(c)

```
1856  CTGACCGCCCTGGGGCGAGCGTCTACATCA/GTATGGCTCTTCCCCGCAAG
      LeuThrAlaLeuGlyAspValTyrIleAsn

1904  GTCTGGGCGTGTGCGCGTGAGGGAATATGGCTAATGACGAGCAG/ATGACGCCTTC
                                                    AlaPhe

1959  GGCACCGCCCACCGGCGCCCACTCCTCCATGGTCGGTGTCGACCTCCCC
      GlyThrAlaHisArgAlaHisSerSerMetValGlyValAspLeuPro

2007  CAGAAGGCCGCCGGCTTCCTCATGAAGAAGGAGCTCGACTACTTCGCG
      GlnLysAlaAlaGlyPheLeuMetLysLysGluLeuAspTyrPheAla

2055  CAGGCCCTCGAGGCGCCCCAGCGTCCCTTCCTCGCCATCCTGGGCGGC
      GlnAlaLeuGluAlaProGlnArgProPheLeuAlaIleLeuGlyGly

2103  GCCAAGGTCTCGGACAAGATCCAGCTCATCGACAACCTGCTGGACAAG
      AlaLysValSerAspLysIleGlnLeuIleAspAsnLeuLeuAspLys

2151  GTCAACACGCTAATCATCTGCGGGCATGCCTTCACCTTCAAGAAG
      ValAsnThrLeuIleIleCysGlyGlyMetAlaPheThrPheLysLys

2199  ACGCTGGACGGCATGTCCATCGGCAACTCGCTCTTTGACGAGGCCGGC
      ThrLeuAspGlyMetSerIleGlyAsnSerLeuPheAspGluAlaGly
```

FIG. 61(d)

2247 GCCAAGACGGTGCGCCTCCCTCATGGACAAGGCCAAGCAGAAGGGTGTC
     AlaLysThrValAlaSerLeuMetAspLysAlaLysGlnLysGlyVal

2295 AAGGTCGTCGTCCCCGTCGACTACATCACCGCCGACAAGTTCGACAAG
     LysValValValProValAspTyrIleThrAlaAspLysPheAspLys

2343 GACGCCAACACGGGCCAAGGCCTCGGCGAGGAGTCCATCAAGCTCCTCTACCGCGAG
     AspAlaAsnThrGlyLysAlaSerAspAlaGlnGlyIleProAspGly

2391 TGGATGGGCCTCGACTGCGGGCGAGGAGTCCATCAAGCTCCTCTACCGCGAG
     TrpMetGlyLeuAspCysGlyGluGluSerIleLysLeuTyrArgGlu

2439 GCCATCGACAACGCCAAGACGCCAAGACCATCCTCTGAACTGCCCCGCCGTC
     AlaIleAspAsnAlaLysThrIleLeuTrpAsnCysProAlaGlyVal

2487 TTCGAGTTCGAGAAGTTCGCCTCGGGAACCAAGGCCACCCTCGACGCC
     PheGluPheGluLysPheAlaSerGlyThrLysAlaThrLeuAspAla

2535 GTCGTCGACGGCGCCCAGAACGCCGGCAAGATTGTCATCATCGGCGGC
     ValValAspGlyAlaGlnAsnAlaGlyLysIleValIleIleGlyGly

2583 GGCGACACCGCTACCGTCGCTGCCAAGTACGGCGTCGAGGACAAGCTC
     GlyAspThrAlaThrValAlaAlaLysTyrGlyValGluAspLysLeu

FIG. 61(e)

```
2631 AGCCACGTATCTACCGGTGGGCGGGCCCAGCCTGGAGCTGCTCGAGGGC
     SerHisValSerThrGlyGlyGlyAlaSerLeuGluLeuLeuGluGly

2679 AAGGAGCTACCCGGCGTGACGGCCCCTCTGAGTAAGTAAGCCTCCA
     LysGluLeuProGlyValThrAlaLeuSerSerLys*

2725 TATCGAGCGAGGGAGTCGGCGATGAATGGCAGGCATGGTTGATGATGGTTGTTGTTTTG
2785 CCCAGGTCGAAGGGTGGCGAGCCTGTAGGGTTGAGAATAGAACTGCCTAGTTTAGCAGT
2845 AACAATGTCGGTGTAAAATTGAGAAAAAAAAACCTTTGTTTGCCATCCAAGTC
2905 GTTGGTCGTATCTCGTGTGAGTCTGAGTCTGTGTAACGAGTGACCCCATTGATCCCATGTA
2965 GTGGTCTGCTGGCTGTCCATGTAGCTGTGCAACACGCAAGGCCGCCAACCCACGTAATA
3025 CCCACCTTGCCCAGAATATTCTAGTCTCAGGCGCCACCAAATCAATCAAAGTTCCAA
3085 CCCGCCACGCTTTCCACGGGCATATCACATCCCTCTCACCGACAATAGACCATCAGCC
3145 CAACCTCCCAACAATATCACACATCTGCCTGACATGGTAATTACCTCTCCCAAAGTACCCCAGCGCC
3205 CGGCGCTTAGCTCTGCCTGACATGGTAATTACCTCTCCCAAAGTACCCCCTCACTCCCT
3265 CTACCCGCATTCGGCTCTAGCGTCCCAAGATACTAGGTACC
```

FIG. 62(a)

```
   1 ATGCATACTACGGATACTAGTAGGGTAATTAGCGGGTTTCCACTCGCACATACGTACACG
  61 TAAGTCGGTGGCTCAGGTTCGGACGAGGGCGGGTACACAGCAGGAGAGAGAGGCTCTTC
 121 GTAGCCTTGCCTCTGCATCCGCCGACCCAGCGCGCGGGCCCAGAGATAGCACAAGCCTG
 181 CACGATTCGTGGCACCCAGGACGCGGGATGCGGGAGTTGCGTAATCGGCTGCTTCTATTTC
 241 AGATGGTGCGAGGGAGTACTCCTACTCACGATCTTGAATCACAGGAGGTCCCCATCAAAG
 301 CCACATGCCGACGTCGTTTACGAGACACGGTACATGGTACATCCGAAGACGGGACAGCAG
 361 GAAGCACCTAAAAGACGCTTCCCTCCGACATGGAAACACCCCATTGGGCCAGGCGGCAAGG
 421 AGCAGGAGGAGCAGGCAGTTGCTTTCGATGATGCTCGCGCCGAACCGTGAT
 481 TAGGTACTGATGCCATCGGTGCCGCACCGGCCCTGCGTCTGCACCTTGCGACCGCGCG
 541 CTACTCGTACTATGCCTACAGGTATGGGCTTTCCGCGTGTCGCCTTGCGACCGCGCG
 601 GCTGCTGACGACCACCCAAGGCACGTAACATGGCGGCACGAAATTTCTCTGCCTGCT
 661 CGTCCTCTTGGTGTGGAGGGTACGAGTGCAGGTATGATGGGACGGCAGAGGAGTGACGG
 721 AGGCTGTGCGGTTGGCACGAGTACTGTAGTCGTAGTACTGTAGGTGCAGCGACTGTG
 781 GTGGTACTGCTAGGTGGAATTGGGTCCAGCAGGCATGCAGCTCCCAGCCACCGTCGTTAA
 841 CCAATCAGTTAAAGCACGCGTCGTTGTTGCCCCGCCCCTTGTCTGGTCGCCTACAAGGCTGCCACACAG
 901 GTCGTGCCCCAGTCGTCGTTGTTGCCCCGCCCCAGTGAGTGCCCGGTGCCCACAAGT
 961 GTAACAACAGCCGCCCCAGGTCCTTGTAGGTGCCCAGTGAGTGCCCGGTGCCCACAAGT
1021 TTCTCGTAGGCATCCACTAGGCGGACTTGGAAGCCATCAGTGATGCTTCCCTCCTTTCC
1081 CCCTCCACATCTCACTCACGTCACGCAAGCCAACCCTCTCCCCCGTCTCCATTCCAT
1141 CTTCTTCTCCACGACCCTTAAGAGTCCCTCGCTGACGTCGACCATCCTTGCTCCC
1201 AGCCCCACGACATCTGCATTCGTCTGGGCTTCTTGACACTCTCGTCATTTCATTTCCTTATAAA
```

FIG. 62(b):

```
1261 ACCTCTTTACCGCTCTTCCCGTAATCCGACGCCATGGAGG/GTACGTGTCG
                                         MetGluGlu

1311 CCGCAACGCACTCCCGCTTCCCCTACTACCCCTATCGCGCATCCATACGGCGCCGCGATG
1371 CCTAGCCATCGCGAGGGTGCAAGCAAGACTTGGCTAACTGTTCTTCGCTTCACAG/AG
1430 GAGGTGCGCCGCCCCTCGTTATCGACAATGG/GTAAGCTCGCCCGCTGTCTC
     GluValAlaAlaLeuValIleAspAsnGly

1479 ACCGACATCCATCGTCCCCCTGGCCTCTGTCGAGATGGGAGCCTCCAGGGTCCCTTCGA
1539 CGAGCGCGTCGATTGCCAAAATCCAAGAGATCGGGCCATACTGAGCCGACACTCGTGTG
1599 TTTTCTGGACATTAGGACTGACTTGATTCTAG/TTCGGGTATGTGCAAGCC
                                    SerGlyMetCysLysAla

1650 GGTTTCGCCGGTGATGATGCTCCCCGAGCTGTTTCC/GTAAGTACCC
     GlyPheAlaGlyAspAspAlaProArgAlaValPhePro

1697 CACTTCCACCCGTCGAGCTCCCCAATTGTCCACCGCCAGGGCGAGAAGGGGCAGAACGG
1757 GGCAAACTGCATCGCAAACATGGCTAATTCGATGCACAG/CGTCCATTGTCGGT
                                           SerIleValGly
```

FIG. 62(c)

```
1811  CGTCCCCGCCACCATGG/GTAAGTTTCCGGCCGCAGCCGACACCTCTC
      ArgProArgHisHisGly

1858  ACCCCCCCCGGGGGCTCCTAAGCGAGTCAGGCGCTGGTTCTGACCGCTGGATACTATAG/
1918  CATCATGATGGCATGGGCCAGAAGGACTCGTCGGTCGGTGACGAG
      IleMetIleGlyMetGlyGlnLysAspSerTyrValGlyLysAspGlu

1964  GCTCAGTCCAAGGTGTGGTATCCTCACCCTGCGCTACCCCATTGAGCAC
      AlaGlnSerLysArgGlyIleLeuThrLeuArgTyrProIleGluHis

2012  GTTGTTGTCACCAACTGGACGACATGGAGAAGATCTGGCACCACACC
      ValValValThrAsnTrpAspAspMetGluLysIleTrpHisHisThr

2060  TTCTACAACGAGCTGCTGTTGCCCCGAGGAGCACCCGGTCCTGCTC
      PheTyrAsnGluLeuArgValAlaProGluHisProValLeuLeu

2108  ACCGAGGGCGCCCATCAACCCCAAGTCCAACCGTGAGAAGATGACCCAG
      ThrGluAlaProIleAsnProLysSerAsnArgGluLysMetThrGln

2156  TTCGTCTTCGAGACCTTCAACGCCCCTGCCTTCTACGTCTTCCATCCAG
      PheValPheGluThrPheAsnAlaProAlaPheTyrValSerIleGln
```

FIG. 62(d)

```
2204  GCCGTCCTGTCACTGTATACGCCCTCCGGCTACGACCGGTATCGTCCTG
      AlaValLeuSerLeuTyrAlaSerGlyArgThrThrGlyIleValLeu

2252  GACTCTGGTGATGGTGTCACCCACGTTGTCCCATCTACGAGGGTTTC
      AspSerGlyAspGlyValThrHisValValProIleTyrGluGlyPhe

2300  GCCCTGCCCCACGCCATTGCCCGTGTCGACATGGTCGGTCGTGATCTC
      AlaLeuProHisAlaIleAlaArgValAspMetValGlyArgAspLeu

2348  ACCGACTACCTCATGAAGATCCTGGCCGAGCGCGGCTACACCTTCTTC
      ThrAspTyrLeuMetLysIleLeuAlaGluArgGlyTyrThrPhePhe

2396  ACCACGGCCGAGCGTGAGATTGTCCGTGACATCAAGGAGGAGCTCTGC
      ThrThrAlaGluArgGluIleValArgAspIleLysGluGluLeuCys

2444  TACGTCGCCCTCGACTTCGAGCAGGAGATCCAGACTGCCGCCCAGAGC
      TyrValAlaLeuAspPheGluGlnGluIleGlnThrAlaAlaGlnSer

2492  TCCAGCCTGGAGAAGTCCTACGAGCTTCCCGACGGCCAGGTCATCACC
      SerSerLeuGluLysSerTyrGluLeuProAspGlyGlnValIleThr
```

FIG. 62(e)

```
2540  ATTGGCAATGAGGCGGCTTCCGTGCTCCGAGGCTCTCTTCCAGCCCTCC
      IleGlyAsnGluArgArgPheArgAlaProGluAlaLeuPheGlnProSer

2588  GTCCTGGGTCTCGAGAGCGGGCATCCACGTCACCACCTTCAACTCC
      ValLeuGlyLeuGluSerGlyGlyIleHisValThrThrPheAsnSer

2636  ATCATGAAGTGCGACGTCGATGTCCGTAAGGATCTGTACGGCAACATT
      IleMetLysCysAspValAspValArgLysAspLeuTyrGlyAsnIle

2684  GTCATGGTAAGTCAGATGCCGGGCCTGGAAGACACCTCATTAGGATCTTGCTAAC
      ValMet

2740  ACCAATTTTTTTTTTAG/TCTGGTGGTACCACCATGTACCCTGGCCTCTCT
                        SerGlyThrThrMetTyrProGlyLeuSer

2790  GACCGTATGCAGAAGGAGATCACTGCTCTTGCTCCTTCTTCCATGAAG
      AspArgMetGlnLysGluIleThrAlaLeuAlaProSerSerMetLys

2838  GTCAAGATCATTGCTCCCCCGGAGGCAAGTACTCCGTCTGGATCGGT
      ValLysIleIleAlaProProGluArgLysTyrSerValTrpIleGly

2886  GGTTCCATTCTGGCTCTGTCCACCTTCCAGCAGATGTGGATCTCG
      GlySerIleLeuAlaSerLeuSerThrPheGlnGlnMetTrpIleSer
```

FIG. 62(f)

2934 AAGCAGGAGTACGAGAGAGCGGCCCCTCCATCGTCCACCGCAAGTGC
     LysGlnGluTyrAspGluSerGlyProSerIleValHisArgLysCys

2982 TTCTAAGGTATGTTGTCGCTGGGAAGCCGGATACCCGAATGTAAGGTTGACAG
     Phe*

3035 GTTCGAAAAGACAAGGCCAACCGGCCAGAACCAAATCCTTCCACCCTCCGCAAAAGAACGC
3095 CAAGATGTCGGAGTCGGTGGCGACCGATGCAACGTCTACTCAGCTGCGCGTATCCCAC
3155 TCAAGTCTCATATTTACGAAAAGTTATTTCACATGGTCAGGCGGTGGTGGGCGTTGCCTT
3215 TTCTCGGAACAGACATGAGACGGCGGCCACTTTGTAGTCGTTAGGGATGCGAGC
3275 CTAGGGGTGTAGGAAGCTGAGGTTGATATACAATAACTTTTTTGCTTCCGTTCTAGAC
3335 TCGTTCAATGGGAAGACGTGACGGAATCGCTTGGCTGTGTCTAATAGCCCAGCTTGATCAGG
3395 CGAGTCGGGTTGTGTTTTCGATGTTGAGAGGTGCACCAGCTATTTGCTCGTTTTTACCAGCAGT
3455 TAGGTATTATGGTCTCTGCCATGCCGCGCTAGTAACCTCCGCACTAGCCGGTTCTTGTCGTTCTTCCTGCTCGCC
3515 GTCCTCTGCCATGCCGCGGCTAGTAACCTCCGCACTAGCCGGTTCTTTGTCGTTCTTCCTGCTCGCC
3575 AGTATTATCCCCCGTAGTACTTGCGCTCTTCTTCTTTGCGCTGGCAGCCTCTTCTGCTT
3635 GATGAGCTTCCTGACTTGCGCTCTTCTTCTTTGCGCTGGCAGCCTCTTCTGCTT
3695 GATGCGCCCGACCATGGCGGACCGGCTCTGCTCCCCGTTGAGCAGCTCGTCGAC 5,574,007

POLYPEPTIDE CAPABLE OF INTERACTING WITH THROMBIN

This application is a continuation of application Ser. No. 07/740,492 filed on Aug. 5, 1991, now abandoned.

BACKGROUND OF THE INVENTION

1. Field of the Invention

The present invention relates to a polypeptide capable of interacting with thrombin. More particularly, the present invention is concerned with a novel, substantially pure polypeptide with a low molecular weight, which interacts with thrombin to form a binding therebetween, thereby exhibiting an activity to inhibit the blood coagulation and platelet aggregation by thrombin and/or an activity to promote the thrombin-catalyzed activation of protein C. The present invention is also concerned with a DNA comprising a nucleotide sequence coding for the polypeptide; a recombinant DNA molecule comprising a replicable expression vector and the DNA; a transformant containing the recombinant DNA molecule; a process for producing the above-mentioned polypeptide; and a pharmaceutical composition comprising the polypeptide.

The polypeptide of the present invention participates in anticoagulation of blood and fibrinolysis with respect to blood coagulation, and has excellent activities of anticoagulation, platelet aggregation inhibition and thrombolysis. The polypeptide of the present invention is therefore useful as an active ingredient of drugs, particularly those for the treatment of diseases involving undesired blood-coagulation, such as myocardial infarction, thrombosis, embolism, obstruction of peripheral blood vessels, arteriosclerosis obliterans, disseminated intravascular coagulation (DIC) syndrome, angina pectoris, transient ischemic attack and toxemia of pregnancy.

In the present specification, amino acids and peptides are represented using abbreviations, as indicated below, approved by the IUPAC-IUB Commission on Biochemical Nomenclature (CBN). With respect to amino acids and the like having isomers, those represented by the following abbreviations are of the L-configuration unless otherwise specified. Further, unless otherwise specified, the left end and right end of the amino acid sequences of peptides are the N-terminus and C-terminus, respectively.

Gln: glutamine residue
Asp: aspartic acid residue
Pro: proline residue
Tyr: tyrosine residue
Val: valine residue
Lys: lysine residue
Glu: glutamic acid residue
Ala: alanine residue
Asn: asparagine residue
Leu: leucine residue
Phe: phenylalanine residue
Gly: glycine residue
His: histidine residue
Ser: serine residue
Thr: threonine residue
Ile: isoleucine residue
Trp: tryptophan residue
Arg: arginine residue
Met: methionine residue
Cys: cysteine residue Polydeoxyribonucleotides and oligodeoxyribonucleotides are represented by sequences of deoxynucleotide residues which are abbreviated as follows:

A: 2'-deoxyadenylic acid residue
C: 2'-deoxycytidylic acid residue
G: 2'-deoxyguanylic acid residue
T: thymidylic acid residue Unless otherwise specified, the left end and the right end of the sequence of deoxynucleotides are the 5' end and 3'end, respectively.

2. Discussion of Related Art

Protein C is known as a protein which is dependent on vitamin K and which plays an important role in the blood coagulation mechanism. In recent years, it has been reported that a substance which interacts with thrombin to form a binding therebetween, thereby exhibiting activities to repress the platelet activation and fibrin formation by the action of thrombin and promote the thrombin-catalyzed activation of protein C, is present in rabbit lung, bovine lung, human lung, human placenta and the like. Such a substance is generally called "thrombomodulin".

N. L. Esmon et al. (see J. Biol. Chem., vol. 257, pages 859–864, 1982) reported that a substance separated from rabbit lung and purified requires calcium ions at the time of activating protein C after forming a bond to thrombin. Further, K. Suzuki et al. (see Biochemica et Biophysica Acta, vol. 882, pages 343–352, 1986) reported that a substance separated from bovine lung and purified also requires calcium ions at the above-mentioned time, and this requirement for calcium ions with respect to a substance separated from human placenta and purified was reported by H. H. Salem et al. (see J. Biol. Chem., vol. 259, pages 12246–12251, 1984). It was reported by S. Kurosawa et al. (see J. Biol. Chem., vol. 262, pages 2206–2212, 1987) that a soluble peptide, obtained by digesting with elastase the above-mentioned substance separated from rabbit lung and purified, exhibits the highest activity at a calcium ion concentration of 0.3 mM in the activation of protein C, and that such a dependence on calcium ion concentration is not observed at the time of the activation of protein C having the Gla domain deleted (such protein C hereinafter referred to as "GDPC").

S. Yamamoto, who is one of the present inventors, and his colleagues have disclosed the cloning of a human-derived thrombomodulin cDNA (see International Application Publication No. WO88/05053).

In accordance with the recent progress of genetic engineering, it is now possible to replace one or more predetermined amino acid residues in a protein with other amino acid residues and also to delete an amino acid sequence from a predetermined site of a protein. Various researches have been made to create a novel protein meeting a particular objective by modifying a natural protein using genetic engineering. With respect to human thrombomodulin, the present inventors (see M. Zushi et al., J. Biol. Chem., vol. 264, pages 10351–10353, 1989) have shown that a polypeptide comprised of 115 amino acid residues has an ability to promote the thrombin-catalyzed activation of protein C.

In the treatment of diseases involving undesired blood coagulation, the administration of a pharmaceutical composition comprising a polypeptide is mainly effected by intravenous drip or local administration by PTCR (percutaneous transluminal coronary recanalization). With respect to the administration of human thrombomodulin, intravenous drip is preferred to local administration by PTCR. Such an administration method is acceptable for a short-term treatment, but it causes grave mental and economic burden on patients who receive a long-term treatment or preventive medication. Further, because the molecular weight of conventional polypeptides is generally large and only a limited portion of the polypeptide chain contributes toward pharmaceutical activity, the dose of a pharmaceutical composition comprising a polypeptide is inevitably large, and this is likely to create a danger of patient antigenecity.

SUMMARY OF THE INVENTION

The present inventors have made extensive and intensive studies with a view toward developing a novel low molecular weight thrombomodulin having an improved activity to obtain a pharmaceutical composition, which is suitable for oral and nasal administrations (less burdensome as compared to intravenous drip and local administration by PTCR), by identifying a region of the above-mentioned peptide comprising 115 amino acid residues, which is essential for exhibiting an activity to inhibit the blood coagulation and platelet aggregation by thrombin and/or an activity to promote the thrombin-catalyzed activation of protein C. As a result, the present inventors have succeeded in identifying a region of thrombomodulin sequence which provides an ability to interact with protein C to form a binding therewith and also identifying an amino acid sequence comprising a thrombin binding site of thrombomodulin. Moreover, the present inventors have found that a polypeptide having the above-mentioned region of thrombomodulin sequence and the above-mentioned amino acid sequence comprising a thrombin binding site is effectively expressed in a microorganism or a cultured animal cell line. On the basis of these novel findings, the present invention has been completed.

Accordingly, it is an object of the present invention to provide a substantially pure, low molecular weight polypeptide capable of effectively exhibiting an activity to inhibit the blood coagulation and platelet aggregation by thrombin and/or an activity to promote the thrombin-catalyzed activation of protein C.

It is another object of the present invention to provide a DNA coding for the above polypeptide.

It is a further object of the present invention to provide a recombinant DNA molecule comprising the above DNA and a vector.

It is still a further object of the present invention to provide a microorganism or a cultured animal cell line transformed with the above recombinant DNA molecule.

It is still a further object of the present invention to provide a process for producing the above-mentioned substantially pure polypeptide by using the above-mentioned transformant.

It is still a further object of the present invention to provide a pharmaceutical composition comprising the above-mentioned substantially pure polypeptide, which is suitable for oral and nasal administrations.

The foregoing and other objects, features and advantages of the present invention will be apparent from the following detailed description and appended claims taken in connection with the accompanying drawings.

BRIEF DESCRIPTION OF THE DRAWINGS

In the accompanying drawings:

FIG. 1 is an illustration of a recombinant plasmid M13mp19TMJ3 obtained in Example 1-(1)-(a) with which a deleter TMd3 is complementarily hybridized, showing the nucleotide sequence around the portion at which the deleter is hybridized with the plasmid, together with the amino acid sequence encoded thereby;

FIG. 2 is an illustration of a recombinant plasmid M13TMD3 obtained in Example 1-(1)-(a) with which a deleter TMd5 is complementarily hybridized, showing the nucleotide sequence around the portion at which the deleter is hybridized with the plasmid, together with the amino acid sequence encoded thereby;

FIG. 3 is an illustration of a recombinant plasmid M13TMD3 obtained in Example 1-(1)-(a) with which a deleter TMd6 is complementarily hybridized, showing the nucleotide sequence around the portion at which the deleter is hybridized with the plasmid, together with the amino acid sequence encoded thereby;

FIG. 4 is an illustration of a recombinant plasmid M13mp19TMJ3 obtained in Example 1-(1)-(a) with which a deleter TMd1 is complementarily hybridized, showing the nucleotide sequence around the portion at which the deleter is hybridized with the plasmid, together with the amino acid sequence encoded thereby;

FIG. 5 is an illustration of a recombinant plasmid M13TMD1 obtained in Example 1-(4)-(a) with which a mutator TMm1 is complementarily hybridized, showing the nucleotide sequence around the portion at which the mutator is hybridized with the plasmid, thereby causing an amino acid substitution, together with the amino acid sequence encoded thereby;

FIG. 6 is an illustration of a recombinant plasmid M13TMD1 obtained in Example 1-(4)-(a) with which a mutator TMm2 is complementarily hybridized, showing the nucleotide sequence around the portion at which the mutator is hybridized with the plasmid, thereby causing an amino acid substitution, together with the amino acid sequence encoded thereby;

FIG. 10 is an illustration of a recombinant plasmid M13TMD7 obtained in Example 1-(1)-(b) with which a mutator TMm3 is complementarily hybridized, showing the nucleotide sequence around the portion at which the mutator is hybridized with the plasmid, thereby causing an amino acid substitution, together with the amino acid sequence encoded thereby;

FIG. 13 is an illustration of a recombinant plasmid M13TMD7 obtained in Example 1-(1)-(b) with which a mutator TMm4 is complementarily hybridized, showing the nucleotide sequence around the portion at which the mutator is hybridized with the plasmid, thereby causing an amino acid insertion, together with the amino acid sequence encoded thereby;

FIG. 14 is an illustration of a recombinant plasmid M13TMD7 obtained in Example 1-(1)-(b) with which a mutator TMm5 is complementarily hybridized, showing the nucleotide sequence around the portion at which the mutator is hybridized with the plasmid, thereby causing an amino acid insertion, together with the amino acid sequence encoded thereby;

FIG. 15 is an illustration of a recombinant plasmid M13TMD7 obtained in Example 1-(1)-(b) with which a mutator TMm6 is complementarily hybridized, showing the nucleotide sequence around the portion at which the mutator is hybridized with the plasmid, thereby causing an amino acid insertion, together with the amino acid sequence encoded thereby;

FIG. 54 is an illustration of a recombinant plasmid M13TMD7 obtained in Example 1-(1)-(b) with which a deleter TMd9 is complementarily hybridized, showing the nucleotide sequence around the portion at which the deleter is hybridized with the plasmid, together with the amino acid sequence encoded thereby;

FIG. 55(a–e) show the entire amino acid sequence of human thrombomodulin polypeptide;

FIG. 61(a–e) shows a nucleotide sequence corresponding to region (A) of FIG. 59 indicated with the mark ⊢⊣, together with the amino acid sequence of the PGK protein which is indicated below the nucleotide sequence;

FIG. 62(a–e) shows a nucleotide sequence corresponding to region (B) of FIG. 60 indicated with the mark ⊢⊣, together with the amino acid sequence of the actin protein which is indicated below the nucleotide sequence;

Figure 7:
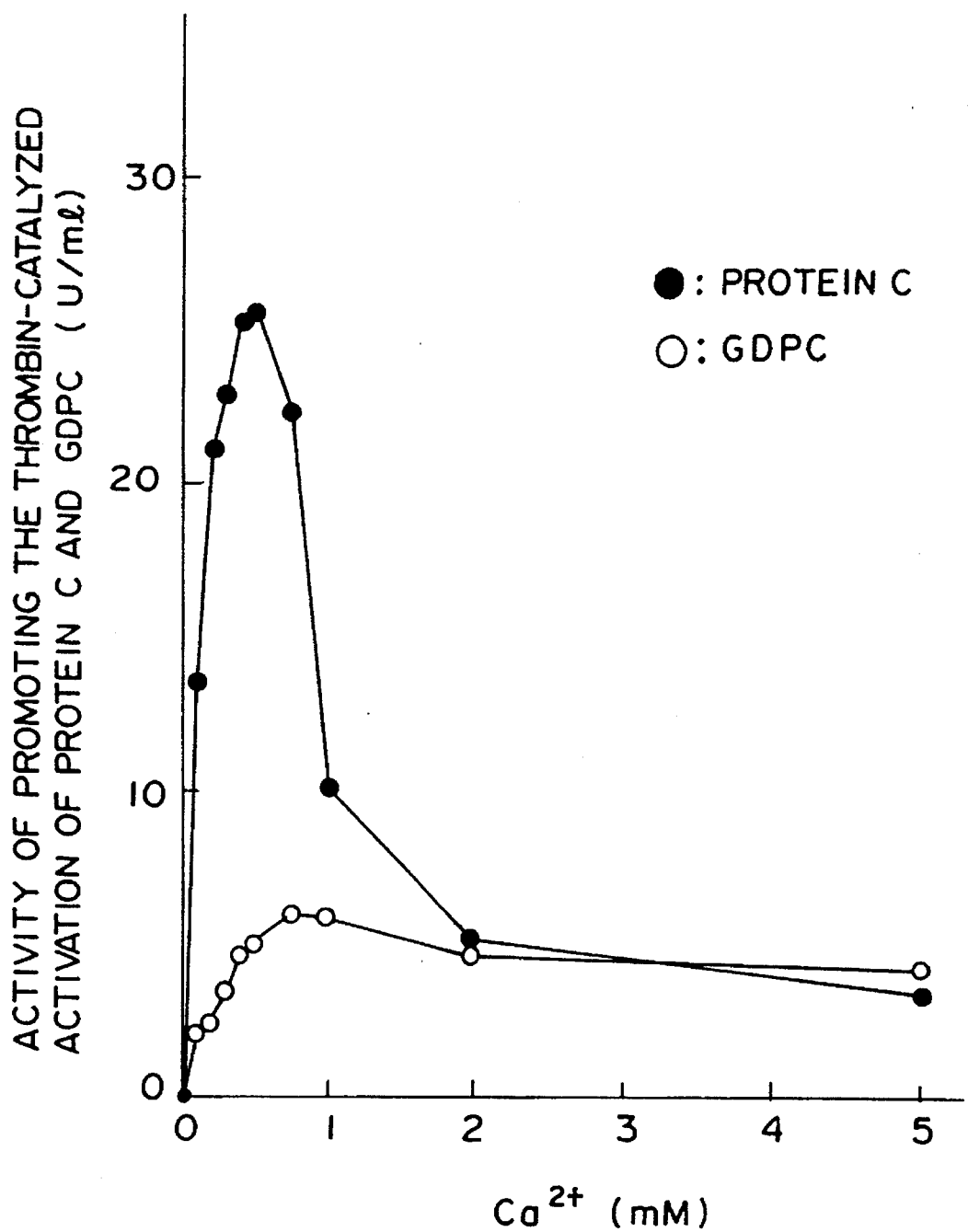
FIG. 7 is a graph showing the effect of calcium ion concentration on the activity of promoting the thrombin-catalyzed activation of each of protein C and GDPC with respect to polypeptide D123Asp obtained in Example 1.

In the drawings, the abbreviations have the following meanings:

B.B: linkage site between BamHI and BglII cm: chloramphenicol acetyltransferase gene Amp: β-lactamase gene acyII: SE-83 cephalosporin C acylase gene PGKP: promoter of *Acremonium chrysogenum* PGK gene PGKT: terminator of *Acremonium chrysogenum* PGK gene ACTP: promoter of *Acremonium chrysogenum* actin gene ACTT: terminator of *Acremonium chrysogenum* actin gene km: neomycin phosphotransferase gene HYB: hygromycin B phosphotransferase gene P: PvuII Ps: PstI M: MluI K: KpnI Sma: SmaI Sa: SalI St: StuI Sc: ScaI X: XhoI Xb: XbaI N: NsiI Nc: NcoI E: EcoRI RV: EcoRV H: HindIII Bs: BssHII Ps.Ns: linkage site between PstI and NsiI 2μ or i: replication origin of yeast 2μ plasmid CYCP: promoter of yeast iso-1-cytochrome C gene CYCT: terminator of yeast iso-1-cytochrome C gene GAPDP: promoter of *Acremonium chrysogenum* GAPD gene L: insertion site of BglII linker (GGAAGATCTTCC)(SEQ. ID. No. 1)

DETAILED DESCRIPTION OF THE INVENTION

In one aspect of the present invention, there is provided a substantially pure polypeptide having an amino acid sequence represented by the formula (I):

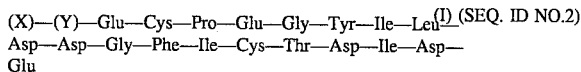
(X)—(Y)—Glu—Cys—Pro—Glu—Gly—Tyr—Ile—Leu— (I) (SEQ. ID NO.2)
Asp—Asp—Gly—Phe—Ile—Cys—Thr—Asp—Ile—Asp—
Glu wherein X represents (a) an amino acid residue selected from the group consisting of Asp, Glu and Gla wherein Gla represents a γ-carboxyglutamic acid residue or (b) a peptide or polypeptide residue consisting of at least two amino acid residues selected from Asp, Glu and Gla, wherein the above-mentioned at least two amino acid residues are all the same or combinations of the Asp, Glu and Gla; and Y represents 0 to 58 amino acid residues.

In the polypeptide of the present invention, Y is preferably a peptide comprising an amino acid sequence represented by the formula (II)(SEQ. ID. No. 3):

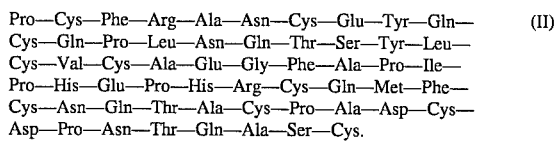
Pro—Cys—Phe—Arg—Ala—Asn—Cys—Glu—Tyr—Gln— (II)
Cys—Gln—Pro—Leu—Asn—Gln—Thr—Ser—Tyr—Leu—
Cys—Val—Cys—Ala—Glu—Gly—Phe—Ala—Pro—Ile—
Pro—His—Glu—Pro—His—Arg—Cys—Gln—Met—Phe—
Cys—Asn—Gln—Thr—Ala—Cys—Pro—Ala—Asp—Cys—
Asp—Pro—Asn—Thr—Gln—Ala—Ser—Cys.

It is preferred that the polypeptide of the present invention further have an amino acid sequence represented by the formula (III)(SEQ. ID. No. 4):

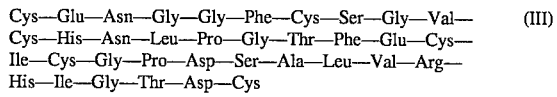
Cys—Glu—Asn—Gly—Gly—Phe—Cys—Ser—Gly—Val— (III)
Cys—His—Asn—Leu—Pro—Gly—Thr—Phe—Glu—Cys—
Ile—Cys—Gly—Pro—Asp—Ser—Ala—Leu—Val—Arg—
His—Ile—Gly—Thr—Asp—Cys attached to the amino acid sequence of the formula (I) at its C-terminus.

In another aspect of the present invention, there is provided a DNA comprising a nucleotide sequence coding for the above-defined polypeptide of the present invention.

In a further aspect of the present invention, there is provided a recombinant DNA molecule comprising a replicable expression vector and the above-defined DNA inserted therein.

In still a further aspect of the present invention, there is provided a transformant comprising a microorganism or cultured animal cell line transformed with the above-defined recombinant DNA molecule.

In still a further aspect of the present invention, there is provided a process for producing the above-defined substantially pure polypeptide of the present invention, which comprises:

(a) providing the above-described transformant comprising a microorganism, such as filamentous fungi, or cultured animal cell line transformed with a recombinant DNA molecule;

(b) culturing the transformant to produce a polypeptide; and (c) isolating the polypeptide from the cultured transformant.

In still a further aspect of the present invention, there is provided a pharmaceutical composition comprising an effective amount of the above-defined substantially pure polypeptide of the present invention, and at least one pharmaceutically acceptable carrier, diluent or excipient. The polypeptide of the present invention for use in this pharmaceutical composition has an activity to inhibit blood coagulation and platelet aggregation by thrombin and/or an activity to promote the thrombin-catalyzed activation of protein C.

In the course of the investigations toward the present invention, the present inventors have identified a site of human thrombomodulin which binds to protein C. Illustratively stated, a DNA fragment having a nucleotide sequence coding for the above-mentioned polypeptide comprised of 115 amino acid residues, which had previously been identified by the present inventors, was subcloned into an M13 phage vector. The M13 phage vector was subjected to a deletion reaction in which portions of the subcloned DNA fragment, which respectively correspond to the first amino acid residue (Val) and the first two (Val Asp) amino acid residues from the N terminus of the polypeptide comprised of 115 amino acid residues, were individually deleted by the customary technique of site-directed mutagenesis, to thereby obtain two types of DNA fragments each coding for a deletion mutant of human thrombomodulin. The two types of DNA fragments were individually inserted in expression vector pSV2 for use in an animal cell and expressed in COS-1 cells. As a result, it has surprisingly been found that a 114-amino acid polypeptide obtained by deleting the N-terminal amino acid residue (Val) from the above 115-amino acid polypeptide has the same level of specific activity as that of the 115-amino acid polypeptide, but a 113-amino acid polypeptide obtained by deleting two amino acid residues (Val Asp) from the N terminus of the 115-amino acid polypeptide is extremely low in specific activity as shown in Example 1 described later. That is, it has surprisingly been found that the aspartic acid residue (hereinafter frequently referred to as "Asp$^{367}$") present at the 367th position of the entire amino acid sequence of human thrombomodulin shown in FIG. 55 is essential for promoting the thrombin-catalyzed activation of protein C.

Moreover, the present inventors prepared a deletion mutant (E45) obtained by deleting 38 amino acids from the C terminus of the 114-amino acid polypeptide, and determined the activity of E45. As a result, it has been found that although E45 has satisfactory activity, the activity thereof is only about one-tenth of that of the 114-amino acid polypeptide.

To analyze the function of Asp$^{367}$, the present inventors subcloned a DNA coding for the amino acid sequence of the 1st to 516th amino acids of the entire amino acid sequence of human thrombomodulin shown in FIG. 55 into an M13 phage vector, and subjected the resultant plasmid to a substitution of the portion coding for Asp$^{367}$ by the conventional technique of site-directed mutagenesis using a synthetic DNA for use in mutagenesis, thereby obtaining a DNA coding for a polypeptide comprised of the 1st to 516th amino acids of the entire amino acid sequence shown in FIG. 55 except that Asp$^{367}$ was substituted with another amino acid residue, such as Ala and Glu. The DNA was expressed in COS-1 cells using expression vector pSV2 for use in an animal cell, and the expression product was purified by ion exchange chromatography and measured with respect to its ability to promote the thrombin-catalyzed activation of protein C. As a result, it has been found that when Asp$^{367}$ is replaced with an amino acid residue having no electric charge, such as Ala, the ability to promote the thrombin-catalyzed activation of protein C is extremely low (as shown in Example 1 described later). It has also been found that when Asp$^{367}$ is replaced with an amino acid residue having a negative charge as in the case of Asp, such as Glu and γ-carboxyglutamic acid residue (hereinafter frequently referred to as "Gla"), the ability to promote the thrombin-catalyzed activation of protein C is enhanced to a level higher than the ability before the mutagenesis. Thus, it has been found that Asp$^{367}$ of human thrombomodulin is a site which provides the capability of binding to protein C and that the negative charge of the side chain of Asp is highly related to this function of Asp$^{367}$. Further, it has unexpectedly been found that Asp$^{367}$ can be replaced with a peptide or polypeptide residue consisting of at least two amino acid residues selected from Asp, Glu and Gla.

Further, to identify a site of human thrombomodulin which binds to thrombin, the present inventors conducted the deletion of a specific amino acid sequence based on the above-mentioned polypeptide comprised of 115 amino acids by the technique of site-directed mutagenesis, to thereby obtain a DNA coding for a polypeptide comprised of the 366th to 442nd amino acid residues of human thrombomodulin and a DNA coding for a polypeptide comprised of the 407th to 480th amino acid residues of human thrombomodulin. These DNAs were individually expressed in COS-1 cells using vector pSV2, and the produced polypeptides were purified and measured with respect to the capability of binding to thrombin. As a result, it was found that both polypeptides had the capability of binding to thrombin. Assuming that the amino acid sequence common to both polypeptides corresponds to the binding site to thrombin, three types of polypeptides were synthesized based on the amino acid sequence of the 406th to 444th amino acids by the customary method using an automatic peptide synthesis machine. The three types of polypeptides were measured with respect to the ability to inhibit the binding of thrombomodulin to thrombin. As a result, it has been found that a polypeptide having a specific amino acid sequence of 19 amino acids, i.e., (Glu-Cys-Pro-Glu-Gly-Tyr-Ile-Leu-Asp-Asp-Gly-Phe-Ile-Cys-Thr-Asp-Ile-Asp-Glu)(SEQ. ID. No. 2), contains the binding site of human thrombomodulin to thrombin as described in Example 2 described later.

Based on the above findings, the present inventors have prepared a novel polypeptide having both an amino acid sequence corresponding to the site of human thrombomodulin which provides the capability of binding to protein C and an amino acid sequence corresponding to the binding site of human thrombomodulin to thrombin (as indicated in Examples 3, 4 and 5). Thus, the present invention has been completed, and there is provided a novel polypeptide having the ability to promote the thrombin-catalyzed activation of protein C. A pharmaceutical composition comprising the novel polypeptide of the present invention can be applied by administration methods other than intravenous drip, such as oral administration and intranasal administration.

The substantially pure polypeptide of the present invention has an amino acid sequence represented by the formula (I)(SEQ. ID. No. 2):

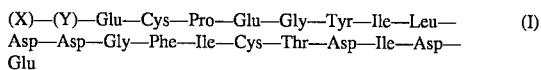

wherein X represents (a) an amino acid residue selected from the group consisting of Asp, Glu and Gla wherein Gla represents a γ-carboxyglutamic acid residue or (b) a peptide or polypeptide residue consisting of at least two amino acid residues selected from Asp, Glu and Gla, wherein said at least two amino acid residues are all the same or combinations of said Asp, Glu and Gla; and Y represents 0 to 58 amino acid residues.

In a preferred embodiment of the present invention, Y of the formula (I) is a peptide comprising an amino acid sequence represented by the formula (II).

In a more preferred embodiment of the present invention, the peptide of formula (I) in which Y is a peptide of formula (II), further has an amino acid sequence represented by formula (III), attached to the amino acid sequence of formula (I) at its C-terminus.

The X of formula (I), corresponding to the binding site of the present polypeptide to protein C, consists of 1 to 20 amino acid residues, preferably 1 to 10 amino acid residues, in view of the number of Gla residues in the Gla domain of protein C to which Gla domain the present polypeptide binds.

Further, it is possible that the polypeptide of the present invention comprising the amino acid sequence of formula (I) has at least one other type peptide or polypeptide attached thereto at its N-terminus and/or C-terminus.

It is also possible to change part of the structure of the polypeptide by natural or artificial mutation without significant change of the activity of the polypeptide. The polypeptide of the present invention includes polypeptides having a structure corresponding to homologous variants of the polypeptide having the above-mentioned amino acid sequence.

The polypeptide of the present invention may or may not contain at least one sugar residue.

The deoxyribonucleic acid of the present invention comprises a nucleotide sequence coding for the polypeptide having the amino acid sequence represented by the formula (I), the nucleotide sequence being unsubstituted or substituted at least at one nucleotide in accordance with the degeneracy of the Genetic Code.

The deoxyribonucleic acid (DNA) of the present invention comprises a nucleotide sequence coding for the amino acid sequence represented by the formula (I) mentioned above. The DNA of the present invention may comprise the nucleotide sequence coding for the amino acid sequence represented by the formula (I) and, attached thereto at its 5' and/or 3' end, at least one nucleotide sequence other than that coding for the amino acid sequence of the formula (I).

According to the present invention, a complementary DNA to the above-mentioned DNA is also provided. According to the present invention, the above-mentioned DNA and the complementary DNA may be complementarily bonded to each other to form a double-stranded DNA.

The structure of the DNA and the structure of the polypeptide deduced therefrom may be partially changed by natural or artificial mutation without causing the main activity of the polypeptide to be changed. Hence, the DNA of the present invention may alternatively have a nucleotide sequence that codes for a polypeptide having a structure corresponding to that of a homologous variant of any of the aforementioned polypeptides.

In accordance with the degeneracy of the Genetic Code, it is possible to replace at least one nucleotide of the nucleotide sequence of a gene by another type of nucleotide without causing the amino acid sequence of the polypeptide produced from the gene to be changed. Hence, the DNA of the present invention may also have any nucleotide sequence that has been changed by replacement in accordance with the degeneracy of the Genetic Code. In this instance, the amino acid sequence deduced from the nucleotide sequence obtained by the above-mentioned substitution is identical with the amino acid sequence as defined above.

The replicable recombinant DNA of the present invention comprises a replicable expression vector and the above-mentioned deoxyribonucleic acid according to the present invention inserted therein. The recombinant DNA is capable, in a transformed microorganism or cell, of expressing a polypeptide of the present invention. Examples of suitable expression vectors include plasmids pBR322, pBR327, pUC18, pUC19, YRp7, YEp24 (ATCC 37051), pPGACY2, pBSFAHY83, pSV2-dhfr (ATCC 37146), pBPV-1(9-1) (ATCC 37111) and the like. In this connection, it is necessary to select an expression vector suitable for a microorganism or cell to be used as a host.

Further, the present invention is directed to a microorganism or cell line transformed with the above-mentioned replicable recombinant DNA molecule. Examples of microorganisms include *Escherichia coli* strains, such as *E. coli* K12 strain 294 (ATCC 31446), *E. coli* B, *E. coli* X1776 (ATCC 31537), *E. coli* C600, and *E. coli* JM105; bacteria belonging to the genus Bacillus, such as *Bacillus subtilis*; Enterobacteria other than *E. coli* strains, such as *Salmonella typhimurium* and *Serratia marcesans*; bacteria belonging to the genus Pseudomonas; *Saccharomyces cerevisiae*; and filamentous fungi, such as *Aspergillus nidulans* and *Acremonium chrysogenum* (ATCC 11550). Examples of cell lines include animal cell lines, such as cell lines VERO (ATCC CCL-81) and HeLa, Chinese hamster ovary (CHO) cell lines, and cell lines WI38, BHK, COS-1, MDCK and the like.

The process for producing the polypeptide of the present invention comprises:

(a) providing a transformant comprising a microorganism or a cultured animal cell line transfomred with a recombinant DNA molecule of the present invention;

(b) culturing the transfomant to produce a polypeptide; and (c) isolating the polypeptide from the cultured transformant.

In the process of the present invention, the above-mentioned DNA of the present invention is ligated to a replicable expression vector at its portion downstream of the DNA region of the vector including a promoter etc. so that the DNA of the present invention can be transcribed properly into mRNA and the proper translation of the mRNA into a polypeptide can be attained. Thus, a replicable expression vector containing the above-mentioned DNA is obtained. Then, cells of a microorganism or cell culture are transformed with the thus obtained replicable recombinant DNA molecule to obtain a transformed microorganism or cell containing the recombinant DNA molecule. The thus obtained transformant is isolated from the parent cells of the microorganism or cell line by means of at least one phenotypical trait imparted with the recombinant DNA molecule. The obtained transformant is cultured to effect expression of the genetic information that is encoded by the above-mentioned deoxyribonucleic acid, thereby producing the polypeptide of the present invention.

For cloning DNA sequences necessary for constructing the DNA and the recombinant DNA molecule according to the present invention, for example, a promoter, an origin of replication, etc., it is preferred to use a host-vector system, in which a prokaryotic cell is employed as a host. Examples of prokaryotic cells include *Escherichia coli* strains, such as *E. coli* K12 strain 294 (ATCC 31446), *E. coli* B, *E. coli* X1776 (ATCC 31537), *E. coli* C600, *E. coli* C600hf1 and *E. coli* W3110 (F⁻,λ⁻, prototrophic, ATCC 27375); bacteria belonging to the genus Bacillus, such as *Bacillus subtilis*; Enterobacteria other than *E. coli*, such as *Salmonella typhimurium* and *Serratia marcesans*; bacteria belonging to the genus Pseudomonas; and *Saccharomyces cerevisiae*. Among these, most preferred is *E. coli* K12 strain 294. When the above-mentioned microorganism is used as a host, a plasmid vector suitable for the above-mentioned microorganism is generally employed as a replicable expression vector for the recombinant DNA molecule. For example, as the plasmid vector for transforming an *E. coli* strain, plasmids pBR322, pBR327, pUC18 and pUC19 may be used. A plasmid vector generally contains an origin of replication, a promoter and a marker gene which imparts to the recombinant DNA a phenotypical trait useful for selecting a cell line transformed with the recombinant DNA. Examples of promoters include a β-lactamase and lactose promoter, a tryptophan promoter and the like. Examples of marker genes include a gene for ampicillin resistance, a gene for tetracycline resistance, a gene for hygromycin resistance and the like. On the other hand, for expressing the DNA of the present invention to produce the polypeptide of the present invention, there may be used not only the above-mentioned host-vector system in which a prokaryotic cell is employed as a host, but also a host-vector system in which a eukaryotic cell, such as cells derived from vertebrates, is employed as a host. Examples of eukaryotic cells include cells, such as the animal cell lines as mentioned before. In order to express the DNA of the present invention in the above-mentioned eukaryotic host cell, the recombinant DNA molecule of the present invention generally contains functional sequences for controlling gene expression, such as an origin of replication, a promoter which is to be located upstream of the DNA of the present invention, a ribosome-binding site, a polyadenylation site and a transcription termination sequence. Such functional sequences to be used for expressing the DNA of the present invention in a eukaryotic cell may be obtained from a virus or viral substance.

For example, a promoter which can be used in the present invention may be obtained from adeno-virus 2, polyoma virus, simian virus 40 (SV40) and the like. Especially, the major late promoter of adenovirus 2 and the early promoter and late promoter of SV40 are preferred. Further, there may also be employed a promoter which is inherently present at a portion upstream of a gene which codes for a human lung-derived peptide having the ability to promote the thrombin-catalyzed activation of protein C, as long as the promoter is suitable for use in the above-mentioned host-vector system.

With respect to an origin of replication, there may be employed endogenous origins, for example, replication origins derived from a virus such as adenovirus, polyoma virus, SV40, vesicular stomatitis virus (VSV) and bovine papilloma virus (BPV). Alternatively, when a vector having such a property that it can be integrated into a host chromosome is used as an expression vector, the origin of replication of the host chromosome may be utilized.

The microorganism or cell line transformed with the replicable recombinant DNA molecule of the present invention is, as mentioned above, selected from parent cells which remain untransformed by means of at least one phenotypical trait imparted by the recombinant DNA molecule. A phenotypical trait may be imparted to the recombinant DNA molecule by inserting at least one marker gene in the recombinant DNA molecule. Alternatively, a marker gene inherent in the replicable expression vector may also be utilized. Examples of marker genes include a gene for drug resistance, for example, neomycin resistance, and a gene coding for dihydrofolate reductase (hereinafter referred to as "DHFR"). In this connection, it should be noted that there are various types of DHFR and, therefore, when a gene coding for a DHFR is used as a marker gene, the host cell to be used must be selected according to the types of DHFR encoded by the marker gene to be employed. For example, when a gene coding for a wild type DHFR is used as a marker gene, it is preferred to use a host cell which is deficient in DHFR. Such a DHFR-deficient strain requires hypoxanthine, glycine and thymidine and, therefore, cannot grow in a medium containing no hypoxanthine, glycine and thymidine. However, when the DHFR-deficient strain is transformed with a recombinant DNA containing a gene coding for DHFR, the strain no longer requires hypoxanthine, glycine and thymidine and can grow even in a medium containing no hypoxanthine, glycine and thymidine. Therefore, transformed cells can easily be selected from the cells remaining untransformed, using as a criterion an auxotrophy with respect to hypoxanthine, glycine and thymidine.

On the other hand, when a gene coding for a mutant DHFR which is poor in affinity to methotrexate (MTX) (the gene is hereinafter referred to as "MTX-resistant DHFR gene") is used as a marker gene, the host cell may contain a gene coding for a normal DHFR, and need not be deficient in DHFR. The reason for this is as follows. The normal DHFR is inhibited by MTX and, therefore, a host cell containing a gene coding for a normal DHFR requires hypoxanthine, glycine and thymidine in the presence of MTX. However, when such a host is transformed with a recombinant DNA containing the MTX-resistant DHFR gene, the transformed cell no longer requires hypoxanthine, glycine and thymidine even in the presence of MTX. Therefore, the transformed cell can be selected from the cells remaining untransformed using as a criterion auxotrophy with respect to hypoxanthine, glycine and thymidine in the presence of MTX. In this connection, a majority of eukaryotic cells are sensitive to MTX and therefore, the MTX-resistant DHFR gene may be advantageously employed as a marker gene.

Further, yeasts, such as *Saccharomyces cerevisiae*, may also be used as a host for expressing the DNA of the present invention. For expressing the DNA of the present invention in the yeast, for example, a plasmid YEp24 may be used as a replicable expression vector. The plasmid YEp24 contains a Ura3 gene and the Ura3 gene may be utilized as a marker gene.

Examples of promoters of the expression vector used for a yeast cell include promoters of genes of enzymes participating in the glycolytic pathway, such as 3-phosphoglycerate kinase or enolase, glyceraldehyde-3-phosphate dehydrogenase, hexokinase, pyruvate decarboxylase, phosphofructokinase, glucose-6-phosphate isomerase and glucokinase, and genes of alcohol dehydrogenase 2, isocytochrome C, acid phosphatase, enzymes participating in the nitrogen metabolism, glyceraldehyde-3-phosphate dehydrogenase, enzymes participating in the utilization of galactose, maltose and lactose, and the like. Among them, promoters of genes of alcohol dehydrogenase 2, isocytochrome C, acid phosphatase, enzymes participating in the nitrogen metabolism, glyceraldehyde-3-phosphate dehydrogenase and enzymes participating in the utilization of galactose, maltose and lactose are more advantageous because the transcription by the action of these promoters can be controlled by changing the culturing conditions for a host.

With respect to an origin of replication, a termination codon and other DNA sequences for controlling the transcription and translation in a yeast cell, any customary sequences may be used as long as they are suitable for a yeast cell.

Filamentous fungi, such as *Aspergillus nidulans* and *Acremonium chrysogenum* (ATCC 11550), can also be employed as a host for expression of the DNA of the present invention. For the expression of the DNA of the present invention with filamentous fungi, for example, pPGACY2 and pBSFAHY83 are employed as expresion vectors, which can be obtained by the method described in Matsuda et al Japanese Patent Application No. 2-219032 (which corresponds to Unexamined Japanese Patent Application Laid-Open Specification No. 4-104792) as described in Reference Examples 1-(1) and 1-(3) and FIGS. 56 and 58.

The promoter and terminator of the expression vector for *Acremonium chrysogenum* include, for example, those of the genes of phosphoglycerate kinase (PGK), glyceraldehyde-3-phosphate dehydrogenase (GAPD), actin and the like. DNA fragments containing these promoters and terminators can be obtained, for example, from a chromosome library of *Acremonium chrysogenum* (according to the method described in Referential Example 2-(1) hereinbelow).

The transformed microorganism or cell line may be cultured in a conventional nutrient medium according to the customary method to express the DNA coding for the polypeptide of the present invention and to produce the polypeptide of the present invention. After the culturing, the polypeptide of the present invention may be isolated from the culture of the transformant by a customary method, for example, by column chromatography, etc.

The thus obtained polypeptide may comprise at least one sugar chain of various types and lengths. Whether or not the resultant polypeptide comprises a sugar chain is dependent on the type of host cell employed. Further, the type and the length of the sugar chain are also dependent on the type of host cell employed.

Generally, it is known that a polypeptide produced by translation from the initiation codon ATG may be processed to form a mature polypeptide when the polypeptide is secreted out of the host cell. In the present invention also, the polypeptide may undergo such a processing. The position at which the polypeptide is processed varies according to the type of host and the culturing conditions. For example, when the polypeptide of the present invention is produced in a transformant cell in an unprocessed immature form comprising the amino acid sequence of the formula (I) and a leader sequence, the immature polypeptide may be processed so that the leader sequence is cut off to form a mature polypeptide. However, as mentioned above, the processed portion of the immature polypeptide varies according to the type of employed host and the culturing conditions for the host. Therefore, the above-mentioned processing does not always occur.

The polypeptide of the present invention may also be expressed with a leader sequence of other proteins. Furthermore, by the use of a specific protein leader sequence, the amino acid residues of the polypeptide following the leader sequence can be modified. For example, by the use of leader sequences of prothrombin, blood coagulation factor IX, blood coagulation factor X, blood coagulation factor VII, protein C, protein S and the like, the glutamic acid residue near the N-terminus of the polypeptide following such leader sequences can be γ-carboxylated [B. Furie et al., Blood, 75, 9 1753–1762 (1990)].

As mentioned above, the polypeptide of the present invention may be produced according to recombinant DNA techniques. Alternatively, the polypeptide of the present invention may be produced by organo-chemical synthesis according to the customary method, for example, using a commercially available automatic polypeptide synthesizer, etc.

The polypeptide of the present invention has the activity to promote the thrombin-catalyzed activation of protein C. Protein C is known as a protein which is dependent on vitamin K and plays an important role in the blood coagulation-fibrinolysis system, and is activated by the action of thrombin. It is known that in the living body, activated protein C inactivates activated factors V and VIII of the blood coagulation system coenzymes, and takes part in the production of plasminogen activator which has thrombolytic activity [Koji Suzuki, Igaku No Ayumi (History of Medicine), Vol. 125, p.901 (1983)]. The polypeptide of the present invention promotes the thrombin-catalyzed activation of protein C, thereby enabling the production of a large quantity of activated protein C which exhibits anticoagulation and thrombolytic activities. Hence, the polypeptide of the present invention greatly contributes to in vivo anticoagulation and thrombolysis.

As mentioned above, the polypeptide of the present invention has anticoagulant, platelet aggregation-inhibiting and thrombolytic activities and, hence, can be used, for example, for the treatment and prevention of diseases, such as myocardial infarction, thrombosis, embolism, obstruction of peripheral blood vessels, arteriosclerosis obliterans, disseminated intravescular coagulation (DIC) syndrome, angina pectoris, transient ischemic attack and toxemia of pregnancy. For the treatment of the above-mentioned diseases, the polypeptide of the present invention may be used in the form of a mixture with a pharmaceutically acceptable carrier, diluent or excipient. That is, an effective amount of the polypeptide of the present invention for treating or preventing the above-mentioned diseases may be mixed with an appropriate amount of a carrier, diluent or excipient to prepare a pharmaceutical composition which is suitable for administration to a patient. The polypeptide of the present invention may be used in the form of not only an injection but also a composition suitable for oral and nasal administrations, for example, administration through nostril mucosa.

The dose of the polypeptide of the present invention per adult varies depending on the age, sex, weight, conditions, etc. of the patient. In general, the dose is about 0.1 to about 200 mg. The present polypeptide may be administered once a day or, if desired, several times a day.

DETAILED DESCRIPTION OF THE PREFERRED EMBODIMENTS

The present invention will be described in more detail with reference to the following Examples and Reference Examples, which should not be construed as limiting the scope of the present invention.

The construction of plasmids to be employed for expression of the polypeptide of the present invention in filamentous fungi will be described in Reference Examples which are described after Examples.

Example 1

Identification of an Amino Acid Sequence of a Portion of the Human Thrombomodulin Which Imparts the Thrombomodulin with the Ability to Bind to Protein C (1) Construction of pSV2TMD7 and pSV2TMD8

(a) Construction of Plasmid M13TMD3

Plasmid pSV2TMJ2 (ATCC No. 67283) described in Example 1-(1) of International Unexamined Patent Application Publication No. W088/05053 is completely digested with restriction enzyme NcoI to cleave the plasmid. Both ends of the cleaved plasmid are treated with E. coli DNA polymerase to make them blunt. Then, the cleaved plasmid is completely digested with restriction enzyme HindIII to obtain a DNA fragment of about 1900 bp. The thus obtained DNA fragment is designated TMJ3. On the other hand, a phage M13mp19 (manufactured and sold by Takara Shuzo Co., Ltd., Japan, catalog No. 3119) is digested with restriction enzymes HindIII and HincII to obtain a vector. The DNA fragment TMJ3 is inserted in the above-obtained vector to obtain recombinant plasmid M13mp19TMJ3.

Separately, a DNA probe for deletion (hereinafter referred to as "deleter") TMd3 having the following nucleotide sequence is organochemically synthesized (SEQ. ID. No. 5):

5'-GGAGGCCGCTCAACAGTCGGTGCCA-3' (25mer)

which hybridizes to a portion of the plasmid M13mp19TMJ3 having the following partial sequence (SEQ. ID. No. 6) as shown in FIG. 1 and which codes for the partial amino acid sequence (SEQ. ID. NO, 7) also shown in FIG. 1:

CAC ATT GGC ACC GAC TGT TGAGCGGCCT CC His Ile Gly Thr Asp Cys

Then, a 285 bp nucleotide sequence is deleted from the above-obtained recombinant plasmid M13mp19TMJ3 by a technique of site-directed mutagenesis using the thus obtained deleter TMd3 in accordance with the method described in Method in Enzymology, 100, 468 (1983), Academic Press.

Illustratively stated, 25 pmol of the deleter TMd3 and 10 pmol of M13 primer M3 (manufactured and sold by Takara Shuzo Co., Ltd., Japan, catalog No. 3831) are phosphorylated at their 5'-ends by means of T4 kinase. To the phosphorylated deleter and primer is added 0.5 pmol of a single-stranded DNA of recombinant plasmid M13mp19TMJ3. The resultant mixture is heated at 95° C. for 5 minutes and then cooled to room temperature. Then, 5 units of E. coli DNA polymerase I (Klenow fragment) and 10 units of T4 DNA ligase are added to the mixture, and the mixture is incubated at 37° C. for 30 min to form a recombinant plasmid in the mixture. The thus obtained mixture is added to a culture of E. coli JM105 (manufactured and sold by Pharmacia Fine Chemicals AB, Sweden, catalog No. 27-1550) to transfect the E. coli with the recombinant plasmid. The E. coli is cultured on an agar plate at 37° C. overnight to thereby form plaques on the agar plate. The plaques are transplanted on a nitrocellulose filter, followed by denaturation with an alkari and neutralization with 0.5M Tris-HCl buffer (pH7.5), and heated at 80° C. for 2 hours. Then, the nitrocellulose filter is subjected to prehybridization at 55° C. for 2 hours in a solution containing 6×SET [0.9M NaCl, 180 mM Tris buffer (pH8.0) and 6 mM EDTA], 5×Denhart's [0.1% (w/v) polyvinyl pyrrolidone and 0.1% (w/v) bovine serum albumin (BSA)], 0.1% SDS and 100 µg/ml denatured salmon sperm DNA. Subsequently, the resultant nitrocellulose filter is subjected to hybridization at 55° C. for 2 hours in a solution having the same composition as that of the above solution except that a $^{32}$P-labeled TMd3 is used instead of the denatured salmon sperm DNA. Then, the nitrocellulose filter is washed with 6×SSC (an aqueous solution containing 0.9M NaCl and 0.09M trisodium citrate) twice at room temperature each for 5 min. Further, the filter is washed with the same solution successively at 55° C., 65° C. and 75° C. The above washing is conducted twice each for 5 min at the respective temperature. Then, X-ray film XAR-5 (manufactured and sold by Eastman Kodak Company, U.S.A.) is contacted with the resultant nitrocellulose filter, and exposed at −80° C. overnight to X-ray. As a result, several tens of strongly exposed black spots are observed on the X-ray film. Each of the spots corresponds to the respective clones which have been transfected with the recombinant plasmid. Six clones are selected from the obtained clones and the recombinant plasmid is isolated from each of the selected clones. Each of the plasmids is analyzed with respect to its restriction sites and nucleotide sequence. The recombinant plasmids of the clones are found to be identical with respect to their restriction sites and nucleotide sequence. The thus obtained DNA fragment is found to have a nucleotide sequence containing initiation codon ATG and, downstream thereof, a nucleotide sequence that codes for a polypeptide comprised of amino acid residues up to the 480th position of the sequence of FIG. 55. This DNA fragment is designated as TMD3, and the recombinant plasmid containing this DNA fragment is designated as M13TMD3. In FIG. 1, there is illustrated the recombinant plasmid M13mp19TMJ3 with which the deleter TMd3 is hybridized, and of which the DNA region corresponding to the DNA fragment TMJ3 is partly deleted.

(b) Construction of Plasmid pSV2TMD7

The recombinant plasmid M13TMD3 obtained in Example 1-(1)-(a) is subjected to a partial deletion of 1044 nucleotides according to the technique of site-directed mutagenesis in substantially the same manner as in Example 1-(1)-(a) except that deleter TMd5 having the following nucleotide sequence (SEQ. ID. No. 8):

5'-GAAGCACGGGTCGGGGAACCCCAGG-3' (25 mer) which is complementary to a portion of the plasmid M13TMD3 having the following partial sequence (SEQ. ID. #9) as shown in FIG. 2 and which codes for the partial amino acid sequence (SEQ. ID. NO. 10) also shown in FIG. 2:

GGC CTG GGG TTC CCC GAC CCG TGC TTC AGA is used instead of the deleter TMd3, to thereby obtain recombinant plasmid M13TMD7 having inserted therein a DNA fragment designated as TMD7. This DNA fragment TMD7 has a nucleotide sequence including initiation codon ATG and, downstream thereof, a nucleotide sequence coding for a peptide comprised of amino acid residues up to the 18th position counted from the amino acid residue corresponding to the initiation codon and the 367th to the 480th amino acid residues of the sequence of FIG. 55. In FIG. 2, there is illustrated the recombinant plasmid M13TMD3 with which the deleter TMd5 is hybridized, and of which the DNA region corresponding to the DNA fragment TMD3 is partly deleted. Further, the recombinant plasmid M13TMD7 DNA is completely digested with restriction enzymes HindIII and BamHI, and a TMD7 DNA fragment of about 580 bp is isolated. On the other hand, plasmid pSV2-dhfr (ATCC No. 37146) is completely digested with restriction enzymes HindIII and BglII to obtain a vector. This vector and the above-mentioned DNA fragment of 580 bp are ligated to each other using T4DNA ligase to obtain plasmid pSV2TMD7.

(c) Construction of Plasmid pSV2TMD8

The recombinant plasmid M13TMD3 obtained in Example 1-(1)-(a) is subjected to a partial deletion of 1047 nucleotides according to the technique of site-directed mutagenesis in substantially the same manner as in Example 1-(1)-(a) except that deleter TMd6 having the following nucleotide sequence (SEQ. ID. NO. 11):

5'-TCTGAAGCACGGGGGGAACCCCAGG-3' (25 mer) which hybridizes to a portion of the plasmid M13TMD3 having the following partial sequence (SEQ. ID No. 12) as shown in FIG. 3 and which codes for the partial amino acid sequence (SEQ. ID. NO. 13) also shown in FIG. 3:

GGC CTG GGG TTC CCC CCG TGC TTC AGA GCC is used instead of the deleter TMd3, to thereby obtain recombinant plasmid M13TMD8 having inserted therein a DNA fragment designated as TMD8. This DNA fragment TMD8 has a nucleotide sequence including initiation codon ATG and, downstream thereof, a nucleotide sequence coding for a peptide comprised of amino acid residues up to the 18th position counted from the amino acid residue corresponding to the initiation codon and the 368th to 480th amino acid residues of the sequence of FIG. 55. In FIG. 3, there is illustrated the recombinant plasmid M13TMD3 with which the deleter TMd6 is hybridized, and of which the DNA region corresponding to the DNA fragment TMD3 is partly deleted. Further, the recombinant plasmid M13TMD8 is completely digested with restriction enzymes HindIII and BamHI, and a TMD8 DNA fragment of about 580 bp is isolated. On the other hand, plasmid pSV2-dhfr (ATCC No. 37146) is completely digested with restriction enzymes HindIII and BglII to obtain a vector. This vector and the above-mentioned DNA fragment of 580 bp are ligated to each other using T4DNA ligase to obtain plasmid pSV2TMD8.

(2) Transfection of Plasmids pSV2TMD7 and pSV2TMD8 into Cells of Cell Line COS-1

Cells of cell line COS-1 (ATCC No. CRL1650) are cultured in Dulbecco's minimal essential medium (hereinafter referred to as "DMEM", manufactured and sold by Flow Laboratories Inc., U.S.A., catalog No. 10-311) containing 10% (v/v) fetal calf serum (hereinafter referred to as "FCS", manufactured and sold by GIBCO, U.S.A.), which is contained in a tissue culture dish. When the culture achieves a logarithmic growth phase, the cells which have grown adhering to each other and to the tissue culture dish are dissociated from the tissue culture dish using a phosphate buffer (PBS) containing 0.25% trypsin and 0.02% EDTA. The dissociated cells are suspended in a 7 mM phosphate buffer (pH7.4) for electroporation containing 272 mM saccharose and 1 mM $MgCl_2$ so that the cell concentration becomes $8 \times 10^6$ cells/ml to thereby obtain a cell suspension. 500 µl of the resultant cell suspension is charged in a cuvette for electroporation (manufactured and sold by Bio-rad Corp., U.S.A., catalog No. 165-2085). Each of the plasmid pSV2TMD7 and pSV2TMD8 DNAs constructed in Example 1-(1) is suspended in a 0.1 mM tris-HCl buffer (pH 8.0) so that the DNA concentration becomes 4 µg/µl. 5 µl of the suspension containing 20 µg of the plasmid DNA is added to the above-mentioned COS-1 cell suspension in the cuvette, and allowed to stand at 0° C. for 10 minutes. Thereafter, the cuvette is transferred into an electroporation apparatus (manufactured and sold by Bio-rad Corp., U.S.A., catalog No. 165-2075), and electric pulse is applied under conditions of 3 µF and 450 V twice at intervals of 30 seconds. The cuvette is allowed to stand at 0° C. for 10 minutes, and the cell suspension is put in 10 ml of DMEM containing 10% (v/v) FCS, placed in a tissue culture dish (diameter: 10 cm). The cell suspension in the tissue culture dish is cultured in a $CO_2$ gas incubator at 37° C. for 24 hours. Thereafter, the culture medium is replaced by 10 ml of DMEM containing no FCS, and further incubation is performed for 48 hours. The cell culture is recovered from the tissue culture dish.

(3) Assay of the Activity of Polypeptides Produced by Culturing COS-1 Cells Transformed by Plasmids pSV2TMD7 and pSV2TMD8 to Promote the Thrombin-catalyzed Activation of Protein C 5 µl of the supernatant of the culture of COS-1 cells transformed by each of plasmids pSV2TMD7 and pSV2TMD8, 3 µl of thrombin (manufactured and sold by Sigma Chemical Company, catalog No. T-6759, 20 ng/µl), 5 µl of 10×Assay Buffer containing 1M NaCl, 30 mM $CaCl_2$, 1% calf serum albumin and 0.5M tris-HCl buffer (pH 8.5)

and 29.5 μl of distilled water are mixed together and allowed to stand at 37° C. for 5 minutes, followed by the addition of 7.5 μl protein C (derived from bovine, 0.2 μg/μl) to the mixture. The reaction is conducted at 37° C. for 30 minutes, and terminated by adding 6.25 μl of a stop solution (20 mM tris-HCl buffer, pH7.5, containing 100 mM NaCl, 0.3$A_{280}$ anti-thrombin III and 100 μg/ml heparin).

The activity of activated protein C is measured by first adding 10 μl of Boc-Leu-Ser-Thr-Arg-MCA (manufactured and sold by Peptide Institute, The Foundation (Japan), 5 mg/ml), 5 μl of 5M CsCl and 495 μl of a substrate reaction buffer (50 mM tris-HCl buffer containing 100 mM NaCl (pH 8.5)), next allowing the reaction to proceed at 37° C. for 20 minutes, then terminating the reaction by adding 55 μl of acetic acid, and finally measuring the concentration of liberated AMC (7-amino-7-methyl-coumarin) by means of a spectrofluorometer (model RF-540, manufactured and sold by Shimadzu Corporation, Japan) at an excitation wavelength of 380 nm and an emission wavelength of 440 nm. The obtained fluorescence intensity is compared with the fluorescence intensity of a solution having a known AMC concentration to determine the amount of the liberated AMC. The value obtained by deducting from this amount the amount of AMC in the case where an aqueous solution containing no polypeptide of the present invention is added, represents the activity of the polypeptide to promote the thrombin-catalyzed activation of protein C. The activity to produce 1 nM of activated protein C per ml of reaction mixture and per minute is defined as 1 u (unit). Results are shown in Table 1.

(4) Determination of the Amount of Polypeptide Produced by Culturing COS-1 Cells Transformed with Each of Plasmids pSV2TMD7 and pSV2TMD8

The amount of polypeptide contained in the supernatant of a culture of COS-1 cells transformed with each of plasmids pSV2TMD7 and pSV2TMD8 is determined according to the method of K. Suzuki et al [J. Biol. Chem. Vol. 264, pp.4872–4876(1989)] according to the enzyme immunoassay (hereinafter referred to as "ELISA") using rabbit anti-human thrombomodulin antibody. Details are as follows.

(a) Construction of Plasmid pSV2TMD1

The recombinant plasmid obtained in Example 1-(1)-(a) is subjected to a partial deletion of 177 nucleotides according to the technique of site-directed mutagenesis in substantially the same manner as in Example 1-(1)-(a) except that deleter TMd1 having the following nucleotide sequence (SEQ. ID. No. 14):

5'-GGAGGCCGCTCAGCCCGAATGCACG-3' (25 mer) which hybridizes to a portion of the plasmid M13mp19TMJ3 having the following partial sequence (SEQ. ID No. 15) as shown in FIG. 4 and which codes for the partial amino acid sequence (SEQ. ID. NO. 16) also shown in FIG. 4:

GGG CTC GTG CAT TCG GGC TGAGCGGCCT CCGTCCAG is used instead of the deleter TMd3, to thereby obtain recombinant plasmid M13TMD1 having inserted therein a DNA fragment designated as TMD1. This DNA fragment TMD1 has a nucleotide sequence including an initiation codon ATG and, downstream thereof, a nucleotide sequence coding for a peptide comprised of amino acid residues up to the 516th position counted from the amino acid residue corresponding to the initiation codon of the sequence of FIG. 55. In FIG. 4, there is illustrated the recombinant plasmid M13mp19TMJ3 with which the deleter TMd1 is hybridized, and of which the DNA region corresponding to the DNA fragment TMJ3 is partly deleted. Further, the recombinant plasmid M13TMD1 DNA is completely digested with restriction enzymes HindIII and BamHI, and a TMD1 DNA fragment of about 1700 bp is isolated. On the other hand, plasmid pSV2-dhfr (ATCC No. 37146) is completely digested with restriction enzymes HindIII and BglII to obtain a vector. This vector and the above-mentioned DNA fragment of 1700 bp are ligated to each other using T4DNA ligase to obtain plasmid pSV2TMD1.

(b) Introduction of Plasmid pSV2TMD1 into an Animal Cell and Purification of a Polypeptide Transfection of each of the plasmid pSV2TMD1 constructed in Example 1-(4)-(a) and plasmid pSV2-dhfr (ATCC No. 37146) into cell line CHO-dhfr⁻ is performed according to the method of F. L. Graham et al [F. L. Graham, Virology, vol. 52, p. 456 (1973)], using calcium phosphate. The cell line CHO-dhfr⁻ has been obtained from Dr. L. Chasin and Dr. G. U. Chasin of Columbia University (U.S.A.). The transfected cell is cultured in Dulbecco's minimal essential medium (DMEM, manufactured and sold by Flow Laboratories Inc., U.S.A.) supplemented with 150 μg/ml proline and 10% dialyzed fetal calf serum (DFCS, manufactured and sold by GIBCO, U.S.A., catalog No. 220-6440AG). After about one-month culturing, colonies of the transformed cell appear. Each cell clone is then successively cultured in media which contain Methotrexate (MTX, manufactured and sold by Wako Pure Chemical Inc., Japan) in concentrations of 20 nM, 200 nM, 2 μM and 20 μM, respectively, to thereby obtain a transformed cell line (9G5E) having high capacity for producing a polypeptide which has an activity to promote the thrombin-catalyzed activation of protein C. The obtained cell line grows in the same culture medium as mentioned above, and cultured in the same medium having as mentioned above except that the serum concentration is reduced to 1%, thereby obtaining 10 liters of culture.

The obtained culture (10 liters) is applied to a Q-Sepharose column (manufactured and sold by Pharmacia Fine Chemicals, Inc. Sweden) equilibrated with 20 mM tris-HCl buffer (pH 7.4) containing 0.2M NaCl. The column is washed with the buffer employed in the equilibration, and eluted with 20 mM tris-HCl buffer (pH 7.4) containing 1M NaCl. The eluate is subjected to a 5-fold dilution with 20 mM Tris-HCl buffer (pH 7.4). Then, the desalted fraction is applied to a diisopropyl-phosphorothrombin modified agarose column (hereinafter referred to as "DIP-thrombin column") prepared by bonding diisopropylphosphorothrombin prepared according to the method of N. L. Esmon et al. [J. Biol. Chem. Vol. 257, p.859 (1982)] to an agarose bromocyanated according to the method of P. Cuatrecasas [J. Biol. Chem. Vol. 245, p.3059 (1970)], which column has been equilibrated with 20 mM phosphate buffer (pH 7.4) containing 0.2M NaCl. This column is washed with the buffer employed in the equilibration, and is eluted with 20 mM phosphate buffer (pH 7.4) containing 1.0M NaCl, to thereby obtain the active fraction. The active fraction is concentrated, and is applied to Sephacryl S-300 column (17-0559-01, manufactured and sold by Pharmacia Fine Chemicals, Inc., Sweden) equilibrated with phosphate buffer saline (PBS). The fraction is developed with the same buffer to obtain an active fraction, which has been concentrated. The thus purified polypeptide is designated as D123Asp.

(c) Preparation of Antibody

An antibody for the purified polypeptide D123Asp is prepared according to the method of E. Harlow et al ["Antibodies a Laboratory Manual, p.92, (1988), published by Cold Spring Harbor Laboratory], in which rabbit (Japanese white species, 4 months old) is immunized with the polypeptide, antiserum is taken from the immuned rabbit and then purified by precipitation using ammonium sulfate.

The reactivity of the obtained antibody with the polypeptide D123Asp is confirmed by the following procedure. Illustratively stated, purified polypeptide (about 10 ng) prepared in Example 1-(4)-(b) is spotted onto a nitrocellulose filter, followed by air drying. Then, the polypeptide spotted on the filter is reacted with the above-obtained purified antibody functions as a primary antibody. Thereafter, the polypeptide is reacted with biotin treated anti-rabbit IgG (manufactured and sold by Zymed Laboratories Inc., U.S.A., Catalog No. 62-1840) prepared with a goat followed by coloring with avidin, biotinylated horseradish peroxidase (manufactured and sold by Amersham Japan, RPN 1051) and 4-chloronaphthol. The immunoreaction product is detected as a dark brown spot.

(d) ELISA

The amount of polypeptide is determined according to the method of K. Suzuki et al [J. Biol Chem. Vol. 264, pp. 4872–4876 (1989)] by ELISA using rabbit anti-human thrombomodulin antibody. Illustratively stated, F(a b')$_2$ antibody is prepared from rabbit anti-human thrombomodulin antibody obtained in Example 1-(4)-(c) according to the method of E. Harlow et al [Antibodies A Laboratory Manual 630 (1988) published by Cold Spring Harbor Laboratory]. The prepared F(a b')$_2$ antibody is diluted with 0.1M sodium bicarbonate buffer (pH 9.2) so that the resultant solution has a concentration of 5 μg/ml. The diluted solution is portionwise charged in each well of a 96-well microtiter plate (manufactured and sold by Dynatech Laboratories, Inc., catalog No. 011-010-7801) in an amount of 100 μl/well. One hour later, each of the wells is washed with 0.1M sodium bicarbonate buffer (pH 9.2), followed by addition of 10% normal rabbit serum (manufactured and sold by 2Flow Laboratories Inc., U.S.A., catalog No. 29-411-49) in an amount of 200 μl/well, thereby performing blocking for 2 hours. Thereafter, each of the wells is washed with 10 mM phosphate buffer (pH 7.0) containing 0.1M NaCl, 1 mM MgCl$_2$, 0.1% BSA and 0.05% Tween-20. Separately, the polypeptide solution to be measured is diluted with a phosphate buffer containing 0.1% BSA, 0.5% gelatin and 0.05% Tween-20 to obtain 100 fold, 1,000 fold, 10,000 fold and 100,000 fold dilutions. The dilutions are charged in the wells in an amount of 100 μl/well, and subjected to a reaction for 2 hours. Each of the wells is washed with the above-mentioned washing buffer, and added thereto is 100 μl of an antibody solution (1 μg/ml) obtained by labeling the above-mentioned F(a b')$_2$ anti-human thrombomodulin antibody with β-galactosidase according to the method of S. Yoshitake et al [Scand. J. Immunol. Vol. 10, pp. 81–86 (1979)]. Reaction is performed for one hour, and after the reaction, each of the wells is washed with the above-mentioned washing buffer. Subsequently, 100 μl of a solution obtained by dissolving 4-MUG (4-methylunberipheryl-β-D-galactoside, manufactured and sold by Sigma Chemical Company, U.S.A., catalog No. M-1633) in PBS in a concentration of 0.1 mg/ml, is charged in each of the wells. The fluorescence is measured at an excitation wavelength of 360 nm and at a measurement wavelength of 450 nm, using a spectrophotofluorometer (manufactured and sold by Pandex Laboratories, Inc., catalog No. 10-015-1) suited for 96-well microtiter plates. Results are shown in Table 1.

(5) Preparation of Asp$^{367}$Mutant (a) Construction of plasmid pSV2TMM1

The recombinant plasmid M13TMD1 obtained in Example 1-(4)-(a) is subjected to a partial mutation of Asp$^{367}$ to Ala$^{367}$ according to the technique of site-directed mutagenesis in substantially the same manner as in Example 1-(1)-(a) except that DNA probe TMm1 for mutation (hereinafter referred to as "mutator") having the following nucleotide sequence (SEQ. ID. No. 17):

5'-CTGAAGCACGGAGCCACGGGCTCCA-3' (25 mer) which hybridizes to a portion of the plasmid M13TMDI having the following partial sequence (SEQ. ID No. 19) as shown in FIG. 5 and which codes for the partial amino acid sequence (SEQ. ID. NO. 20) also shown in FIG. 5:

TGT GTG GAG CCC GTG GAC CCG TGC TTC AGA GCC is used instead of the deleter TMd3, to thereby obtain recombinant plasmid M13TMM1 having inserted therein a DNA fragment designated as TMM1. This DNA fragment TMM1 has a nucleotide sequence including initiation codon ATG and, downstream thereof, a nucleotide sequence coding for a polypeptide (SEQ. ID. No. 18) comprised of amino acid residues up to the 516th position counted from the amino acid residue corresponding to the initiation codon of the sequence of FIG. 55, wherein the 367th Asp is changed to Ala. FIG. 5 shows a hybridization of mutator TMm1 with recombinant plasmid M13TMD1, in which Asp$^{367}$ is changed to Ala$^{367}$. Further, recombinant plasmid M13TMM1 DNA is completely digested with restriction enzymes HindIII and BamHI, and a TMM1 DNA fragment of about 1700 bp is isolated. On the other hand, plasmid pSV2-dhfr(ATCC No. 37146) is completely digested with restriction enzymes HindIII and BglII to obtain a vector. This vector and the above-mentioned DNA fragment of 1700 bp are ligated to each other using T4 DNA ligase to obtain plasmid pSV2TMM1.

(b) Construction of Plasmid pSV2TMM2

The recombinant plasmid M13TMD1 obtained in Example 1-(4)-(a) is subjected to a partial mutation of Asp$^{367}$ to Glu$^{367}$ according to the technique of site-directed mutagenesis in substantially the same manner as in Example 1-(1)-(a) except that mutator TMm2 having the following nucleotide sequence (SEQ. ID. No. 21):

5'-CTGAAGCACGGTTCCACGGGCTCCA-3' (25 mer) which hybridizes to a portion of the plasmid M13TMDI having the following partial sequence (SEQ. ID No. 23) as shown in FIG. 6 and which codes for the partial amino acid sequence (SEQ. ID. NO. 24) also shown in FIG. 6:

TGT GTG GAG CCC GTG GAC CCG TGC TTC AGA GCC is used instead of the deleter TMd3, to thereby obtain recombinant plasmid M13TMM2 having inserted therein a DNA fragment designated as TMM2. This DNA fragment TMM2 has a nucleotide sequence including initiation codon ATG and, downstream thereof, a nucleotide sequence coding for a polypeptide (SEQ. ID. No. 22) comprised of amino acid residues up to the 516th position counted from the amino acid residue corresponding to the initiation codon of the sequence of FIG. 55, wherein the 367th Asp is changed to Glu. FIG. 6 shows the recombinant plasmid M13TMD1 hybridized with mutator TMm2 to thereby change Asp$^{367}$ to Glu$^{367}$. Further, recombinant plasmid M13TMM2 DNA is completely digested with restriction enzymes HindIII and BamHI, and a TMM2 DNA fragment of about 1700 bp is isolated. On the other hand, plasmid pSV2dhfr (ATCC No. 37146) is completely digested with restriction enzymes HindIII and BglII to obtain a vector. This vector and the above-mentioned DNA fragment of 1700 bp are ligated to each other using T4DNA ligase to obtain plasmid pSV2TMM2.

(c) Transfection of Asp$^{367}$ Mutant into Cells of Cell Line COS-1

Transfection of plasmids pSV2TMD1, pSV2TMM1 and pSV2TMM2 into cell line COS-1 is performed according to the method described in Example 1-(2). With respect to each of the plasmids, electroporation is performed 90 times, and about 900 ml of culture is obtained.

(d) Purification and Quantitative Analysis of Polypeptide Produced by Asp$^{367}$ Mutant Culture (900 ml) obtained in Example 1-(5)-(c) is applied to Q-sepharose column (manufactured and sold by Pharmacia Fine Chemicals, Inc., Sweden, catalog No. 17-0510-01) equilibrated with 5 mM phosphate buffer (pH 7.4). The column is washed with 5 mM phosphate buffer (pH 7.4) containing 0.18M NaCl, and eluted with 5 mM phosphate buffer (pH 7.4) containing 0.28M NaCl. The eluate is dialyzed using 5 mM phosphate buffer (pH 7.4) having Ca ions removed by means of Chelex 100 (manufactured and sold by Bio Rad, U.S.A., catalog No. 143-2832).

Subsequently, according to ELISA described in Example 1-(4), the amount of each polypeptide is determined. As a result, it is found that the amount of each of the polypeptides is about 50 μg.

The polypeptides isolated from the supernatants of cultures of cell line COS-1 transfected with plasmids pSV2TMM1 and pSV2TMM2 are designated as D123Ala and D123Glu, respectively.

Figure 8:
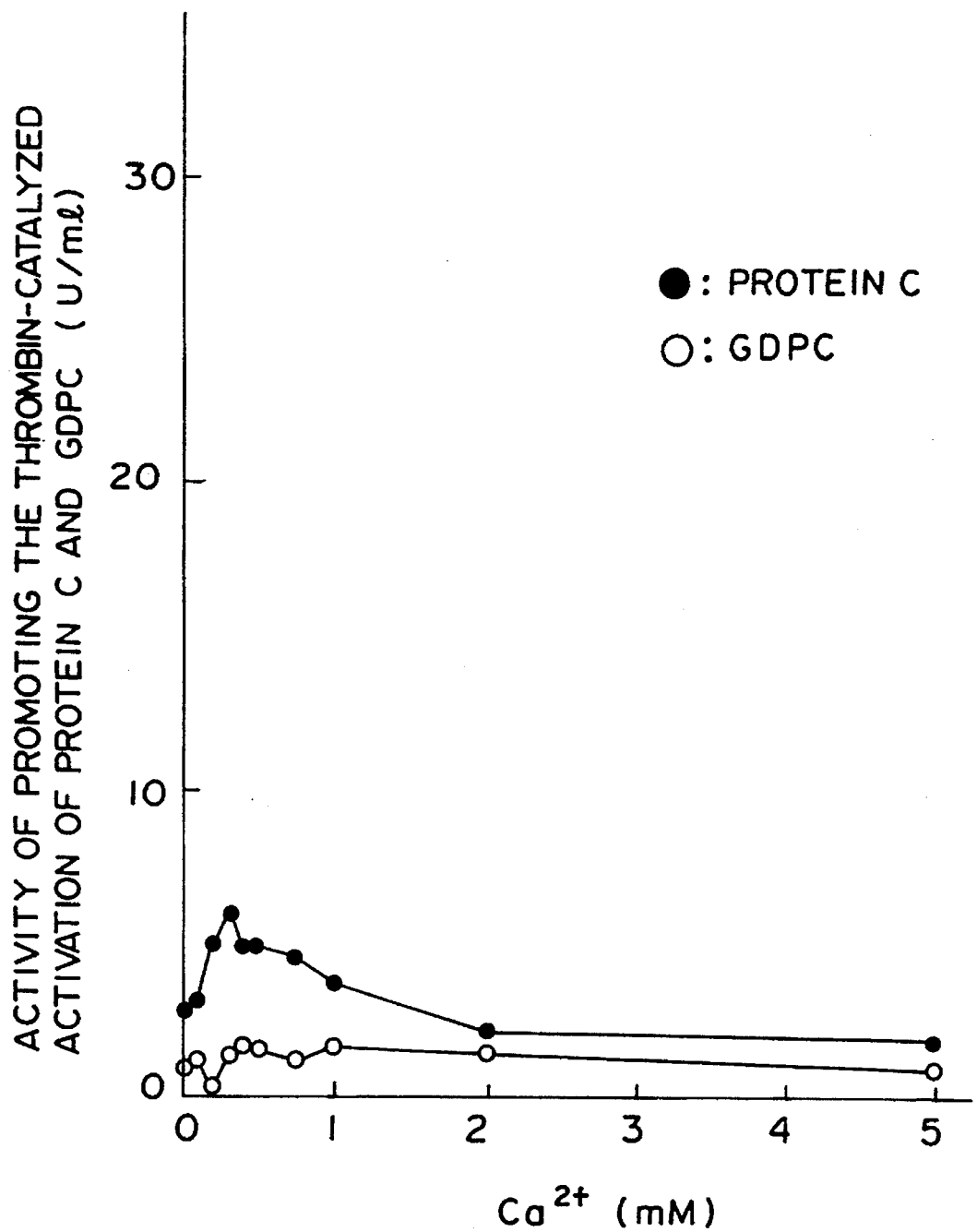
FIG. 8 is a graph showing the effect of calcium ion concentration on the activity of promoting the thrombin-catalyzed activation of each of protein C and GDPC with respect to polypeptide D123Ala obtained in Example 1.
Figure 9:
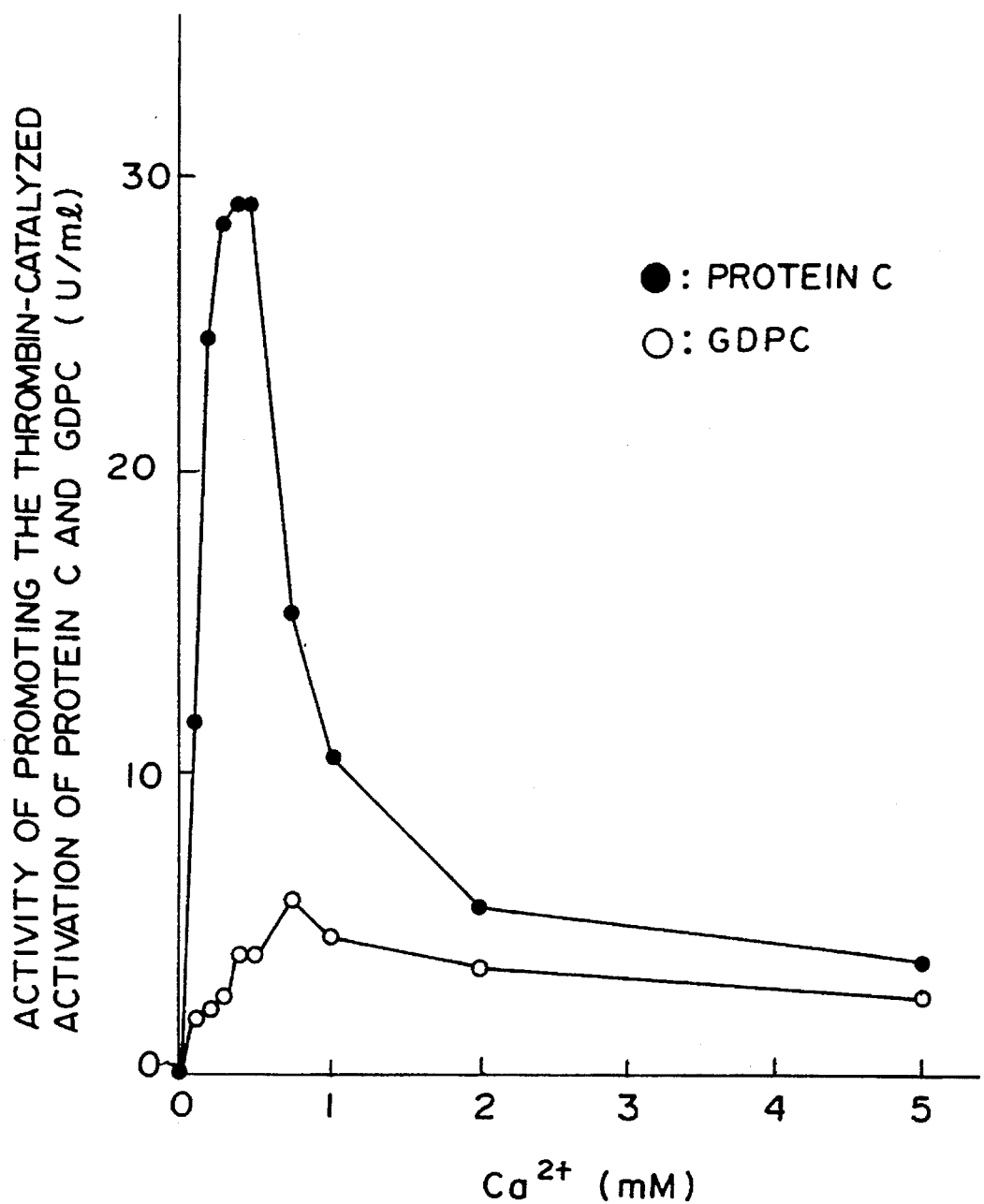
FIG. 9 is a graph showing the effect of calcium ion concentration on the activity of promoting the thrombin-catalyzed activation of each of protein C and GDPC with respect to polypeptide D123Glu obtained in Example 1.

(e) Assay for the Activity of Polypeptide Produced by Asp$^{367}$ Mutant to Promote the Thrombin-catalyzed Activation of protein C With respect to the polypeptide solutions (0.4 μg/ml) purified and quantitated in Example 1-(5)-(d), the activity of polypeptides to promote the thrombin-catalyzed activation of protein C is measured according to the method described in Example 1-(3). The CaCl$_2$ concentration of 10×Assay buffer is adjusted so that the activities at calcium ion concentrations of 0 to 5 mM are determined. Also, with respect to protein C having no Gla domain (hereinafter referred to as "GDPC") which is prepared by chymotrypsin treatment according to the method of N. L. Esmon [J. Biol. Chem. Vol. 258, pp. 5548–5553 (1983)]and which is used instead of protein C, the activity measurement is carried out within the same range of calcium concentration. Results are shown in FIGS. 7–9.

D123Asp is found to have a high activity exhibiting the highest value at calcium concentrations of from 0.4 to 0.5 mM, in the activation of protein C. On the other hand, in the activation of GDPC, such a characteristic dependency on calcium ion concentrations is not observed, and low activity is observed over a wide range of calcium ion concentrations.

On the other hand, D123Ala is found to have low activity in the activation of both protein C and GDPC. With respect to D123Glu, the activity similar to that of D123Asp is observed, but the activity of D123Glu is as high as 1.2 times that of D123Asp in the activation of protein C.

Example 2

Identification of an Amino Acid Sequence Coding for Human Thrombomodulin, Which Contains a Binding Site to Thrombin (1) Preparation of Synthetic Polypeptide The synthesis of polypeptides is performed by an automatic peptide synthesizer (model 431A, manufactured and sold by Applied Biosystems Inc., U.S.A.) according to the customary solid phase synthesis method, using a phenyl acetomethyl resin (PAM resin) as a support. The following three new types of polypeptides are prepared by synthesis through the study of the amino acid sequence from the 406th to the 444th position of human thrombomodulin.

Polypeptide A: Met-Phe-Cys-Asn-Gln-Thr-Ala-Ala-Pro-Ala-Asp-Cys-Asp (SEQ. ID. No. 25)

Polypeptide B: Ala-Cys-Pro-Ala-Asp-Ala-Asp-Pro-Asn-Thr-Gln-Ala-Ser-Cys-Glu (SEQ. ID. No. 26)

Polypeptide C: Glu-Cys-Pro-Glu-Gly-Tyr-Ile-Leu-Asp-Asp-Gly-Phe-Ile-Cys-Thr-Asp-Ile-Asp-Glu (SEQ. ID. No. 27)

In the synthesis of polypeptide A, PAM-aspartic acid resin (manufactured and sold by Applied Biosystem Inc., U.S.A., catalog No. 400092) prepared by bonding t-butyloxycarbonyl-aspartic acid β-benzyl ester with PAM resin is used as a starting material. To the C-terminus of the PAM-aspartic acid resin, amino acids protected by Boc are successively combined one by one, i.e., first Boc-Cys (4-CH$_3$OBzl), second Boc-Asp (OBzl) and so on are successively combined. With respect to the polypeptides B and C, PAM-glutamic acid resin (manufactured and sold by Applied Biosystems Inc., U.S.A., catalog No. 400096) prepared by bonding t-butyloxycarbonyl glutamic acid gamma-benzyl ester with PAM resin is used as a starting material. To the C-terminus of the PAM-glutamic acid resin, amino acids protected by Boc are successively bonded one by one.

The following protective amino acids are used:
t-butyloxycarbonyl-L-alanine (Boc-Ala), t-butyloxycarbonyl-L-asparatic acid β-benzyl ester [Boc-Asp (OBzl)], t-butyloxycarbonyl-L-glutamic acid benzyl ester [Boc-Glu (OBzl)], t-butyloxycarbonyl-S-p-methoxybenzyl-L-cysteine [Boc-Cys (4-CH$_3$OBzl)], t-butyloxycarbonyl-L-phenylalanine (Boc-Phe), t-butyloxycarbonyl-L-Asparagine (Boc-Asn), t-butyloxycarbonyl-L-Glutamine (Boc-Gln), t-butyloxycarbonyl-L-Proline (Boc-Pro), t-butyloxycarbonyl-O-benzyl-L-Threonine [Boc-Thr (Bzl)], t-butyloxycarbonyl-O-benzyl-L-Serine [Boc-Ser (Bzl)], t-butyloxycarbonyl-O-2-bromobenzyloxy-carbonyl-L-Tyrosine [Boc-Tyr (BrBzl)], t-butyloxycarbonyl-glycine (Boc-Gly), t-butyloxycarbonyl-L-Isoleucine (Boc-Ile), and t-butyloxycarbonyl- L-leucine (Boc-Leu).

The resultant resin (1 g) having a protected peptide bonded thereto is put in a vessel for a reaction with hydrogen fluoride, and anisol (0.5 ml) is added to permeate it into the resin. Then, 10 ml of hydrogen fluoride is added, and incubated at 0° C. for one hour. Thereafter, the remaining hydrogen fluoride is immediately distilled off and acetic acid (1%) is added to the residue to extract a polypeptide. The thus obtained solution is washed with ether, and then lyophilized, to thereby obtain a crude polypeptide.

(2) Crosslinking and Purification of Synthetic Peptides

According to the method of J. Ryan [J. Biol. Chem., 264, 20283–20287 (1989)], disulfide bonds are formed in the intramolecular structure of each of the three types of peptides synthesized in Example 2-(1), and the obtained peptides are purified. Illustratively stated, the synthesized peptides are purified by HPLC, and the purified peptides are subjected to amino acid analysis to confirm that the syntheses have correctly been carried out. Then, the peptides are separately dissolved in a 0.18 mM K$_3$Fe(CN)$_6$ solution containing 8M urea so that the final concentration of each of the peptides becomes 100 μg/ml. The thus obtained peptide solutions are stirred at room temperature for 12 days to thereby crosslink the peptides. The crosslinking of the peptides is confirmed by HPLC. Trifluoroacetic acid (40%) is added to each of the crosslinking reaction mixtures so that the pH value of each mixture becomes 2.5. The obtained mixtures are individually purified using Waters Bondapak column (1.9×30 cm) and are dried under a reduced pressure to obtain 30 mg of each of the desired synthetic peptides. HPLC analysis shows that each of the resultant synthetic peptides has a purity of at least 99%, and that the amino acid sequences of the obtained three types of peptides are idential to those indicated in Example 2-(1).

(3) Determination of the Activities of the Synthetic Peptides to Inhibit the Binding of Thrombin to Thrombomodulin The acitvity of each of the synthetic peptides to inhibit the binding of thrombin to thrombomodulin is determined by the following method. D123Asp purified in Example 1-(4)-(b) is diluted with 0.1M sodium bicarbonate buffer (pH 9.2) so that the final concentration of D123Asp becomes 1.5 μg/ml. 100 μl of the diluent is dispensed to each well of a flat-bottomed 96 well-microtiter plate for ELISA. The plate is allowed to stand for 3 hours, and then each well is washed with 0.1M sodium bicarbonate buffer (pH 9.2). 150 μl of 50 mM Tris-HCl buffer (pH 7.5) containing 0.1M NaCl and 1% BSA is dispensed to each well, and the plate is allowed to stand for 2 hours so that each well is subjected to blocking. To each well of the plate is added a solution obtained by reacting thrombin (0 to 0.4 μg/μl), which has been diluted with a washing solution {50 mM Tris-HCl buffer (pH 7.5) containing 0.5% BSA and 0.05% Tween-20}, with various concentrations of the synthetic peptide solutions at 37° C. for 30 minutes, and a reaction is conducted at room temperature for 1 hour. The plate is washed again with the above-mentioned washing solution. To each well of the plate is added 100 μl of 50 mM Tris-HCl buffer (pH 8.0) containing 0.1M NaCl, in which 200 μM H-D-Phe-Pip-Arg-pNA (Kabi Virum, Sweden, catalog No. S2238) has been dissolved, to thereby liberate pNA (paranitroanilin). A few hours later, the absorbance of the liberated pNA is measured at a wavelength of 410 nm. To determine the inhibition constant (Ki) of each of the synthetic peptides, 100/v in which v represents the thrombin activity (expressed in %) at the time when a peptide having a predetermined concentration is added, assuming the thrombin activity in the absence of a peptide as 100%, is plotted in rectangular coordinates against the concentration of the peptide to-obtain a graph (Dixon plot). The inhibition constant (Ki) is defined as the reading of the intersection of the plotted line with the abscissa. The results are shown in Table 2.

Example 3

Preparation of a Novel Polypeptide Having the Activity to Promote the Thrombin-catalyzed Activation of Protein C (1) Construction of Plasmid pSV2TMM3

The recombinant plasmid M13TMD7 obtained in Example 1-(1)-(b) is partialy mutated by the technique of site-directed mutagenesis in substantially the same manner as in Example 1-(1)-(a) except that mutater TMm3 having the following nucleotide sequence (SEQ. ID. No. 28):

5'-GAAGCACGGTTCGGGGAACCCCAGG-3' (25 mer) which hybridizes to a portion of the plasmid M13TMD7 having the following partial sequence (SEQ. ID No. 30) as shown in FIG. 10 and which codes for the partial amino acid sequence (SEQ. ID. NO. 31) also shown in FIG. 10:

GGC CTG GGG TTC CCC GAC CCG TGC TTC AGA is used instead of the deleter TMd3, to thereby obtain recombinant plasmid M13TMM3 having a DNA fragment designated TMM3 inserted therein. The DNA fragment TMM3 has a nucleotide sequence comprising initiation codon (ATG) and, downstream thereof, a nucleotide sequence coding for a peptide (SEQ. ID. No. 29) comprised of amino acid residues up to the 18th position counted from the amino acid residue corresponding to the initiation codon and the 367th to 480th amino acid residues, in which the 367th Asp is replaced by Glu, of the sequence of FIG. 55. In FIG. 10, there is illustrated the recombinant plasmid M13TMD7 with which the mutator TMm3 is hybridized, and in which Asp is replaced by Glu.

Further, the obtained plasmid M13TMM3 DNA is completely digested with restriction enzymes HindIII and BamHI to obtain a TMM3 DNA fragment of about 580 bp. On the other hand, plasmid pSV2-dhfr (ATCC No. 37146) is completely digested with restriction enzymes HindIII and BglII to obtain a vector. This vector and the above-mentioned DNA fragment of about 580 bp are ligated to each other using T4 DNA ligase to obtain plasmid pSV2TMM3.

(2) Transfection of Plasmids pSV2TMD7 and pSV2TMM3 into Cell Line COS-1

According to the method described in Example 1-(2), transfection of plasmids pSV2TMD7 and pSV2TMM3 into cell line COS-1 is performed. Illustratively stated, to a culture of cell line COS-1 are individually added suspensions of the plasmids pSV2TMD7 and pSV2TMM3. The obtained mixtures are individually subjected to electroporation 90 times so that cell line COS-1 is transfected with each of the plasmids. The resultant suspensions are cultured to thereby obtain 90 ml of each of the cultures.

(3) Purification and Quantitative Determination of Polypeptides Produced by Cell Line COS-1 Transfected with plasmids pSV2TMD7 and pSV2TMM3

90 ml of each of the cultures obtained in Example 3-(2) is applied to a Q-Sepharose column equilibrated with 5 mM phosphate buffer (pH 7.4). The column is washed with 5 mM phosphate buffer (pH 7.4) containing 0.15M NaCl, and eluted with 5 mM phosphate buffer (pH 7.4) containing 1.0M NaCl. The thus obtained eluate is subjected to dialysis for desalting. The dialysate is applied to a DIP-thrombin column equilibrated with 20 mM phosphate buffer (pH 7.4) containing 0.2M NaCl to adsorb an active fraction thereto. The column is washed with the same buffer as used for the above adsorption and equilibration, and eluted with 20 mM phosphate buffer (pH 7.4) containing 1.0M NaCl to obtain an active fraction. The obtained active fraction is applied again to the DIP-thrombin column equilibrated with 20 mM phosphate buffer (pH 7.4) containing 0.2M NaCl, washed with the same buffer as used for the adsorption and equlibration, and eluted with 20 mM phosphate buffer (pH 7.4) containing 1.0M NaCl to obtain an active fraction.

Subsequently, the obtained active fraction is dialyzed against 5 mM phosphate buffer (pH 7.4) from which calcium ion has been removed by means of Chelex 100 (manufactured and sold by Bio Rad Co., Ltd., U.S.A., Catalog No. 143-2832), followed by concentration by means of Centricon (Amicon Co., Ltd., Catalog No. 4205) to obtain a purified polypeptide. The purified polypeptide is subjected to qunatitative determination according to ELISA described in Example 1-(4)-(d). The amount of a polypeptide obtained from each of the cultures obtained in Example 3-(2) is 50 μg. The polypeptide purified from the culture of cell line COS-1 transfected with pSV2TMD7 is designated as E456Asp, and the polypeptide purified from the culture of cell line COS-1 transfected with pSV2TMM3 is designated as E456Glu.

Figure 11:
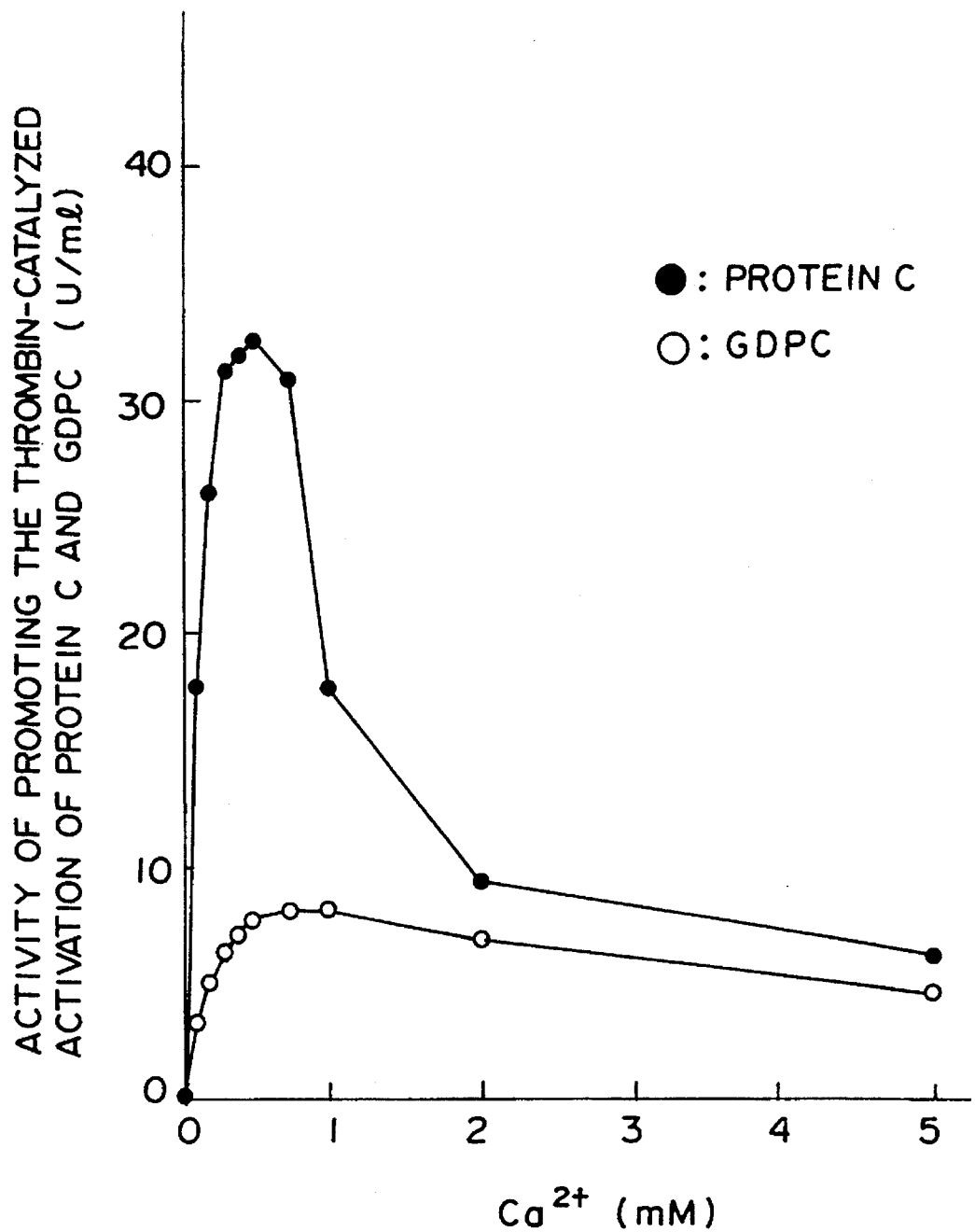
FIG. 11 is a graph showing the effect of calcium ion concentration on the activity of promoting the thrombin-catalyzed activation of each of protein C and GDPC with respect to polypeptide E456Asp obtained in Example 3.
Figure 12:
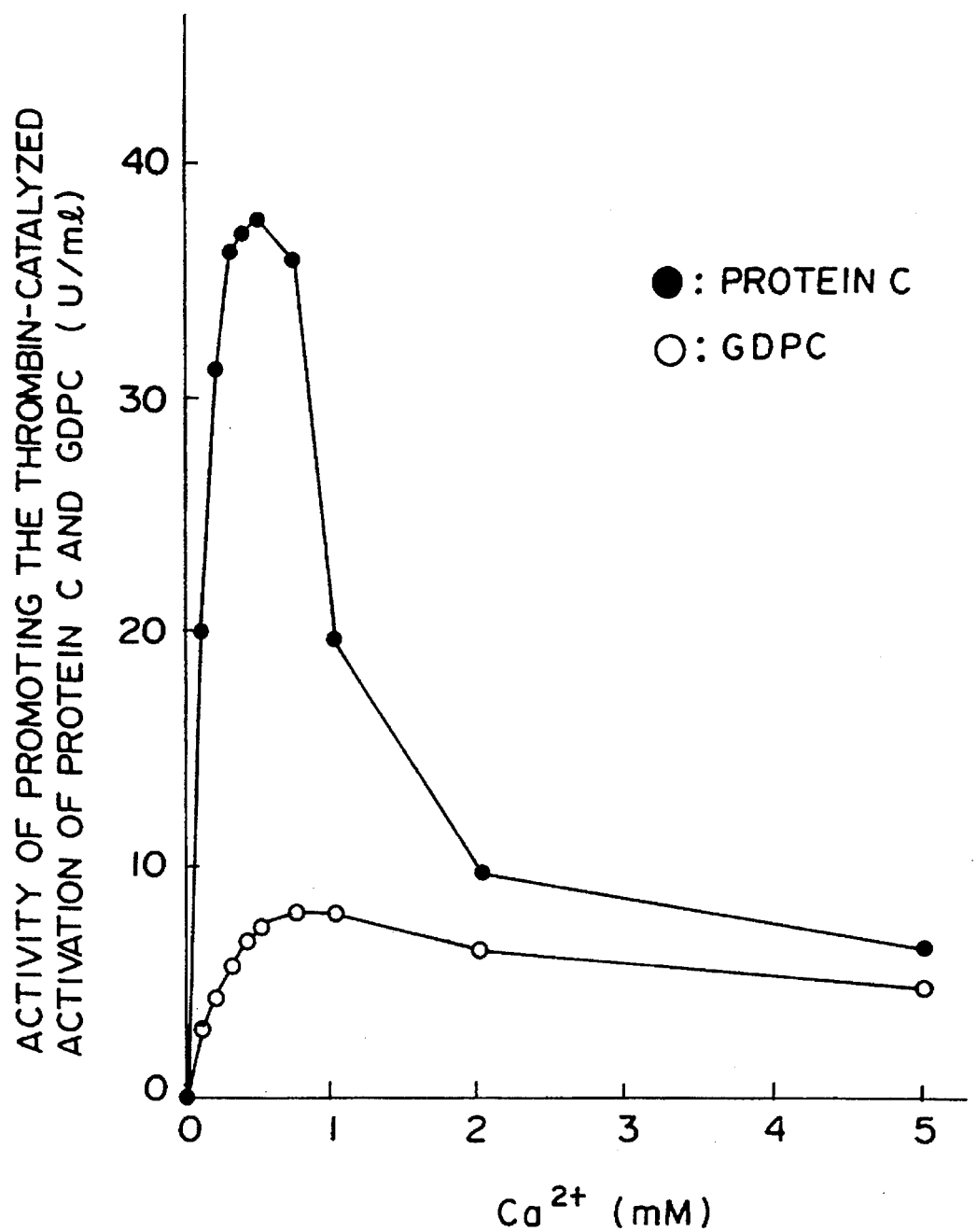
FIG. 12 is a graph showing the effect of calcium ion concentration on the activity of promoting the thrombin-catalyzed activation of each of protein C and GDPC with respect to polypeptide E456Glu obtained in Example 3.
Figure 16:
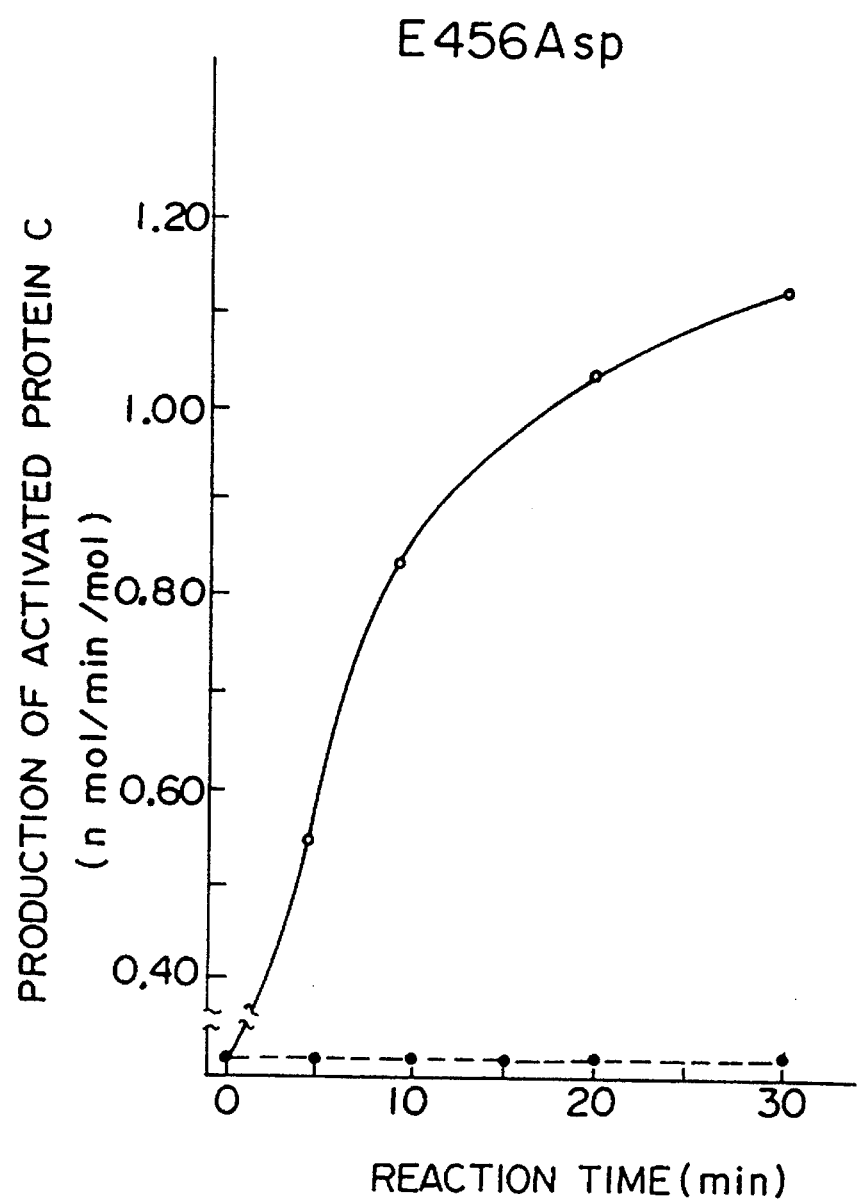
FIG. 16 is a graph showing the relationship between the amount of the activated protein C formed by the reaction of protein C with thrombin and the reaction time, in which a comparison is made between the presence (o) of and the absence (●) of polypeptide E456Asp purified in Example 4(5)
Figure 17:
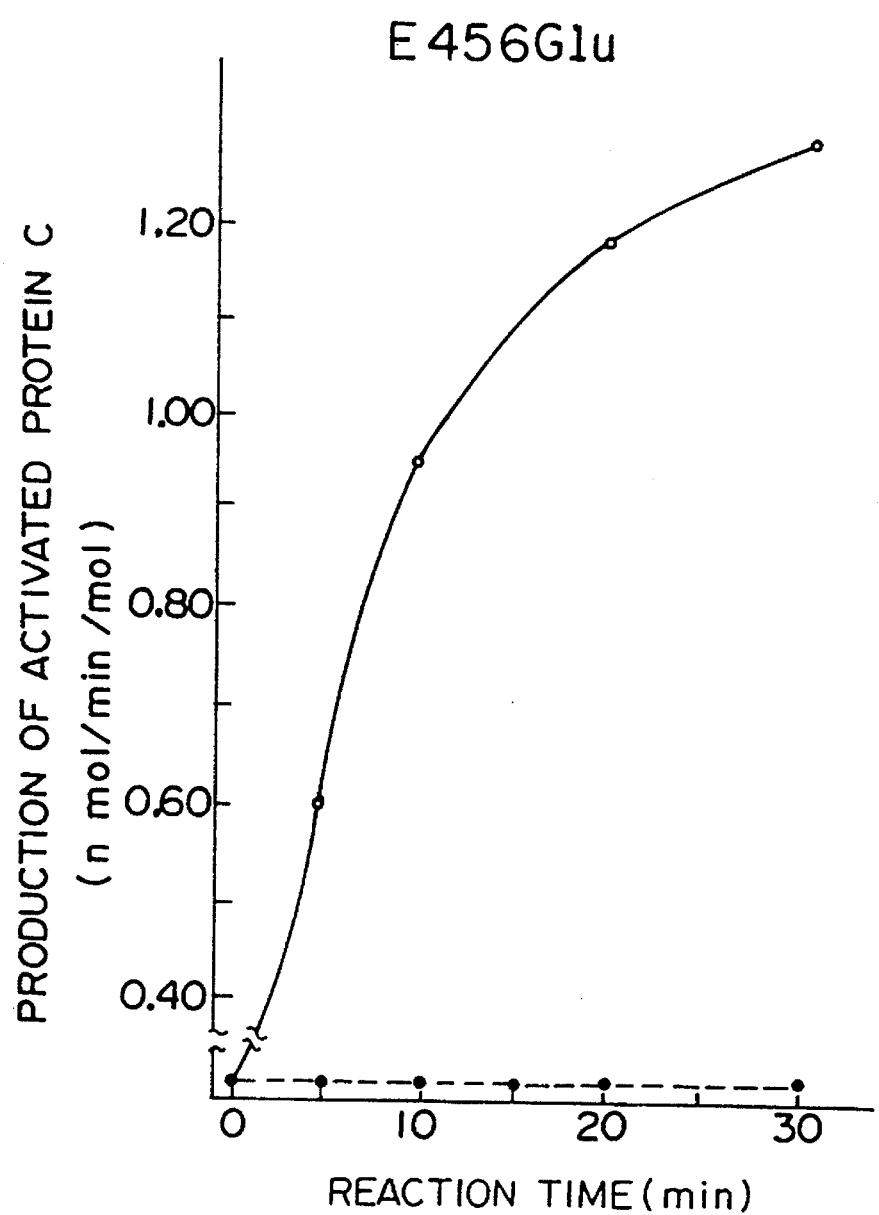
FIG. 17 is a graph showing the relationship between the amount of the activated protein C formed by the reaction of protein C with thrombin and the reaction time, in which a comparison is made between the presence (o) of and the absence (●) of polypeptide E456Glu purified in Example 4(5)
Figure 18:
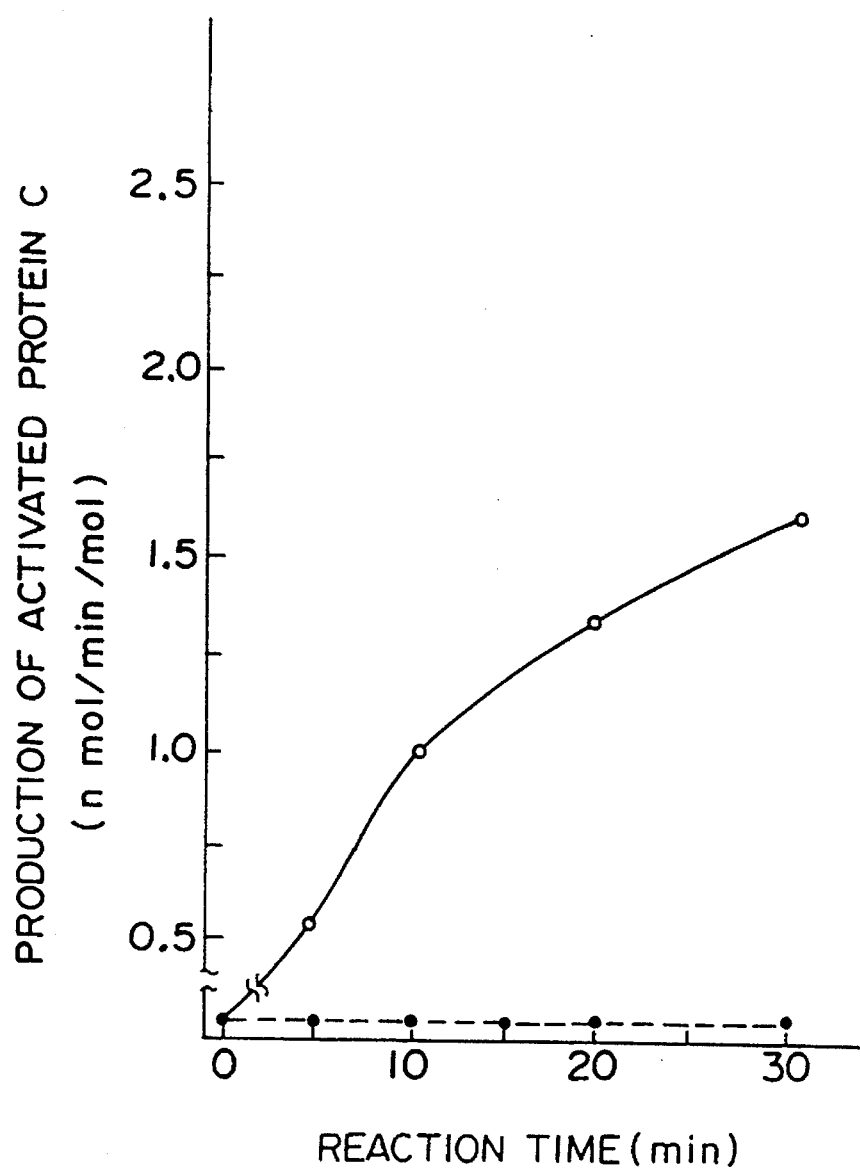
FIG. 18 is a graph showing the relationship between the amount of the activated protein C formed by the reaction of protein C with thrombin and the reaction time, in which a comparison is made between the presence (o) of and the absence (●) of polypeptide E456Asp2 purified in Example 4(5)
Figure 19:
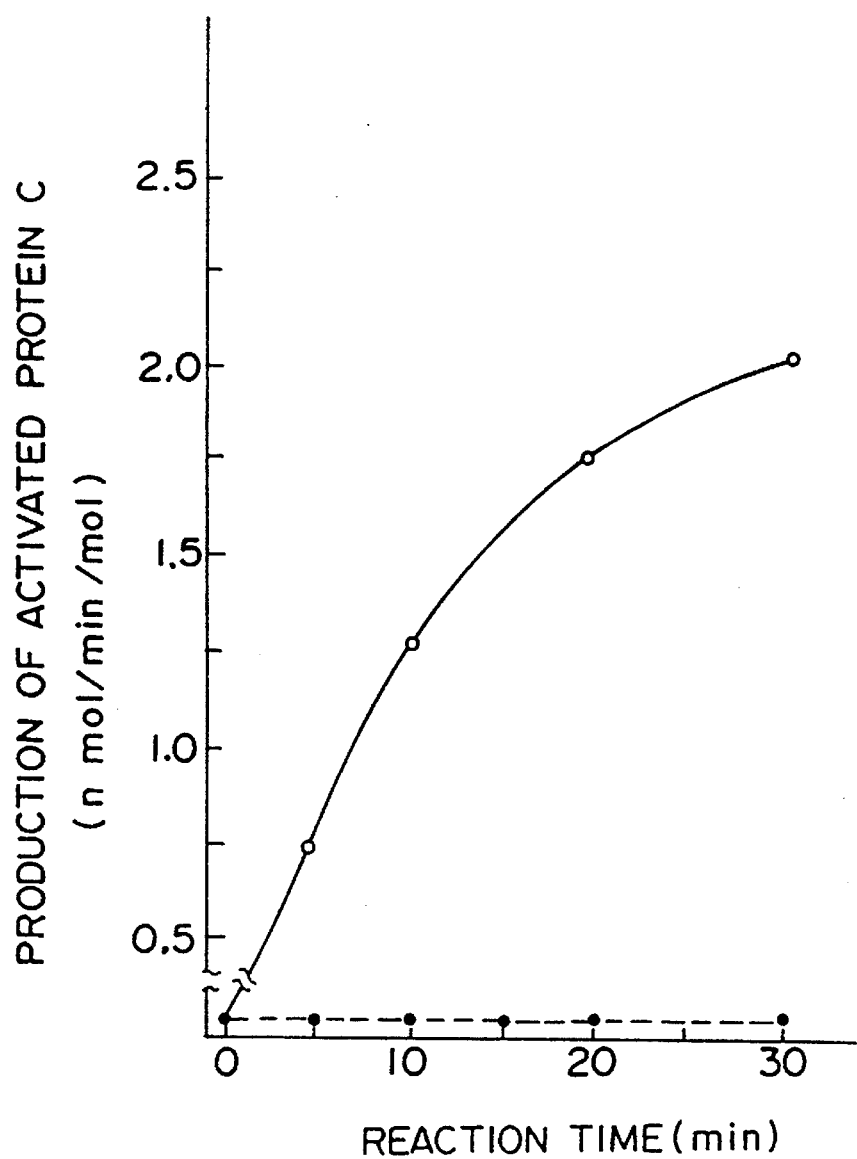
FIG. 19 is a graph showing the relationship between the amount of the activated protein C formed by the reaction of protein C with thrombin and the reaction time, in which a comparison is made between the presence (o) of and the absence (●) of polypeptide E456Asp3 purified in Example 4(5)
Figure 20:
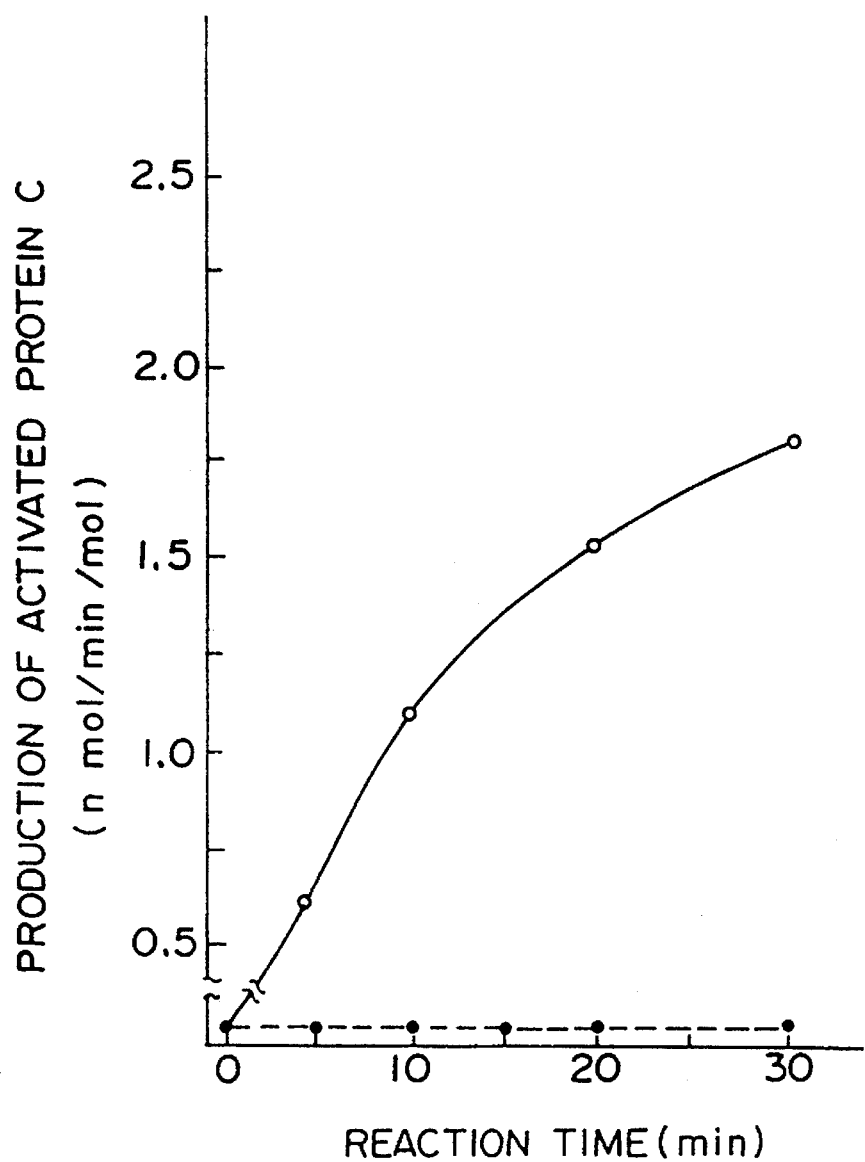
FIG. 20 is a graph showing the relationship between the amount of the activated protein C formed by the reaction of protein C with thrombin and the reaction time, in which a comparison is made between the presence (o) of and the absence (●) of polypeptide E456GluAsp purified in Example 4(5)
Figure 21:
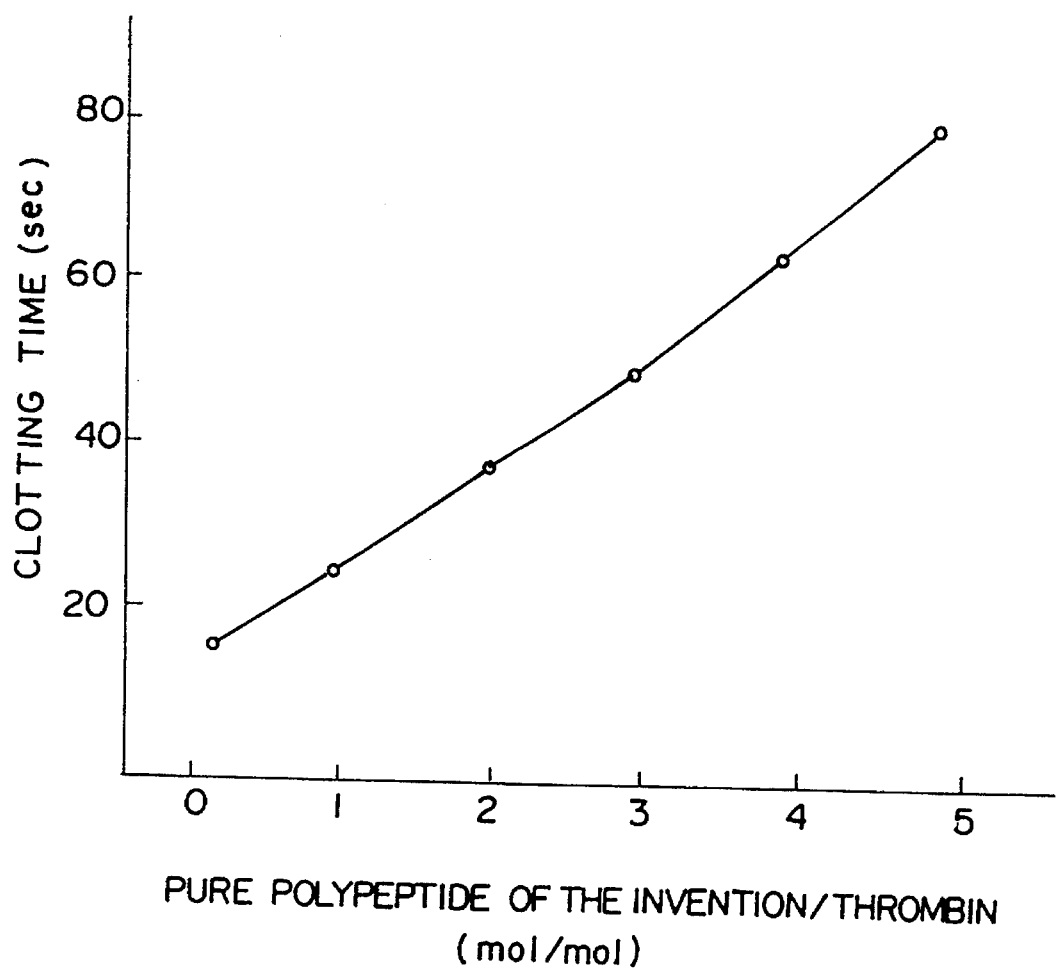
FIG. 21 is a graph showing the relationship between the clotting time of a fibrinogen solution to which polypeptide E456Asp of the present invention purified in Example 4(5) was added and the amount of the added purified polypeptide.
Figure 22:
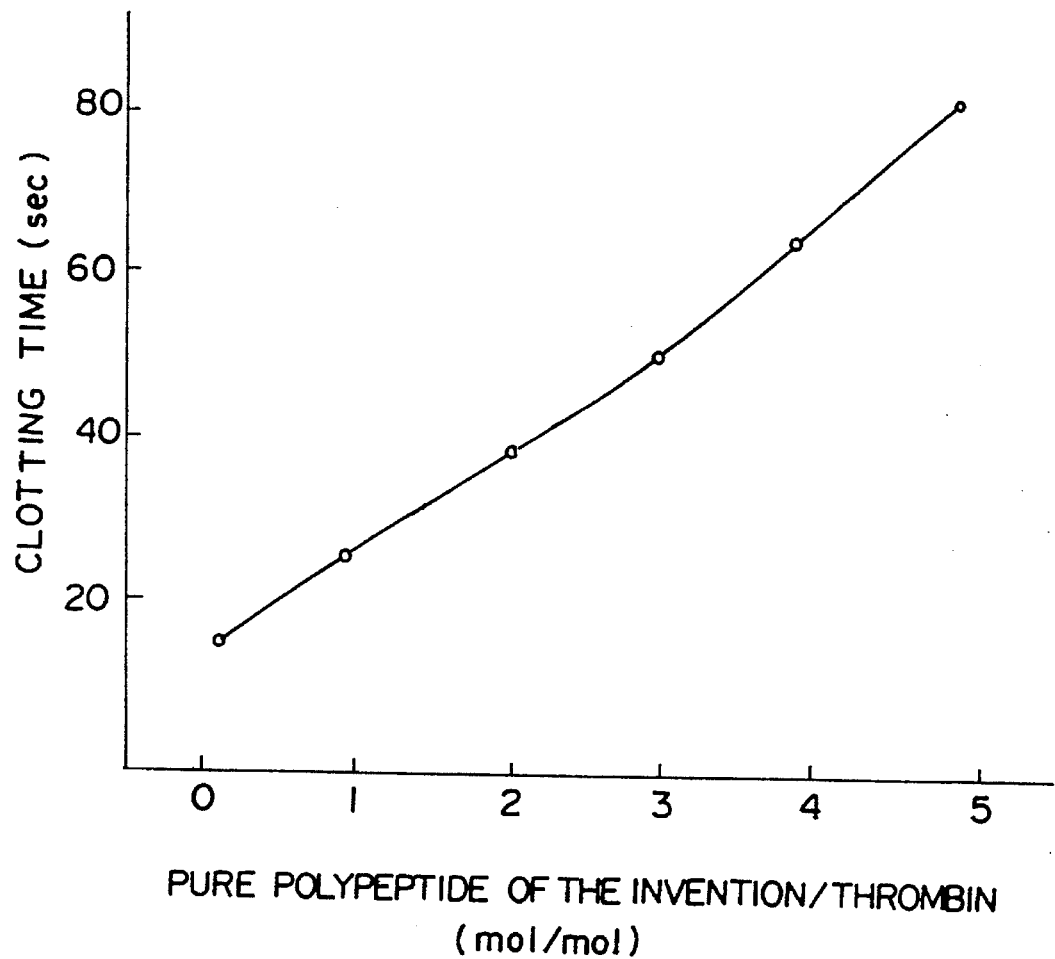
FIG. 22 is a graph showing the relationship between the clotting time of a fibrinogen solution to which polypeptide E456Glu of the present invention purified in Example 4(5) was added and the amount of the added purified polypeptide.
Figure 23:
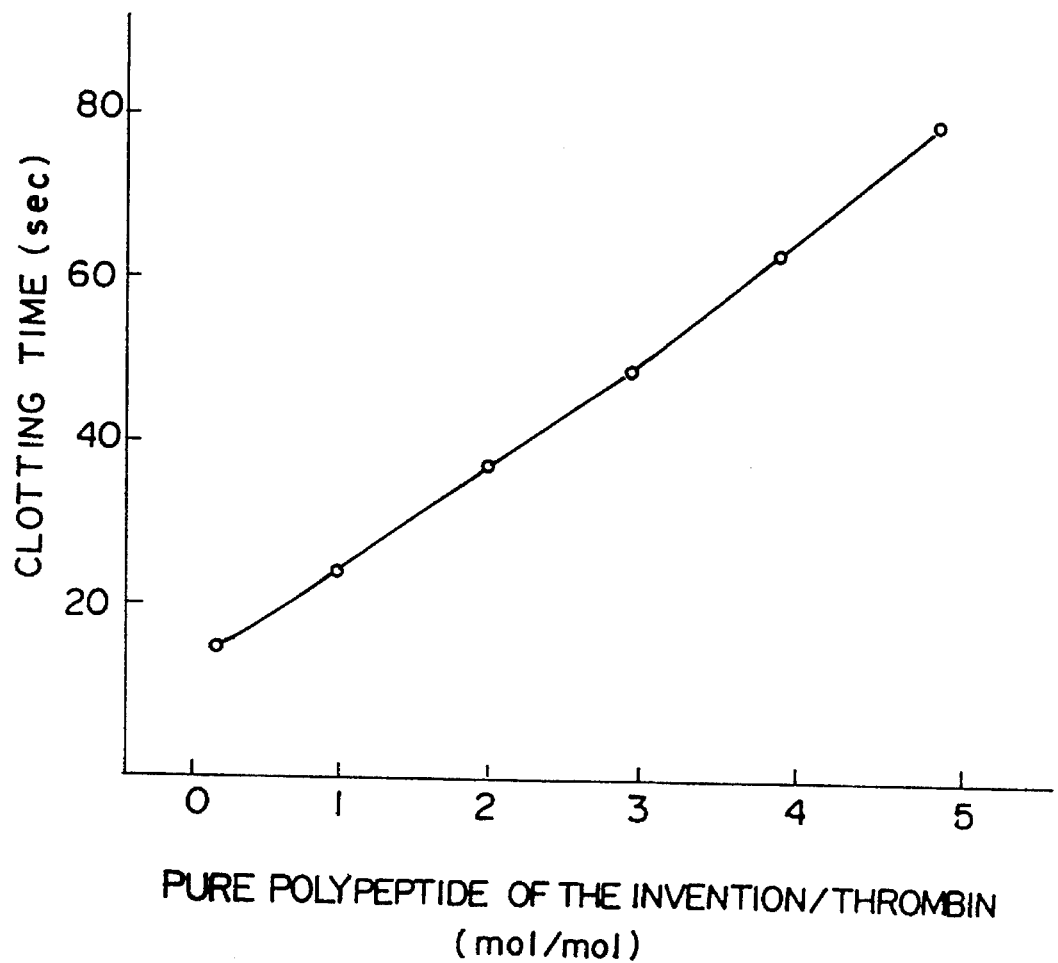
FIG. 23 is a graph showing the relationship between the clotting time of a fibrinogen solution to which polypeptide E456Asp2 of the present invention purified in Example 4(5) was added and the amount of the added purified polypeptide.
Figure 24:
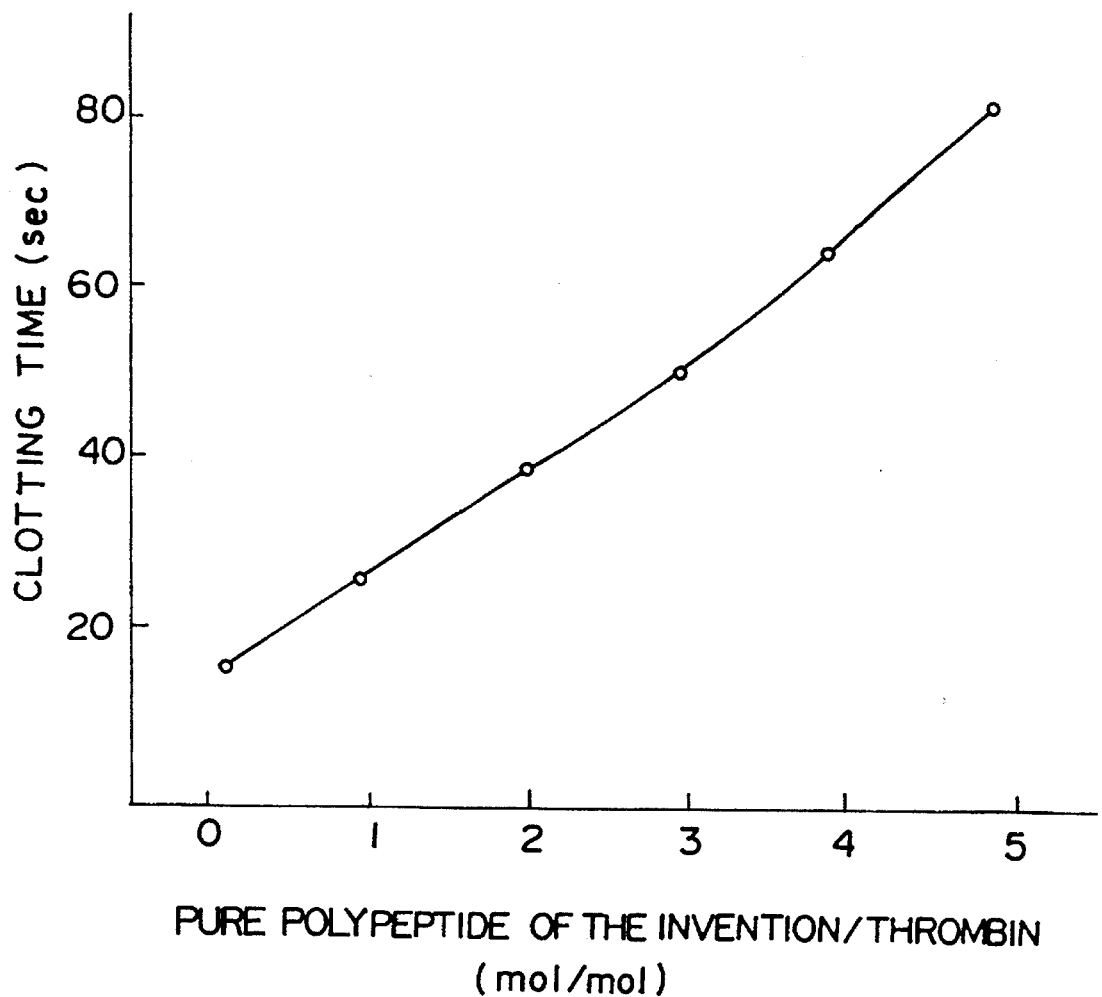
FIG. 24 is a graph showing the relationship between the clotting time of a fibrinogen solution to which polypeptide E456Asp3 of the present invention purified in Example 4(5) was added and the amount of the added purified polypeptide.
Figure 25:
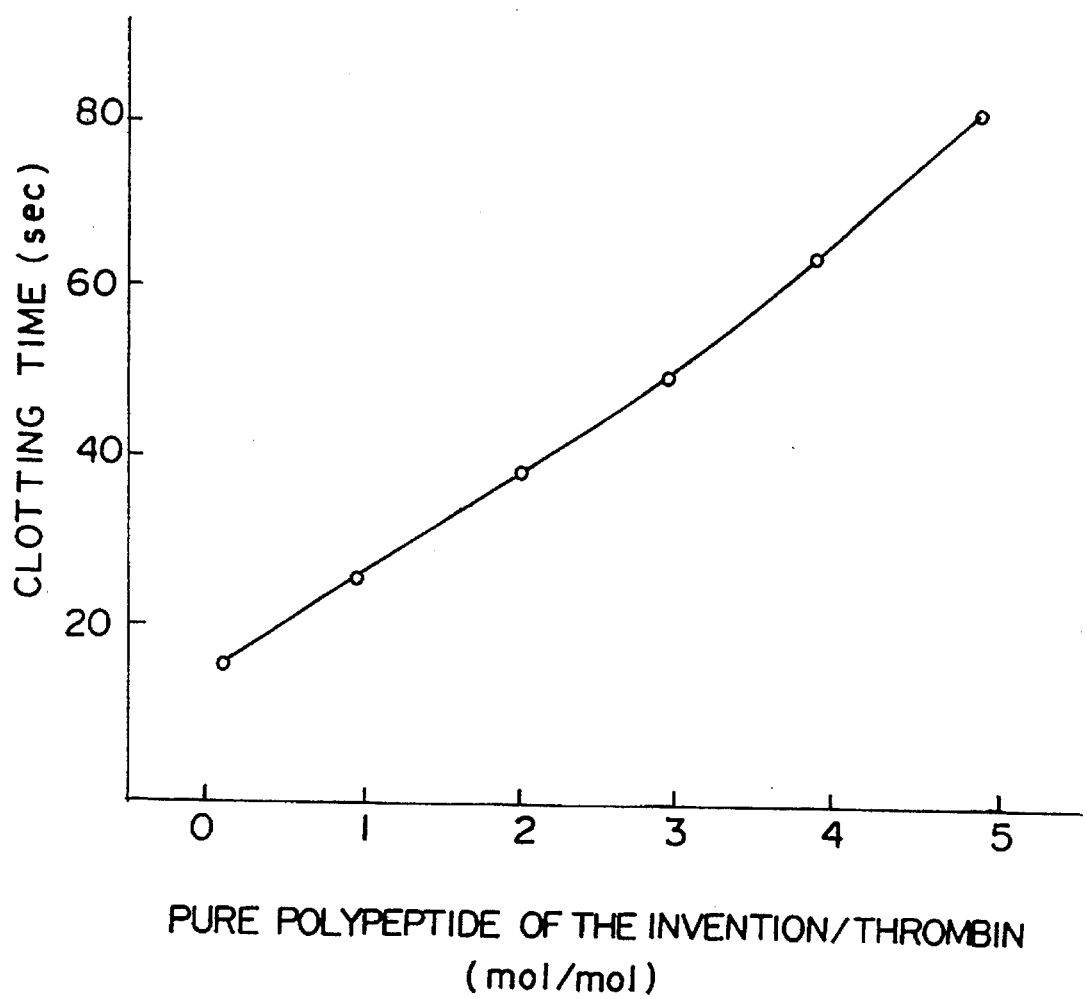
FIG. 25 is a graph showing the relationship between the clotting time of a fibrinogen solution to which polypeptide E456GluAsp of the present invention purified in Example 4(5) was added and the amount of the added purified polypeptide.
Figure 26:
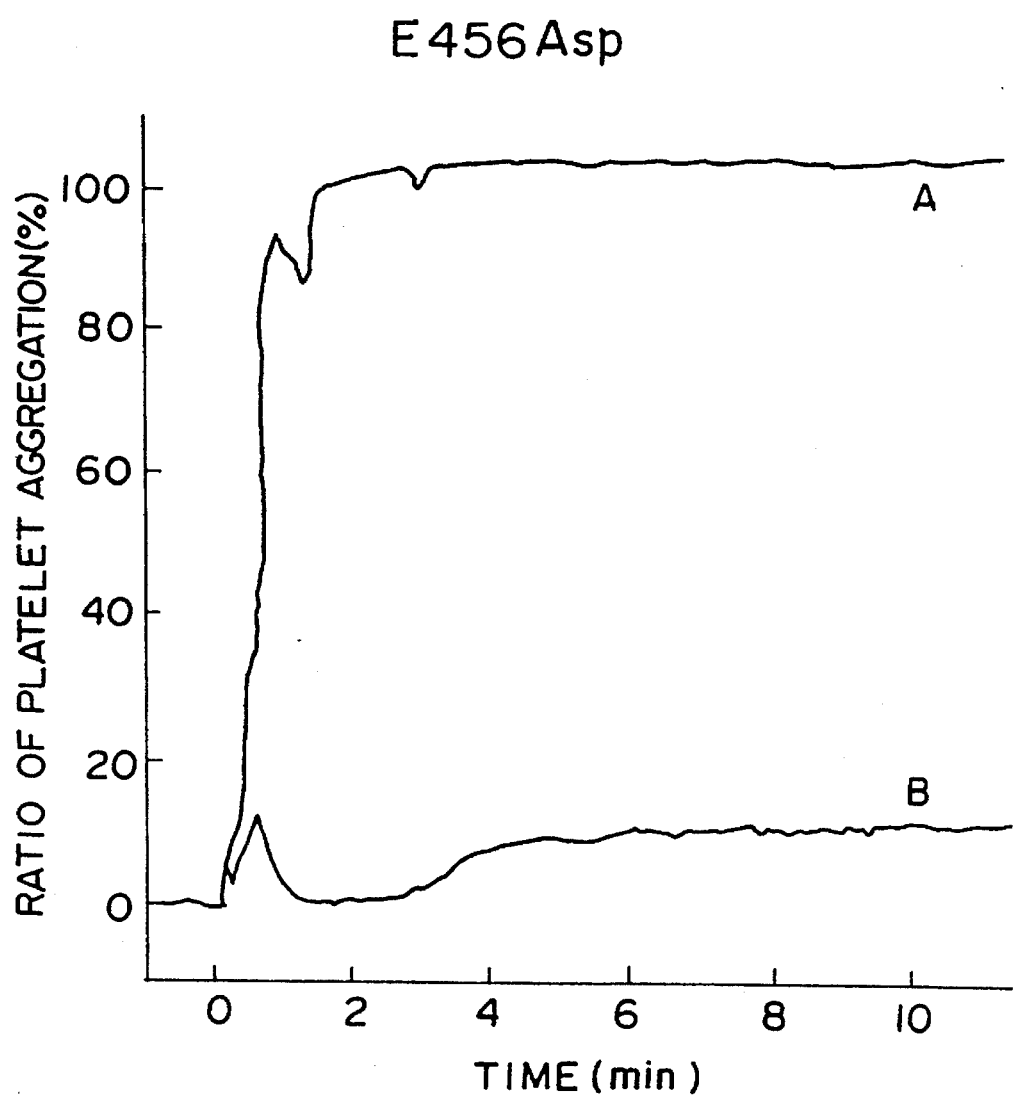
FIG. 26 is a graph showing the relationship between the thrombin-catalyzed platelet aggregation and the time, in which a comparison is made between the presence (B) of and the absence (A) of polypeptide E456Asp of the present invention purified in Example 4(5)
Figure 27:
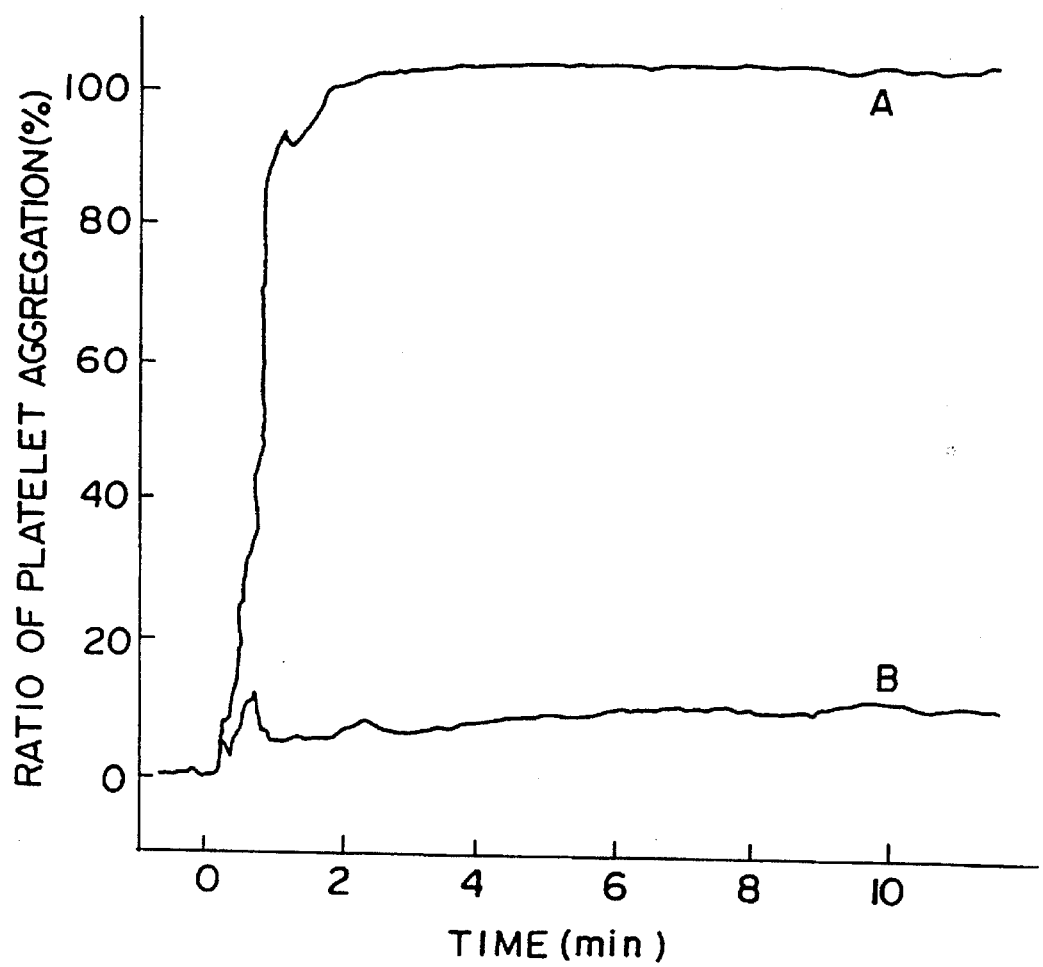
FIG. 27 is a graph showing the relationship between the thrombin-catalyzed platelet aggregation and the time, in which a comparison is made between the presence (B) of and the absence (A) of polypeptide E456Glu of the present invention purified in Example 4(5)
Figure 28:
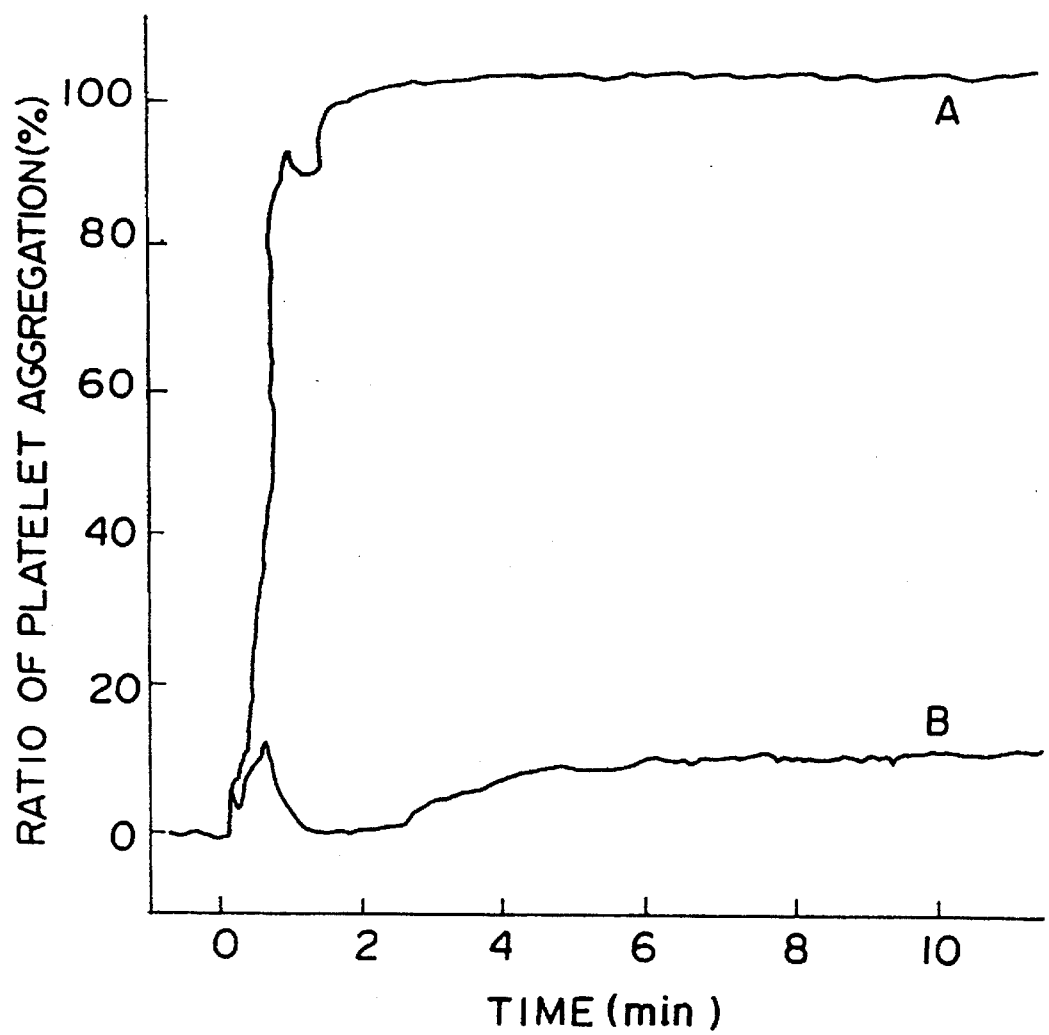
FIG. 28 is a graph showing the relationship between the thrombin-catalyzed platelet aggregation and the time, in which a comparison is made between the presence (B) of and the absence (A) of polypeptide E456Asp2 of the present invention purified in Example 4(5)
Figure 29:
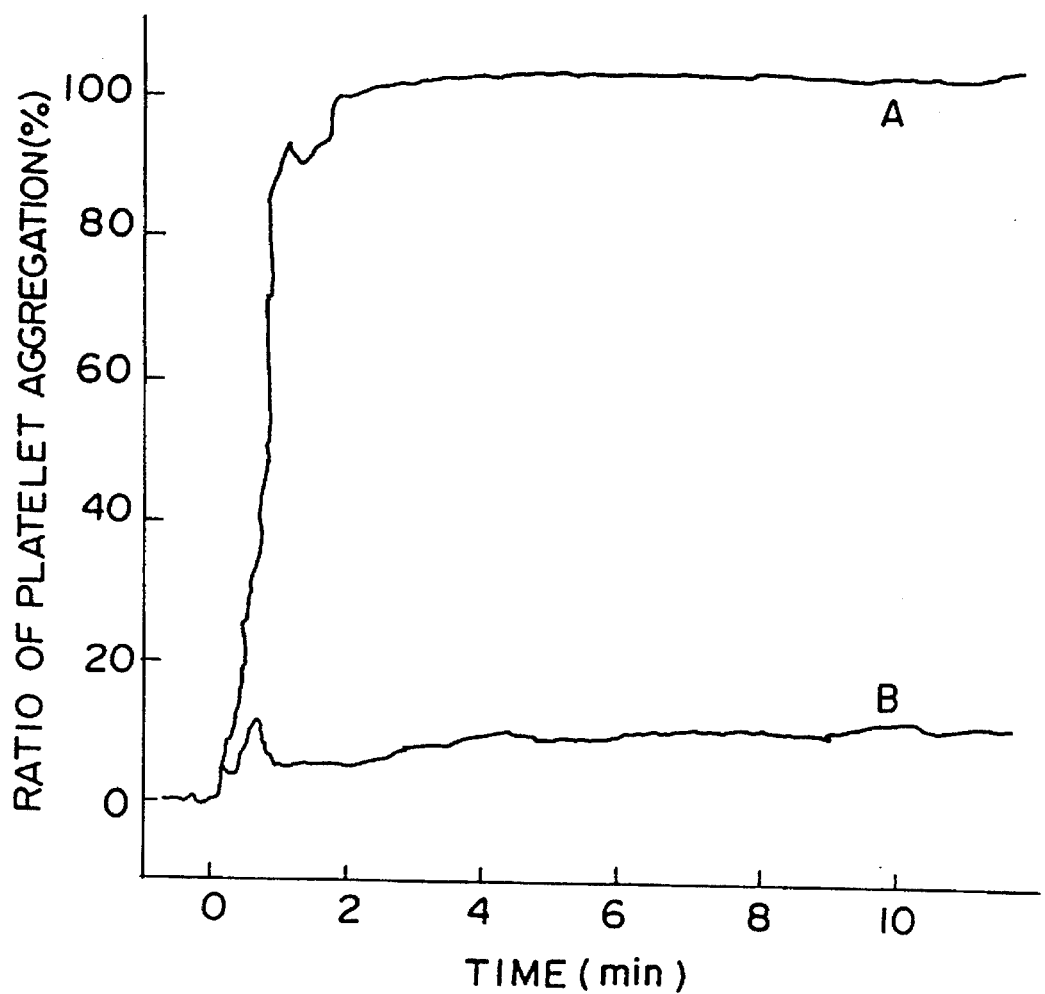
FIG. 29 is a graph showing the relationship between the thrombin-catalyzed platelet aggregation and the time, in which a comparison is made between the presence (B) of and the absence (A) of polypeptide E456Asp3 of the present invention purified in Example 4(5)
Figure 30:
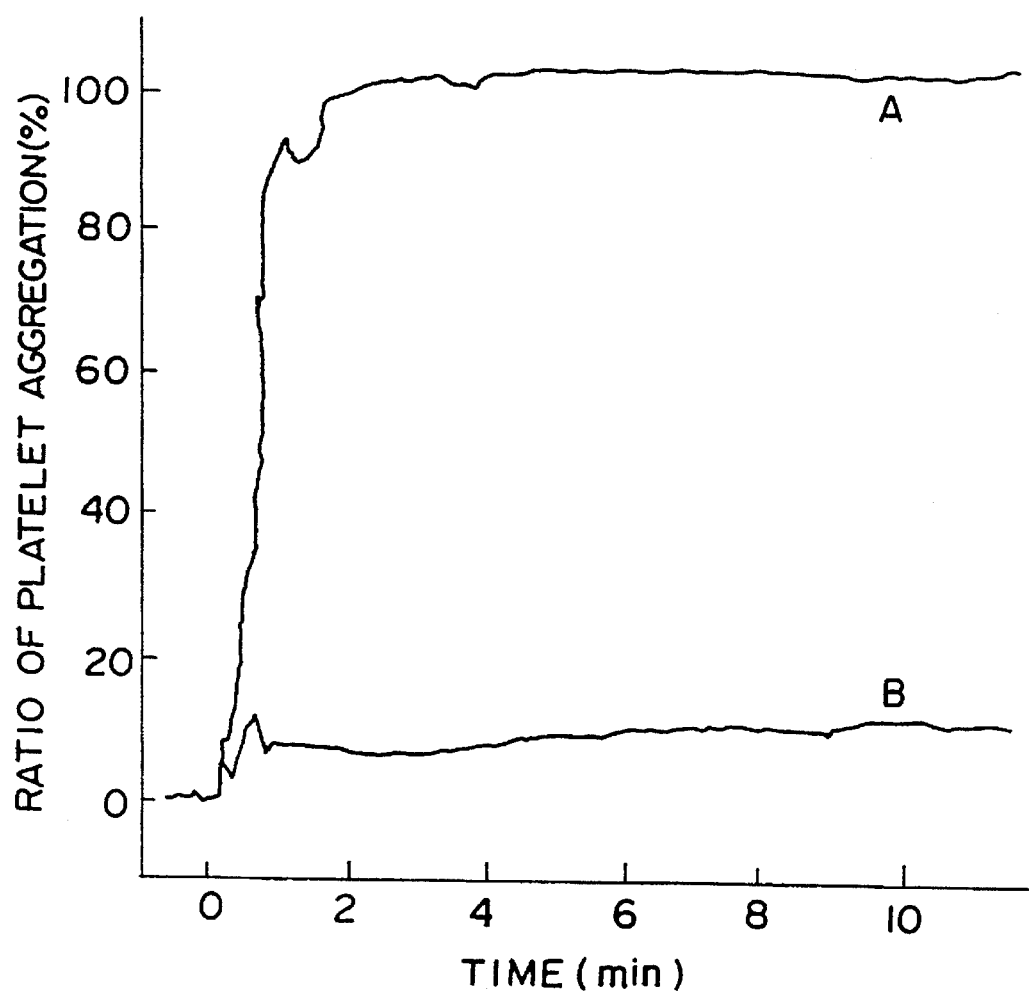
FIG. 30 is a graph showing the relationship between the thrombin-catalyzed platelet aggregation and the time, in which a comparison is made between the presence (B) of and the absence (A) of polypeptide E456GluAsp of the present invention purified in Example 4(5)

(4) Assay for the Activity of Each of the Polypeptides E456Asp and E456Glu to Promote the Thrombin-catalyzed Activation of Protein C The polypeptides described in Example 3-(3) are individually subjected to assay for the activity to promote the thrombin-catalyzed activation of protein C according to the method as described in Example 1-(3). The results are shown in FIGS. 11 and 12. As shown in FIG. 11, E456Asp exhibits a high activity to promote the thrombin-catalyzed activation of protein C, which shows a maximum value at a calcium ion concentration of 0.4 to 0.5 mM. On the other hand, in the case of the activation of GDPC, such a specific dependence on the calcium ion concentration is not observed, and on a whole, a low activity is detected to promote the activation of GDPC. As shown in FIG. 12, the activity of E456Glu is similar to that of E456Asp, however, with respect to the promotion of the thromobin-catalyzed activation of protein C, E456Glu exhibits an activity as high as 1.3 times that of E456Asp.

Example 4

Preparation of a Novel Polypeptide Having the Ability to Promote the Thrombin-catalyzed Activation of Protein C (1) Construction of Plasmid pSV2TMM4

Three additional nucleotides are inserted in the recombinant plasmid M13TMD7 obtained in Example 1-(1)-(b) by the technique of site-directed mutagenesis in substantially the same manner as in Example 1-(1)-(a) except that mutator TMm4 having the following nucleotide sequence (SEQ. ID. No. 32):

5'-GAAGCACGGGTCGTCGGGGAACCCCAGG-3' (28 mer) which hybridizes to a portion of the plasmid M13TMD7 having the following partial sequence (SEQ. ID No. 34) as shown in FIG. 13 and which codes for the partial amino acid sequence (SEQ. ID. NO. 35) also shown in FIG. 13:

GGC CTG GGG TTC CCC GAC CCG TGC TTC AGA is used instead of the deleter TMd3, to thereby obtain recombinant plasmid M13TMM4 having a DNA fragment designated TMM4 inserted therein. The DNA fragment TMM4 has a nucleotide sequence comprising initiation codon (ATG) and, downstream thereof, a nucleotide sequence coding for a polypeptide (SEQ. ID. No. 33) comprised of amino acid residues up to the 18th position counted from the amino acid residue corresponding to the initiation codon and the 367th to 480th amino acid residues, in which another Asp is inserted in the position before the 367th Asp, of the sequence of FIG. 55. In FIG. 13, there is illustrated the recombinant plasmid M13TMD7 with which the mutator TMm4 is hybridized, and in which three additional nucleotides are inserted.

Further, the obtained plasmid M13TMM4 is completely digested with restriction enzymes HindIII and BamHI to obtain a TMM4 DNA fragment of about 580 bp. On the other hand, plasmid pSV2-dhfr (ATCC No. 37146) is completely digested with restriction enzymes HindIII and BglHI to obtain a vector. This vector and the above-mentioned TMM4 DNA fragment of about 580 bp are ligated to each other using T4 DNA ligase to thereby obtain plasmid pSV2TMM4.

(2) Construction of Plasmid pSV2TMM5

Six additional nucleotides are inserted in the recombinant plasmid M13TMD7 obtained in Example 1-(1)-(b) by the technique of site-directed mutagenesis in substantially the same manner as in Example 1-(1)-(a) except that mutater TMm5 having the following nucleotide sequence (SEQ. ID. No. 36):

5'-GAAGCACGGGTCGTCGTCGGGGAAC-CCCAGG-3' (31 mer) which hybridizes to a portion of the plasmid M13TMD7 having the following partial sequence (SEQ. ID No. 38) as shown in FIG. 14 and which codes for the partial amino acid sequence (SEQ. ID. NO. 39) also shown in FIG. 14:

GGC CTG GGG TTC CCC GAC CCG TGC TTC AGA is used instead of the deleter TMd3, to thereby obtain recombinant plasmid M13TMM5 having a DNA fragment designated TMM3 inserted therein. The DNA fragment TMM3 has a nucleotide sequence comprising initiation codon (ATG) and, downstream thereof, a nucleotide sequence coding for a polypeptide (SEQ. ID. No. 37) comprised of amino acid residues up to the 18th position counted from the amino acid residue corresponding to the initiation codon and the 367th to 480th amino acid residues, in which two Asps are inserted in the position before the 367th Asp, of the sequence of FIG. 55. In FIG. 14, there is illustrated the recombinant plasmid M13TMD7 with which the mutator TMm5 is hybridized, and in which six additional nucleotides are inserted.

Further, the obtained plasmid M13TMM5 is completely digested with restriction enzymes HindIII and BamHI, and a TMM5 DNA fragment of about 580 bp is isolated. On the other hand, plasmid pSV2-dhfr (ATCC No. 37146) is completely digested with restriction enzemes HindIII and BglII to obtain a vector. This vector and the above-mentioned TMM5 DNA fragment of about 580 bp are ligated to each other using T4 DNA ligase to thereby obtain plasmid pSV2TMM5.

(3) Construction of Plasmid pSV2TMM6

Three additional nucleotides are inserted in the recombinant plasmid M13TMD7 obtained in Example 1-(1)-(b) by the technique of site-directed mutagenesis in substantially the same manner as in Example 1-(1)-(a) except that mutator TMm6 having the following nucleotide sequence:

5'-GAAGCACGGGTCTTCGGGGAACCCCAGG-3' (28 mer) which hybridizes to a portion of the plasmid M13TMD7 having the following partial sequence (SEQ. ID No. 42) shown in FIG. 15 and which codes for the partial amino acid sequence (SEQ. ID. NO. 43) also shown in FIG. 15:

GGC CTG GGG TTC CCC GAC CCG TGC TTC AGA is used instead of the deleter TMd3, to thereby obtain recombinant plasmid M13TMM6 having a DNA fragment designated TMM6 inserted therein. The DNA fragment TMM6 has a nucleotide sequence comprising initiation codon (ATG) and, downstream thereof, a nucleotide sequence coding for a polypeptide (SEQ. ID. No. 41) comprised of amino acid residues up to the 18th position counted from the amino acid residue corresponding to the initiation codon and the 367th to 480th amino acid residues, in which another Glu is inserted in the position before the 367th Asp, of the sequence of FIG. 55. In FIG. 15, there is illustrated the recombinant plasmid M13TMD7 with which the mutator TMm6 is hybridized, and in which three additional nucleotides are inserted.

Further, the obtained plasmid M13TMM6 is completely digested with restriction enzymes HindIII and BamHI to obtain a TMM4 DNA fragment of about 580 bp. On the other hand, plasmid pSV2-dhfr (ATCC No. 37146) is completely digested with restriction enzyemes HindIII and BglII to obtain a vector. This vector and the above-mentioned TMM4 DNA fragment of about 580 bp are ligated to each other using T4 DNA ligase to thereby obtain plasmid pSV2TMM6.

(4) Transfection of Plasmids pSV2TMD7, pSV2TMM3, pSV2TMM4, pSV2TMM5 and pSV2TMM6 into Cell Line COS-1

According to the method described in Example 1-(2), transfection of each of plasmids pSV2TMD7, pSV2TMM3, pSV2TMM4, pSV2TMM5 and pSV2TMM6 obtained above into cell line COS-1 is performed. Illustratively stated, to the culture of cell line COS-1 are individually added suspensions of the plasmids pSV2TMD7, pSV2TMM3, pSV2TMM4, pSV2TMM5 and pSV2TMM6. The resultant mixtures are individually subjected to electroporation 90 times so that cell line COS-1 is transfected with each of the plasmids. The resultant mixtures are cultured to thereby obtain 900 ml of each of the cultures.

(5) Purification and Quantitative Determination of Polypeptides Produced by Cell Line COS-1 Transfected with Plasmids pSV2TMD7, pSV2TMM3, pSVTMM4, pSVTMM5 and pSVTMM6

900 ml of each of the cultures obtained in Example 4-(4) is purified according to the method described in Example 3-(3), and the absorbances thereof are individually measured. The value of the molecular extinction coefficient for general proteins, which is 10.0 ($E^{1\%}_{1cm} \cdot 280$ nm=10.0), is applied to each of the purified polypeptides. Based on this coefficient, the amounts of the purified polypeptides are individually calculated from the absorbances thereof, and are found to be about 50 μg.

Further, the purified polypeptides are individually subjected to SDS-polyacrylamide gel electrophoresis using a 15 to 25% acrylamide concentration gradient, and CBB staining is performed to observe any stained bands. Only one band is found for each of the purified polypeptides.

The polypeptide purified from the culture of cell line COS-1 transfected with pSV2TMD7 is designated as E456Asp, the polypeptide purified from the culture of cell line COS-1 transfected with pSV2TMM3 is designated as E456Glu, the polypeptide purified from the culture of cell line COS-1 transfected with pSV2TMM4 is designated as E456Asp2, the polypeptide purified from the culture of cell line COS-1 transfected with pSV2TMM5 is designated as E456Asp3, and the polypeptide purified from the culture of cell line COS-1 transfected with pSV2TMM6 is designated as E456GluAsp.

(6) Assay for the Activity to Promote the Thrombin-catalyzed Activation of Protein C With respect to the polypeptides purified and quantitated in Example 4-(5), the activity to promote the thrombin-catalyzed activation of protein C is asssayed by the following method.

To 0.02M Tris-HCl buffer (pH 8.5) containing 0.1M NaCl, 0.5 mM $CaCl_2$ and 10 mg/ml BSA are added 50 μg/ml protein C, 5 nM thrombin and 5 nM of each of the purified polypeptides of the present invention, and reacted at 37° C. To each of the reaction mixtures are added 300 μg/ml antithrombin III (manufactured and sold by Sigma Chemical Company, U.S.A.) and 5 mM EDTA to terminate the reaction. Then, the amount of the activated protein C produced by the reaction is determined by the method described in Example 1-(3) in which a synthetic substrate is used.

The results are shown in FIGS. 16 to 20. When any of the polypeptides of the present invention is not added, the production of the activated protein C is not observed (broken line). On the other hand, when one of the polypeptides of the present invention is added, the amount of produced protein C is increased with the lapse of reaction time (solid line).

(7) Measurement of Anticoagulating Activity

The activity of each of the polypeptides of the present invention to inhibit the thrombin-catalyzed conversion of fibrinogen to fibrin so as to inhibit blood coagulation, is determined by measuring clotting time using Coagulometer KC-10A (manufactured and sold by Heinrich Amelung A.G., Germany). Illustratively stated, to 0.05M Tris-HCl buffer (pH 7.5) containing 5 mM $CaCl_2$ and 0.1M NaCl is added 3.0 μg of fibrinogen (Fraction I, manufactured and sold by Sigma Chemical Company, U.S.A.). To the resultant mixture is added 0 to 50 nM of each of the purified polypeptides of the present invention. Then, 10 nM thrombin is added to the mixture in such an amount that the total amount of the mixture becomes 0.4 ml, and then the coagulation time of the mixture is measured.

The results are shown in FIGS. 21 to 25. It has been confirmed that the higher the amount of each of the added purified polypeptides relative to the amount of thrombin, the longer the clotting time.

(8) Measurement of Platelet Aggregation-inhibiting Activity

The activity of each of the polypeptides of the present invention to inhibit the thrombin-catalyzed platelet aggregation is evaluated using platelet aggregation measuring apparatus HEMA TRACER IV (manufactured and sold by NIKO Bioscience, Inc., Japan). Measurement is carried out according to the manual attached thereto. When 40 μl of a 20 NIH unit/ml thrombin solution (manufactured and sold by SIGMA Chemical Co., U.S.A., T 6759) is added to 180 μl of a Platelet Rich Plasma (PRP) platelet solution ($3 \times 10^5$ cells/μl) and incubated, the aggregation of platelets occurs. By contrast, when one of the purified polypeptides of the present invention is added in a molar amount equal to or more than that of thrombin to be added and allowed to stand at 37° C. for 2 minutes before the addition of 20 μl of thrombin (40 NIH unit/ml) to a platelet solution, the aggregation of platelets does not occur even after incubation. The aggregation of platelets is determined on the basis of the transparency, assuming the transparency of Platelet Poor Plasma (PPP) solution as 100%. The ratio of platelet aggregation is plotted against the incubation time (0 min: the time when thrombin or a mixture of thrombin and one of the polypeptides is added to the PRP solution). The results are shown in FIGS. 26 to 30. It is confirmed that the platelet aggregation is inhibited when one of the polypeptides of the present invention is added.

Example 5

Expression for E456Glu, Using Prothrombin Leader Peptide (1) Construction of Plasmid pSV2PTTMM3

Figure 31B:
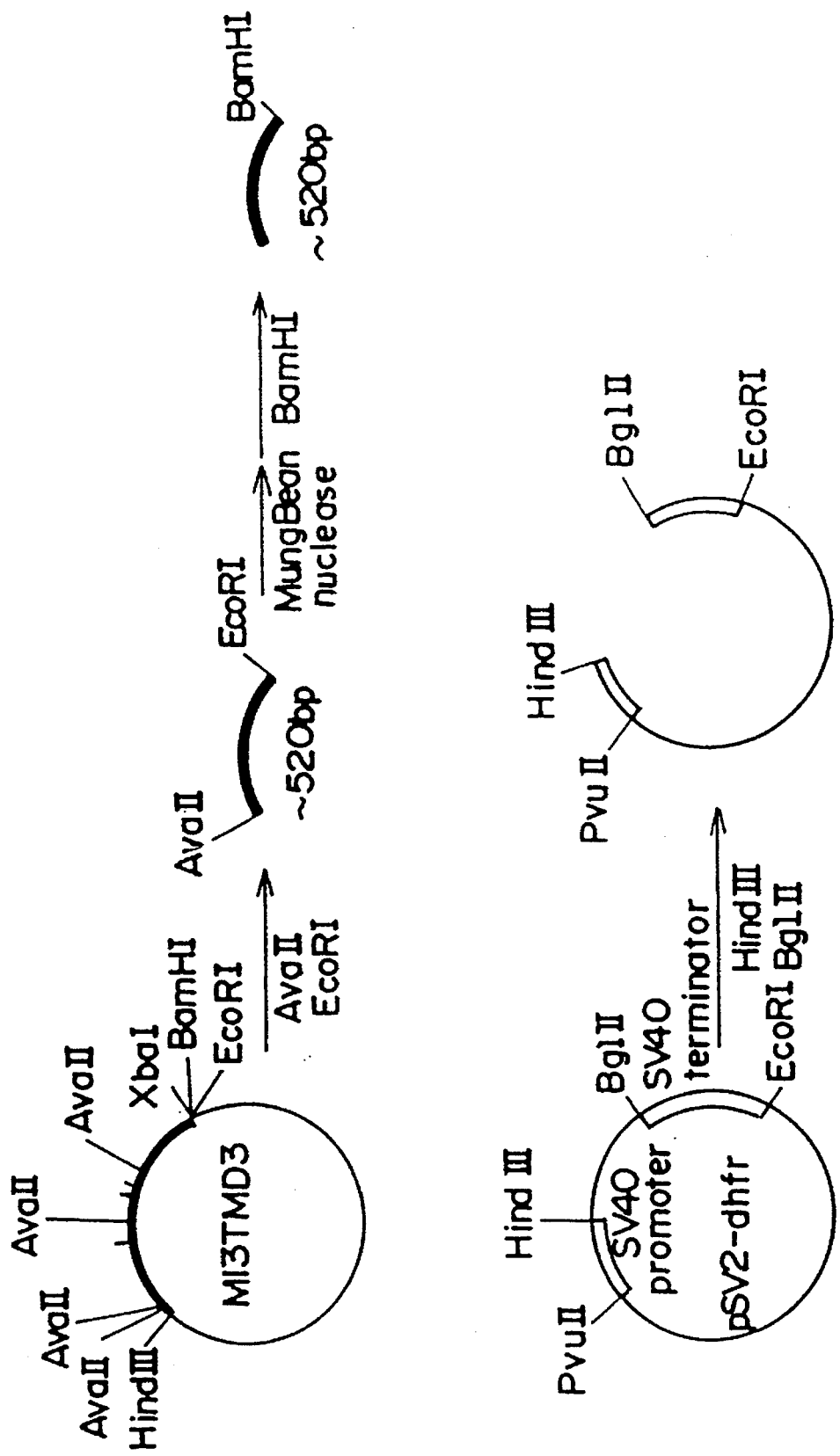
FIG. 31(a–c) shows a flow chart illustrating the construction of plasmid pSV2PTTMM3.
Figure 31C:
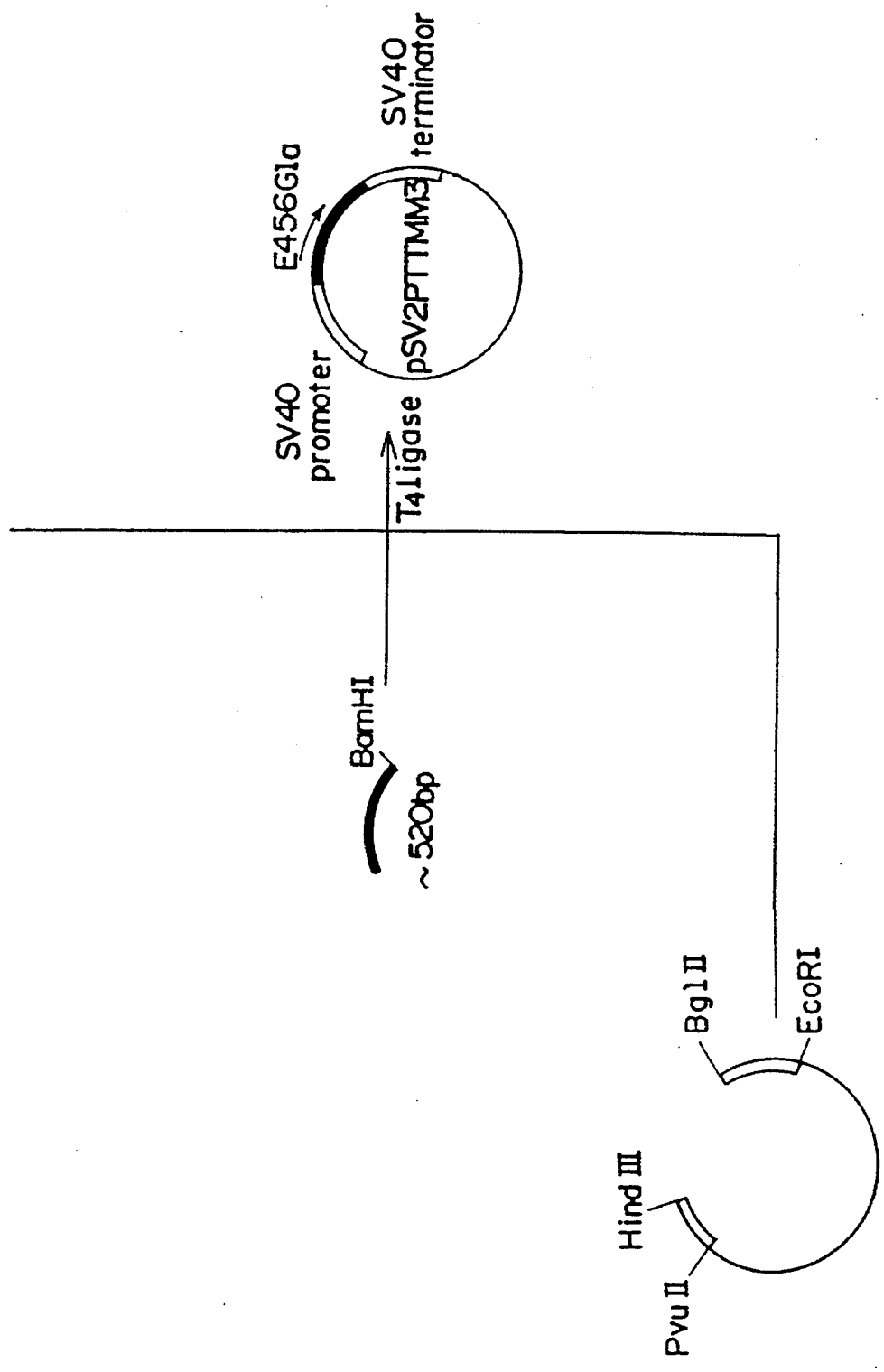

According to the process shown in FIG. 31(*a–c*), plasmid pSV2PTTMM3 for expression of a gene coding for E456Glu using prothrombin leader peptide is constructed.

(a) Preparation of PTTM Linker

PTTM linker having a nucleotide sequence shown in FIG. 31(a) is prepared in order to express a gene coding for E456Glu by means of prothrombin leader peptide under the control of SV40 promoter. The preparation method is detailed as follows.

First, four types of oligonucleotides respectively having the following nucleotide sequences are individually synthesized using DNA synthesizer model 380A (manufactured and sold by Applied Biosystems, U.S.A.) according to the customary method, (1) 5'-AGCTTAGCTGACACACTATGGCG-CACGTCCGAGGCTTGCAGCTGCCTG GCTGC-CTGGCCCTGGCTGCCCTGTGT-3', (SEQ. ID. No. 44)

(2) 5'-AGCCTTGTGCACAGCCAGCATGTGTTC-CTGGCTCCTCAGCAAGCACG GTCGCTGCTC-GAGCGGGTCCGGCGACCCGTGGAA-3', (SEQ. ID. No. 45)

(3) 5'-GTGCACAAGGCTACACAGGGCAGC-CAGGGCCAGGCAGCCAGGCAGCT GCAAGC-CTCGGACGTGCGCCATAGTGTGTCAGCTA-3', (SEQ. ID. No. 46) and (4) 5'-TTCCACGGGTCGCCGGACCCGCTCGAG-CAGCGACCGTGCTTGCTGAG GAGCCAGGAA-CACATGCTGGCT-3' (SEQ. ID. No. 47).

Subsequently, the 5'- end of each of oligonucleotides (2) and (3) is phosphorylated by T4 polynucleotide kinase. Then, phosphorylated oligonucleotide (2) is mixed with oligonucleotide (1) whereas phosphorylated oligonucleotide (3) is mixed with oligonucleotide (4), followed by annealing to obtain PTTM linker.

(b) Construction of Plasmid pSV2PTTMM3

Plasmid M13TMD3 prepared in Example 1-(1)-(a) is completely digested with restriction enzymes AvaII and EcoRI to obtain an AvaII-EcoRI DNA fragment of about 520 bp comprising a nucleotide sequence coding for E456Asp. This DNA fragment is isolated and purified. The purified DNA fragment is treated with Mung Bean Nuclease (manufactured and sold by Takara Shuzo Co., Ltd, Japan, 2420A) to make both ends of the fragment blunt. The resultant fragment is digested with BamHI to thereby obtain a fragment of about 520 bp. On the other hand, plasmid pSV2-dhfr (ATCC No. 37146) is completely digested with restriction enzymes HindIII and BglII to obtain a vector. This vector, the above-mentioned DNA fragment of about 520 bp and the PTTM linker prepared in Example 5-(1)-(a) are ligated using T4 DNA ligase to thereby obtain plasmid pSV2PTTMM3.

(2) Construction of Plasmid pSV2PTTMM6

Figure 32B:
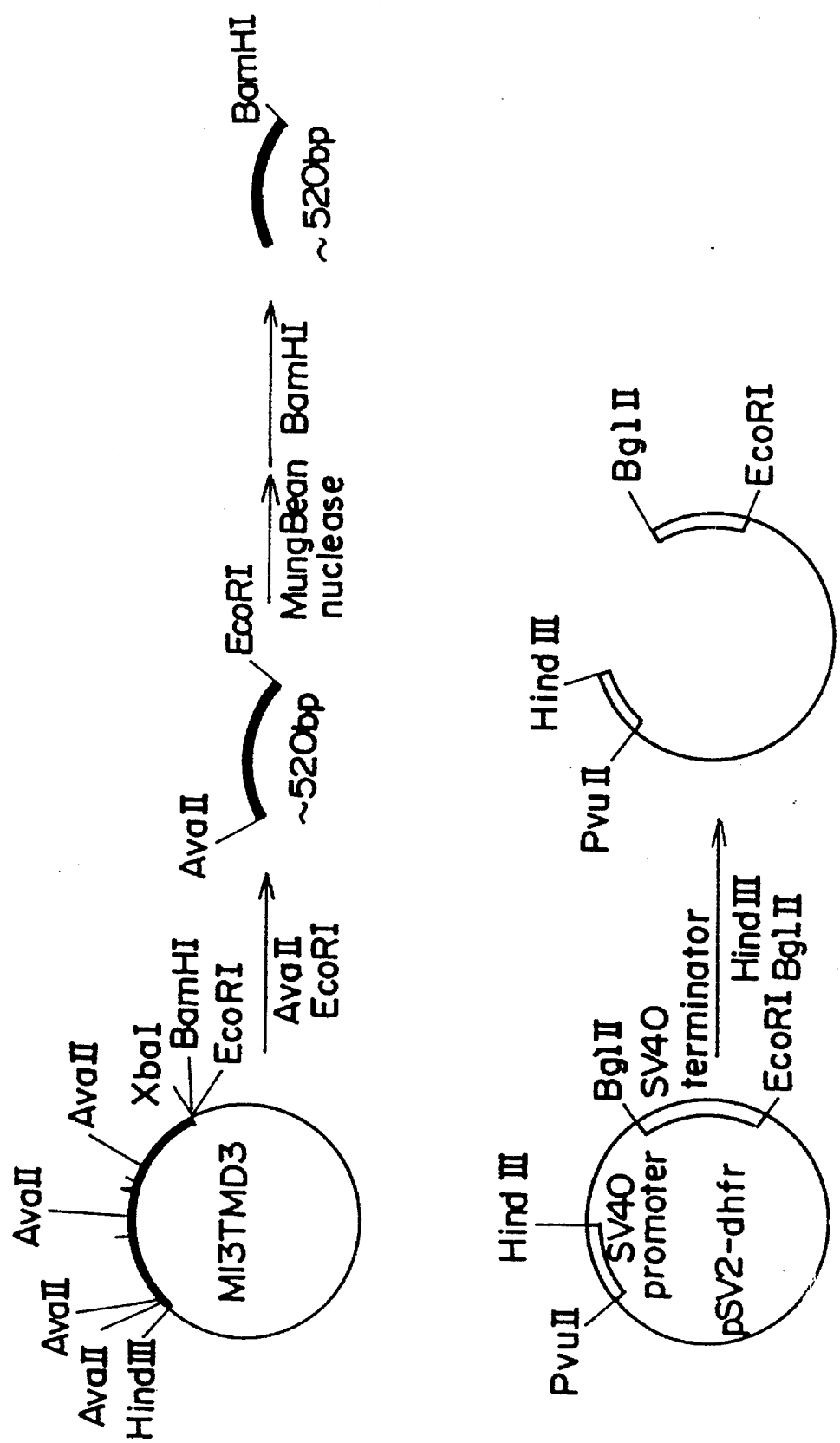
FIG. 32(a–c) shows a flow chart illustrating the construction of plasmid pSV2PTTMM6.
Figure 32C:
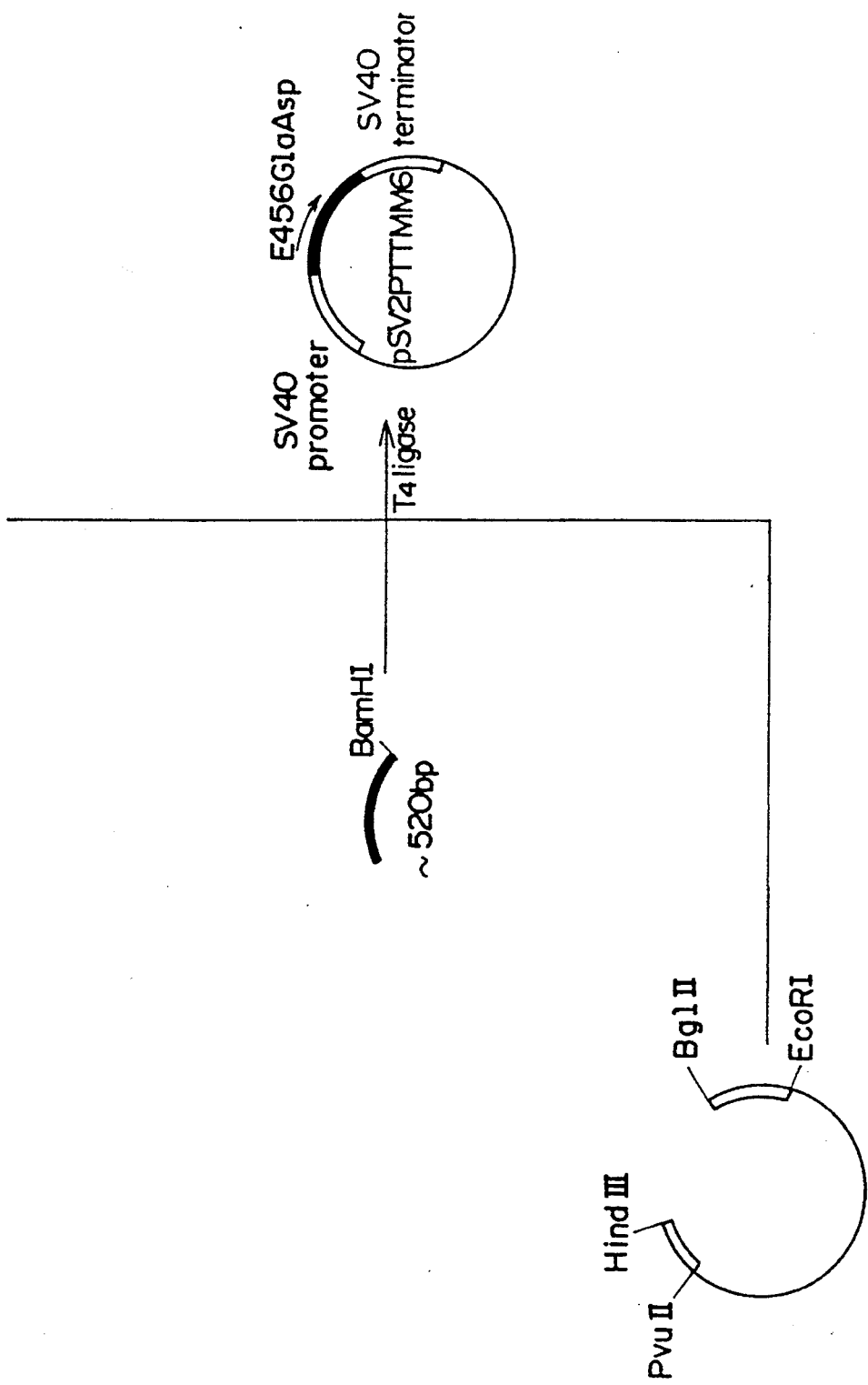

According to the process shown in FIG. 32, plasmid pSV2PTTMM6 for expression of a gene coding for E456GluAsp using prothrombin leader peptide is constructed.

(a) Preparation of PTTM2 Linker

PTTM2 linker having a nucleotide sequence shown in FIG. 32(a) is prepared in order to express a gene coding for E456GluAsp by prothrombin leader peptide under the control of SV40 promoter. The preparation method is detailed as follows.

First, four types of oligonucleotides respectively having the following nucleotide sequences are individually synthesized using DNA synthesizer model 380A, (manufactured and sold by Applied Biosystems, U.S.A.) according to the customary method, (1) 5'-AGCTTAGCTGACACACTATGGCG-CACGTCCGAGGCTTGCAGCTGCCT GGCTGC-CTGGCCCTGGCTGCCCTGTGT-3', (SEQ. ID. No. 44)

(2) 5'-AGCCTTGTGCACAGCCAGCATGTGTTC-CTGGCTCCTCAGCAAGCACG GTCGCTGCTC-GAGCGGGTCCGGCGACCCGTGGAAGAC-3', (SEQ. ID. No. 48)

(3) 5'-GTGCACAAGGCTACACAGGGCAGC-CAGGGCCAGGCAGCCAGGCAGCT GCAAGC-CTCGGACGTGCGCCATAGTGTGTCAGCTA-3', (SEQ. ID. No. 46) and (4) 5'-GTCTTCCACGGGTCGCCGGACCCGCTC-GAGCAGCGACCGTGCTTGCT GAGGAGCCAG-GAACACATGCTGGCT-3' (SEQ. ID. No. 49).

Subsequently, the 5'- end of each of oligonucleotides (2) and (3) is phosphorylated by T4 polynucleotide kinase. Then, phosphorylated oligonucleotide (2) is mixed with oligonucleotide (1) whereas phosphorylated oligonucleotide (3) is mixed with oligonucleotide (4), followed by annealing to obtain PTTM linker.

(b) Construction of plasmid pSV2PTTMM6

Plasmid M13TMD3 prepared in Example 1-(1)-(a) is completely digested with restriction enzymes AvaII and EcoRI to obtain an AvaII-EcoRI DNA fragment of about 520 bp comprising a nucleotide sequence coding for E456Asp. This DNA fragment is isolated and purified. The purified DNA fragment is treated with Mung Bean Nuclease (manufactured and sold by Takara Shuzo Co., Ltd, Japan) to make both ends of the fragment blunt. The resultant fragment is digested with BamHI to thereby obtain a fragment of about 520 bp. On the other hand, plasmid pSV2-dhfr (ATCC No. 37146) is completely digested with restriction enzymes HindIII and BamHI to obtain a vector. This vector, the above-mentioned DNA fragment of about 520 bp and the PTTM2 linker prepared in Example 5-(2)-(a) are ligated using T4 DNA ligase to thereby obtain plasmid pSV2PTTMM6.

(3) Transfection of Plasmids pSV2PTTMM3 and pSV2PTTMM6 into Cell Line CHO

Plasmid pSV2PTTMM3 is transfected into cell line CHO according to the method described in Example 1-(4)-(b). Colonies of the transformed cell appear about a month later. Each of the obtained cells is successively cultured in media which contain Methotrexate in concentrations of 20 nM and 200 nM, respectively, to thereby create a cell line (PTTM) having high capacity for producing a polypeptide having the activity to promote the thrombin-catalyzed activation of protein C. This cell line is cultured in DMEM which has been supplemented with proline, DFCS and vitamin $K_1$ (Aquamephyton, manufactured and sold by Merck Sharp and Dohome Co., Ltd.) at concentrations of 150 µg/µl, 10% and 5 µg/ml, respectively. The resultant cells are further cultured in substantially the same DMEM as mentioned above, except that the concentration of DFCS is decreased to 1%, thereby obtaining 1 liter of culture.

Transfection of plasmid pSV2PTTMM6 into cell line CHO and subsequent culturing of the obtained transfected cells are conducted in substantially the same manner as described above, to thereby create a cell line (PTTM2) having high capacity for producing a polypeptide having the activity to promote the thrombin-catalyzed activation of protein C. As a result, 1 liter of culture is obtained.

(4) Purification and Quantitative Determination of Each of Polypeptides 1 liter of each of the cultures of PTTM and PTTM2 cells obtained in Example 5-(3) is purified according to the method described in Example 3-(3). The absorbance of each of the purified polypeptides is measured. The value of the molecular extinction coefficient for general proteins, which is 10.0 ($E^{1\%}_{1cm}$.280 nm=10.0), is applied to each of the purified polypeptides, and based on this coefficient, the amount of each of the purified polypeptides is calculated from the absorbance and found to be about 50 μg.

Further, the purified polypeptides are individually subjected to SDS-polyacrylamide gel electrophoresis using a 5 to 10% acrylamide concentration gradient, and CBB staining is performed to observe any stained bands. Only one band is found with respect to each of the polypeptides.

The polypeptide purified from the culture of PTTM cells transfected with pSV2PTTMM3 is designated as E456Gla, and the other polypeptide purified from the culture of PTTM2 cells transfected with pSV2PTTMM6 is designated as E456GlaAsp.

Figure 33:
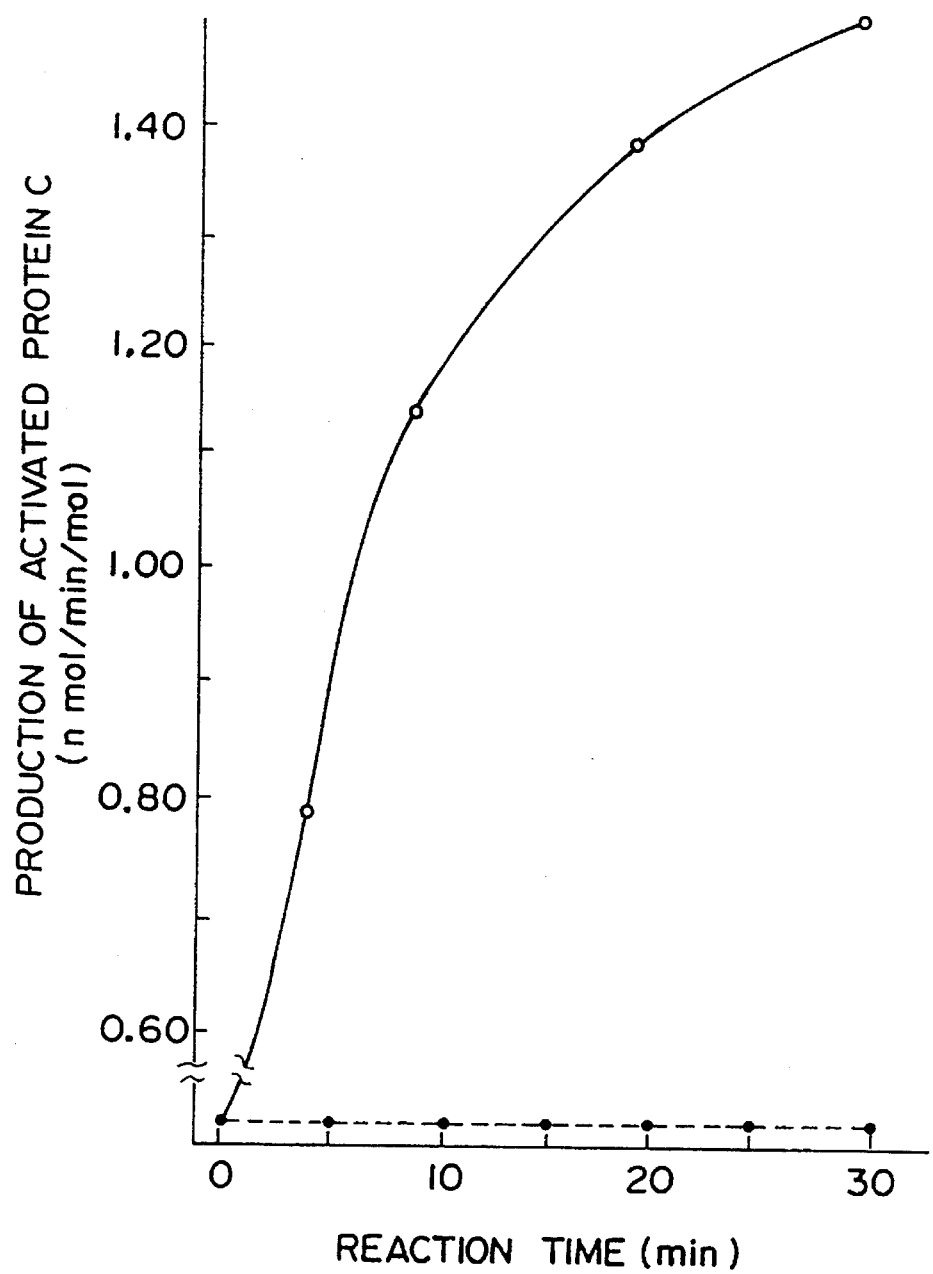
FIGS. 33 and 34 are graphs showing the relationships between the amount of the activated protein C formed by the reaction of protein C with thrombin and the reaction time, in which a comparison is made between the presence (o) of and the absence (●) of the polypeptide of the present invention, namely polypeptide E456Gla of the present invention purified in Example 5(4) for FIG. 33 and polypeptide E456Glu of the present invention purified in Example 3(3) for FIG. 34.
Figure 34:
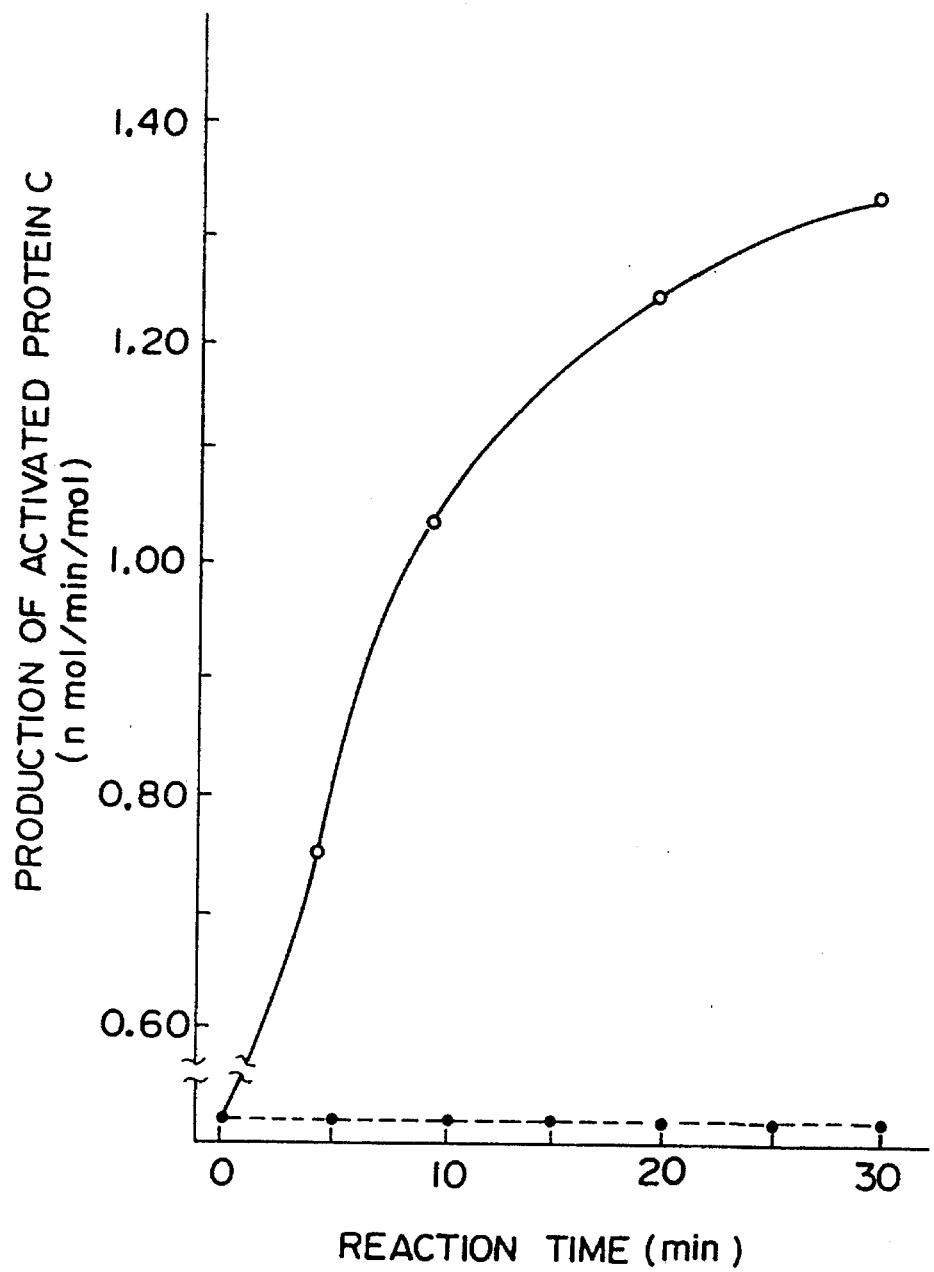
Figure 35:
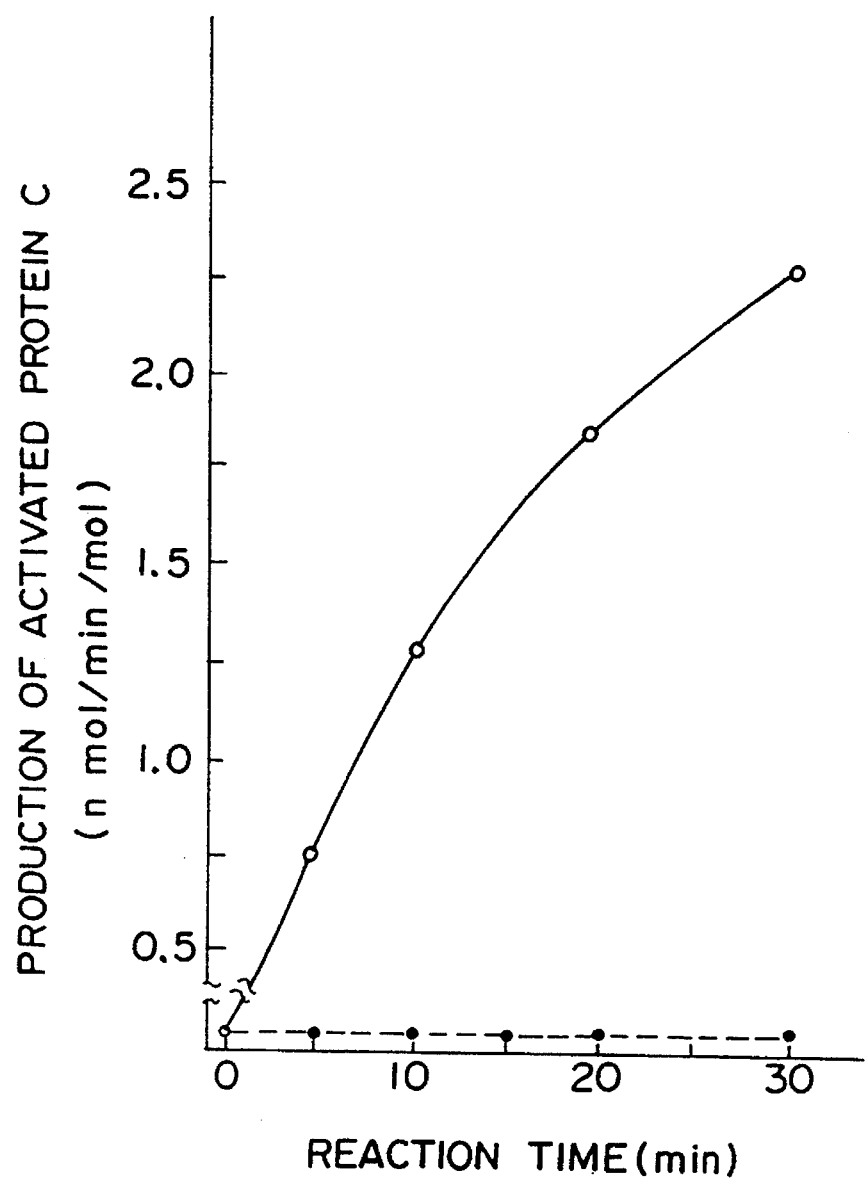
FIG. 35 is a graph showing the relationship between the amount of the activated protein C formed by the reaction of protein C with thrombin and the reaction time, in which a comparison is made between the presence (o) of and the absence (●) of polypeptide E456GlaAsp of the present invention purified in Example 5(4)

(5) Assay for the Activity to Promote the Thrombin-catalyzed Activation of Protein C With respect to the polypeptide E456Glu purified in Example 3-(3), the value of the molecular extinction coefficient for general proteins, which is 10.0 ($E^{1\%}_{1cm}$280 nm=10.0), is applied to the polypeptide. Based on this coefficient, the amount of the polypeptide is calculated from the absorbance thereof. Further, with respect to this polypeptide E456Glu and the polypeptides E456Gla and E456GlaAsp purified and quantitated in Example 5-(4), the activities to promote the thrombin-catalyzed activation of protein C are individually assayed according to the method described in Example 4-(6). The results of the assay with respect to the polypeptides E456Gla and E456Glu are shown in FIGS. 33 and 34, and the results of the assay with respect to the polypeptide E456GlaAsp is shown in FIG. 35. When none of the polypeptides of the present invention is added, the production of activated protein C is not observed (broken line). By contrast, when each of the polypeptides E456Gla, E456GlaAsp and E456Glu of the present invention is added, the amount of produced protein C is increased with the lapse of reaction time (solid line). 30 Min after the polypeptide addition, the amount of protein C activated in the presence of E456Gla is 20% larger than that of protein C activated in the presence of E456Glu. 30 Min after the polypeptide addition, the amount of protein C activated in the presence of E456GlaAsp is 80% larger than that of protein C activated in the presence of E456Glu.

(6) Confirmation of Gamma-carboxyglutamic Acid (a) Determination of an N-terminal Amino Acid Sequence Polypeptides E456Gla and E456GlaAsp, which have been purified by the procedure described above, are individually analyzed as follows.

Each of polypeptides E456Gla and E456GlaAsp is dialyzed against a 0.1% (v/v) aqueous solution of sodium dodecyl sulfate (SDS) at room temperature for 16 hours to obtain a sample for the analysis of amino acid sequence. Using an amino acid sequencer (Model 470A, manufactured and sold by Applied Biosystems Inc., U.S.A.), Edman degradation is successively effected starting from the N-terminus according to the method of R. M. Hewick et al.[J. Biol. Chem., Vol. 256, p. 7990 (1981)]. Liberated phenylthiohydantoin amino acid is analyzed using an apparatus for high performance liquid chromatography (SP 8100, manufactured and sold by Spectra Physics, U.S.A.) and ZORVAX ODS column (manufactured and sold by E. I. du Pont de Nemours and Company, U.S.A.) to determine the amino acid sequence. As a result, it is found that the polypeptide E456Gla has the following amino acid sequence (SEQ. ID. No. 50).

Pro-Val-X-Pro-X-Phe-Arg-Ala-

Polypeptide E456GlaAsp is found to have the following amino acid sequence (SEQ. ID. No. 51).

Pro-Val-X-Asp-Pro-X-Phe-Arg-Ala-

In the above two amino acid sequences, X denotes that no amino acid is detected.

(b) Confirmation of Gamma-carboxyglutamic Acid

Each of polypeptides E456Gla and E456GlaAsp, which have been purified by the procedure described above, is subjected to amino acid analysis according to the method of M. J. Jorgensen et al.[J. Biol. Chem., 262, 14, 6729–6734 (1987)], as follows.

Each of the purified polypeptides is hydrolyzed in 2M potassium hydroxide at 110° C. for 22 hours. The hydrolysate is subjected to amino acid analysis using an amino acid analyzer (Model 119CL, manufactured and sold by Beckman City Hope Medical Institute, U.S.A) equipped with data system (Model 126, manufactured and sold by Beckman City of Hope Medical Institute, U.S.A.), to thereby confirm gamma-carboxyglutamic acid.

(7) Measurement of Anticoagulating Activity

Figure 36:
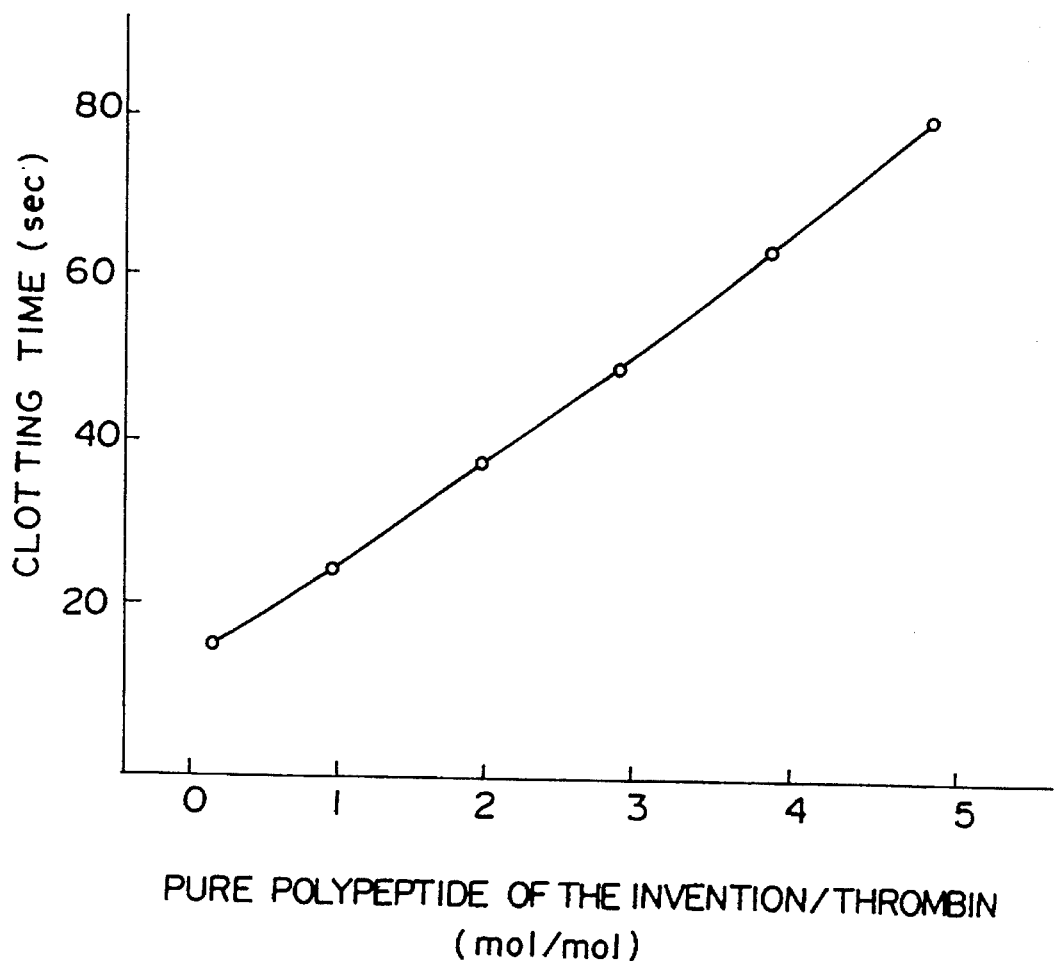
FIG. 36 is a graph showing the relationship between the clotting time of a fibrinogen solution to which polypeptide E456Gla of the present invention purified in Example 5(4) was added and the amount of the added purified polypeptide.
Figure 37:
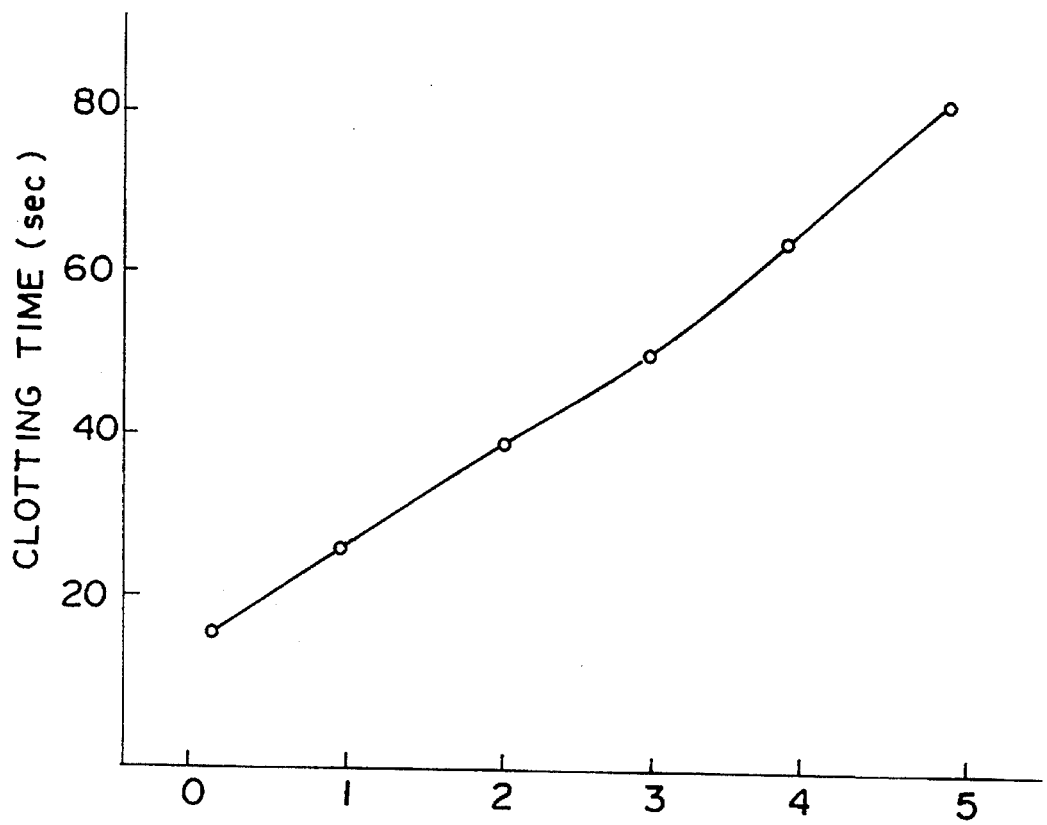
FIG. 37 is a graph showing the relationship between the clotting time of a fibrinogen solution to which polypeptide E456GlaAsp of the present invention purified in Example 5(4) was added and the amount of the added purified polypeptide.

The activity of the polypeptides of the present invention to inhibit the thrombin-catalyzed conversion of fibrinogen to fibrin so as to substantially inhibit blood coagulation is measured according to the method of Example 4-(7). The results for polypeptide E456Gla and polypeptide E456GlaAsp are shown in FIGS. 36 and 37, respectively. It is confirmed that the higher the amount of the purified polypeptide added relative to the amount of thrombin, the longer the clotting time.

(8) Confirmation of Platelet Aggregation-inhibiting Activity

Figure 38:
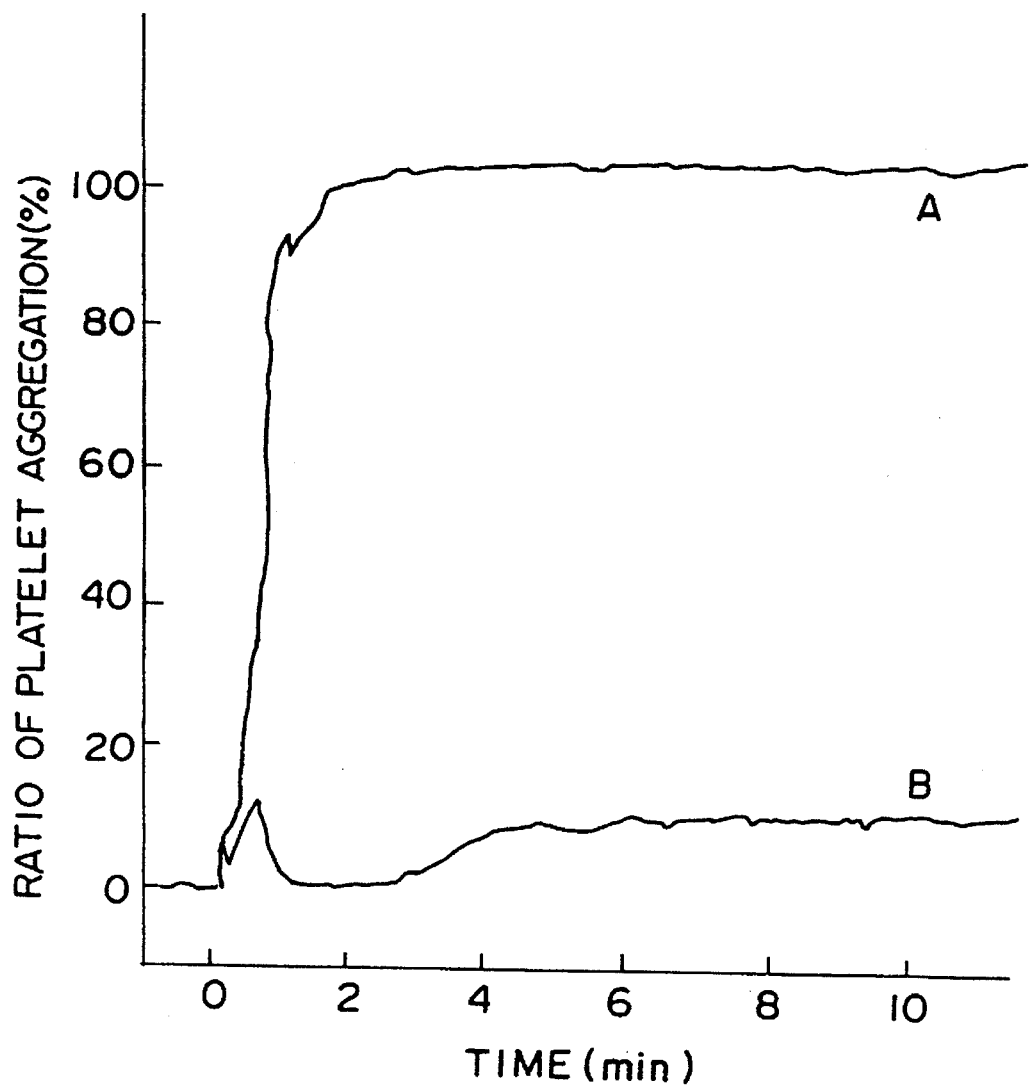
FIG. 38 is a graph showing the relationship between the thrombin-catalyzed platelet aggregation and the time, in which a comparison is made between the presence (B) of and the absence (A) of polypeptide E456Gla of the present invention purified in Example 5(4)
Figure 39:
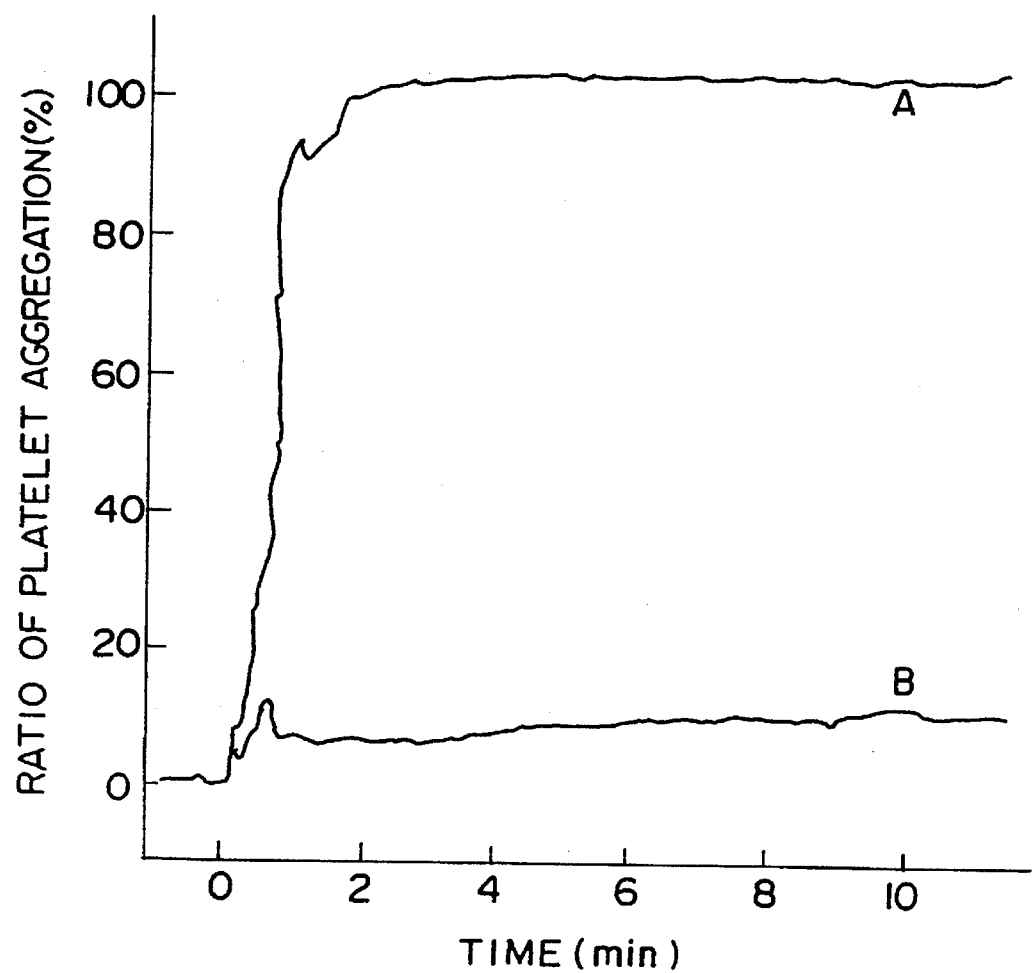
FIG. 39 is a graph showing the relationship between the thrombin-catalyzed platelet aggregation and the time, in which a comparison is made between the presence (B) of and the absence (A) of polypeptide E456GlaAsp of the present invention purified in Example 5(4)

The activity of the peptides of the present invention to substantially inhibit the thrombin-catalyzed platelet aggregation is measured according to the method of Example 4-(8). The results for polypeptide E456Gla and polypeptide E456GlaAsp are shown in FIGS. 38 and 39, respectively. It is confirmed that, when each of the polypeptides of the present invention is added, the platelet aggregation is inhibited.

Example 6

Expression of Polypeptides E456Asp and E456Glu in *Acremonium chrysogenum*

(1) Construction of plasmid pMTMD7

Figure 40:
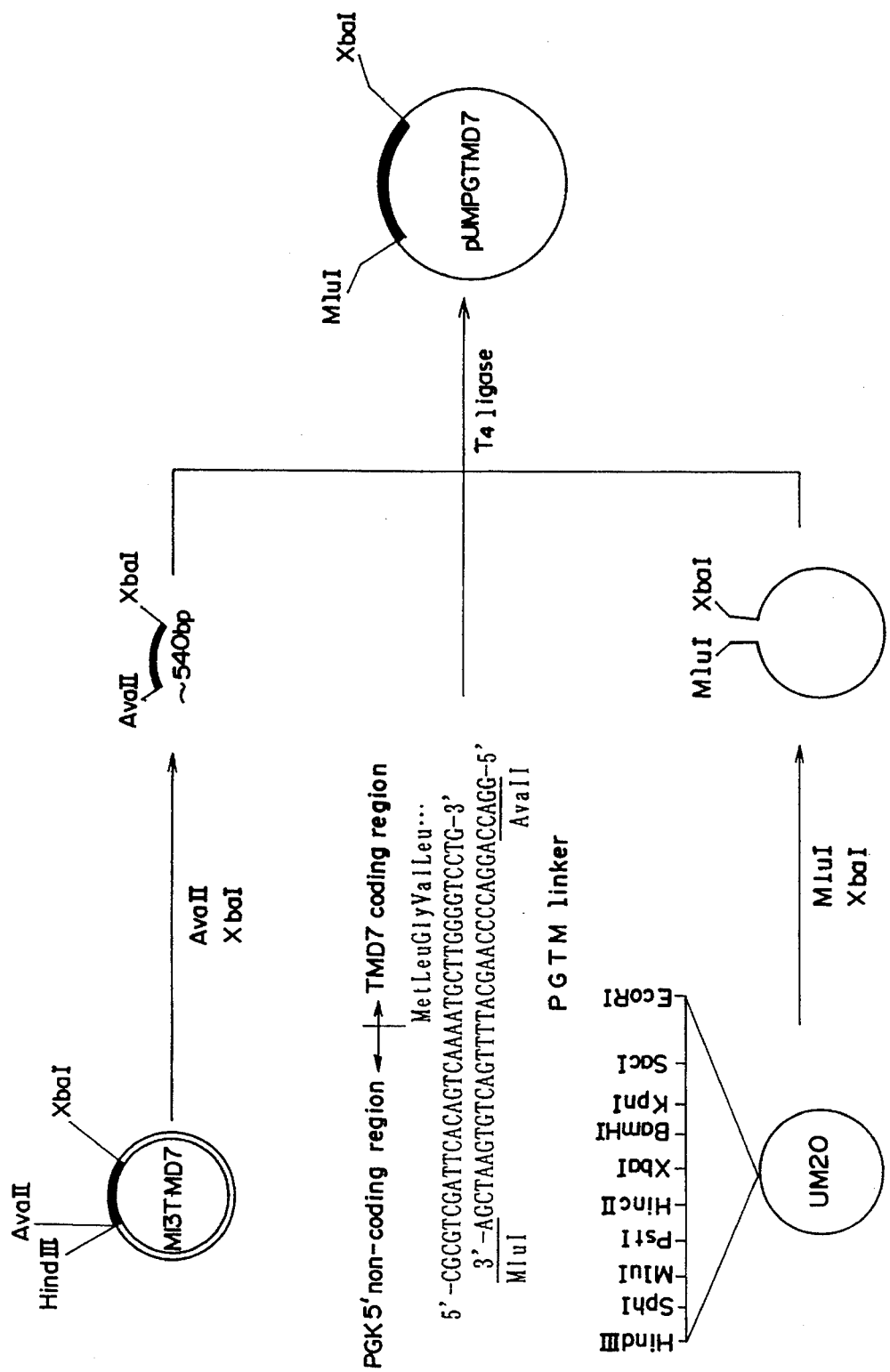
FIG. 40 shows a flow chart illustrating the construction of plasmid pUMPGTMD7.
Figure 41:
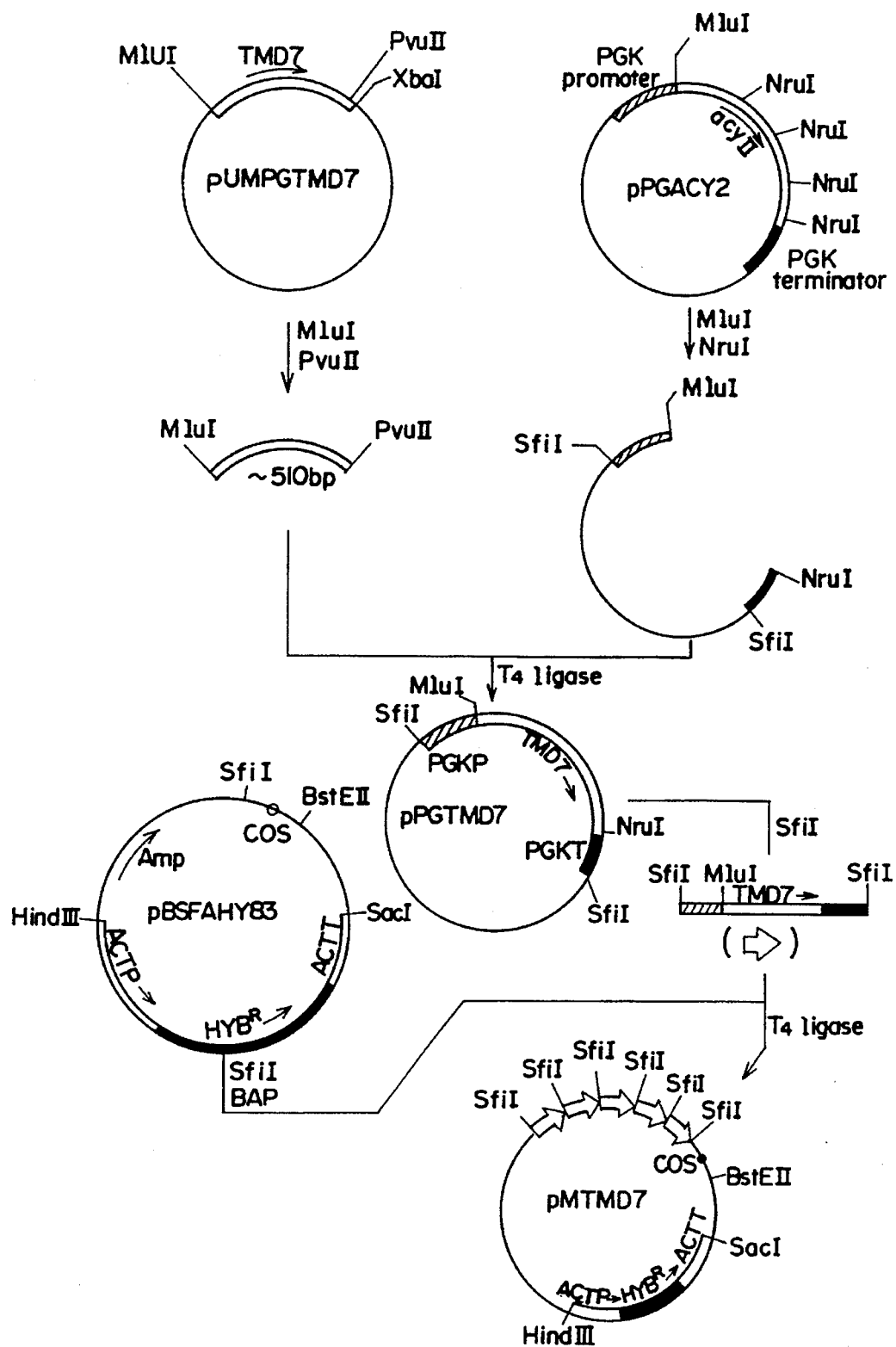
FIG. 41 shows a flow chart illustrating the construction of plasmid pMTMD7.

According to the steps shown in FIGS. 40 and 41, plasmid pMTMD7 for expression of a gene coding for polypeptide E456Asp under the control of PGK promoter derived from *Acremonium chrysogenum* is constructed.

(a) Preparation of a PGTM Linker

A PGTM linker having a nucleotide sequence shown in FIG. 40 is prepared in order to coincide the position of the initiation codon of the gene coding for polypeptide E456Asp to the position of the initiation codon of PGK gene (SEQ. ID. No. 52) and (SEQ. ID. No. 53) derived from *Acremonium chrysogenum*. The details of the procedure are described below.

Two types of oligonucleotides having the following nucleotide sequences:

(1) 5'-CGCGTCGATTCACAGTCAAAATGCT-TGGGGTCCTG-3', (SEQ. ID. No. 52) and (2) 5'-GGACCAGGACCCCAAGCATTTTGACTGT-GAATCGA-3' (SEQ. ID. No. 54)

are synthesized by the conventional method using an automatic DNA synthesizer (Model 380-A, manufactured and sold by Applied Biosystem Co., Ltd.). The obtained two types of oligonucleotides are mixed and annealed to thereby obtain a PGTM linker.

(b) Construction of Plasmid pUMpGTMD7

The plasmid M13TMD7, which has been obtained in Example 1-(1)-(b), is transfected into a host which has no methylating activity, and a double stranded plasmid DNA is prepared from the resultant transformant, followed by complete digestion with restriction enzymes AvaII and XbaI to obtain a purified AvaII-XbaI fragment of about 540 bp containing a nucleotide sequence coding for polypeptide E456Asp, which fragment has a portion of the N-terminus coding region deleted. On the other hand, UM20 manufactured and sold by International Biotechnologies, Inc., U.S.A., catalog No. 33700) is digested with restriction enzymes MluI and XbaI to obtain a purified MluI-XbaI fragment of about 7.3 kb. Then, these two fragments and the PGTM linker obtained in the above procedure are ligated to each other to obtain plasmid pUMPGTMD7.

(c) Construction of Plasmid pPGTMD7

Plastamid pUMPGTMD7 obtained in the above procedure is completely digested with restriction enzymes MluI and PvuII to obtain a purified MluI-PvuII fragment of about 510 bp containing a gene coding for polypeptide E456Asp and a portion of PGK5' non-coding region. On the other hand, plasmid pPGACY2 obtained according to the method of Matsuda et al.(Japanese-Patent Application 2-219032, see Reference Examples described later), which plasmid contains PGK promoter and PGK terminator both derived from *Acremonium chrysogenum*, is digested with restriction enzymes MluI and NruI to obtain a purified DNA fragment of about 4.8 kb. These DNA fragments are ligated to each other using T4 DNA ligase to obtain plasmid pPGTMD7.

(d) Construction of Plasmid pMTMD7

The above constructed plasmid pPGTMD7 comprising an expression unit for polypeptide E456Asp (hereinafter referred to as "E456Asp expression unit") comprised the PGK promoter derived from *Acremonium chrysogenum*, the gene coding for polypeptide E456Asp and the PGK terminator derived from *Acremonium chrysogenum*, is digested with restriction enzyme SfiI to obtain a DNA fragment of 2.6 kb containing the E456Asp expression unit. On the other hand, plasmid pBSFAHY 83 obtained according to the method of Matsuda et al. (Japanese Patent Application 2-219032, see Reference Example described later) is digested with restriction enzyme SfiI, followed by the treatment with alkaline phosphatase. Then, the fragments obtained above are ligated to each other by means of T4 DNA ligase under conditions such that the concentration of the fragment containing the E456Asp expression unit is higher than that of the other fragment. The thus obtained ligated plasmid DNA is introduced into *E. coli* HB101, to thereby obtain a transformant. The transformant is spread on L-broth agar medium containing ampicillin (100 µg/ml), and allowed to grow at 37° C. overnight to thereby form colonies. 10 Colonies are chosen at random, and from each of them, a recombinant cosmid DNA is obtained. The obtained recombinant cosmid DNA is digested with restriction enzyme BstEII, and subjected to agarose gel electrophoresis, to thereby select one recombinant cosmid having inserted therein a large number of E456Asp expression units per vector molecule. The selected recombinant cosmid is designated as pMTMD7, which is prepared in a large amount. It is presumed that at least 5 copies of E456Asp expression unit are contained in the resultant pMTMD7, from the analysis of the results obtained above.

(2) Construction of Plasmid pMTMM3

Figure 42:
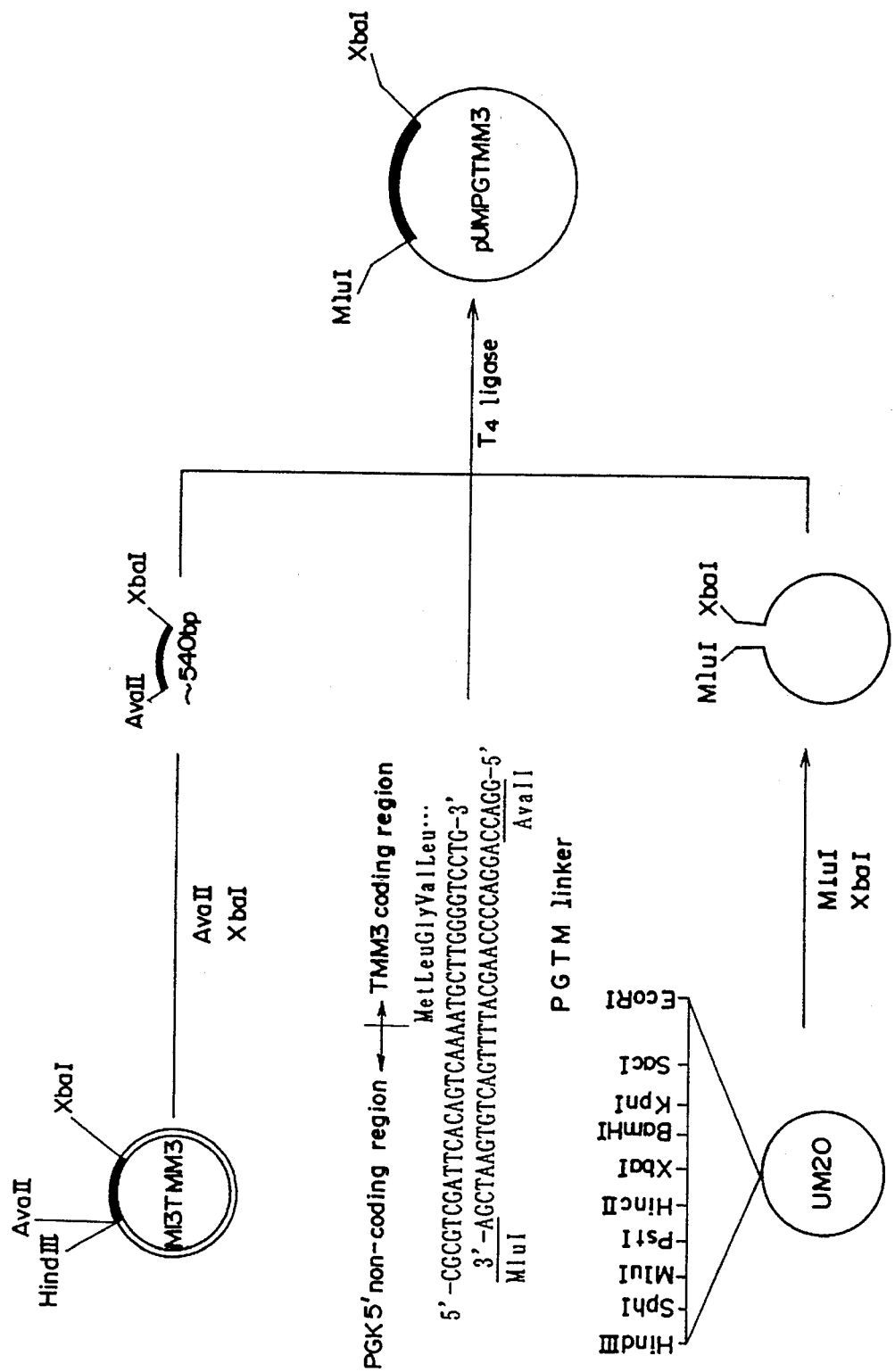
FIG. 42 shows a flow chart illustrating the construction of plasmid pUMPGTMM3.
Figure 43:
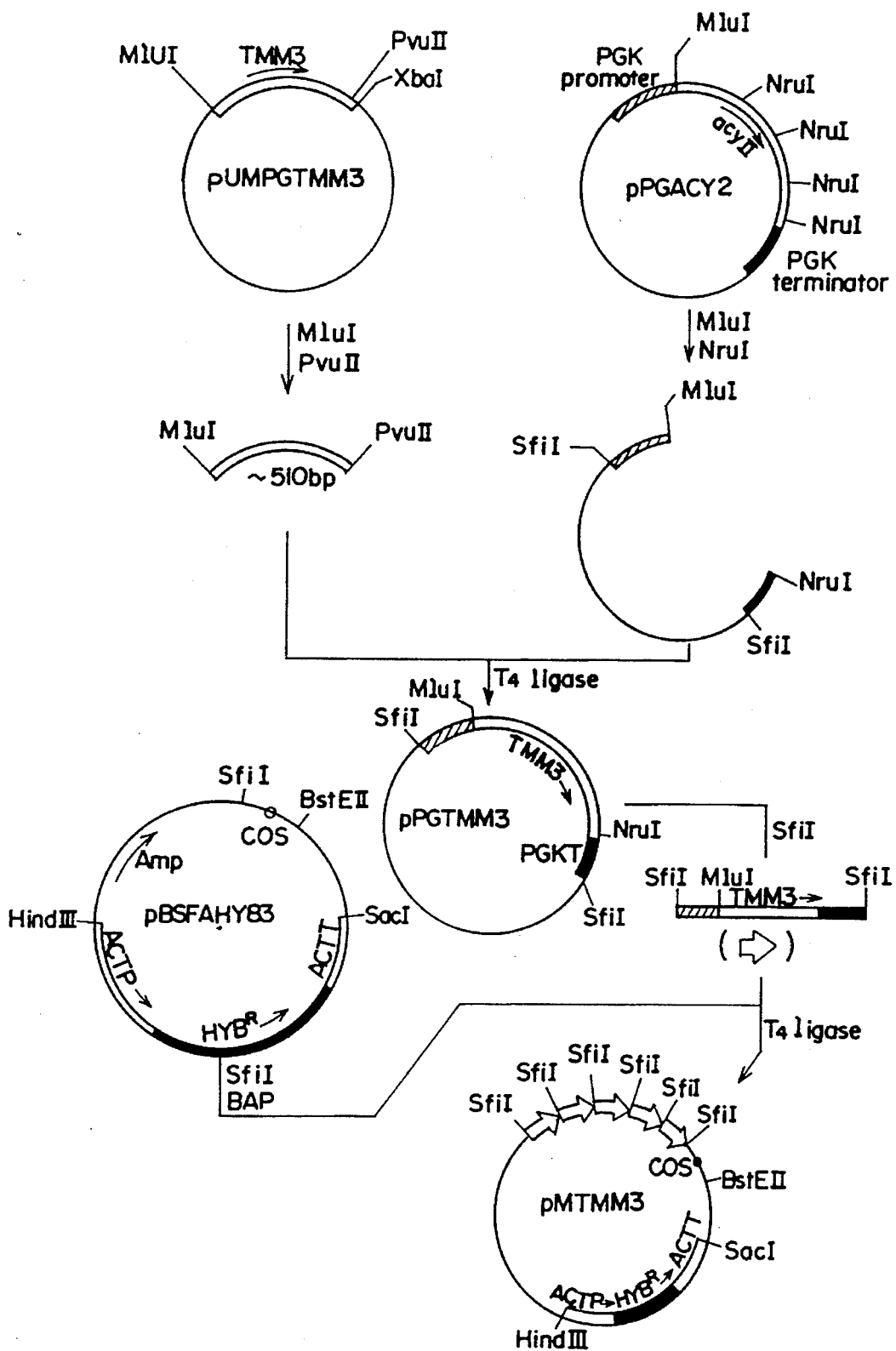
FIG. 43 shows a flow chart illustrating the construction of plasmid pMTMM3.

Substancially the same procedure as described in Example 6-(1) is repeated in accordance with the method indicated in FIGS. 42 and 43 to thereby obtain plasmid pMTMM3 for expression of a gene coding for polypeptide E456Glu under the control of PGK promoter derived from *Acremonium chrysogenum*.

(a) First, the plasmid M13TMM3 obtained in Example 3-(1) is completely digested with restriction enzymes AvaII and XbaI to obtain a purified AvaII-XbaI fragment of about 540 bp containing a nucleotide sequence coding for polypeptide E456Glu, which gene has a portion of the N-terminus coding region deleted. On the other hand, UM20(manufactured and sold by International Biotechnologies, Inc., U.S.A., catalog No. 33700) is digested with restriction enzymes MluI and XbaI to obtain a purified MluI-XbaI fragment of about 7.3 kb. Then, these two DNA fragments and the PGTM linker obtained in Example 6-(1)-(a) are ligated by means of T4 DNA ligase to obtain plasmid pUMPGTMM3.

(b) Construction of Plasmid pPGTMM3

The plasmid pUMPGTMM3 obtained in Example 6-(2)-(a) is completely digested with restriction enzymes MluI and PvuII to obtain a purified MluI-PvuII fragment of about 510 bp containing a gene coding for polypeptide E456Glu and a portion of PGK5' non-coding region. On the other hand, plasmid pPGACY2 containing *Acremonium chrysogenum* PGK promoter and PGK terminator obtained according to the method of Matsuda et al (Japanese Patent Application No. 2-219032, see Reference Example described later) is digested with restriction enzymes MluI and NruI to obtain a purified MluI-NruI fragment of about 4.8 kb. Then, these two DNA fragments are ligated to each other by means of T4DNA ligase to obtain plasmid pPGTMM3.

(c) Construction of Plasmid pMTMM3

The above constructed plasmid pPGTMM3 comprising an expression unit for polypeptide E456Glu (hereinafter referred to as "E456Glu expression unit") comprised PGK promoter derived from *Acremonium chrysogenum*, the gene coding for polypeptide E456Glu and the PGK terminator derived from *Acremonium chrysogenum*, is digested with restriction enzyme SfiI to obtain a DNA fragment of 2.6 kb containing the E456Glu expression unit. On the other hand, plasmid pBSFAHY83 obtained according to the method of Matsuda et al. (Japanese Patent Application 2-219032, see Reference Example described later) is digested with restriction enzyme SfiI, followed by treatment with alkaline phosphatase. Then, the fragments obtained above are ligated to each other by means of T4 DNA ligase under conditions such that the concentration of the fragment containing the E456Glu expression unit is higher than that of the other fragment. The thus obtained ligated plasmid DNA is introduced into *E. coli* HB101, to thereby obtain a transformant. The transformant is spread on L-broth agar medium containing ampicillin (100 µg/ml), and allowed to grow at 37° C. overnight to thereby form colonies. 10 Colonies are chosen at random, and from each colony, a recombinant cosmid DNA is obtained. The obtained recombinant cosmid DNA is digested with restriction enzyme BstEII, and subjected to agarose gel electrophoresis, to thereby select one recombinant cosmid having inserted therein a large number of E456Glu expression units per vector molecule. The selected recombinant cosmid is designated as pMTMM3, which is prepared in a large amount. It is presumed that at least 5 copies of E456Glu expression unit are contained in the resultant pMTMM3, from the analysis of the results obtained above.

(3) Introduction of Plasmids pMTMD7 and pMTMM3 into *Acremonium chrysogenum*

(a) Preparation of Protoplast

The culture media for preparing protoplasts have the following composition:

CM culture medium: media comprised of 20 g of sucrose, 0.5 g of potassium dihydrogen phosphate, 0.5 g of dipotassium hydrogen phosphate, 0.5 g of potassium chloride, 0.5 g of magnesium sulfate.$7H_2O$, 0.01 g of iron (II) sulfate.$7H_2O$, 3 g of sodium nitrate, 4 g of yeast extract, and 10 g of peptone dissolved in 1 liter of distilled water;

CM solid medium: CM culture medium supplemented with 1.5% of agar;

GAG culture medium: medium comprised of 40 g of glycerol, 4 g of asparagine, 0.1 g of calcium chloride, 0.1 g of sodium chloride, 25 ml of trace metal solution [comprised of 4 g of magnesium sulfate.$7H_2O$, 0.4 g of ferrous (II) sulfate.$7H_2O$, 0.16 g of manganese sulfate.$4H_2O$, and 0.4 g of zinc sulfate.$7H_2O$, and 0.04 g of anhydrous copper sulfate dissolved in 1 liter of distilled water], and 30 ml of 0.1M phosphate buffer solution (pH 7.0) dissolved in 1 liter of distilled water; and P-buffer: 0.6M potassium chloride, 0.01M magnesium chloride and 0.025M calcium chloride.

A mycelium of *Acremonium chrysogenum* (ATCC No. 11550) grown at 30° C. for 5 days on CM solid medium is inoculated into 50 ml of CM medium, and cultured at 30° C. for 3 days on a rotary shaker (250 r.p.m). Subsequently, 1 ml of the resultant culture is inoculated into 50 ml of GAG culture medium, and cultured at 30° C. for 20 hours. 50 ml of the culture thus obtained is subjected to centrifugation at 3500 r.p.m for 10 minutes, to thereby precipitate the mycelium. The mycelium is washed with a 0.9% NaCl solution, and suspended in 20 ml of McIlvain buffer (0.1M citric acid, 0.2M sodium phosphate, pH7.3) containing 0.01M dithiothreitol. The suspension is kept at 30° C. for 1 hour while gently shaking. Then, the culture is subjected to centrifugation at 3200 r.p.m for 10 minutes, to thereby precipitate the mycelium. The mycelium is washed with P-buffer, suspended in 10 ml of P-buffer containing Novozyme (manufactured and sold by Novo Industry, Denmark) at a concentration of 10 mg/ml, and subjected to gentle shaking at 30° C. for 1 hour. The resultant reaction mixture is subjected to centrifugation at 800 r.p.m for 30 seconds, to thereby obtain a supernatant. The supernatant is filtered by means of a filter paper (Toyo Filter Paper 5A), to thereby separate the mycelium from the protoplast. The filtrate is then subjected to centrifugation at 3000 r.p.m for 5 minutes to precipitate the protoplast, and the protoplast is washed with P-buffer once and suspended in P-buffer so that the concentration of the protoplast becomes $3 \times 10^8$/ml.

(b) Transformation of Protoplast with pMTMD7 and pMTMM3 and Culturing Thereof

To 0.1 ml of the protoplast suspension obtained in Example 6-(3)-(a) is first added 10 μl of a solution containing 5 μg each of plasmids pMTMD7 and pMTMM3, and then 0.05 ml of PEG solution, followed by gentle stirring. The resultant mixture is allowed to stand on ice for 25 minutes, and then 1 ml of PEG solution containing 25% polyethylene glycol (about 4000), 0.01M tris-buffer (pH 8.0), 0.05M calcium chloride and 0.6M potassium chloride, is added. The mixture is allowed to stand at room temperature for 30 minutes.

The thus obtained transformed protoplast suspention is portionwise spread on a plate containing 25 ml of a protoplast regeneration medium (which is the BRM medium described in Isogai et al.: Agric. Biol. Chem. 1987, 51, 2321–2329) each in an amount of 0.2 ml, followed by incubation at 15° C. for 20 hours. Then, 5 ml of BRM medium containing 4.5 mg of hygromycin B and kept at 50° C., is superposed on the above plate, followed by incubation at 28° C. for 14 days. As a result, 70 strains of transformants hereinafter referred to as "HYB transformants") which have been rendered resistant to hygromycin B, appear.

(c) Measurement of the Activity of a Supernatant of Transformant Culture to Promote the Thrombin-catalyzed Activation of Protein C Three strains isolated from each of the above HYB transformants produced using plasmids pMTMD7 and pMTMM3 are individually inoculated into 30 ml of CM medium, followed by culturing while shaking (220 r.p.m) at 30° C. for 3 days. 1 ml of each of the resultant cultures is subjected to centrifugation at 1500 r.p.m for 5 minutes to obtain a supernatant. The supernatant is recovered, and subjected to measurement of activity to promote the thrombin-catalyzed activation of protein C in accordance with the method described in Example 1-(3).

All of the strains thus obtained exhibit the activity. On the other hand, *Acremonium chrysogenum* (ATCC No. 11550), which has not been transformed, does not exhibit the activity. Results are shown in Table 3.

(4) Purification of Polypeptides E456Asp and E456Glu

Each of strains D71 and M31 obtained in the above procedure is inoculated into 500 ml of CM culture medium, followed by culturing while shaking (220 r.p.m) at 30° C. for 5 days. Then, the resultant culture is subjected to centrifugation to recover 500 ml of a supernatant. From the recovered supernatant, the polypeptide of the present invention is purified according to the method of Example 3-(3). The molecular extinction coefficient for general proteins, which is 10.0 ($E_{1cm}^{1\%}$.280 nm=10.0), is assigned to the purified polypeptide of the present invention. Based on this coefficient, the amount of the purified polypeptide is calculated from the absorbance thereof, which is found to be about 50 μg. The purified polypeptide is subjected to SDS-polyacrylamide gel electrophoresis using a 5 to 10% acrylamide concentration gradient, and CBB staining is performed. As a result, two 24K and 22K bands are observed.

Figure 44:
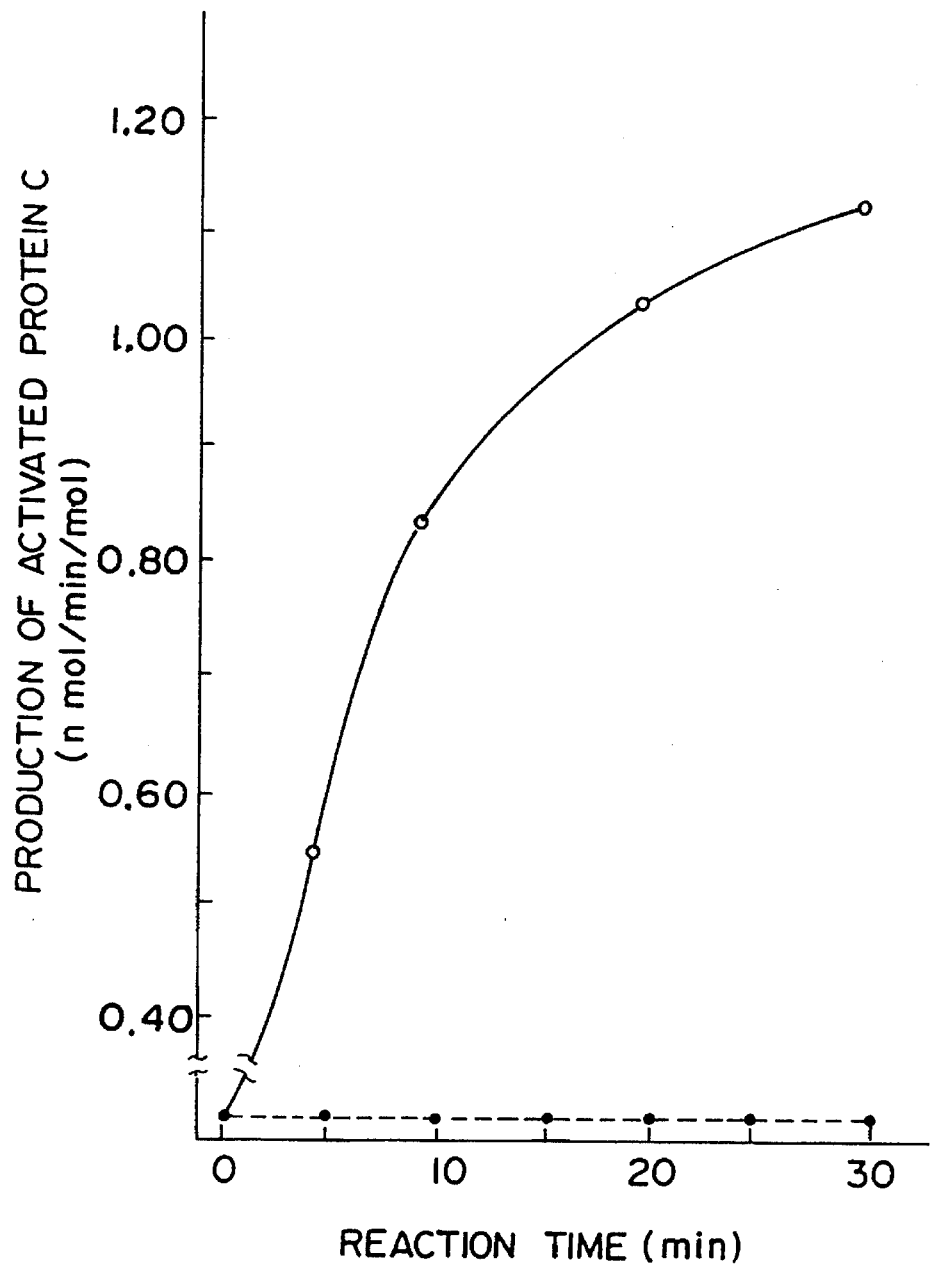
FIGS. 44 and 45 are graphs showing the relationships between the amount of the activated protein C formed by the reaction of protein C with thrombin and the reaction time, in which a comparison is made between the presence (o) of and the absence (●) of the polypeptide of the present invention, namely, polypeptides E456Asp and E456Glu of the present invention purified in Example 6(4) for FIG. 44 and FIG. 45, respectively.
Figure 45:
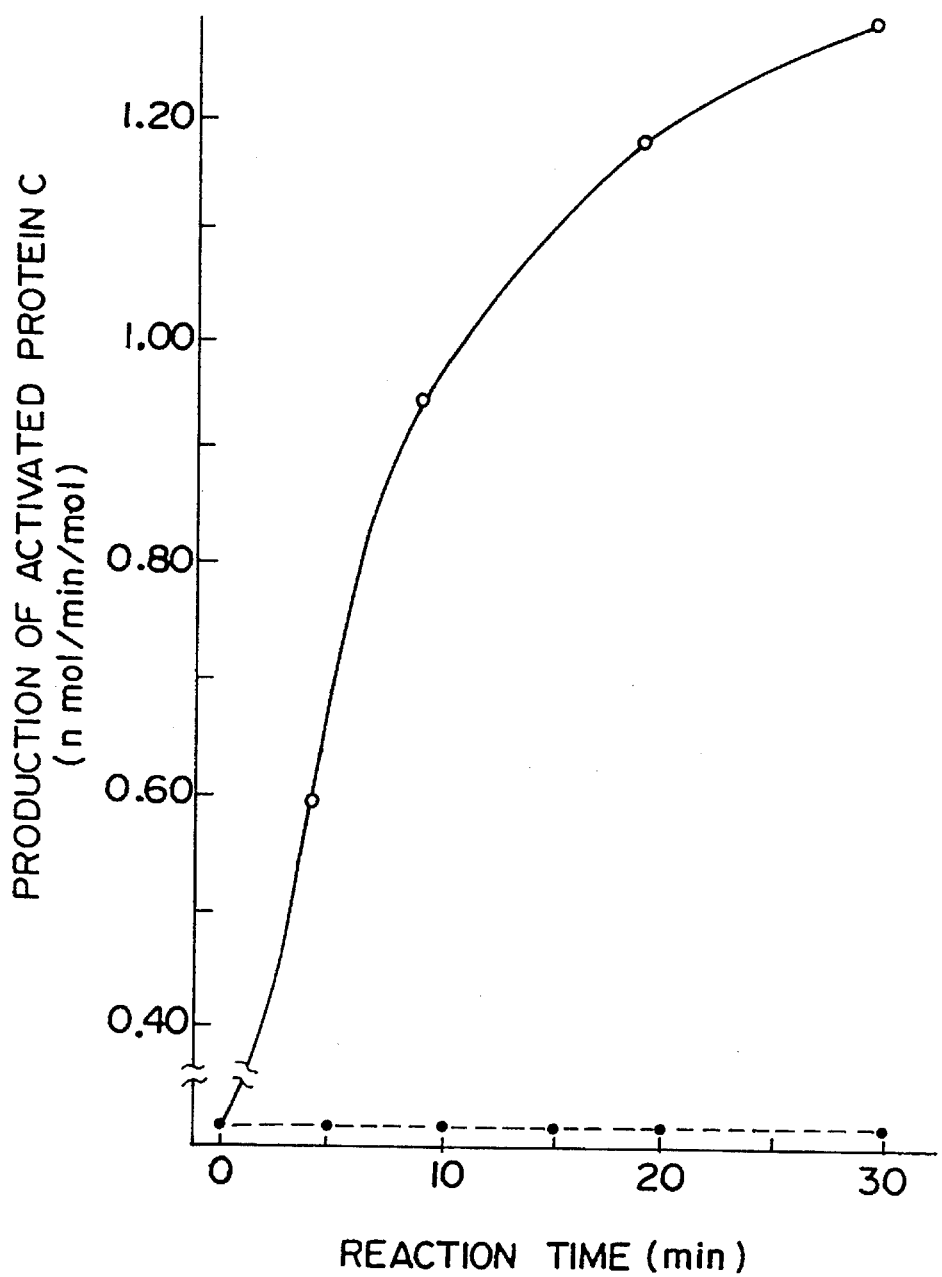

(5) Confirmation of the Activity to Promote the Thrombin-catalyzed Activation of Protein C With respect to each of polypeptides E456Asp and E456Glu purified by the above procedure, the activity to promote the thrombin-catalyzed activation of protein C is determind according to the method of Example 4-(6). The results are shown in FIGS. 44 and 45. When none of the polypeptides of the present invention is added, the formation of activated protein C is not observed (broken line). On the other hand, when any one of polypeptides E456Asp and E456Glu of present invention are added, the amount of activated protein C is increased with the lapse of reaction time (solid line).

(6) Measurement of Anticoagulating Activity

Figure 46:
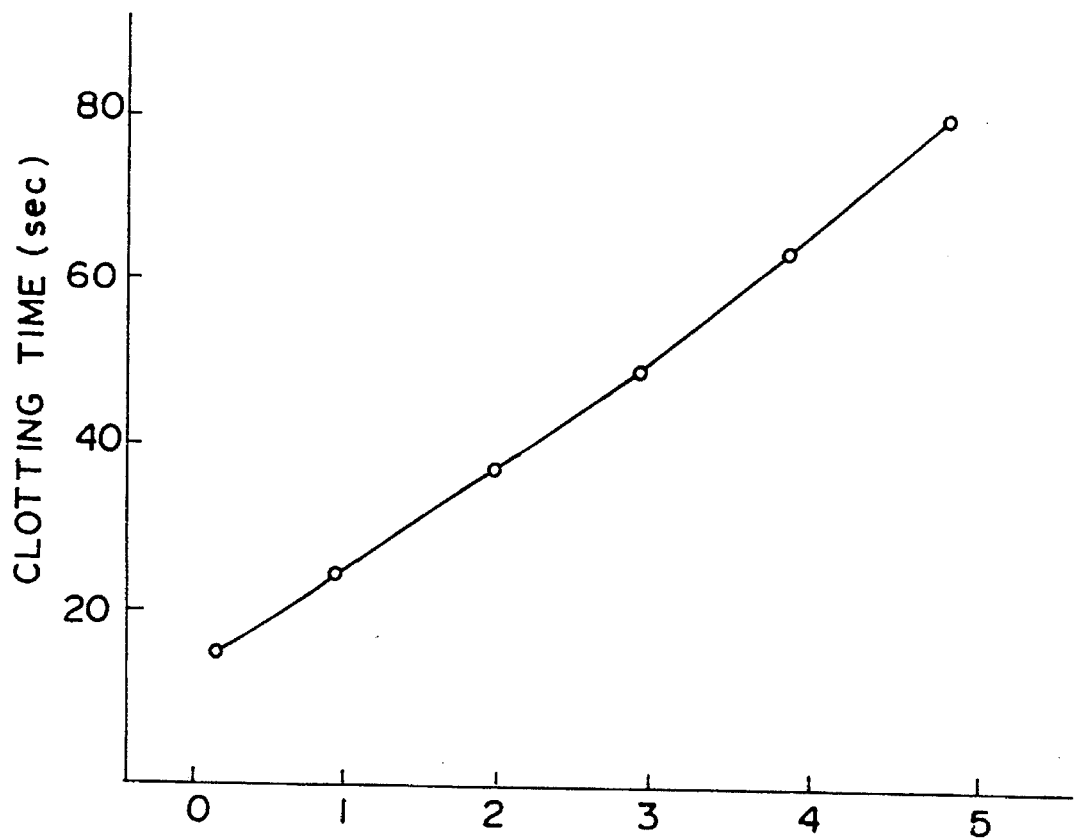
FIGS. 46 and 47 are graphs showing the relationships between the clotting time of a fibrinogen solution, to which polypeptides E456Asp and E456Glu of the present invention purified in Example 6(4) were individually added, and the amount of each of the added purified polypeptides.
Figure 47:
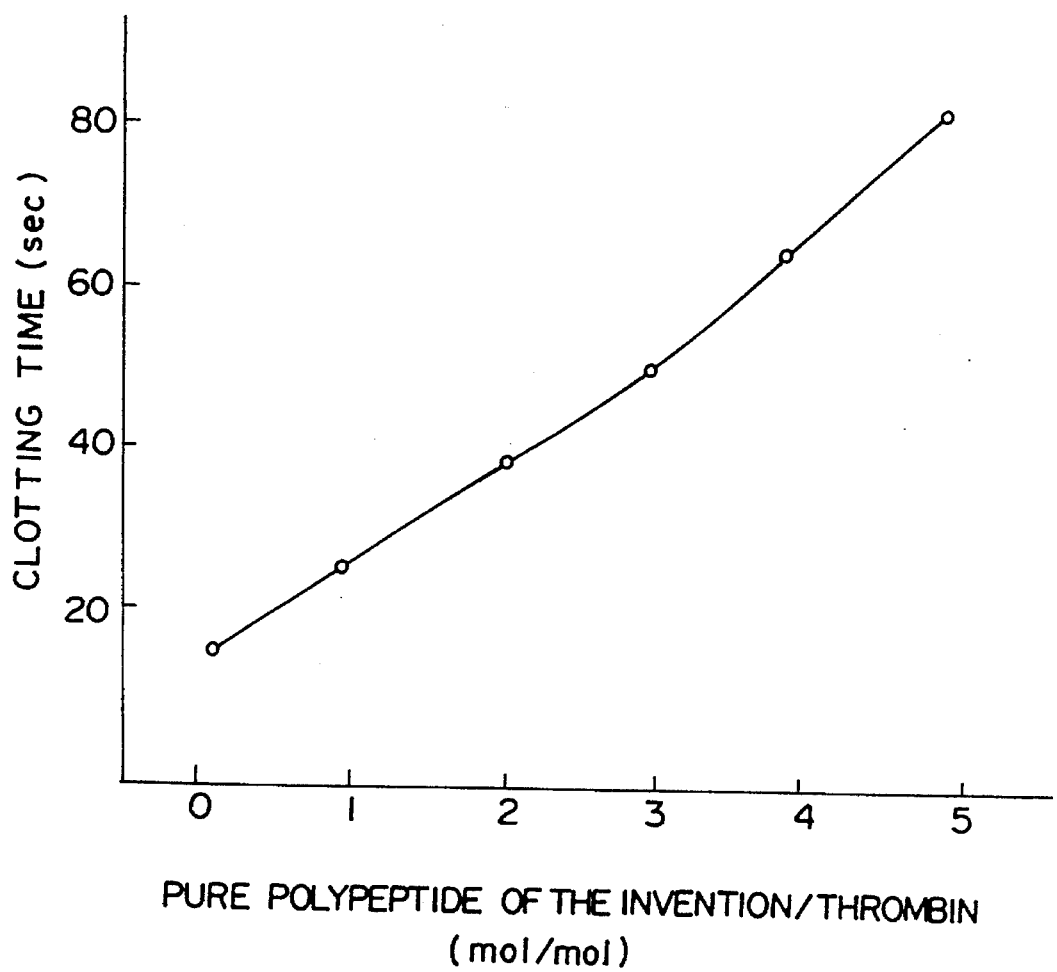

The activity of the polypeptides of the present invention to inhibit the thrombin-catalyzed conversion of fibrinogen to fibrin so as to thereby substantially inhibit blood coagulation is measured according to the method of Example 4-(7). The results for polypeptide E456Asp and polypeptide E456Glu are shown in FIGS. 46 and 47, respectively. It is confirmed that the higher the amount of the purified polypeptide added relative to the amount of thrombin, the longer the clotting time.

(7) Confirmation of Platelet Aggregation-inhibiting Activity

Figure 48:
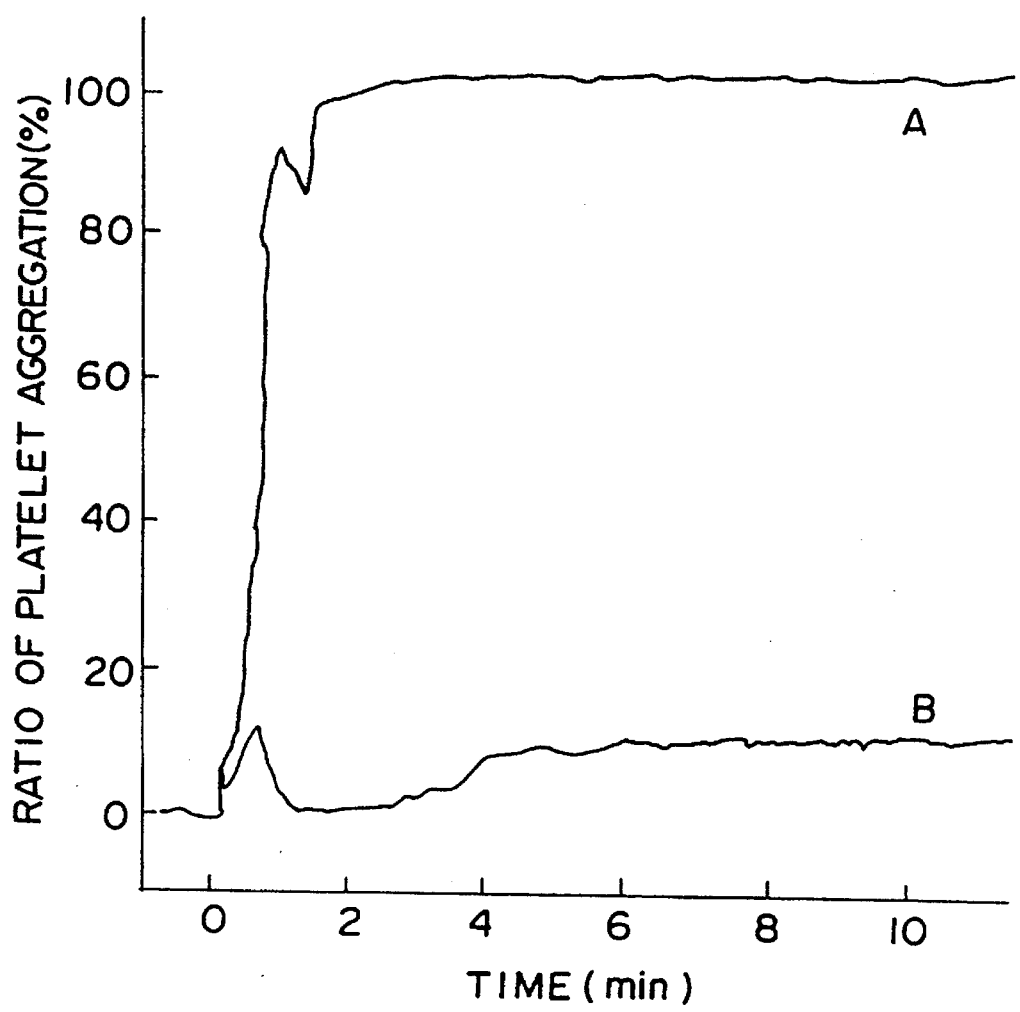
FIGS. 48 and 49 are graphs showing the relationships between the thrombin-catalyzed platelet aggregation and the time, in which a comparison is made between the presence (B) of and the absence (A) of the polypeptide of the present invention, namely, polypeptides E456Asp and E456Glu of the present invention purified in Example 6(4) for FIG. 48 and FIG. 49, respectively.
Figure 49:
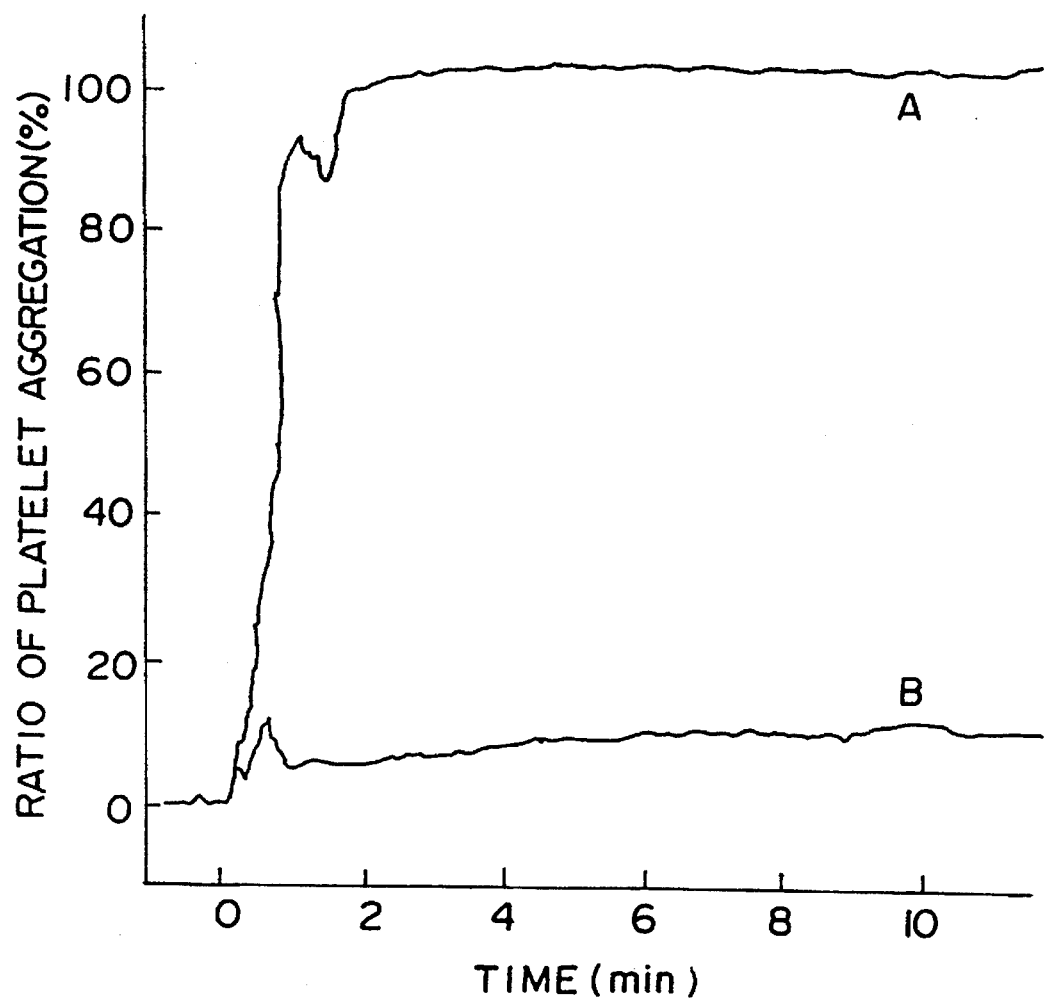

The activity of the peptides of the present invention to substantially inhibit the thrombin-catalyzed platelet aggregation is measured according to the method of Example 4-(8). The results for polypeptide E456Asp and polypeptide E456Glu are shown in FIGS. 48 and 49, respectively. It is confirmed that, when each of the polypeptides of the present invention is added, the platelet aggregation is inhibited.

TABLE 1

| Plasmid | Sample | Activity (u/ml) | Amount of polypeptide (mg/ml) | Specific activity (u/mg) |
| --- | --- | --- | --- | --- |
| pSV2TMD7 | culture | 1210 | 2.803 | 5809 |
| pSV2TMD8 | culture | 7 | 0.510 | 14 |
| Control | COS-1 cell culture | not detected | not detected | — |

TABLE 2

| Polypeptide | Inhibition constant (Ki) (μM) |
| --- | --- |
| Polypeptide A | no inhibiting activity |
| Polypeptide B | no inhibiting activity |
| Polypeptide C | 95 |

TABLE 3

| Strain | Plasmid | Specific activity (u/ml) |
| --- | --- | --- |
| D71 | pMTMD7 | 910 |
| D72 | pMTMD7 | 745 |
| D73 | pMTMD7 | 370 |
| M31 | pMTMM3 | 926 |
| M32 | pMTMM3 | 800 |
| M33 | pMTMM3 | 482 |
| Acremonium chrysogenum (ATCC11550) | — | 0 |

Example 7

Culturing of D71 Strain

D71 strain obtained in Example 6 is inoculated into each of 30 ml of MM medium and 30 ml of CM medium. Separately, D71 is inoculated into the same types of media each containing 50 μg/ml of Antipain (a protease inhibitor manufactured and sold by Sigma Chemical Company, U.S.A., catalog No. A6271). The inoculated media are subjected to culturing at 30° C. for 2 days while shaking at 220 rpm. 1 ml of each of the resultant cultures is centrifuged at 15,000 r.p.m for 5 minutes to thereby collect a supernatant. The supernatant is measured with respect to the activity of promoting the thrombin-catalyzed activation of protein C in the same manner as in Step (3) of Example 1. The results are shown in Table 4. As is apparent from Table 4, the cultures obtained by using the culture media containing Antipain exhibit activities which are as high as 3 to 4 times those of the cultures obtained by using the culture media containing no Antipain.

Example 8

Purification of Polypeptide Produced by D71 Strain (1) Culturing of D71 Strain

D71 strain obtained in Example 6 is inoculated into 100 ml of CM medium and cultured at 30° C. for 5 days while shaking at 220 rpm and then centrifuged at 5000 r.p.m for 20 minutes to thereby collect cells. The cells are inoculated into 1 liter of MM medium containing 50 μg/ml of Antipain (manufactured and sold by Sigma Chemical Company, U.S.A., catalog No. A6271) and cultured at 28° C. for 4 days. 1 liter of the supernatant of the obtained culture is filtered by means of a filter having a pore size of 0.22 μm.

(2) Purification by DIP-thrombin Column

The culture obtained in the step (1) above is absorbed onto Q Sepharose column which has been equilibrated with 20 mM phosphate buffer (pH 7.4), and then washed with 5 mM phosphate buffer (pH 7.4) containing 0.15M NaCl, followed by elution with 5 mM phosphate buffer (pH 7.4) containing 0.3M NaCl. The obtained fraction is dialyzed to effect desalting.

A DIP-thrombin (diisopropylphosphoro-thrombin), which has been prepared according to the method of N. L. Esmon et al. [J. Biol. Chem., Vol. 257, p. 859 (1982)], is bonded to an agarose which has been treated with cyanogen bromide according to the method of P. Cuatrecasas [J. Biol. Chem., Vol. 245, p. 3059 (1970)], to thereby prepare DIP-thrombin-agarose. The DIP-throm- bin-agarose is packed in a column to prepare a DIP-thrombin-agarose column (hereinafter referred to as "DIP-thrombin column"). The column is equilibrated with 20 mM phosphate buffer (pH 7.4) containing 0.2M NaCl. Then, the above-mentioned fraction is applied to the column to thereby adsorb the active fraction onto the column, and the column is washed with the same buffer as used for equilibration, followed by elution with 20 mM phosphate buffer (pH 7.4) containing 1.0M NaCl, thereby collecting active fractions. The active fractions are dialyzed to effect desalting. The dialysate thus obtained is further applied to a DIP-thrombin column which has been equilibrated with 20 mM phosphate buffer (pH 7.4) containing 0.2M NaCl, thereby adsorbing the active fractions onto the column. The column is then washed with the same buffer as used for equilibration and elution is conducted with 20 mM phosphate buffer (pH 7.4) containing 1.0M NaCl, thereby collecting purified active fractions. The purified product is measured with respect to the absorbance at 280 nm. The value of the molecular extinction coefficient for general proteins, which is $10.0(E_1{}_{cm}{}^{1\%} \cdot 280 \text{ nm}=10.0)$ is applied to the purified product. Based on this coefficient, the amount of the purified product is calculated from the absorbance for the fractions containing the purified product, and is found to be about 1 mg.

Figure 50:
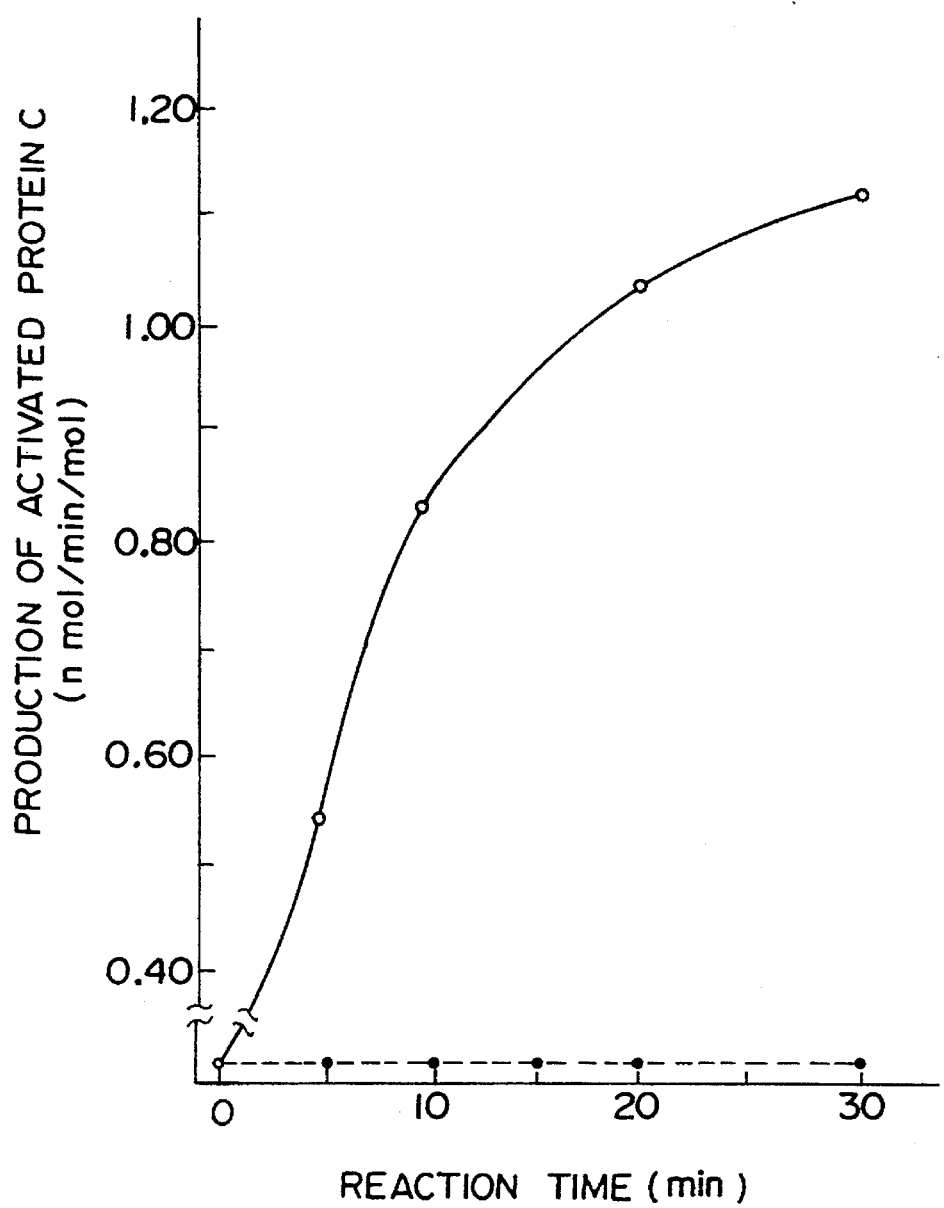
FIG. 50 is a graph showing the relationship between the amount of the activated protein C formed by the reaction of protein C with thrombin and the reaction time, in which a comparison is made between the presence (o) of and the absence (●) of polypeptide E456Asp purified in Example 8(2)

With respect to the thus obtained purified polypeptide (E456Asp), the activity of promoting the thrombin-catalyzed activation of protein C is measured in the same manner as in the step (3) of Example 1. As a result, as shown in FIG. 50, it is found that when the polypeptide of the present invention is absent, no formation of activated protein C is observed (as indicated by a broken line in FIG. 50) whereas when the polypeptide of the present invention (E456Asp) is present, the amount of protein C formed is increased with the lapse of the reaction time.

Figure 53:
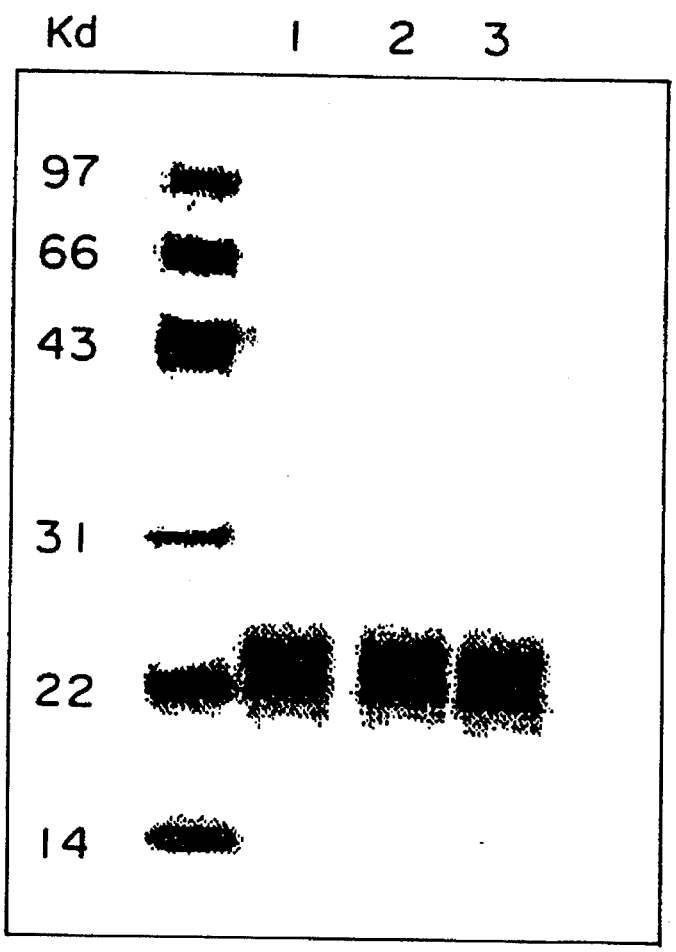
FIG. 53 is a schematic illustration of an SDS-polyacrylamide electrophoresis pattern of polypeptide E456Asp purified in Examples 8-(2), (4) and (5)

Further, the purified product is subjected to SDS-polyacrylamide gel electrophoresis using SDS-PAG plate 15/25 1010 (manufactured and sold by Daiichi Kagaku Yakuhin Co., Japan) and using a 15 to 25% gel gradient, and the gel is subjected to CBB (Coomassie Brilliant Blue) staining to observe any stained bands. As a result, as shown in FIG. 53 (lane 1) two bands are found, one at a molecular weight of 24 k and the other at a molecular weight of 22 k.

(3) Preparation of Anti-TM (Thrombomodulin) Monoclonal Antibody Column (a) Obtainment of Anti-TM Monoclonal Antibody Preparation of anti-TM monoclonal antibody is conducted in accordance with the method of Maruyama et al. [J. Biol.

Chem., 260, 15432 (1985)]. That is, a Balb/c mouse is immunized several times using, as an antigen, purified TM (thrombomodulin) prepared from placenta. Then, spleen cells are taken from the mouse and subjected to cell fusion with mouse myeloma cells of an appropriate cell line, using a cell fusion promoter, such as polyethylene glycol. Examples of mouse myeloma cells which can be used for cell fusion include P3-X63-Ag8-U1 cell (P3-U1) [see Yelton et al, Current Topics in Microbiology and Immunology, 81, 1 (1978)]. The fused cells are subjected to selection by means of an appropriate selective medium, such as HAT (hypoxanthine-aminopterin-thymidine), thereby detecting hybridoma cells. Then, the supernatant of the culture is collected, and screened with respect to an antibody against TM by ELISA (enzyme-linked immunosorbent assay) using TM as a solid phase antigen. Hybridoma cells which produce an antibody against TM are cloned by an appropriate method, such as limiting dilution. As a result, two types of anti-TM monoclonal antibodies are obtained, and designated as anti-TM monoclonal antibodies 1 and 2.

(b) Determination of Epitope of Monoclonal Antibody

The binding of anti-TM monoclonal antibodies 1 and 2 to thrombin is detected as follows. TM purified in item (b) of step (4) of Example 1 is diluted with 0.1M sodium bicarbonate buffer (pH 9.2) to a concentration of 2.5 µg/ml, and put on a flat-bottom microtiter plate for ELISA having 96 wells in an amount of 50 µl/well and allowed to stand still for 3 hours. Then, the wells are washed with 0.1M sodium bicarbonate buffer (pH 9.2), and PBS containing 1% BSA is put in the wells in an amount of 100 µl/well, followed by effecting a blocking overnight at 4° C. Subsequently, culture supernatants respectively containing anti-TM monoclonal antibodies 1 and 2 are individually put in the wells in an amount of 50 µl/well and reacted at 25° C. for 2 hours. Then, thrombin which has been diluted with PBS to a concentration of 1 µg/ml is put in the wells in an amount of 50 µl/well and reacted at 25° C. for 30 minutes, followed by washing with PBS. Then, H-D-Phe-Pip-Arg-pNA (manufactured and sold by Kabi Virum, Sweden, catalog No. S2238) which has been dissolved in PBS at a concentration of 0.3 mg/ml, is added to the wells in an amount of 100 µl/well and reacted at 37° C. for 1 hour, followed by the determination of free pNA (para-nitroaniline) at a detection wavelength of 410 nm. The results are shown in Table 5. In the case where a culture medium containing no monoclonal antibody is added, thrombin binds to E456Asp and does, in a state combined with E456Asp, decomposes S2238 to thereby form pNA. Anti-TM monoclonal antibody 1 inhibits the binding of thrombin to TM, thereby forming a reduced amount of pNA. On the other hand, anti-TM monoclonal antibody 2 does not inhibit the binding of thrombin to TM so that the formation of pNA is not reduced as in the case of no addition of an antibody. Thus, it has been found that anti-TM monoclonal antibody 1 recognizes the binding site of TM to thrombin and that anti-TM monoclonal antibody 2 recognizes a portion of TM other than the binding site thereof to thrombin.

Further, the effects of anti-TM monoclonal antibodies 1 and 2 on the activity of TM to promote the thrombin-catalyzed activation of protein C, are examined as follows. 100 µl of each of culture supernatants respectively containing anti-TM monoclonal antibodies 1 and 2 is individually mixed with 100 µl of TM (30 u/ml) purified in item (b) of step (4) of Example 1 and reacted at 4° C. for 14 hours. Then, the activity of promoting the thrombin-catalyzed activation of protein C is measured in the same manner as in step (3) of Example 1. The results are shown in Table 6. Both of anti-TM monoclonal antibodies 1 and 2 inhibit the promotion by TM of the thrombin-catalyzed activation of protein C. This shows that both of anti-TM monoclonal antibodies 1 and 2 recognizes an active site of TM which participates in the promotion of the thrombin-catalyzed activation of protein C. The active site of TM which participates in the promotion of the thrombin-catalyzed activation of protein C includes two essential sites, i.e., a binding site to protein C and a binding site to thrombin. It has thus been found that anti-TM monoclonal antibody 1 recognizes the binding site of TM to thrombin and anti-TM monoclonal antibody 2 recognizes another active site of TM, probably the binding site to protein C.

(c) Preparation of Monoclonal Antibody Column

The two types of monoclonal antibodies derived from ascites obtained by multiplying hybridoma in the abdominal cavity of a hybridoma-histocompatible animal, such as a nude mouse, are purified by a customary separation and purification technique, such as salting out, ion exchange chromatography and protein A-column chromatography. The thus purified anti-TM monoclonal antibodies are individually subjected to coupling with CNBr-activated Sepharose 4B (Pharmacia Fine Chemicals AB, Sweden, catalog No. 52-1153-00-AI) in accordance with a manual issued by Pharmacia Fine Chemicals AB (Affinity Chromatograph Principles & Methods), to thereby obtain monoclonal antibody columns. The thus obtained columns are respectively designated as anti-TM monoclonal antibody columns 1 and 2.

(4) Purification by Anti-TM-Monoclonal Antibody Column 1

Figure 51:
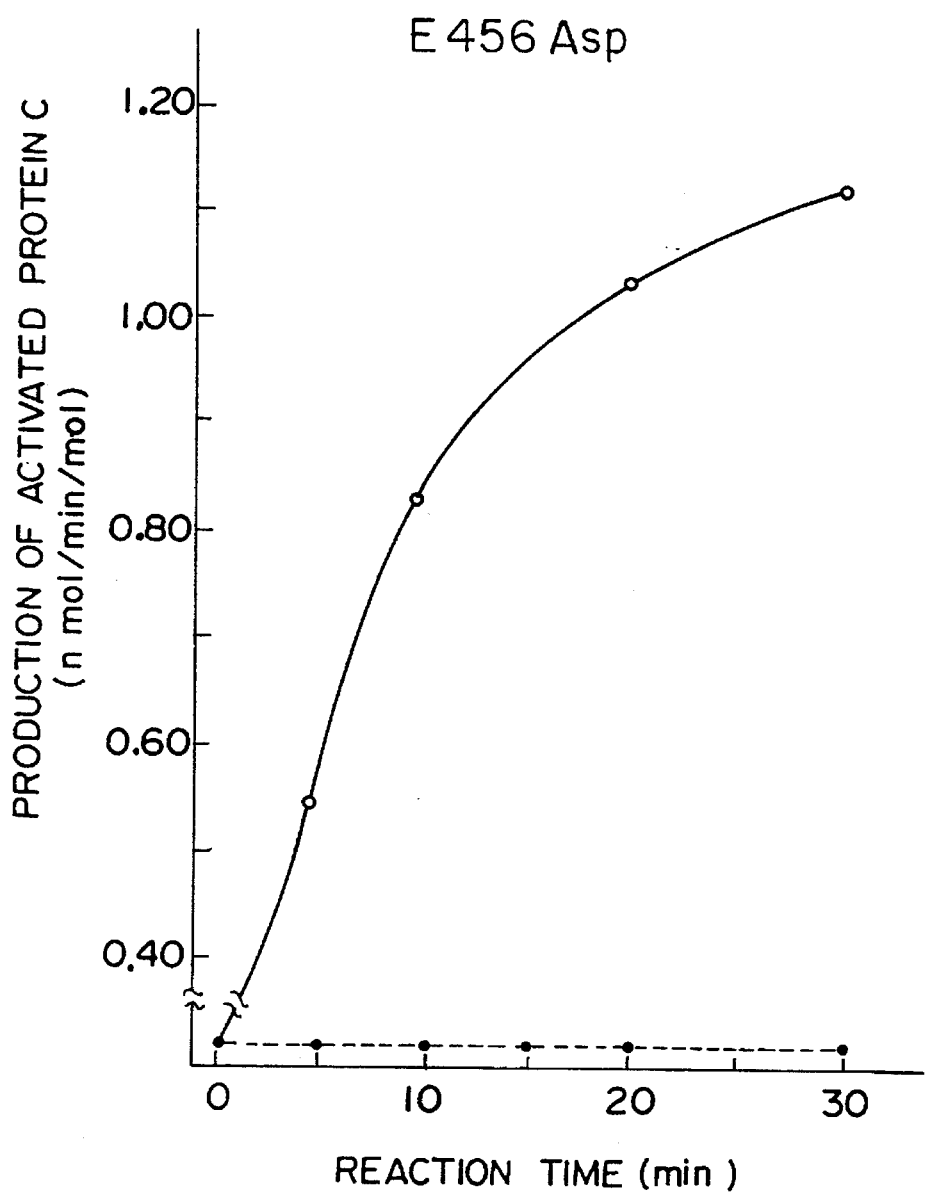
FIG. 51 is a graph showing the relationship between the amount of the activated protein C formed by the reaction of protein C with thrombin and the reaction time, in which a comparison is made between the presence (o) of and the absence (●) of polypeptide E456Asp purified in Example 8(4)

The culture obtained in Example 8-(1) is applied to a Q-sepharose column which has been equilibrated with a 20 mM phosphate buffer (pH 7.4). The column is washed with 5 mM phosphate buffer (pH 7.4) containing 0.15M NaCl, and eluted with 5 mM phosphate buffer (pH 7.4) containing 0.3M NaCl. To the eluate is added sodium chloride so that the concentration of sodium chloride becomes 0.5M. Then, the mixture is applied to anti-TM-monoclonal antibody column 1 prepared in Example 8-(3) and equilibrated with a 20 mM phosphate buffer (pH 7.4) containing 0.5M NaCl. The column is washed with the same buffer as used for the equilibration of the column, and eluted with 0.2M glycine-HCl buffer (pH 2.5) containing 0.5M NaCl. The molecular extinction coefficient for general proteins, which is 10.0 ($E_1$ $cm^{1\%}$ 0.280 nm=10.0), is assigned to the purified polypeptide of the present invention. Based on this coefficient, the amount of the polypeptide is calculated from the absorbance thereof and is found to be about 1 mg. The activity of polypeptide E456Asp purified by the above procedure to promote the thrombin-catalyzed activation of protein C is measured according to the method described in Example 1-(3). As shown in FIG. 51, when polypeptide E456Asp of the present invention is not added, no formation of activated protein C is observed (broken line). On the other hand, when the polypeptide E456Asp of the present invention is added, the amount of activated protein C is increased with the lapse of reaction time (solid line).

Further, the purified polypeptide is subjected to SDS-polyacrylamide gel electrophoresis using a 15 to 25% acrylamide concentration gradient (manufactured and sold by Daiichi Pure Chemicals Co., Ltd., SDS-PAG plate 15/25 1010), and CBB (coomassie brilliant blue) staining is performed. Two bands respectively corresponding to a molecular weight of 24 k and a molecular weight of 22 k are observed, as shown in FIG. 53 (lane 2).-

(5) Purification by Anti-TM-Monoclonal Antibody Column 2

Figure 52:
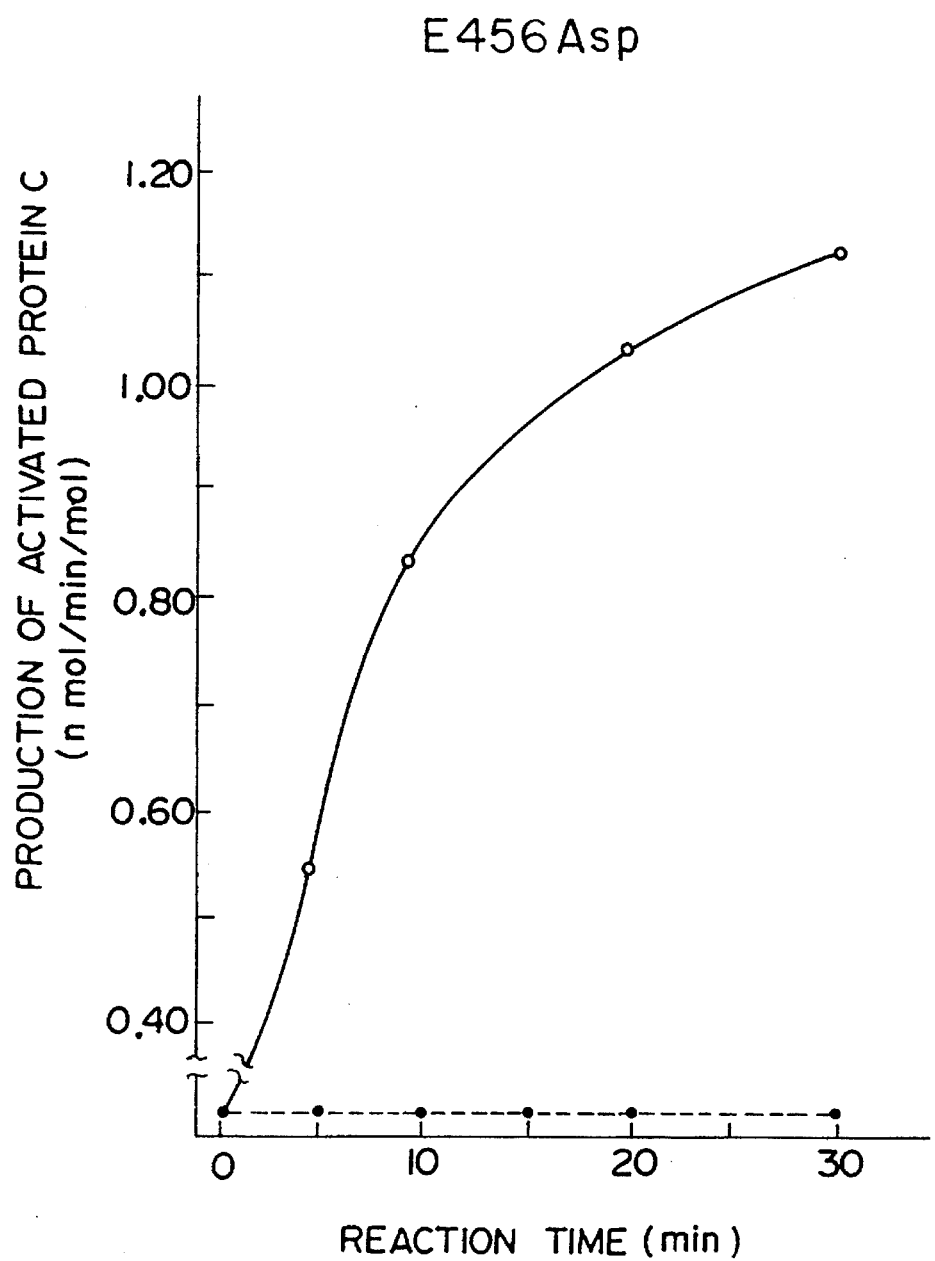
FIG. 52 is a graph showing the relationship between the amount of the activated protein C formed by the reaction of protein C and formed by the reaction of protein C with thrombin and the reaction time, in which a comparison is made between the presence (o) of and the absence (●) of polypeptide E456Asp purified in Example 8(5)

The culture obtained in Example 8-(1) is applied to a Q-sepharose column which has been equilibrated with a 20 mM phosphate buffer (pH 7.4). The column is washed with 5 mM phosphate buffer (pH 7.4) containing 0.15M NaCl, and eluted with 5 mM phosphate buffer (pH 7.4) containing 0.3M NaCl. To the eluate is added sodium chloride so that the concentration of sodium chloride becomes 0.5M. Then, the mixture is applied to anti-TM-monoclonal antibody column 2 prepared in Example 8-(3) and equilibrated with a 20 mM phosphate buffer (pH 7.4) containing 0.5M NaCl. The column is washed with the same buffer as used for the equilibration of the column, and eluted with 0.1M acetic acid buffer (pH 4.0) containing 0.5M NaCl. Thereafter, the eluate is desalted by dialysis. The molecular extinction coefficient for general proteins, which is 10.0 ($E_{1\ cm}^{1\%}$ 0.280 nm=10.0), is assigned to the purified polypeptide of the present invention. Based on this coefficient, the amount of the polypeptide is calculated from the absorbance thereof, and is found to be about 1 mg. The activity of polypeptide E456Asp purified by the above procedure to promote the thrombin-catalyzed activation of protein C is measured according to the method described in Example 1-(3). As shown in FIG. 52, when polypeptide E456Asp of the present invention is not added, no formation of activated protein C is observed (broken line). On the other hand, when the polypeptide E456Asp of the present invention is added, the amount of activated protein C is increased with lapse of reaction time (solid line).

Further, the purified polypeptide is subjected to SDS-polyacrylamide gel electrophoresis using a 15 to 25% acrylamide concentration gradient (manufactured and sold by Daiichi Pure Chemicals Co., Ltd., SDS-PAG plate 15/25 1010), and CBB (coomassie brilliant blue) staining is performed. Two bands respectively corresponding to a molecular weight of 24 k and a molecular weight of 22K are observed, as shown in FIG. 53 (lane 3).

(6) Confirmation of N-terminal Amino Acid Sequence

With respect to each of purified E456Asp polypeptide obtained in Example 8-(2), -(4) and -(5), 2 µg is dialyzed against water to prepare a sample for amino acid-sequence analysis. Next, using an amino acid sequencer (manufactured and sold by Applied Biosystems Inc., U.S.A., Model 470A), Edman degradation is successively performed from the N-terminus according to the method of R. M. Hewick et al. [J. Biol. Chem., 256., 7990 (1981)]. Liberated phenylthiohydantoin amino acid is analyzed using HPLC (manufactured and sold by Spectra Physics, U.S.A., SP 8100) and Zorvax ODS Column (manufactured by E.I. du Pont de Nemours and Company, U.S.A.), and an N-terminal amino acid sequence is determined. As a result, it is found that all of the polypeptides have the following amino acid sequence:

Asp-pro-X-Phe-Arg-Ala-Asn-X-Glu-Tyr-Gln-X-Gln-Pro-Leu-X-Gln-Thr-Ser-Tyr (X is an unidentified amino acid residue) (SEQ. ID No. 52).

EXAMPLE 9

(1) Construction of Plasmid pSV2TMD9

Recombinant plasmid M13TMD7 obtained in Example 1-(1)-(b) is subjected to a deletion of 114 nucleotides according to the technique of site-directed mutagenesis in substantially the same manner as in Example 1-(1)-(a) except that deleter TMd9 having the following nucleotide sequence (SEQ. ID No. 56):

5'-CGGAGGCCGCTCAGATGTCCGTGCA-3' (25 mer) which hybridizes to a portion of the plasmid M13TMD7 having the following partial sequence (SEQ. ID No. 57) as shown in FIG. 54 and which codes for the partial amino acid sequence (SEQ. ID No. 58) also shown in FIG. 54:

TTC ATC TGC ACG GAC ATC TGAGCGGCCT CCGTCCAG is used instead of the deleter TMd3, to thereby obtain recombinant plasmid M13TMD9 having inserted therein a DNA fragment designated as TMD9. This DNA fragment TMD9 has a nucleotide sequence comprising initiation codon ATG and, downstream thereof, a nucleotide sequence coding for a peptide comprised of amino acid residues up to the 18th position counted from the amino acid residue corresponding to the initiation codon and the 367th to the 442nd amino acid residues of the sequence of FIG. 55 (SEQ. ID No. 59). In FIG. 54, there is illustrated the recombinant plasmid M13TMD7 with which the deleter TMd9 is hybridized, and of which the DNA region corresponding to the DNA fragment TMD7 is partly deleted. Further, the recombinant plasmid M13TMD9 is completely digested with restriction enzymes HindIII and BamHI to obtain a vector. This vector and the above-mentioned DNA fragment of 580 bp are ligated to each other using T4 DNA ligase to obtain plasmid pSV2TMD9.

(2) Transfection of pSV2TMD1, pSV2TMD7 and pSV2TMD9 into Cell Line COS-1

Transfection of pSV2TMD1 constructed in Example 1-(4)-(a), pSV2TMD7 constructed in Example 1-(1)-(b) and pSV2TMD9 constructed in Example 9-(1) into COS-1 cells is conducted according to the method of Example 1-(2). Electropolation is conducted 30 times for each of the plasmids, thereby obtaining about 300 ml of a culture.

(3) Purification and Quantitative Determination of Polypeptides 300 ml of the culture obtained in Example 9-(2) is purified according to the method of Example 3-(3). Quantitative analysis by means of sandwich ELISA using rabbit anti-human thrombomodulin antibody prepared in Example 1-4-(c) and anti-human monoclonal antibody 1 prepared in Example 8-(3), shows production of 30 µg of purified polypeptide. The polypeptide purified from the culture of COS-1 cells obtained by transfection of pSV2TMD1 is designated as D123Asp; the polypeptide purified from the culture of COS-1 cells obtained by transfection of pSV2TMD7 is designated as E456Asp; and the polypeptide purified from the culture of COS-1 cells obtained by transfection of pSV2TMD9 is designated as E45.

(4) Measurement of the Activity to Promote the Thrombin-catalyzed Activation of Protein C With respect to the polypeptide purified in Example 9-(3), the activity to promote the activation of protein C is measured according to the following method. That is, 10 µl of a peptide solution (10 nM), 10 µl of thrombin (15 nM), 10 µl of protein C (3.2 µM), 10 µl of 10×Assay buffer [0.5M Tris HCl (pH 7.5) containing 1% BSA, 1M NaCl and 20 mM CaCl$_2$] and 60 µl of distilled water are mixed together. The mixture is reacted at 37° C. for one hour, and antithrombin III and hepalin are added at final concentrations of 100 nM and 1u/ml, respectively, thereby stopping the reaction. To measure the concentration of activated protein C, the concentration of AMC (7-amino-7-methyl-coumarin) liberated from a 200 µM substrate of Boc-Leu-Ser-Thr-Arg-MCA in a buffer containing 0.05M Tris HCl (pH 8.0) and 0.1M CsCl is measured at an excitation wavelength of 380 nm and a measuring wavelength of 440 nm. The results are shown in Table 7.

TABLE 4

| Strain | Medium | Antipain | Activity (u/ml) |
|---|---|---|---|
| D71 | MM | absent | 1000 |
| D71 | CM | absent | 900 |
| D71 | MM | present | 4000 |
| D71 | CM | present | 3500 |

TABLE 5

| Monoclonal antibody | A410 absorbancy |
|---|---|
| 1 | 0.156 |
| 2 | 0.742 |
| absent (medium only) | 0.757 |

TABLE 6

| Monoclonal antibody | Activity (u/ml) |
|---|---|
| 1 | 0 |
| 2 | 0 |
| absent (medium only) | 15.5 |

TABLE 7

| peptide | production of activated protein C (pmol) |
|---|---|
| D123Asp | 18.6 |
| E456Asp | 18.3 |
| E45 | 1.7 |

REFERENCE EXAMPLES

The abbreviations employed in Reference Examples are as follows:

Maniatis Laboratory Manual: T. Maniatis et al., Molecular Cloning A Laboratory Manual published by Cold Spring Harbor Laboratory, 1982

N-3 seed medium: medium comprised of 40 g of corn steep liquor, 20 g of beet, 2 g of ammonium acetate and 40 g of hydrochloric acid hydrolysate of starch, dissolved in 1 liter of water main medium: medium comprised of 30 g of beet, 40 g of defatted soybean, 10 g of corn steep liquor, 5 g of ammonium acetate, 7 g of ammonium sulfate, 8 g of calcium sulfate, 15 g of calcium carbonate, 60 g of hydrochloric acid hydrolysate of starch and 41,5 g of methyl oleate, contained in 1 liter of water CMG medium: medium comprised of 20 g of glucose, 0.5 g of potassium dihydrogen phosphate, 0.5 g of dipotassium hydrogen phosphate, 0.5 g of potassium chloride, 0,5 g of magnesium sulfate (heptahydrate), 0.01 g of iron (II) sulfate (heptahydrate), 3 g of sodium nitrate, 4 g of yeast extract and 10 g of peptone, dissolved in 1 liter of water CM medium: medium comprised of 20 g of sucrose, 0.5 g of potassium dihydrogen phosphate, 0.5 g of dipotassium hydrogen phosphate, 0.5 g of potassium chloride, 0.5 g of magnesium sulfate (heptahydrate), 0.01 g of iron (II) sulfate (heptahydrate), 3 g of sodium nitrate, 4 g of yeast extract and 10 g of peptone, dissolved in 1 liter of water CM solid medium: CM medium containing 1.5% of agar GAG medium: medium comprised of 40 g of glycerol, 4 g of asparagine, 0.1 g of calcium chloride, 0.1 g of sodium chloride, 25 ml of solution containing minute amounts of metals [4 g of magnesium sulfate (heptahydrate), 0.4 g of iron (II) sulfate (heptahydrate), 0.16 g of manganese sulfate (tetrahydrate), 0.4 g of zinc sulfate (heptahydrate) and 0.04 g of anhydrous copper sulfate, dissolved in 1 liter of water] and 30 ml of 0.1M phosphate buffer (pH 7.0), contained in water P-buffer: buffer containing 0.6M potassium chloride, 0.01M magnesium chloride, and 0.025M calcium chloride PEG solution: solution containing 25% polyethylene glycol (molecular weight: about 4000), 0.01M Tris HCl (pH 8.0), 0.05M calcium chloride and 0.6M potassium chloride.

REFERENCE EXAMPLE 1

Reference Example 1-(1)

Construction of pPGACY2

Figure 56:
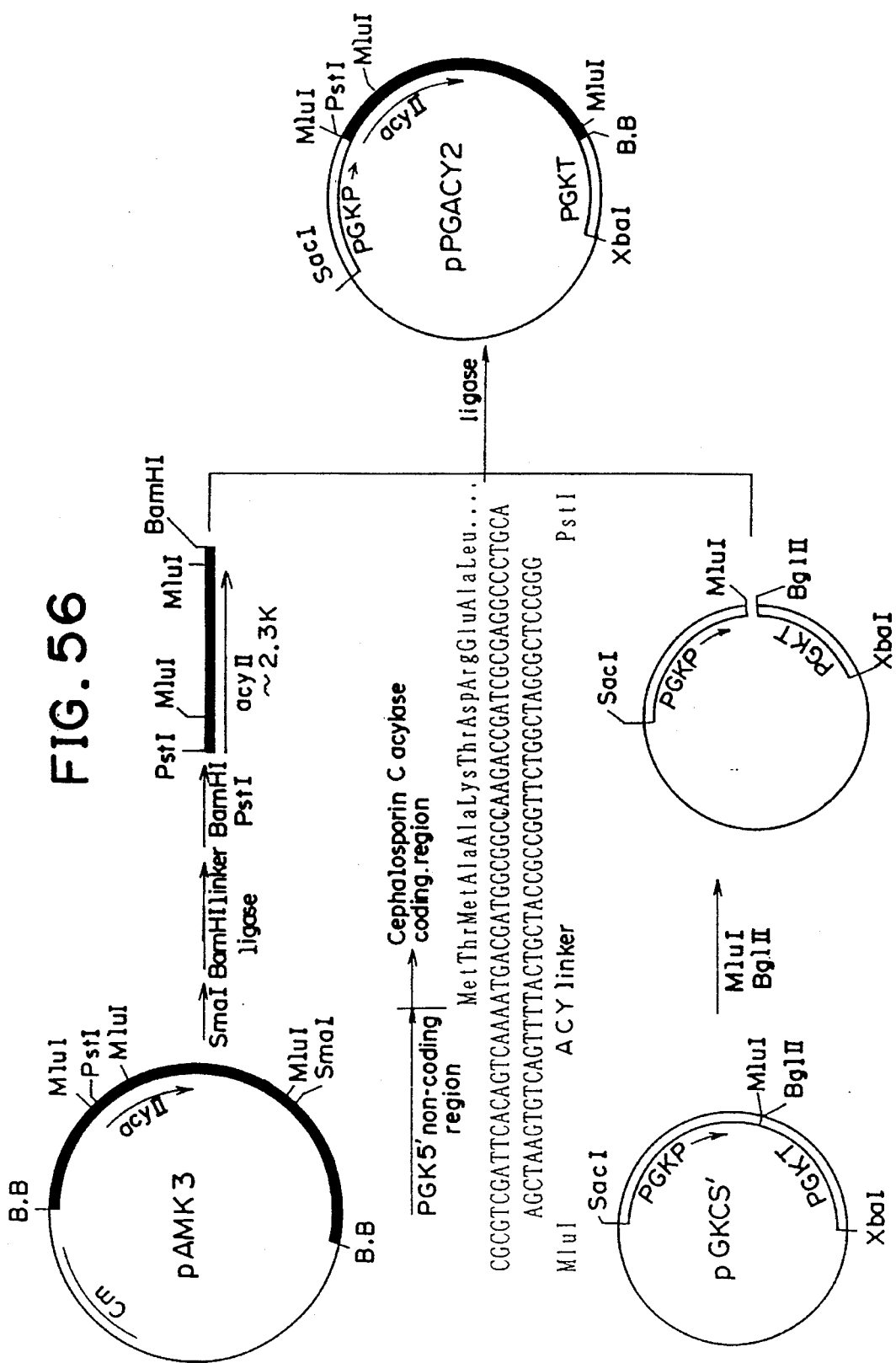
FIG. 56 shows a flow chart illustrating the construction of plasmid pPGACY2.

According to the procedure shown in FIG. 56, plasmid pPGACY2 for expressing cephalosporin C acylase gene derived from strain SE-83 (deposited at Fermentation Research Institute, Japan under accession number 7649) under the control of PGK promoter derived from *Acremonium chrysogenum*, is constructed. Each of the steps of the procedure is described below in detail.

(i) Preparation of ACY Linker

In order for the initiation codon of cephalosporin C acylase gene to correctly coincide with the site of the initiation codon of *Acremonium chrysogenum* PGK gene of, ACY linker having a nucleotide sequence shown in FIG. 56 is prepared as follows.

First, according to the conventional method, there are synthesized four types of oligonucleotides having the following sequences:

1) CGCGTCGATTCACAGTCAAAATGACGAT (SEQ. ID No. 60)

2) GGCGGCCAAGACCGATCGCGAGGCCCTGCA (SEQ. ID No. 61)

3) GCCGCCATCGTCATTTTGACTGTGAATCGA (SEQ. ID No. 62) and

4) GGGCCTCGCGATCGGTCTTG, (SEQ. ID No. 63) using an automatic DNA synthesizer (manufactured and sold by Applied Biosystems Inc., U.S.A., DNA Synthesizer Model 380-A).

Next, the 5'-terminal of each of the above-mentioned oligonucleotides 2) and 3) is phosphorylated with T4 polynucleotide kinase, and mixed with oligonucleotides 1) and 4) for annealing, followed by ligation with T4 DNA ligase, thereby obtaining ACY linker (SEQ. ID No. 65), which codes for the partial amino acid sequence shown in FIG. 56 (SEQ. ID No. 65).

(ii) Preparation of pPGACY2

First, pAMK3 is digested with SmaI to thereby render it linear. BamHI linker is linked to the linearized pAMK3 with T4 DNA ligase, and digested simultaneously with PstI and BamHI to obtain a purified PstI-BamHI fragment (2.3 kb) containing cephalosporin C acylase gene derived from SE-83 strain which lacks a part of the N-terminal coding region. On the other hand, pGKCS' is digested with MluI and BglII, and a DNA fragment of about 4.8 kb is isolated and purified.

Next, these two types of fragments and the ACY linker obtained in step (i) above are ligated with T4 DNA ligase, thereby obtaining pPGACY2. The construction method of plasmid pAMK3 used in this Reference Example 1 as the supply source of cephalosporin C acylase derived from SE-83 is described in Japanese Patent Application Laid-Open Specification No. 61-152286 and literature of Matsuda et al. [Journal of Bacteriology (1987) 169, 5815–5820]. Plasmid pGKCS' used as the supply source of the PGK promoter and PGK terminator derived from *Acremonium chrysogenum* has a structure wherein fragments containing the PGK promoter and the PGK terminator derived from *Acremonium chrysogenum* are ligated through a unique restriction enzyme site in an arrangement suitable for expression, and the construction method thereof is described in Reference Example 2-(2) given later.

In Reference Example 1-(1), isolation of a DNA fragment produced by digestion with a restriction enzyme is conducted by 1% agarose gel electrophoresis. Isolation of the DNA fragment from the agarose gel and purification of the isolated DNA fragment are carried out with GENE CLEAN™ (manufactured and sold by Funakoshi Pharmaceutical Co., Ltd., Japan) according to the protocol attached thereto. Further, basic operations, including ligation reaction of DNA fragments, transformation of *E. coli* using the plasmid produced from the above reaction, and preparation and analysis of the plasmid from the obtained transformant, are all carried out according to the method described in Maniatis Laboratory Manual.

REFERENCE EXAMPLE 1-(2)

Transformation of *Acremonium Chrysogenum* with pPGACY2

By simultaneous transfection with pPGACY2 and pACTHY83, a transformant of *Acremonium chrysogenum* (new *Acremonium chrysogenum* having the activity to produce cephalosporin C acylase) is obtained. That is, pACTHY83 employed in Reference Example 1-(2) is a transformation vector for *Acremonium chrysogenum* having a hygromycin B phosphotransferase expression unit (an expression unit in which the promoter and terminator of an actin gene derived from *Acremonium chrysogenum* and a hygromycin B phosphotransferase gene derived from bacteria are ligated in an arrangement suitable for expression), which can function in *Acremonium chrysogenum*. The construction method thereof is described in Reference Example 2.

(i) Preparation of Protoplast

Mycelium of *Acremonium chrysogenum* IS-5 cultured on CM solid medium at 30° C. for five days is innoculated onto 50 ml of CM medium, and then incubated on a rotary stirrer (250 rpm) at 30° C. for three days. 1 ml of the resultant cell suspension is innoculated onto 50 ml of GAG medium, and incubated at 30° C. for 20 hours. 50 ml of the thus obtained culture is subjected to centrifugation at 3500 rpm for 10 min to precipitate the mycelium. The precipitated mycelium is washed with 0.9% NaCl solution, and suspended in 20 ml of Mcilvaene buffer (containing 0.1M citric-acid and 0.2M sodium phosphate, pH 7.3) containing 0.01M dithiothreitol, followed by gentle shaking at 30° C. for one hour. Subsequently, the mycelium is precipitated by centrifugation at 3200 rpm for 10 min. The precipitate is washed with P-buffer, and suspended in 10 ml of P-buffer containing Novozyme (manufactured and sold by Novo Industry, Denmark) at a concentration of 10 mg/ml, followed by gentle shaking at 30° C. for one hour. The resultant mixture is subjected to centrifugation at 800 rpm for 30 sec, and the obtained supernatant is filtered through a filter papter (Toyo Filter Papter 5A), to thereby separate a protoplast from the mycelium. Then, the filtrate is centrifuged at 3000 rpm for five minutes to precipitate the protoplast, and the precipitate is washed with P-buffer once and suspended in P-buffer at a protoplast concentration of $3 \times 10^8$ cells/ml.

(ii) Transformation of Protoplast with pPGACY2 and pACTHY83

To 0.1 ml of the protoplast suspension obtained in Reference Example 1-(1) are added 10 μl of a solution containing 5 μg of pPGACY2 and 5 μg of pACTHY83 and then 0.05 ml of PEG solution, followed by gentle stirring. The resultant mixture is allowed to stand on ice for 25 min, and 1 ml of the same PEG solution as used above is added. The resultant mixture is allowed to stand at room temperature for 30 min. The thus obtained transformant protoplast suspension is portionwise spread on a plate containing 25 ml of protoplast regeneration medium (which is BRM medium described in Isogai et al., Argic. Biol. Chem. 1987, 51, 2321–2329) in an amount of 0.2 ml, followed by incubation at 15° C. for 20 hours. Next, 5 ml of BRM medium containing 4.5 mg of hygromycin B and kept at 50° C. is superposed on the above plate, followed by incubation at 28° C. for 14 days. As a result, 70 strains of transformants which have been rendered resistant to hygromycin B (hereinafter referred to simply as "HYB transformants") appear.

REFERENCE EXAMPLE 1-(3)

Figure 57:
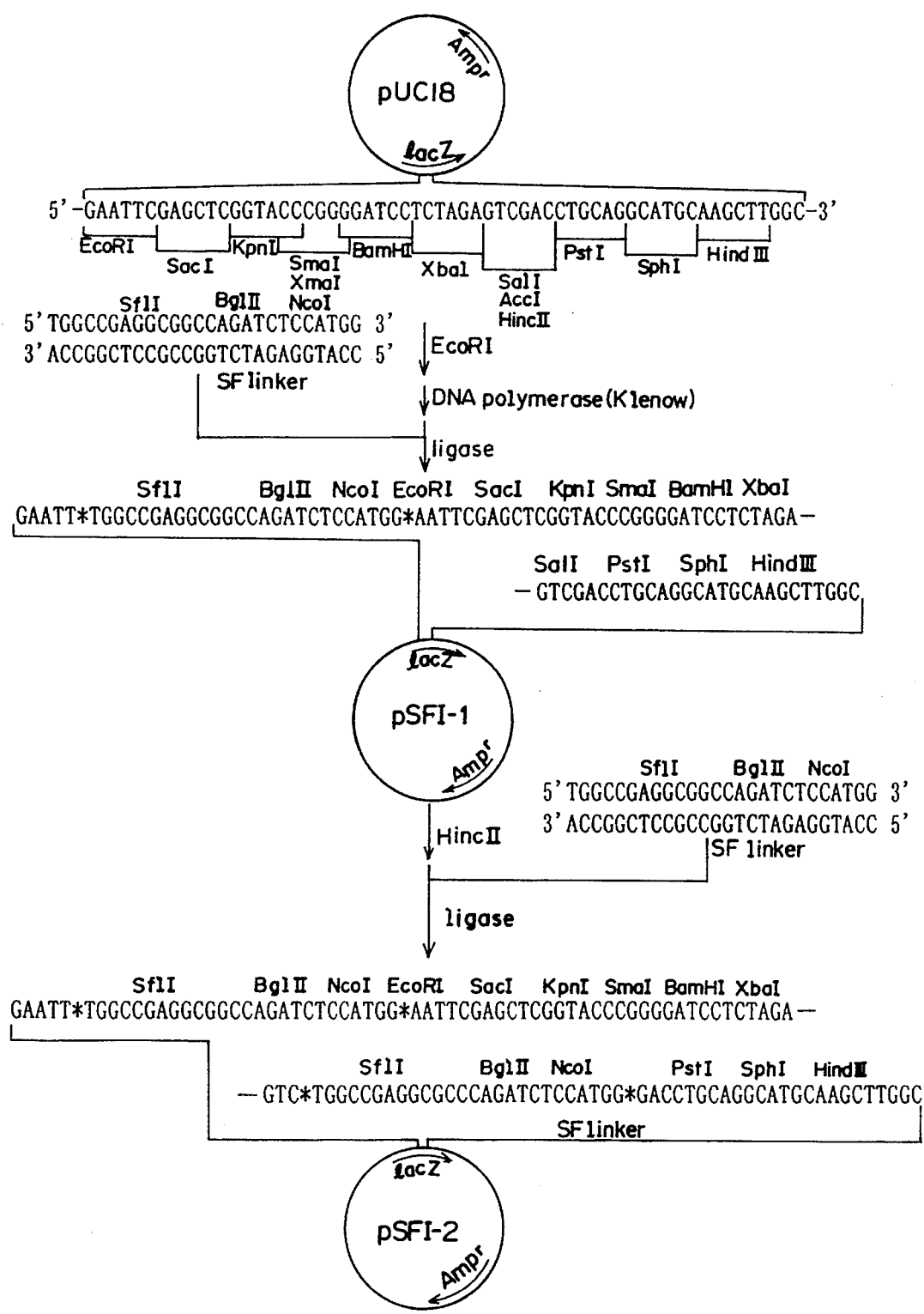
FIG. 57 shows a flow chart illustrating the construction of plasmids pSFI-I and pSFI-2.
Figure 58:
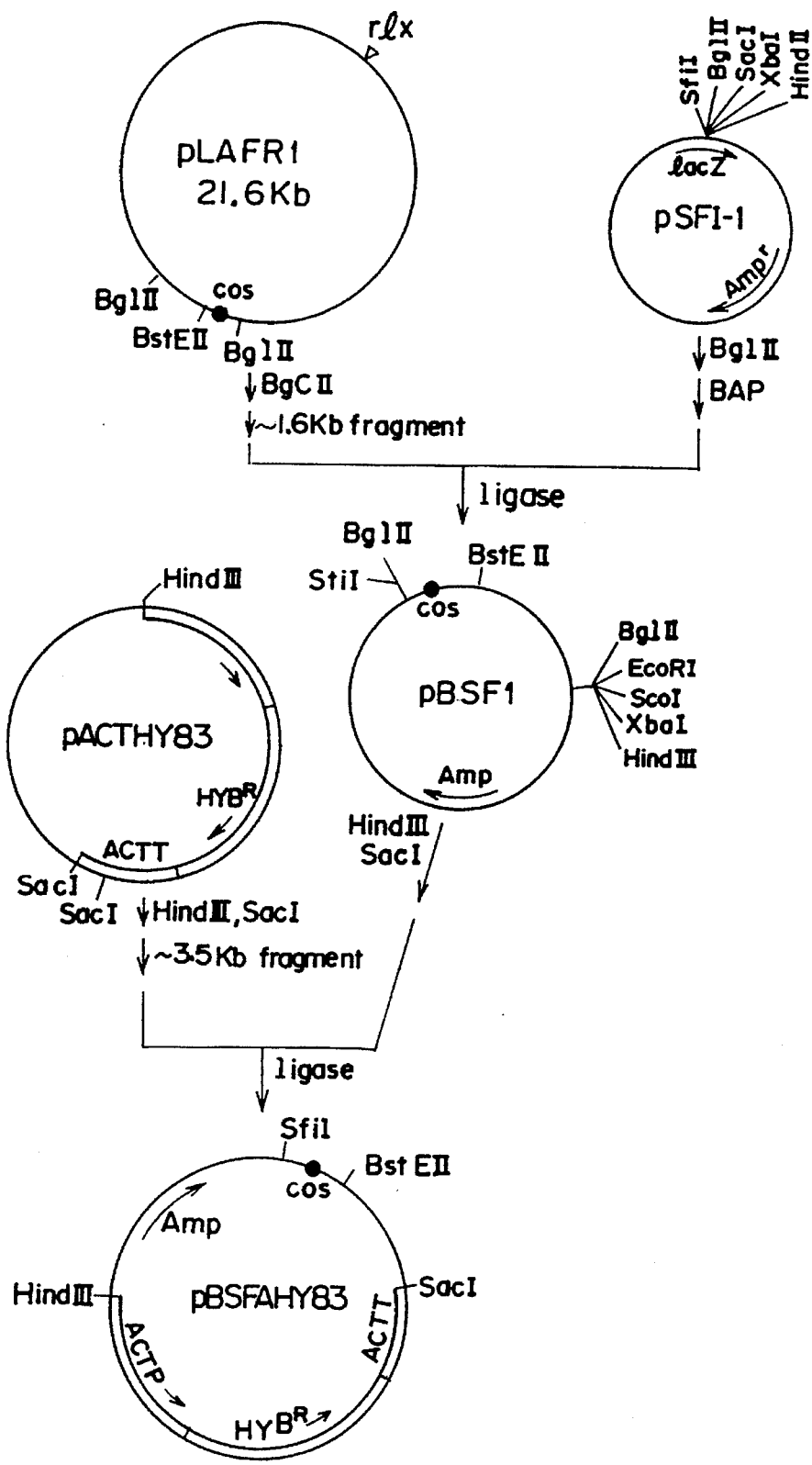
FIG. 58 shows a flow chart illustrating the construction of plasmids pBSFAHY83 in which *Acremonium chrysogenum* has been introduced.

According to the procedure shown in FIGS. 57 and 58, pBSFAHY83 is constructed. Each of the steps of the procedure will be described below.

(i) Construction of pSFI-2 (FIG. 57)

First, pUC18 (manufactured and sold by Takara Shuzo Co., Ltd., Japan) is digested with ECoRI (SEQ. ID No. 66), and the produced cohesive end is converted to blunt end with a DNA polymerase (Klenow fragment) and four types of deoxynucleotide triphosphate. Next, the above fragment is ligated using T4 DNA ligase to an SF linker (synthesized as two single stranded DNAs according to the conventional method using a DNA synthesizer) having the following sequence (SEQ. ID No. 67):

5'TGGCCGAGGCGGCCAGATCTCCATGG3'

3'ACCGGCTCCGCCGGTCTAGAGGTACC5', thereby obtaining pSFI-1.

The nucleotide sequence of a multiple cloning site of pSFI-1 is determined according to the conventional method, and it is confirmed that the sequence of the above-mentioned SF linker and the insertion orientaion of the linker in pSFI-1 are as shown in FIG. 57 (SEQ. ID No. 61). Into HincII site of the thus obtained pSFI-1 is inserted the above-mentioned SF linker (SEQ. ID No. 67) in the orientation shown in FIG. 57, thereby obtaining pSFI-2 (SEQ. ID No. 69). The confirmation of the insertion orientation is carried out in the same manner as in the case of pSFI-1. As shown in FIG. 57, pSFI-2 has a structure having a large number of cloning sites between SfiI sites, and hence pSFI-2 is a vector suitable for preparation of a fragment which can be ligated only in a single orientation.

(ii) Construction of pBSFAHY83 (FIG. 58)

pLAFR1 (ATCC No. 37167) which is a cosmid vector for a broad spectrum of Gram-negative bacterium hosts is digested with BglII, followed by separation and purification of a fragment of 1.6 kb having COS site. This fragment is ligated to pSFI-1, which has been digested with BglII and subjected to alkaline phosphatase treatment (see step (i) above), with T4 DNA ligase, thereby obtaining pBSF1. Subsequently, pACTHY83 is digested with HindIII and SacI, followed by separation and purification of an HYB expression unit fragment of 3.5 kb (see Reference Example 1-(2)]. The resultant fragment is inserted in pBSF1 at a site between HindIII and SacI, to thereby obtain pBSFAHY83.

The thus obtained pBSFAHY83 is a cosmid vector which is suitable for cloning SfiI fragments prepared using the above pSFI-2 in a state such that a large number of SfiI fragments are ligated in the same orientation and for introducing the ligated fragment into *Acremonium chrysogenum*. The construction method of pPGKM5 employed in the present step is illustrated in Reference Example 2. In the above step, basic operations, including separation and purification of a DNA fragment produced by digestion with a restriction enzyme, ligation reaction between DNA fragments, transformation of *E. coli* with a plasmid produced by the reaction, and construction of a plasmid from the obtained transformant and analysis of the purified plasmid, are carried out in accordance with the methods described in Reference Example 1-(1) and Maniatis Laboratory Manual.

REFERENCE EXAMPLE 2-(1)

[Isolation of *Acremonium chrysogenum* Phosphoglycerate Kinase (PGK) Gene]

(i) Preparation of Gene Library of *Acremonium chrysogenum*

The total DNA of *Acremonium chrysogenum* IS-5 strain (deposited at Fermentation Research Institute, Japan under the accession number FERM BP-11232) is extracted according to the method employed by Johnstone et al with respect to *Aspergillus nidulans* (see I. L. Johnstone et al, EMBO J., 4, 1307–1311, 1985). About 60 μg of the total DNA is partially digested with restriction enzyme MboI, and then treated with alkaline phosphatase. On the other hand, 10 μg of λ-vector EMBL3 (manufactured and sold by Promega Co., USA) is completely digested with BamHI and EcoRI and subjected to isopropanol precipitation, to thereby remove the short linker EcoRI-BamHI fragment. Next, about 1 μg of the above-obtained partially digested DNA fragment is subjected to ligation reaction with about 2 μg of the vector having a BamHi terminus by the use of T4 ligase, followed by packaging into a λ-phage particle. The thus obtained recombinant phage suspension is diluted to an appropriate concentration, and used for infecting *Escherichia coli* NM539 (manufactured and sold by Promega Co., USA) to form plaques, and the number of plaques formed is counted. As a result, it is found that the phage suspension contains $3 \times 10^5$ particles of the recombinant phage. This phage suspension is stored at 4° C. as a gene library of *Acremonium chrysogenum*. In the above procedure, the preparation of the donor DNA and the vector, and the ligation reaction therebetween are conducted by the methods described by Frischauf et al (J. Mol. Biol., 170, 827–842, 1983). In addition, the packaging of the DNA into the λ-phage particle is performed by using Packaging extract (manufactured and sold by Promega Co., USA) in accordance with protocol attached to the same.

(ii) Preparation of Probe

The total DNA of *Saccharomyces cerevisiae* is digested with HindIII and inserted into the HindIII site of PBR327 (ATCC 37516), to thereby obtain a gene library. The gene library is screened by the synthetic oligonucleotide of the sequence: 5'-CAGATCATCAAGAAGTAATTATCT- 3' (SEQ. ID No. 70) which has been designed based on the nucleotide sequence of the Saccharomyces PGK gene reported by Hitzeman et al (see Nucleic Acids Res., 10, 7791–7808, 1982), to thereby obtain plasmid pYPGK1 which contains a HindIII fragment of 2.9 kb containing the entire PGK gene derived from *Saccharomyces cerevisiae*. 20 μg of plasmid pYPGK1 is digested with HindIII and EcoRI and subjected to 1% agarose gel electrophoresis, followed by the collection and purification of a fragment of 2.9 kb according to the method described at p.164–165 of the Maniatis Laboratory Manual. About 200 ng of the thus obtained fragment is labeled with [α-$^{32}$P] deoxycytidinetriphosphate (dCTP) (50 μCi) by using Nick translation kit (manufactured and sold by Takara Shuzo Co., Ltd., Japan) in accordance with the protocol attached to the same. After heating the reaction mixture at 70° C. for 10 minutes, the labeled fragment is purified by Nick-column (manufactured and sold by Pharmacia Fine Chemicals AB, Sweden), to thereby obtain a probe having a radioactivity of about $10^7$ cpm (hereinafter this probe is referred to as "YP-probe").

(iii) Screening by Hybridization

*E. coli* NM539 is infected with an aliquot of the phage suspension (gene library) obtained in Step (i) above and the infected NM539 is cultured on four plates to form a total of $2 \times 10^4$ plaques. According to the method of Benton et al (see W. D. Benton et al., Science, 196, 180–182, 1977), these plaques are transferred onto a nitrocellulose filter, followed by denaturation with alkali and neutralization treatment, thereby fixing the DNA. Then, these plaques are hybridized with YP-probe obtained in Step (ii) above. Hybridization is performed at 42° C. for 16 hours in a solution containing 30% formamide, 5xDenhardt's, 5xSSPE, 0.1% SDS, and YP-probe at a final concentration of $5 \times 10^5$ cpm/ml. Then, the filter is washed twice in a 6xSSC solution containing 0.1% SDS at room temperature for 10 minutes, followed by washing in 1xSSC solution containing 0.1% SDS at 42° C. for 30 minutes. Next, using an intensifier screen, autoradiography is carried out at −80° C. for 16 hours. As a result, seven positive spots are found. The phage is collected from agar portions corresponding to four of these seven positive spots, and subjected to plaque hybridization in the same manner as described above, to thereby obtain four pure positive phage clones. These clones are designated as λ-PGK1, λ-PGK2, λ-PGK3, and λ-PGK4, respectively.

(iv) Subcloning of PGK Gene and the Determination of the Location

From the four phage clones obtained in Step (iii) above, DNA is extracted by the method described by Grossberger (see Nucleic Acids Research, 15, 6737). Then the λ-DNA is digested with BamHI and then subjected to agarose gel electrophoresis, followed by Southern hybridization using YP-probe (with respect to the method, see Southern, J. Mol. Biol., 98, 503–517, 1975). In the above procedure, hybridization and washing of the filter are conducted in the same manner as in Step (iii). As a result, it is found that only the BamHI fragment of about 5.5 kb which is present in all clones is hybridized with the above mentioned YP-probe. The fragment is collected from the agarose gel and purified by the use of Gene·Clean™ (manufactured and sold by Funakoshi Pharmaceutical Co., Ltd., Japan) according to the protocol attached to the same. On the other hand, pUC18 (manufactured and sold by Takara Shuzo Co., Ltd., Japan) for use as a vector is digested with BamHI, followed by alkaline phosphatase treatment. Then, the above fragment and the vector are ligated to each other by means of T4 ligase, and introduced into *E. coli* JM105 according to the method described at p.252–253 of Maniatis Laboratory Manual. The resultant transformant is cultured on a L-broth agar medium containing ampicillin (Amp) (100 μg/ml) and 5-bromo-4-chloro- 3-indolyl-β-galactoside (X-Gal) (0.004%), thereby obtaining white colonies. 6 colonies are selected therefrom and subjected to extraction of the plasmid DNA by the rapid, small-scale isolation method (described at p.368–369 of Maniatis Laboratory Manual), and the thus obtained plasmid DNAs are analyzed through digestion with BamHI. As a result, it is found that the plasmid DNAs of 5 clones of the 6 clones have the desired fragment inserted therein. Further, the plasmid DNAs are analyzed by the Southern hybridization in the same manner as described above and as a result, it is confirmed that the insert in the clones is the desired fragment. One of the thus obtained plasmids is designated as "pPGK5".

Figure 59:
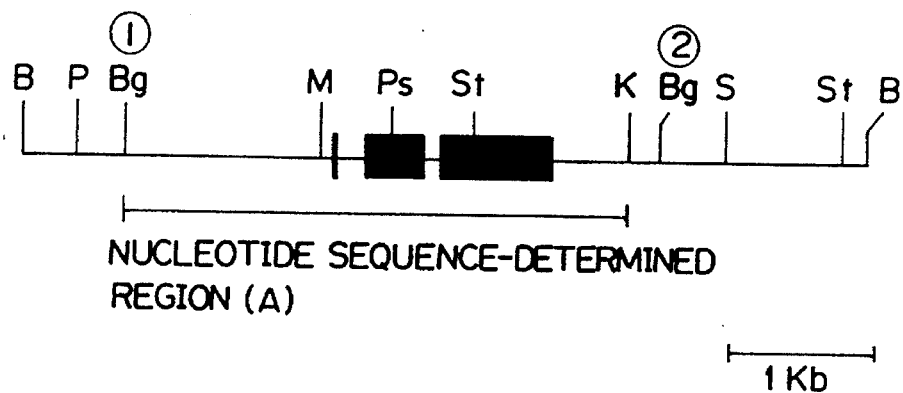
FIGS. 59 and 60 respectively show a restriction map of a DNA fragment containing *Acremonium chrysogenum* PGK gene and a restriction map of a DNA fragment containing *Acremonium chrysogenum* actin gene, wherein the portions marked ■ represent the exons of the above-mentioned genes (the 5'-terminus of the first exon and the 3'-terminus of the final exon have not yet been determined)

Plasmid pPGK5 is digested with various restriction enzymes, and then subjected to agarose gel electrophoresis, thereby obtaining the restriction map of the 5.5 kb insert shown in FIG. 59. Subsequently, in order to determine the location of the region coding for PGK, Southern hybridization is performed between each of the fragments obtained by the digestion of PGK5 with various restriction enzymes and the YP-probe. As a result, it is found that the PstI-StuI fragment of about 0.7 kb contains at least a portion of the region coding for PGK.

(v) Determination of the Nucleotide Sequence of the PGK Gene

The PstI-StuI fragment of about 0.7 kb which has been found to contain a portion of the coding region of the PGK gene is subcloned into the SmaI-PstI site of each of M13mp18 and M13mp19 and a portion of the nucleotide sequence thereof is determined by the method of Sanger et al (Sanger, F., Science, 214, 1981). Then, the nucleotide sequence determined is compared with the nucleotide sequence of the PGK gene which is already known, to thereby determine the orientation of the gene and the portion of the PGK protein coded for by this region. The nucleotide sequence is further determined toward upstream and downstream of this region, to thereby determine the nucleotide sequence of 3306 bp covering the entire region indicated by an underline in FIG. 59. The determination of the nucleotide sequence mentioned above is performed by using a sequencing kit (manufactured and sold by Takara Shuzo Co., Ltd., Japan) in accordance with the protocol attached to the kit. The entire nucleotide sequence determined and the translation product deduced therefrom are shown in FIG. 61(a–e) and (SEQ. ID No. 72).

This nucleotide sequence is analyzed by a computer using a software for processing genetic information (manufactured and sold by SDC Software Kaihatsu Kabushiki Kaisha, Japan). As a result, the following facts [items (1)–(3)] are found and, thus, it is confirmed that the gene isolated in the above procedure is a genuine PGK gene:

(1) The PKG gene of *Acremonium chrysogenum* codes for a protein comprised of 418 amino acid residues and having a molecular weight of 44,300 dalton.

(2) The coding region of this PKG gene is divided by 2 introns respectively of 145 bp and 64 bp. The locations of these introns are the same as those of the introns in the PGK gene of *Aspergillus nidulans* which is a filamentous fungi, although the lengths of the introns are different therefrom.

(3) The primary structure of the protein deduced from the nucleotide sequence of this PGK gene is very similar to those of the PGK genes respectively of human, *Saccharomyces cerevisiae* and *Aspergillus nidulance,* and exhibits homologies of 68%, 70% and 75% thereto, respectively.

BglII(1)-KpnI fragment [nucleotide sequence-determined region (A) in FIG. 59] whose structure has thus been determined covers a region up to 1251 bp upstream of the initiation codon (ATG) of the PGK gene, and hence the desired PGK promoter is considered to be present on this fragment. This assumption is strongly supported by the following Reference Example 2-(2) and (3).

REFERENCE EXAMPLE 2-(2) [Construction of pPGKM5]

Figure 63:
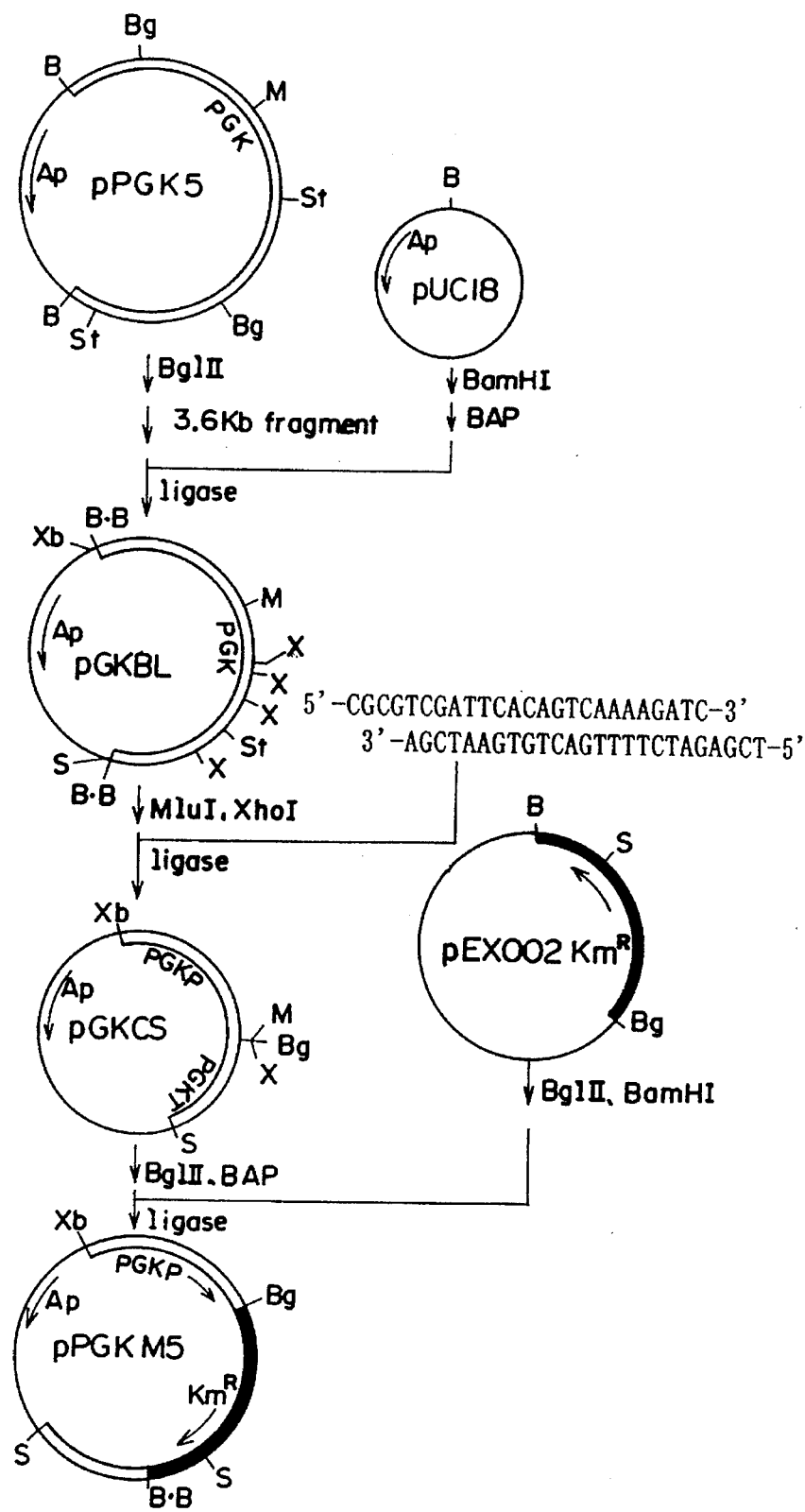
FIG. 63 shows a flow chart illustrating the construction of plasmid pPGKM5.

According to the steps shown in FIG. 63, plasmid pGKM5 is constructed for the expression of bacterium derived neomycin phosphotransferase gene (hereinafter referred to as "$Km^R$ gene") under the control of a PGK promoter derived from *Acremonium chrysogenum*. Each step is explained as follows.

(i) Preparation of pGKBL

Plasmid pPGK5 obtained in Reference Example 2-(1)-(iv) above is digested with BglII and a fragment of 3.6 kb containing PGK gene is isolated and purified. The fragment is inserted to the BamHI site of pUC18 prepared in Reference Example 2-(1)-(iv) above, thereby obtaining pGKBL. At the same time, another plasmid in which the same fragment as mentioned above is inserted in the reverse orientation relative to the orientation of pGKBL, is also obtained, and the plasmid is designated as pGKBL'.

(ii) Preparation of pGKCS

Plasmid pGKBL obtained in Step (i) above is digested with MluI and XhoI, and a fragment of 4.8 kb is isolated and purified. The fragment is ligated to a synthetic linker represented by the following formula, thereby obtaining pGKCS:

5' CGCGTCGATTCACAGTCAAAAGATC-3,

3' AGCTAAGTGTCAGTTTTCTAGAGCT-5'

Further, substantially the same operation as mentioned above is conducted except that pGKBL' is used instead of pGKBL, thereby constructing pGKCS'. pGKCS and pGKCS' are plasmids having a structure such that fragments containing PGK promoter and terminator each derived from *Acremonium chrysogenum* are ligated through unique restriction sites (BglII and XhoI) in an arrangement suitable for expression, and these plasmids are useful as starting materials for constructing vectors for the expression of various types of foreign genes in *Acremonium chrysogenum*. The above-mentioned linker is synthesized as two single strands using DNA synthesizer model 380-A manufactured and sold by Applied Biosystems, according to the conventional method.

(iii) Construction of Plasmid pPGKM5

Plasmid pEX002 is digested with restriction enzymes BamHI and BglII to obtain a fragment of about 1.5 kb containing $Km^R$ gene, and the obtained fragment is purified. The resultant fragment is ligated to plasmid pGKCS according to the orientation illustrated in FIG. 63, which has been digested with BglII and treated with alkaline phosphatase, thereby obtaining plasmid pPGKM5. The plasmid pEX002 used above is an expression vector for *E. coli* having lac UV5 promoter and a $Km^R$ gene derived from transposon 5(Tu5), and the method for the construction thereof is disclosed in Japanese Patent Application Laid-Open Specification No. 63-74488.

In Reference Example 2-(2), DNA fragments digested with restriction enzymes are isolated by 1% agarose gel electrophoresis, and the fragments are recovered from the agarose gel by means of Gene Clean™ (manufactured and sold by Funakoshi Pharmaceutical Co., Ltd., Japan) according to the instructions of the protocol attached thereto. Basic operations, including ligation of a plasmid to a DNA fragment, transformation of *E. coli* and construction and analysis of plasmid prepared by subcloning, are performed according to the methods described in Maniatis Laboratory Manual.

REFERENCE EXAMPLE 2-(3) (Transformation of *Acremonium chrysogenum* with Plasmid pPGKM5)

(i) Preparation of Protoplast

Mycellia (corresponding to about 1 cm²) of *Acremonium chrysogenum* IS-5 grown at 30° C. for 5 days on CM solid medium are inoculated in 50 ml of CM culture medium, and incubated on a rotary shaker (250 rpm) at 30° C. for 3 days. 1 ml of the resultant culture is inoculated in 50 ml of GAG culture medium, and incubated on the rotary shaker (250 rpm) at 30° C. for 20 hours. 50 ml of the obtained culture is subjected to centrifugation at 3,500 rpm for 10 minutes, to thereby collect the mycellia as a precipitate. The collected mycellia are washed with 0.9% NaCl solution, and suspended in 20 ml of Mcilvaene buffer (containing 0.1M citric acid and 0.2M sodium phosphate, pH 7.3) containing 0.01M dithiothreitol, followed by gentle shaking at 30° C. for 1 hour. Then, the suspension is subjected to centrifugation at 3,200 rpm for 10 minutes to thereby collect the mycellia as a precipitate. The resultant mycellia are washed with P-buffer, and suspended in 10 ml of P-buffer containing Novozyme (manufactured and sold by NOVO Industry, Denmark) at a concentration of 10 mg/ml, followed by gentle shaking at 30° C. for 1 hour. The thus obtained mixture is subjected to centrifugation at 800 rpm for 30 seconds, and the resultant supernatant is filtered through a filter paper (Toyo Filter Paper 5A), to thereby separate the mycellia from protoplast. The filtrate is then subjected to centrifugation at 3,000 rpm for 5 minutes to precipitate the protoplast, and the obtained protoplast is washed with P-buffer once, and suspended in P-buffer at a protoplast concentration of $3 \times 10^8$/ml.

(ii) Transformation of Protoplast with Plasmid pPGKM5

To 0.1 ml of the protoplast suspension obtained in (i) above are added 10 μl of a solution containing 5 μg of plasmid pPGKM5 and then 0.05 ml of PEG solution, followed by gentle stirring. The resultant mixture is allowed to stand on ice for 25 minutes, and then 1 ml of PEG solution is added thereto. The mixture is further allowed to stand at room temperature for 30 minutes. The thus obtained transformed protoplast suspension is portionwise spread on a plate containing 25 ml of protoplast regeneration medium (which is BRM medium described in Isogai et al: Argic. Biol. Chem. 1987, 51, 2321–2329) in an amount of 0.2 ml, followed by incubation at 15° C. for 20 hours. Then, 5 ml of BRM medium containing 3 mg of G418 and kept at 50° C., is superposed on the above plate, and the resultant plate is incubated at 28° C. for 10 to 20 days. Thereafter, G418-resistant transformant cell lines selected. The above procedure is repeated several times, to thereby obtain 50 to 150 G418-resistant transformant cell lines per 5.5 μg of plasmid pPGKM5. By contrast, when the same testing as described above is carried out using plasmid pEX002 as a control, only 0 to 2 G418-resistant transformant cell lines are obtained. These results strongly suggest that the XbaI-BglII fragment included in plasmid pPGKM5 contains the promoter of *Acremonium chrysogenum* PGK gene. The nucleotide sequence of the XbaI-BglII fragment is as shown below (SEQ. ID No. 75):

```
AGATCTTTCAGGATGGTGCTGATGGGGGCGAGGGGCAAAACA
CCACCGGGTGATCCTCGACGTGGAGGTTGTGATAGAAGGAGA
GCAAGGGGACGATGATGATGTGGACCTTGTGATTGAGGAGGA
TCATGGCGATGAGGATGAGGAAGAGGATTTACCCGATCTGAT
CGATCCTCCCCCGAACGACGGGGACCAGGAGCGGGAGGGAGC
AGCCGGGCACGAGGCGATCAGGCGCGAGGGTCAAGAACCAGA
CCGACAAGGCCAGCACCAAGAACAGGAACCGGCAGCACCGGA
GGCACCCGCAGCGGACGAGCAGCTCCCGCCACAGAACAACCA
CGAAGTACCGCCCGCCCCGCCGGCCAACCGCGTCGGTCTGGG
CACCGTCCTGTCCAACTTCTCAAACCAGCTCGTCAGCGCCCT
CATCCTGCCGGGAATCTCCTTCGCCATGGGCGAAGCTCTACG
GGTGGCGCTCCCCGCCAGGTGGACACAGTCGTCTCTGTGCCC
CTTTAGGAACGCCCTCCGGGCCTACTCCAGCAGCAGTGGGGT
CGCAGCCTCGTGGGTGGGTGCCTGTACGTGTGATCAAGGACG
TGATCCGGGTCTACGCCAAGCACCGCAAGGTGGCGGCTATGG
GCAACCGGCGGGTCAGAAACGTGGACCGGCCAAGGAGGAACG
CGGGCTCGTCGAGATGAAATCCAGTGATACAACGCAGCATGG
GAACGGAGTTTGGGCTGGCCAGGGTAGATGACGGTATCCAAG
GATTATACTATTAATATAGCGACTACTAGTAATTACTACTGG
GCAGAGTCTACCGCCCAACGTTGGTATGGGTTATTTGTAAAC
GTTCCACGCCAATCTTTTCCACCGTCAGAATCGGCGTATCAT
TGCAATTGACGGCACCAGAATGATGCGTTGGTACTAATAGTA
GGTACGAGGTAACAACAGTAAAGATACTGCCATTATAGAAAG
AGGAAGTCGCTCCCTCGGCAATGCCGCGCCACAAGCGCCTTT
GGCCGAGGACGCCGGAACCCAAACGCAGATCAGATCGGGGGC
AACGGGAAGCTTAGGGACGGAAATGGGGTAATACGAGTAATA
ATCCCCCACCACCACCAAGAAGCTCCCAACCCAAAAGCTTCC
TGCGTCCTTTTCACCCCGCCATCTTCTCCCGACAGAAAGACA
AAACAACCCACCATACCACTCCACAGAGCATTGTTCTTCTCC
TTCAGGACTACCACGCGTCGATTCACAGTCAAA
```

By Southern hybridization using as a probe the PstI fragment (about 900 bp) of plasmid pEX002 containing most of the entire coding region of Km$^R$ gene, it is confirmed that the plasmid pPGKM5 used for transfection is correctly inserted in the chromosome of the above-obtained G418-resistant transformant cell lines.

REFERENCE EXAMPLE 2-(4) (Cloning of Actin Gene)

(i) Screening of Clones Containing Actin Gene by Hybridization

Using $^{32}$P-labeled HinfI fragment of 400 bp (manufactured and sold by WAKO PURE CHEMICAL Industries Ltd., Japan) containing the third exon of human β-actin gene as a probe (hereinafter, referred to as ACT probe), *Acremonium chrysogenum* gene library prepared in Reference Example 2-(1)-(i) is subjected to screening under the same condition as described in Reference Example 2-(3), to thereby obtain 4 phages hybridized with the probe.

(ii) Subcloning of Actin Gene and Determination of the Site Thereof

Figure 60:
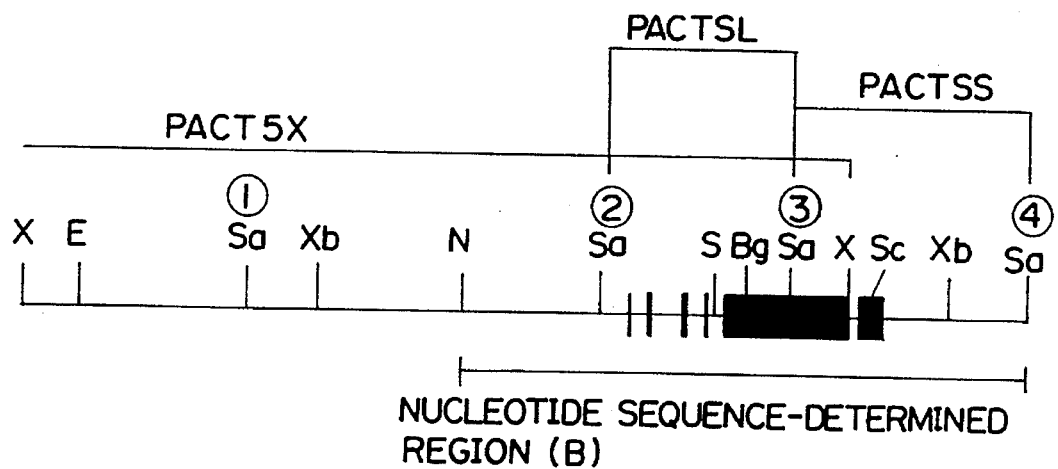

Subcloning of actin gene is performed. Illustratively stated, DNA is extracted from one of the phage clones obtained in step (i), and is designated as λ-ACT5. The obtained λ-ACT5 DNA is digested with restriction enzymes XhoI and SalI, and is subjected to agarose gel electrophoresis, followed by Southern hybridization using the above-mentioned ACT-probe. As a result, it is found that one XhOI fragment of about 5.4 kb and two SalI fragments of about 1.3 kb and about 1.5 kb are hybridized with the ACT-probe. These three fragments (XhoI fragment of about 5.4 kb, SalI fragment of about 1.5 kb and SalI fragment of about 1.3 kb) are individually inserted into SalI site of pUC18 plasmid to thereby obtain plasmids pACT5X, pACT5SS and pACT5SL. Subsequently, partial restriction maps of these plasmids are individually prepared and, by overlapping them, a partial restriction map of the DNA fragment of about 6 kb which is believed to contain actin gene, is prepared as shown in FIG. 60.

Southern hybridization is performed under substantially the same conditions as described in Reference Example 2-(1)-(iv), except that ACT probe is used.

(iii) Determination and Analysis of the Nucleotide Sequence of Actin Gene

The results of step (ii) strongly suggest that the SmaI-XhoI fragment of about 0.7 kb contains at least a portion of the coding region for actin, which correspons to the third exon of human β-Actin. Accordingly, first, the nucleotide sequence of this portion is determined. By comparing this nucleotide sequence with the known actin gene, the presumptions are made with respect to the orientation of the nucleotide sequence, the presence or absence of an intron and the identification of the portion of actin protein coded for by this region. Subsequently, by conducting a nucleotide sequence determination from the region toward both upstream direction and downstream direction, the nucleotide sequence of 3748 bp entirely covering region (B) shown by underline in FIG. 60 is finally determined. The determined entire nucleotide sequence and the amino acid sequence of a presumed translation product are shown in FIG. 62(*a–f*) (SEQ. ID No. 77). The obtained nucleotide sequence and the amino acid sequence are compared with those known with respect to actin gene. As a result, the following observations are obtained, and it is confirmed that the gene isolated through the above-mentioned steps is the authentic actin gene.

1) Actin gene isolated from *Acremonium chrysogenum* codes for the amino acid sequence of a protein having a molecular weight of 41,800 dalton, which comprises 375 amino acid residues. The number of amino acid residues is equal to that of actins other than actin (alpha type) from vertebrate skeletal muscle.

2) Amino acid sequence presumed from the nucleotide sequence shown in FIG. 62(*a–f*) is quite similar to that of known actin. The amino acid sequence of the actin according to the present invention exhibits 92% homology with the actin of *Saccharomyces cerevisiae*, and exhibits 90% homology with the known gamma-type human actin. The NsiI-SalI fragment (FIG. 60) isolated and having the structure determined as mentioned above, includes the actin gene initiation codon and, upstream thereof toward the 5' end, 1293 bp nucleotides, and hence it is believed that the desired actin promoter is present in the fragment. The following Reference Examples 2-(5) and 2-(6) strongly support that the above presumptions are correct.

REFERENCE EXAMPLE 2-(5) (Construction of Plasmid pAC-THY83)

Figure 64:
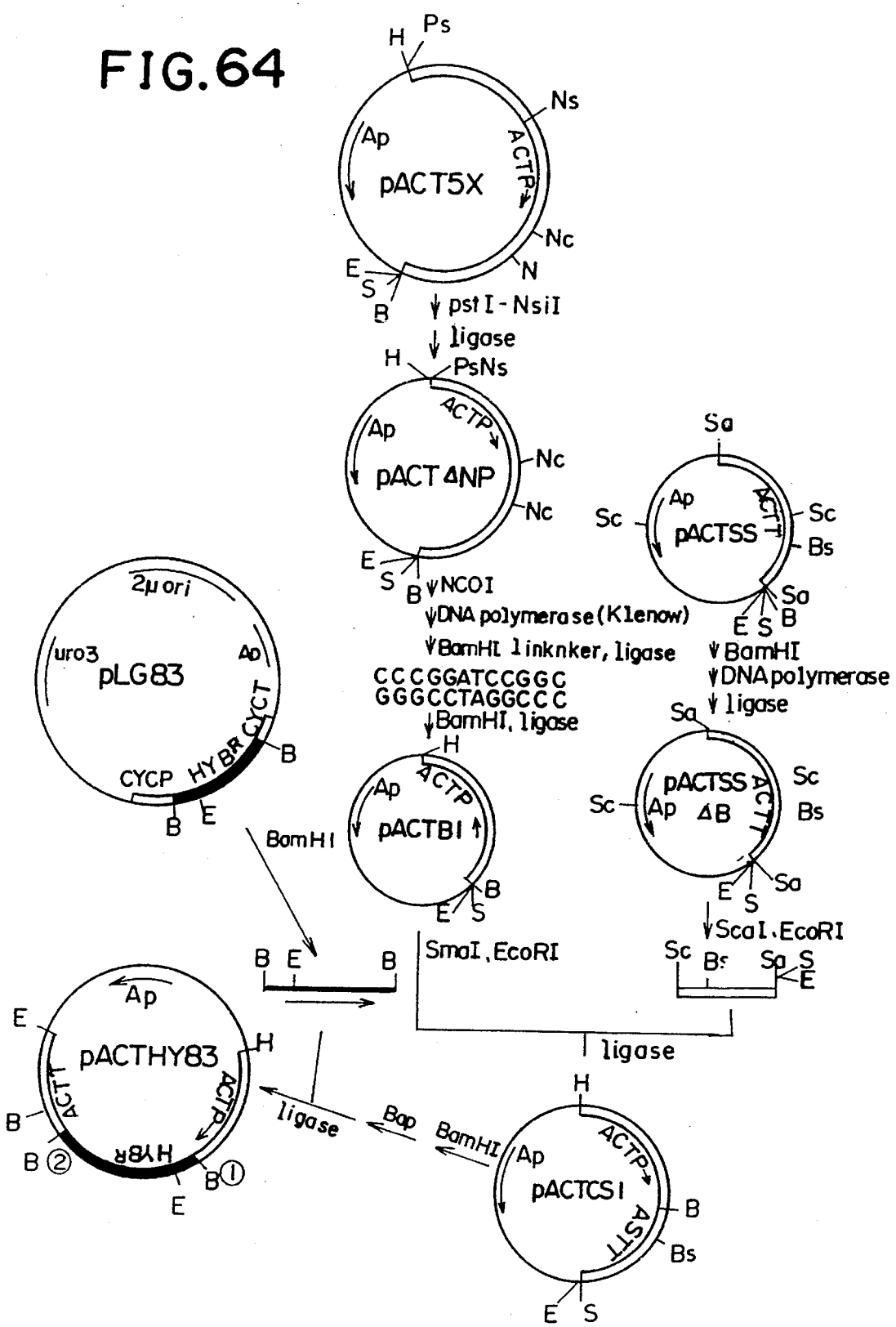
FIG. 64 shows a flow chart illustrating the construction of plasmid pACTHY83.

In accordance with the steps shown in FIG. 64, plasmid pACTHY83 is constructed for expressing hygromycine B phosphotransferase gene (hereinafter referred to as "HYB$^R$ gene") derived from bacteria under the control of actin promoter derived from *Acremonium chrysogenum*. Each of the steps is described below.

(i) Construction of Plasmid pACTΔNP

Plasmid pACT5X obtained in Reference Example 2-(4)-(ii) is simultaneously digested with restriction enzymes NsiI and PstI to obtain a DNA fragment of about 5.3 kb. Then, the obtained DNA fragment of about 5.3 kb is subjected to self-cyclyzation using T4 DNA ligase to construct plasmid pACTΔNP.

(ii) Construction of Plasmids pACTB1, pACTB2 and pACTB3

Plasmid pACTΔNP obtained step (i) is digested with restriction enzyme NcoI to produce cohesive ends. The cohesive ends are treated with DNA polymerase Klenow fragment (hereinafter referred to as "DNA-pol,) and four types of deoxyribonucleotidetriphosphates (deoxyadenosyn triphosphate, deoxyguanosyn triphosphate, deoxycytidyn triphosphate and thymidyne triphosphate, hereinafter referred to as "4dNTPS") to thereby convert them to blunt ends. Then BamHI linker (manufactured and sold by Takara Shuzo Co., Ltd., Japan) having the 5'-end thereof phosphorylated and having the following nucleotide sequence (SEQ. ID No. 78):

5'CCCGGATCCGGG 3'
3'GGGCCTAGGCCC 5' is ligated to the above-mentioned blunt ends using T4 DNA ligase, followed by complete digestion with BamHI. The thus obtained digest is subjected to agarose gel electrophoresis to thereby obtain a DNA fragment of about 4 kb. The resultant fragment is purified, and the purified fragment of about 4 kb is self-cyclized using T4 DNA ligase to obtain plasmid pACTB1. In substantially the same manner, plasmids pACTB2 and pACTB3 are produced using two other types of BamHI linkers which are different from the above-mentioned linker in the nucleotide sequence and the number of nucleotides.

These other BamHI linkers are also manufactured and sold by Takara Shuzo Co., Ltd., Japan, and have the following sequences:

5'CCGGATCCGG 3' (SEQ. ID No. 79) 5' CGGATCCG 3' (SEQ. ID No. 80)
3'GGCCTAGGCC 5', 3' GCCTAGGC 5'.

(iii) Construction of Plasmids pACTCS1, pACTCS2 and pACTCS3

Plasmid pACTSS obtained in Reference Example 2-(4)-(ii) is digested with BamHI, and both ends of the resultant DNA are rendered blunt using DNA pol. and 4dNTPS. The DNA having blunt ends is self cyclized using T4 DNA ligase, thereby obtaining plasmid pACTSSΔBam having BamHI site deleted. This plasmid is digested with ScaI and EcoRI, and a fragment of about 0.9 kb believed to contain actin gene terminator is separated and purified. This fragment is inserted in pACTBI between SmaI and EcoRI sites, thereby obtaining pACTCS1. The above-mentioned fragment of about 0.9 kb is inserted in pACTB2 and pACTB3 between SmaI and EcoRI sites, thereby obtaining pACTCS2 and pACTCS3, respectively. The thus obtained three types of plasmids each have a structure such that a fragment containing *Acremonium chrysogenum* actin promoter is linked through unique restriction site BamHI (positioned just downstream of actin initiation codon ATG) with a fragment containing *Acremonium chrysogenum* actin terminator in an arrangement suited for expression. These plasmids are starting materials useful for the construction of a vector in which various desired genes are expressed in *Acremonium chrysogenum* to produce a fused protein. By using any one of these three types of plasmids, each of the desired genes can be ligated in an actin gene reading frame.

(iv) Construction of Plasmid pACTHY83

Plasmid pLG83 (obtained from Professor Julian Davies of Pasteur Laboratory) is digested with BamHI, and a fragment of about 1.3 kb containing HYB$^R$ gene is separated and purified. This fragment is ligated to pACTCS1 which has been digested with BamHI and treated with alkaline phosphatase in the orientation shown in FIG. 64, thereby obtaining plasmid pACTHY83. The above-mentioned pLG83 is a vector for yeast containing HYB$^R$ gene, and the properties thereof are described in published literature [see Critz et al., Gene (1983) 25, 179–188]. The basic operations performed in Reference Example 2-(5), such as the separation and purification of restriction digested fragments, the ligation of each of fragments to a plasmid, the transformation of *E. coli* and the preparation and analyses of plasmids resulting from subcloning, are substantially the same as those performed in Reference Example 2-(2).

What is claimed is:

1. A substantially pure polypeptide essentially free of other human proteins, said polypeptide consisting of an amino acid sequence represented by the following formula (amino acids 368–480 of SEQ. ID No. 59)

(X)—Pro—Cys—Phe—Arg—Ala—Asn—Cys—Glu—Tyr—
Gln—Cys—Gln—Pro—Leu—Asn—Gln—Thr—Ser—Tyr—
Leu—Cys—Val—Cys—Ala—Glu—Gly—Phe—Ala—Pro—
Ile—Pro—His—Glu—Pro—His—Arg—Cys—Gln—Met—
Phe—Cys—Asn—Gln—Thr—Ala—Cys—Pro—Ala—Asp—
Cys—Asp—Pro—Asn—Thr—Gln—Ala—Ser—Cys—Glu—
Cys—Pro—Glu—Gly—Tyr—Ile—Leu—Asp—Asp—Gly—
Phe—Ile—Cys—Thr—Asp—Ile—Asp—Glu—Cys—Glu—
Asn—Gly—Gly—Phe—Cys—Ser—Gly—Val—Cys—His—
Asn—Leu—Pro—Gly—Thr—Phe—Glu—Cys—Ile—Cys—
Gly—Pro—Asp—Ser—Ala—Leu—Val—Arg—His—Ile—
Gly—Thr—Asy—Cys wherein X is selected from the group consisting of Glu, Gla, Asp—Asp, Asp—Asp—Asp, Glu-Asp and Gla-Asp, wherein Gla represents a γ-carboxyglutamic acid residue.

2. A pharmaceutical composition comprising a substantially pure polypeptide according to claim 1, and at least one pharmaceutically acceptable carrier, diluent or excipient.

3. The pharmaceutical composition according to claim 2, wherein said polypeptide has an activity to inhibit blood coagulation and platelet aggregation by thrombin and/or an activity to promote the thrombin-catalyzed activation of protein C.

4. The substantially pure polypeptide according to claim 1, wherein X is Glu.

5. The substantially pure polypeptide according to claim 1, wherein X is Gla.

6. The substantially pure polypeptide according to claim 1, wherein X is Asp—Asp.

7. The substantially pure polypeptide according to claim 1, wherein X is Asp—Asp—Asp.

8. The substantially pure polypeptide according to claim 1, wherein X is Glu-Asp.

9. The substantially pure polypeptide according to claim 1, wherein X is Gla-Asp.

10. A substantially pure polypeptide essentially free of other human proteins, said polypeptide consisting of an amino acid sequence represented by the formula (amino acids 19–516 of SEQ. ID No. 59):

Ala—Pro—Ala—Glu—Pro—Gln—Pro—Gly—Gly—Ser—
Gln—Cys—Val—Glu—His—Asp—Cys—Phe—Ala—Leu—
Tyr—Pro—Gly—Pro—Ala—Thr—Phe—Leu—Asn—Ala—
Ser—Gln—Ile—Cys—Asp—Gly—Leu—Arg—Gly—His—
Leu—Met—Thr—Val—Arg—Ser—Ser—Val—Ala—Ala—
Asp—Val—Ile—Ser—Leu—Leu—Leu—Asn—Gly—Asp—
Gly—Gly—Val—Gly—Arg—Arg—Arg—Leu—Trp—Ile—
Gly—Leu—Gln—Leu—Pro—Pro—Gly—Cys—Gly—Asp—
Pro—Lys—Arg—Leu—Gly—Pro—Leu—Arg—Gly—Phe—
Gln—Trp—Val—Thr—Gly—Asp—Asn—Asn—Thr—Ser—
Tyr—Ser—Arg—Trp—Ala—Arg—Leu—Asp—Leu—Asn—
Gly—Ala—Pro—Leu—Cys—Gly—Pro—Leu—Cys—Val—
Ala—Val—Ser—Ala—Ala—Glu—Ala—Thr—Val—Pro—
Ser—Glu—Pro—Ile—Trp—Glu—Glu—Gln—Gln—Cys—
Glu—Val—Lys—Ala—Asp—Gly—Phe—Leu—Cys—Glu—
Phe—His—Phe—Pro—Ala—Thr—Cys—Arg—Pro—Leu—
Ala—Val—Glu—Pro—Gly—Ala—Ala—Ala—Ala—
Val—Ser—Ile—Thr—Tyr—Gly—Thr—Pro—Phe—Ala—
Ala—Arg—Gly—Ala—Asp—Phe—Gln—Ala—Leu—Pro—
Val—Gly—Ser—Ser—Ala—Ala—Val—Ala—Pro—Leu—
Gly—Leu—Gln—Leu—Met—Cys—Thr—Ala—Pro—Pro—
Gly—Ala—Val—Gln—Gly—His—Trp—Ala—Arg—Glu—
Ala—Pro—Gly—Ala—Trp—Asp—Cys—Ser—Val—Glu—
Asn—Gly—Gly—Cys—Glu—His—Ala—Cys—Asn—Ala—
Ile—Pro—Gly—Ala—Pro—Arg—Cys—Gln—Cys—Pro—
Ala—Gly—Ala—Ala—Leu—Gln—Ala—Asp—Gly—Arg—
Ser—Cys—Thr—Ala—Ser—Ala—Thr—Gln—Ser—Cys—
Asn—Asp—Leu—Cys—Glu—His—Phe—Cys—Val—Pro—
Asn—Pro—Asp—Gln—Pro—Gly—Ser—Tyr—Ser—Cys—
Met—Cys—Glu—Thr—Gly—Tyr—Arg—Leu—Ala—Ala—
Asp—Gln—His—Arg—Cys—Glu—Asp—Val—Asp—Asp—
Cys—Ile—Leu—Glu—Pro—Ser—Pro—Cys—Pro—Gln—
Arg—Cys—Val—Asn—Thr—Gln—Gly—Gly—Phe—Glu—
Cys—His—Cys—Tyr—Pro—Asn—Tyr—Asp—Leu—Val—
Asp—Gly—Glu—Cys—Val—Glu—Pro—Val—Glu—Pro—
Cys—Phe—Arg—Ala—Asn—Cys—Glu—Tyr—Gln—Cys—
Gln—Pro—Leu—Asn—Gln—Thr—Ser—Tyr—Leu—Cys—
Val—Cys—Ala—Glu—Gly—Phe—Ala—Pro—Ile—Pro—
His—Glu—Pro—His—Arg—Cys—Gln—Met—Phe—Cys—
Asn—Gln—Thr—Ala—Cys—Pro—Ala—Asp—Cys—Asp—
Pro—Asn—Thr—Cln—Ala—Ser—Cys—Glu—Cys—Pro—
Glu—Gly—Tyr—Ile—Leu—Asp—Asp—Gly—Phe—Ile—
Cys—Thr—Asp—Ile—Asp—Glu—Cys—Glu—Asn—Gly—
Gly—Phe—Cys—Ser—Gly—Val—Cys—His—Asn—Leu—
Pro—Gly—Thr—Phe—Glu—Cys—Ile—Cys—Gly—Pro—
Asp—Ser—Ala—Leu—Val—Arg—His—Ile—Gly—Thr—
Asp—Cys—Asp—Ser—Gly—Lys—Val—Asp—Gly—Gly—
Asp—Ser—Gly—Ser—Gly—Glu—Pro—Pro—Pro—Ser—
Pro—Thr—Pro—Gly—Ser—Thr—Leu—Thr—Pro—Pro—
Ala—Val—Gly—Leu—Val—His—Ser—Gly.

11. A pharmaceutical composition comprising a substantially pure polypeptide according to claim 10, and at least one pharmaceutically acceptable carrier, diluent or excipient.

12. The pharmaceutical composition according to claim 11, wherein said polypeptide has an activity to inhibit blood coagulation and platelet aggregation by thrombin and/or an activity to promote the thrombin-catalyzed activation of protein C.

* * * * *

SEQUENCE LISTING ( 1 ) GENERAL INFORMATION:

( i i i ) NUMBER OF SEQUENCES: 80

( 2 ) INFORMATION FOR SEQ ID NO:1:

( i ) SEQUENCE CHARACTERISTICS:
        ( A ) LENGTH: 12 base pairs
        ( B ) TYPE: nucleic acid
        ( C ) STRANDEDNESS: both
        ( D ) TOPOLOGY: linear ( i i ) MOLECULE TYPE: DNA (synthetic)

( i x ) FEATURE:
        ( A ) NAME/KEY: -
        ( B ) LOCATION: 1..12
        ( D ) OTHER INFORMATION: /label=oligonucleotide
            / note="BamHI linker"

( x i ) SEQUENCE DESCRIPTION: SEQ ID NO:1:

GGAAGATCTT CC  12

( 2 ) INFORMATION FOR SEQ ID NO:2:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY: Peptide
        ( B ) LOCATION: 1..19
        ( D ) OTHER INFORMATION: /label=peptide
            / note="Peptide I, fragment of thrombin binding
            polypeptide."

( x i ) SEQUENCE DESCRIPTION: SEQ ID NO:2:

Glu Cys Pro Glu Gly Tyr Ile Leu Asp Asp Gly Phe Ile Cys Thr Asp
1               5                   10                  15

Ile Asp Glu ( 2 ) INFORMATION FOR SEQ ID NO:3:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: internal ( i x ) FEATURE:
        ( A ) NAME/KEY: Peptide
        ( B ) LOCATION: 1..58
        ( D ) OTHER INFORMATION: /label=peptide
            / note="Peptide II; preferred sequence linked to
            N-terminus of thrombin binding polypeptide
        (Peptide I)."

( x i ) SEQUENCE DESCRIPTION: SEQ ID NO:3:

| Pro | Cys | Phe | Arg | Ala | Asn | Cys | Glu | Tyr | Gln | Cys | Gln | Pro | Leu | Asn | Gln |
| 1   |     |     |     | 5   |     |     |     |     | 10  |     |     |     |     | 15  |     |

| Thr | Ser | Tyr | Leu | Cys | Val | Cys | Ala | Glu | Gly | Phe | Ala | Pro | Ile | Pro | His |
|     |     |     | 20  |     |     |     |     | 25  |     |     |     |     | 30  |     |     |

| Glu | Pro | His | Arg | Cys | Gln | Met | Phe | Cys | Asn | Gln | Thr | Ala | Cys | Pro | Ala |
|     |     | 35  |     |     |     |     | 40  |     |     |     |     | 45  |     |     |     |

| Asp | Cys | Asp | Pro | Asn | Thr | Gln | Ala | Ser | Cys |
|     | 50  |     |     |     |     | 55  |     |     |     |

( 2 ) INFORMATION FOR SEQ ID NO:4:

( i ) SEQUENCE CHARACTERISTICS:
        ( A ) LENGTH: 36 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: C-terminal ( i x ) FEATURE:
        ( A ) NAME/KEY: Peptide
        ( B ) LOCATION: 1..36
        ( D ) OTHER INFORMATION: /label=peptide
           / note="Peptide III; preferred peptide to be
           attached to C-terminus of thrombin binding
           polypeptide, Peptide I."

( x i ) SEQUENCE DESCRIPTION: SEQ ID NO:4:

| Cys | Glu | Asn | Gly | Gly | Phe | Cys | Ser | Gly | Val | Cys | His | Asn | Leu | Pro | Gly |
| 1   |     |     |     | 5   |     |     |     |     | 10  |     |     |     |     | 15  |     |

| Thr | Phe | Glu | Cys | Ile | Cys | Gly | Pro | Asp | Ser | Ala | Leu | Val | Arg | His | Ile |
|     |     |     | 20  |     |     |     |     | 25  |     |     |     |     | 30  |     |     |

| Gly | Thr | Asp | Cys |
|     |     |     | 35  |

( 2 ) INFORMATION FOR SEQ ID NO:5:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( i v ) ANTI-SENSE: YES ( i x ) FEATURE:
        ( A ) NAME/KEY: -
        ( B ) LOCATION: 1..25
        ( D ) OTHER INFORMATION: /label=oligonucleotide
           / note="Lower strand of "deleter TMd3"in Figure
           1."

( x i ) SEQUENCE DESCRIPTION: SEQ ID NO:5:

GGAGGCCGCT CAACAGTCGG TGCCA                                                25

( 2 ) INFORMATION FOR SEQ ID NO:6:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (plasmid)

( i v ) ANTI-SENSE: NO ( i x ) FEATURE:
    ( A ) NAME/KEY: -
    ( B ) LOCATION: 1..30
    ( D ) OTHER INFORMATION: /label=oligonucleotide
        / note="Upper strand of "deleter TMd3"in Figure 1."

( i x ) FEATURE:
    ( A ) NAME/KEY: CDS
    ( B ) LOCATION: 1..18
    ( D ) OTHER INFORMATION: /product="TMd3 amino acids"

( x i ) SEQUENCE DESCRIPTION: SEQ ID NO:6:

```
CAC ATT GGC ACC GAC TGT TGAGCGGCCT CC                    30
His Ile Gly Thr Asp Cys
 1               5
```

( 2 ) INFORMATION FOR SEQ ID NO:7:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: protein ( x i ) SEQUENCE DESCRIPTION: SEQ ID NO:7:

```
His Ile Gly Thr Asp Cys
 1               5
```

( 2 ) INFORMATION FOR SEQ ID NO:8:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: DNA (synthetic)

( i v ) ANTI-SENSE: YES ( i x ) FEATURE:
    ( A ) NAME/KEY: -
    ( B ) LOCATION: 1..25
    ( D ) OTHER INFORMATION: /label=oligonucleotide
        / note="Lower strand of "deleter TMd5"in Figure 2."

( x i ) SEQUENCE DESCRIPTION: SEQ ID NO:8:

```
GAAGCACGGG TCGGGGAACC CCAGG                              25
```

( 2 ) INFORMATION FOR SEQ ID NO:9:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: DNA (plasmid)

( i v ) ANTI-SENSE: NO ( i x ) FEATURE:
    ( A ) NAME/KEY: -
    ( B ) LOCATION: 1..30
    ( D ) OTHER INFORMATION: /label=oligonucleotide
        / note="Upper strand of "deleter TMd5"in Figure 2."

( i x ) FEATURE:
    ( A ) NAME/KEY: CDS
    ( B ) LOCATION: 1..30
    ( D ) OTHER INFORMATION: /product="TMd5 amino acids"

( x i ) SEQUENCE DESCRIPTION: SEQ ID NO:9:

```
GGC  CTG  GGG  TTC  CCC  GAC  CCG  TGC  TTC  AGA                30
Gly  Leu  Gly  Phe  Pro  Asp  Pro  Cys  Phe  Arg
 1                  5                        10
```

( 2 ) INFORMATION FOR SEQ ID NO:10:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

```
Gly  Leu  Gly  Phe  Pro  Asp  Pro  Cys  Phe  Arg
 1                  5                        10
```

( 2 ) INFORMATION FOR SEQ ID NO:11:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (synthetic)

( i v ) ANTI-SENSE: YES ( i x ) FEATURE:
        ( A ) NAME/KEY: -
        ( B ) LOCATION: 1..25
        ( D ) OTHER INFORMATION: /label=oligonucleotide
           / note="Lower strand of "deleter TMd6"in Figure 3."

( x i ) SEQUENCE DESCRIPTION: SEQ ID NO:11:

```
TCTGAAGCAC  GGGGGGAACC  CCAGG                                   25
```

( 2 ) INFORMATION FOR SEQ ID NO:12:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (plasmid)

( i v ) ANTI-SENSE: NO ( i x ) FEATURE:
        ( A ) NAME/KEY: -
        ( B ) LOCATION: 1..30
        ( D ) OTHER INFORMATION: /label=oligonucleotide
           / note="Upper strand of "deleter TMd6"in Figure 3."

( i x ) FEATURE:
        ( A ) NAME/KEY: CDS
        ( B ) LOCATION: 1..30
        ( D ) OTHER INFORMATION: /product="TNd6 amino acids"

( x i ) SEQUENCE DESCRIPTION: SEQ ID NO:12:

```
GGC  CTG  GGG  TTC  CCC  CCG  TGC  TTC  AGA  GCC                30
```

```
Gly  Leu  Gly  Phe  Pro  Pro  Cys  Phe  Arg  Ala
 1              5                        10
```

( 2 ) INFORMATION FOR SEQ ID NO:13:

( i ) SEQUENCE CHARACTERISTICS:
    ( A ) LENGTH: 10 amino acids
    ( B ) TYPE: amino acid
    ( D ) TOPOLOGY: linear ( i i ) MOLECULE TYPE: protein ( x i ) SEQUENCE DESCRIPTION: SEQ ID NO:13:

```
Gly  Leu  Gly  Phe  Pro  Pro  Cys  Phe  Arg  Ala
 1              5                        10
```

( 2 ) INFORMATION FOR SEQ ID NO:14:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: DNA (synthetic)

( i v ) ANTI-SENSE: YES ( i x ) FEATURE:
    ( A ) NAME/KEY: -
    ( B ) LOCATION: 1..25
    ( D ) OTHER INFORMATION: /label=oligonucleotide
      / note="Lower strand of "deleter TMd1"in Figure
      4."

( x i ) SEQUENCE DESCRIPTION: SEQ ID NO:14:

GGAGGCCGCT CAGCCCGAAT GCACG    25

( 2 ) INFORMATION FOR SEQ ID NO:15:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( i i ) MOLECULE TYPE: DNA (plasmid)

( i v ) ANTI-SENSE: NO ( i x ) FEATURE:
    ( A ) NAME/KEY: -
    ( B ) LOCATION: 1..36
    ( D ) OTHER INFORMATION: /label=oligonucleotide
      / note="Upper strand of "deleter TMd1"in Figure
      4."

( i x ) FEATURE:
    ( A ) NAME/KEY: CDS
    ( B ) LOCATION: 1..18
    ( D ) OTHER INFORMATION: /product="deleter TMd1 amino
      acids"

( x i ) SEQUENCE DESCRIPTION: SEQ ID NO:15:

```
GGG  CTC  GTG  CAT  TCG  GGC  TGAGCGGCCT CCGTCCAG    36
Gly  Leu  Val  His  Ser  Gly
 1              5
```

( 2 ) INFORMATION FOR SEQ ID NO:16:

( i ) SEQUENCE CHARACTERISTICS:
    ( A ) LENGTH: 6 amino acids
    ( B ) TYPE: amino acid ( D ) TOPOLOGY: linear ( i i ) MOLECULE TYPE: protein ( x i ) SEQUENCE DESCRIPTION: SEQ ID NO:16:

Gly Leu Val His Ser Gly
 1               5

( 2 ) INFORMATION FOR SEQ ID NO:17:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (synthetic)

( i v ) ANTI-SENSE: YES ( i x ) FEATURE:
        ( A ) NAME/KEY: -
        ( B ) LOCATION: 1..25
        ( D ) OTHER INFORMATION: /label=oligonucleotide
              / note="Lower strand of "mutator TMm1"in Figure
              5."

( i x ) FEATURE:
        ( A ) NAME/KEY: CDS
        ( B ) LOCATION: complement (3..23)
        ( D ) OTHER INFORMATION: /function="changes CVEPVDPCFRA to
              CVEPVAPCFRA in M13TMD1"
              / product="mutator TMm1 amino acids"

( x i ) SEQUENCE DESCRIPTION: SEQ ID NO:17:

CTGAAGCACG GAGCCACGGG CTCC                    2 4

( 2 ) INFORMATION FOR SEQ ID NO:18:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: protein ( x i ) SEQUENCE DESCRIPTION: SEQ ID NO:18:

Glu Pro Val Ala Pro Cys Phe
 1               5

( 2 ) INFORMATION FOR SEQ ID NO:19:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (plasmid)

( i v ) ANTI-SENSE: NO ( i x ) FEATURE:
        ( A ) NAME/KEY: -
        ( B ) LOCATION: 1..33
        ( D ) OTHER INFORMATION: /label=oligonucleotide
              / note="Upper strand of "mutator TMm1"in Figure
              5."

( i x ) FEATURE:
        ( A ) NAME/KEY: CDS
        ( B ) LOCATION: 1..33
        ( D ) OTHER INFORMATION: /function="wild type M13TMD1
              sequence"

/ product="M13TMD1 amino acids"

( x i ) SEQUENCE DESCRIPTION: SEQ ID NO:19:

```
TGT  GTG  GAG  CCC  GTG  GAC  CCG  TGC  TTC  AGA  GCC              33
Cys  Val  Glu  Pro  Val  Asp  Pro  Cys  Phe  Arg  Ala
 1              5                        10
```

( 2 ) INFORMATION FOR SEQ ID NO:20:

( i ) SEQUENCE CHARACTERISTICS:
      ( A ) LENGTH: 11 amino acids
      ( B ) TYPE: amino acid
      ( D ) TOPOLOGY: linear ( i i ) MOLECULE TYPE: protein ( x i ) SEQUENCE DESCRIPTION: SEQ ID NO:20:

```
Cys  Val  Glu  Pro  Val  Asp  Pro  Cys  Phe  Arg  Ala
 1              5                        10
```

( 2 ) INFORMATION FOR SEQ ID NO:21:

( i ) SEQUENCE CHARACTERISTICS:
      ( A ) LENGTH: 25 base pairs
      ( B ) TYPE: nucleic acid
      ( C ) STRANDEDNESS: single
      ( D ) TOPOLOGY: linear ( i i ) MOLECULE TYPE: DNA (synthetic)

( i v ) ANTI-SENSE: YES ( i x ) FEATURE:
      ( A ) NAME/KEY: -
      ( B ) LOCATION: 1..25
      ( D ) OTHER INFORMATION: /label=oligonucleotide
         / note="Lower strand of "mutator TMm2"in Figure
         6."

( i x ) FEATURE:
      ( A ) NAME/KEY: CDS
      ( B ) LOCATION: complement (3..23)
      ( D ) OTHER INFORMATION: /function="changes CVEPVDPCFRA to
         CVEPVEPCFRA in M13TMD1"
         / product="mutator TMm2 amino acids"

( x i ) SEQUENCE DESCRIPTION: SEQ ID NO:21:

```
CTGAAGCACG  GTTCCACGGG  CTCCA                                      25
```

( 2 ) INFORMATION FOR SEQ ID NO:22:

( i ) SEQUENCE CHARACTERISTICS:
      ( A ) LENGTH: 7 amino acids
      ( B ) TYPE: amino acid
      ( D ) TOPOLOGY: linear ( i i ) MOLECULE TYPE: protein ( x i ) SEQUENCE DESCRIPTION: SEQ ID NO:22:

```
Glu  Pro  Val  Glu  Pro  Cys  Phe
 1              5
```

( 2 ) INFORMATION FOR SEQ ID NO:23:

( i ) SEQUENCE CHARACTERISTICS:
      ( A ) LENGTH: 33 base pairs
      ( B ) TYPE: nucleic acid
      ( C ) STRANDEDNESS: single
      ( D ) TOPOLOGY: linear ( i i ) MOLECULE TYPE: DNA (plasmid)

```
          ( i v ) ANTI-SENSE: NO ( i x ) FEATURE:
                    ( A ) NAME/KEY: -
                    ( B ) LOCATION: 1..33
                    ( D ) OTHER INFORMATION: /label=oligonucleotide
                          / note="Upper strand of "mutator TMm2"in Figure
                              6."

( i x ) FEATURE:
                    ( A ) NAME/KEY: CDS
                    ( B ) LOCATION: 1..33
                    ( D ) OTHER INFORMATION: /function="wild type M13TMD1
                              sequence"
                          / product="M13TMD1 amino acids"

( x i ) SEQUENCE DESCRIPTION: SEQ ID NO:23:

TGT  GTG  GAG  CCC  GTG  GAC  CCG  TGC  TTC  AGA  GCC                         33
Cys  Val  Glu  Pro  Val  Asp  Pro  Cys  Phe  Arg  Ala
 1             5                        10

( 2 ) INFORMATION FOR SEQ ID NO:24:

( i ) SEQUENCE CHARACTERISTICS:
                    ( A ) LENGTH: 11 amino acids
                    ( B ) TYPE: amino acid
                    ( D ) TOPOLOGY: linear ( i i ) MOLECULE TYPE: protein ( x i ) SEQUENCE DESCRIPTION: SEQ ID NO:24:

Cys  Val  Glu  Pro  Val  Asp  Pro  Cys  Phe  Arg  Ala
 1             5                        10

( 2 ) INFORMATION FOR SEQ ID NO:25:

( i ) SEQUENCE CHARACTERISTICS:
                    ( A ) LENGTH: 13 amino acids
                    ( B ) TYPE: amino acid
                    ( D ) TOPOLOGY: linear ( i i ) MOLECULE TYPE: peptide ( v ) FRAGMENT TYPE: internal ( i x ) FEATURE:
                    ( A ) NAME/KEY: Peptide
                    ( B ) LOCATION: 1..13
                    ( D ) OTHER INFORMATION: /label=peptide
                          / note="synthetic peptide from thrombomodulin for
                              study of thrombin binding site."

( x i ) SEQUENCE DESCRIPTION: SEQ ID NO:25:

Met  Phe  Cys  Asn  Gln  Thr  Ala  Ala  Pro  Ala  Asp  Cys  Asp
      1             5                        10

( 2 ) INFORMATION FOR SEQ ID NO:26:

( i ) SEQUENCE CHARACTERISTICS:
                    ( A ) LENGTH: 15 amino acids
                    ( B ) TYPE: amino acid
                    ( D ) TOPOLOGY: linear ( i i ) MOLECULE TYPE: peptide ( v ) FRAGMENT TYPE: internal ( i x ) FEATURE:
                    ( A ) NAME/KEY: Peptide
                    ( B ) LOCATION: 1..15
                    ( D ) OTHER INFORMATION: /label=peptide
                          / note="synthetic peptide from thrombomodulin for
                              study of thrombin binding site."
```

( x i ) SEQUENCE DESCRIPTION: SEQ ID NO:26:

Ala Cys Pro Ala Asp Ala Asp Pro Asn Thr Gln Ala Ser Cys Glu
1               5                   10                  15

( 2 ) INFORMATION FOR SEQ ID NO:27:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY: Peptide
        ( B ) LOCATION: 1..19
        ( D ) OTHER INFORMATION: /label=peptide
            / note="synthetic peptide from thrombomodulin for
            study of thrombin binding site."

( x i ) SEQUENCE DESCRIPTION: SEQ ID NO:27:

Glu Cys Pro Glu Gly Tyr Ile Leu Asp Asp Gly Phe Ile Cys Thr Asp
1               5                   10                  15

Ile Asp Glu ( 2 ) INFORMATION FOR SEQ ID NO:28:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (synthetic)

( i v ) ANTI-SENSE: YES ( i x ) FEATURE:
        ( A ) NAME/KEY: -
        ( B ) LOCATION: 1..25
        ( D ) OTHER INFORMATION: /label=oligonucleotide
            / note="Lower strand of "mutator TMm3"in Figure
            10."

( i x ) FEATURE:
        ( A ) NAME/KEY: CDS
        ( B ) LOCATION: complement (1..24)
        ( D ) OTHER INFORMATION: /function="changes GLGFPDPCFR to
            GLGFPEPCFR in M13TMD7"
            / product="mutator TMm3 amino acids"

( x i ) SEQUENCE DESCRIPTION: SEQ ID NO:28:

GAAGCACGGT TCGGGGAACC CCAGG                      25

( 2 ) INFORMATION FOR SEQ ID NO:29:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: protein ( x i ) SEQUENCE DESCRIPTION: SEQ ID NO:29:

Leu Gly Phe Pro Glu Pro Cys Phe
1               5

( 2 ) INFORMATION FOR SEQ ID NO:30:

( i ) SEQUENCE CHARACTERISTICS:
  ( A ) LENGTH: 30 base pairs
  ( B ) TYPE: nucleic acid
  ( C ) STRANDEDNESS: single
  ( D ) TOPOLOGY: linear ( i i ) MOLECULE TYPE: DNA (plasmid)

( i v ) ANTI-SENSE: NO ( i x ) FEATURE:
  ( A ) NAME/KEY: -
  ( B ) LOCATION: 1..30
  ( D ) OTHER INFORMATION: /label=oligonucleotide
    / note="Upper strand of "mutator TMm3" in Figure 10."

( i x ) FEATURE:
  ( A ) NAME/KEY: CDS
  ( B ) LOCATION: 1..30
  ( D ) OTHER INFORMATION: /function="wild type M13TMD7 sequence"
    / product="M13TMD7 amino acids"

( x i ) SEQUENCE DESCRIPTION: SEQ ID NO:30:

| GGC | CTG | GGG | TTC | CCC | GAC | CCG | TGC | TTC | AGA | 30 |
|-----|-----|-----|-----|-----|-----|-----|-----|-----|-----|----|
| Gly | Leu | Gly | Phe | Pro | Asp | Pro | Cys | Phe | Arg |    |
| 1   |     |     |     | 5   |     |     |     |     | 10  |    |

( 2 ) INFORMATION FOR SEQ ID NO:31:

( i ) SEQUENCE CHARACTERISTICS:
  ( A ) LENGTH: 10 amino acids
  ( B ) TYPE: amino acid
  ( D ) TOPOLOGY: linear ( i i ) MOLECULE TYPE: protein ( x i ) SEQUENCE DESCRIPTION: SEQ ID NO:31:

| Gly | Leu | Gly | Phe | Pro | Asp | Pro | Cys | Phe | Arg |
|-----|-----|-----|-----|-----|-----|-----|-----|-----|-----|
| 1   |     |     |     | 5   |     |     |     |     | 10  |

( 2 ) INFORMATION FOR SEQ ID NO:32:

( i ) SEQUENCE CHARACTERISTICS:
  ( A ) LENGTH: 27 base pairs
  ( B ) TYPE: nucleic acid
  ( C ) STRANDEDNESS: single
  ( D ) TOPOLOGY: linear ( i i ) MOLECULE TYPE: DNA (synthetic)

( i v ) ANTI-SENSE: YES ( i x ) FEATURE:
  ( A ) NAME/KEY: -
  ( B ) LOCATION: 1..28
  ( D ) OTHER INFORMATION: /label=oligonucleotide
    / note="Lower strand of "mutator TMm4" in Figure 13."

( i x ) FEATURE:
  ( A ) NAME/KEY: CDS
  ( B ) LOCATION: complement (1..24)
  ( D ) OTHER INFORMATION: /function="Changes GLGFPDPCFR to GLGFPDDPFR in M13TMD7"
    / product="TMm4 amino acids"

( x i ) SEQUENCE DESCRIPTION: SEQ ID NO:32:

GAAGCACGGG TCGTCGGGGA ACCCCAG    27

( 2 ) INFORMATION FOR SEQ ID NO:33:

( i ) SEQUENCE CHARACTERISTICS:

(A) LENGTH: 9 amino acids
(B) TYPE: amino acid
(D) TOPOLOGY: linear (ii) MOLECULE TYPE: protein (xi) SEQUENCE DESCRIPTION: SEQ ID NO:33:

Leu Gly Phe Pro Asp Asp Pro Cys Phe
 1               5

(2) INFORMATION FOR SEQ ID NO:34:

(i) SEQUENCE CHARACTERISTICS:
   (A) LENGTH: 30 base pairs
   (B) TYPE: nucleic acid
   (C) STRANDEDNESS: single
   (D) TOPOLOGY: linear (ii) MOLECULE TYPE: DNA (plasmid)

(iv) ANTI-SENSE: NO (ix) FEATURE:
   (A) NAME/KEY: -
   (B) LOCATION: 1..30
   (D) OTHER INFORMATION: /label=oligonucleotide
        / note="Upper strand of "mutator TMm4"in Figure
        13."

(ix) FEATURE:
   (A) NAME/KEY: CDS
   (B) LOCATION: 1..30
   (D) OTHER INFORMATION: /function="wild type M13TMD7
        sequence"
        / product="M13TMD7 amino acids"

(xi) SEQUENCE DESCRIPTION: SEQ ID NO:34:

GGC CTG GGG TTC CCC GAC CCG TGC TTC AGA                    30
Gly Leu Gly Phe Pro Asp Pro Cys Phe Arg
 1               5                  10

(2) INFORMATION FOR SEQ ID NO:35:

(i) SEQUENCE CHARACTERISTICS:
   (A) LENGTH: 10 amino acids
   (B) TYPE: amino acid
   (D) TOPOLOGY: linear (ii) MOLECULE TYPE: protein (xi) SEQUENCE DESCRIPTION: SEQ ID NO:35:

Gly Leu Gly Phe Pro Asp Pro Cys Phe Arg
 1               5                  10

(2) INFORMATION FOR SEQ ID NO:36:

(i) SEQUENCE CHARACTERISTICS:
   (A) LENGTH: 31 base pairs
   (B) TYPE: nucleic acid
   (C) STRANDEDNESS: single
   (D) TOPOLOGY: linear (ii) MOLECULE TYPE: DNA (synthetic)

(iv) ANTI-SENSE: YES (ix) FEATURE:
   (A) NAME/KEY: -
   (B) LOCATION: 1..31
   (D) OTHER INFORMATION: /label=oligonucleotide
        / note="Lower strand of "mutator TMm5"in Figure
        14."

(ix) FEATURE:

(A) NAME/KEY: CDS
(B) LOCATION: complement (1..30)
(D) OTHER INFORMATION: /function="changes GLGFPDPCFR to
  GLGFPDDDPCFR in M13TMD7"
  / product="mutator TMm5 amino acids"

(xi) SEQUENCE DESCRIPTION: SEQ ID NO:36:

GAAGCACGGG TCGTCGTCGG GGAACCCCAG G    31

(2) INFORMATION FOR SEQ ID NO:37:

(i) SEQUENCE CHARACTERISTICS:
  (A) LENGTH: 10 amino acids
  (B) TYPE: amino acid
  (D) TOPOLOGY: linear (ii) MOLECULE TYPE: protein (xi) SEQUENCE DESCRIPTION: SEQ ID NO:37:

Leu Gly Phe Pro Asp Asp Asp Pro Cys Phe
 1               5                  10

(2) INFORMATION FOR SEQ ID NO:38:

(i) SEQUENCE CHARACTERISTICS:
  (A) LENGTH: 30 base pairs
  (B) TYPE: nucleic acid
  (C) STRANDEDNESS: single
  (D) TOPOLOGY: linear (ii) MOLECULE TYPE: DNA (plasmid)

(iv) ANTI-SENSE: NO (ix) FEATURE:
  (A) NAME/KEY: -
  (B) LOCATION: 1..30
  (D) OTHER INFORMATION: /label=oligonucleotide
    / note="Upper strand of "mutator TMm5"in Figure
    14."

(ix) FEATURE:
  (A) NAME/KEY: CDS
  (B) LOCATION: 1..30
  (D) OTHER INFORMATION: /function="wild type M13TMD7
    sequence"
    / product="M13TMD7 amino acids"

(xi) SEQUENCE DESCRIPTION: SEQ ID NO:38:

GGC CTG GGG TTC CCC GAC CCG TGC TTC AGA    30
Gly Leu Gly Phe Pro Asp Pro Cys Phe Arg
 1               5                  10

(2) INFORMATION FOR SEQ ID NO:39:

(i) SEQUENCE CHARACTERISTICS:
  (A) LENGTH: 10 amino acids
  (B) TYPE: amino acid
  (D) TOPOLOGY: linear (ii) MOLECULE TYPE: protein (xi) SEQUENCE DESCRIPTION: SEQ ID NO:39:

Gly Leu Gly Phe Pro Asp Pro Cys Phe Arg
 1               5                  10

(2) INFORMATION FOR SEQ ID NO:40:

(i) SEQUENCE CHARACTERISTICS:
  (A) LENGTH: 28 base pairs
  (B) TYPE: nucleic acid
  (C) STRANDEDNESS: single (D) TOPOLOGY: linear (ii) MOLECULE TYPE: DNA (synthetic)

(iv) ANTI-SENSE: YES (ix) FEATURE:
(A) NAME/KEY: -
(B) LOCATION: 1..28
(D) OTHER INFORMATION: /label=oligonucleotide
/ note="Lower strand of "mutator TMm6"in Figure 15."

(ix) FEATURE:
(A) NAME/KEY: CDS
(B) LOCATION: complement (1..27)
(D) OTHER INFORMATION: /function="changes GLGFPDPCFR to GLGFPEDPCFR in M13TMD7"
/ product="mutator TMm6 amino acids"

(xi) SEQUENCE DESCRIPTION: SEQ ID NO:40:

GAAGCACGGG TCTTCGGGGA ACCCCAGG                    28

(2) INFORMATION FOR SEQ ID NO:41:

(i) SEQUENCE CHARACTERISTICS:
(A) LENGTH: 9 amino acids
(B) TYPE: amino acid
(D) TOPOLOGY: linear (ii) MOLECULE TYPE: protein (xi) SEQUENCE DESCRIPTION: SEQ ID NO:41:

Leu Gly Phe Pro Glu Asp Pro Cys Phe
 1               5

(2) INFORMATION FOR SEQ ID NO:42:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: DNA (plasmid)

(iv) ANTI-SENSE: NO (ix) FEATURE:
(A) NAME/KEY: -
(B) LOCATION: 1..30
(D) OTHER INFORMATION: /label=oligonucleotide
/ note="Upper strand of "mutator TMm6"in Figure 15."

(ix) FEATURE:
(A) NAME/KEY: CDS
(B) LOCATION: 1..30
(D) OTHER INFORMATION: /function="wild type M13TMD7 sequence"
/ product="M13TMD7 amino acids"

(xi) SEQUENCE DESCRIPTION: SEQ ID NO:42:

GGC CTG GGG TTC CCC GAC CCG TGC TTC AGA           30
Gly Leu Gly Phe Pro Asp Pro Cys Phe Arg
 1               5                   10

(2) INFORMATION FOR SEQ ID NO:43:

(i) SEQUENCE CHARACTERISTICS:
(A) LENGTH: 10 amino acids
(B) TYPE: amino acid
(D) TOPOLOGY: linear (ii) MOLECULE TYPE: protein (xi) SEQUENCE DESCRIPTION: SEQ ID NO:43:

Gly Leu Gly Phe Pro Asp Pro Cys Phe Arg
 1               5                  10

(2) INFORMATION FOR SEQ ID NO:44:

(i) SEQUENCE CHARACTERISTICS:
        (A) LENGTH: 74 base pairs
        (B) TYPE: nucleic acid
        (C) STRANDEDNESS: single
        (D) TOPOLOGY: linear (ii) MOLECULE TYPE: DNA (synthetic)

(iv) ANTI-SENSE: NO (ix) FEATURE:
        (A) NAME/KEY: -
        (B) LOCATION: 1..74
        (D) OTHER INFORMATION: /label=oligonucleotide
            / note="5'portion of upper strand of PTTM linker, Figure 31."

(xi) SEQUENCE DESCRIPTION: SEQ ID NO:44:

```
AGCTTAGCTG ACACACTATG GCGCACGTCC GAGGCTTGCA GCTGCCTGGC TGCCTGGCCC    60

TGGCTGCCCT GTGT                                                      74
```

(2) INFORMATION FOR SEQ ID NO:45:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ii) MOLECULE TYPE: DNA (synthetic)

(iv) ANTI-SENSE: NO (ix) FEATURE:
        (A) NAME/KEY: -
        (B) LOCATION: 1..81
        (D) OTHER INFORMATION: /label=oligonucleotide
            / note="3'portion of upper strand of PTMM linker, Figure 31."

(xi) SEQUENCE DESCRIPTION: SEQ ID NO:45:

```
AGCCTTGTGC ACAGCCAGCA TGTGTTCCTG GCTCCTCAGC AAGCACGGTC GCTGCTCGAG    60

CGGGTCCGGC GACCCGTGGA A                                              81
```

(2) INFORMATION FOR SEQ ID NO:46:

(i) SEQUENCE CHARACTERISTICS:
        (A) LENGTH: 83 base pairs
        (B) TYPE: nucleic acid
        (C) STRANDEDNESS: single
        (D) TOPOLOGY: linear (ii) MOLECULE TYPE: DNA (synthetic)

(iv) ANTI-SENSE: YES (ix) FEATURE:
        (A) NAME/KEY: -
        (B) LOCATION: 1..73
        (D) OTHER INFORMATION: /label=oligonucleotide
            / note="3'portion of lower strand of PTTM linker, Figure 31."

(xi) SEQUENCE DESCRIPTION: SEQ ID NO:46:

GTGCACAAAG GCTACACAGG GCAGCCAGGG CCAGGCAGCC AGGCAGCTGC AAGCCTCGGA    60

CGTGCGCCAT AGTGTGTCAG CTA    83

(2) INFORMATION FOR SEQ ID NO:47:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: DNA (synthetic)

(iv) ANTI-SENSE: YES (ix) FEATURE:
        (A) NAME/KEY: -
        (B) LOCATION: 1..69
        (D) OTHER INFORMATION: /label=oligonucleotide
            / note="5'portion of lower strand of PTTM linker,
            Figure 31."

(xi) SEQUENCE DESCRIPTION: SEQ ID NO:47:

TTCCACGGGT CGCCGGACCC GCTCGAGCAG CGACCGTGCT TGCTGAGGAG CCAGGAACAC    60

ATGCTGGCT    69

(2) INFORMATION FOR SEQ ID NO:48:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (ii) MOLECULE TYPE: DNA (synthetic)

(iv) ANTI-SENSE: NO (ix) FEATURE:
        (A) NAME/KEY: -
        (B) LOCATION: 1..84
        (D) OTHER INFORMATION: /label=oligonucleotide
            / note="3'portion of upper strand of PTTM2
            linker, Figure 32."

(xi) SEQUENCE DESCRIPTION: SEQ ID NO:48:

AGCCTTGTGC ACAGCCAGCA TGTGTTCCTG GCTCCTCAGC AAGCACGGTC GCTGCTCGAG    60

CGGGTCCGGC GACCCGTGGA AGAC    84

(2) INFORMATION FOR SEQ ID NO:49:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: DNA (synthetic)

(iv) ANTI-SENSE: YES (ix) FEATURE:
        (A) NAME/KEY: -
        (B) LOCATION: 1..71
        (D) OTHER INFORMATION: /label=oligonucleotide
            / note="5'portion of lower strand of PTTM2
            linker, Figure 32."

(xi) SEQUENCE DESCRIPTION: SEQ ID NO:49:

GTCTTCCACG GGTCGCCGGA CCCGCTCGAG CAGCGACCGT GCTTGCTGAG GAGCCAGGAA    60

CACATGCTGG CT 72

( 2 ) INFORMATION FOR SEQ ID NO:50:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY: Peptide
        ( B ) LOCATION: 1..8
        ( D ) OTHER INFORMATION: /label=peptide
            / note="peptide E456Gla"

( x i ) SEQUENCE DESCRIPTION: SEQ ID NO:50:

Pro Val Xaa Pro Xaa Phe Arg Ala
1               5

( 2 ) INFORMATION FOR SEQ ID NO:51:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY: Peptide
        ( B ) LOCATION: 1..9
        ( D ) OTHER INFORMATION: /label=peptide
            / note="polypeptide E456GlaAsp"

( x i ) SEQUENCE DESCRIPTION: SEQ ID NO:51:

Pro Val Xaa Asp Pro Xaa Phe Arg Ala
1               5

( 2 ) INFORMATION FOR SEQ ID NO:52:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (synthetic)

( i v ) ANTI-SENSE: NO ( i x ) FEATURE:
        ( A ) NAME/KEY: -
        ( B ) LOCATION: 1..35
        ( D ) OTHER INFORMATION: /label=oligonucleotide
            / note="Upper strand of PGTM linker, Figure 40."

( i x ) FEATURE:
        ( A ) NAME/KEY: CDS
        ( B ) LOCATION: 21..35
        ( D ) OTHER INFORMATION: /function="leader peptide"
            / product="TMD7 coding region"

( x i ) SEQUENCE DESCRIPTION: SEQ ID NO:52:

CGCGTCGATT CACAGTCAAA ATG CTT GGG GTC CTG 35
                        Met Leu Gly Val Leu
                         1               5

( 2 ) INFORMATION FOR SEQ ID NO:53:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: protein ( x i ) SEQUENCE DESCRIPTION: SEQ ID NO:53:

Met Leu Gly Val Leu
1               5

( 2 ) INFORMATION FOR SEQ ID NO:54:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (synthetic)

( i v ) ANTI-SENSE: YES ( i x ) FEATURE:
        ( A ) NAME/KEY: -
        ( B ) LOCATION: 1..35
        ( D ) OTHER INFORMATION: /label=oligonucleotide
           / note="Lower strand of PGTM linker, Figure 40."

( x i ) SEQUENCE DESCRIPTION: SEQ ID NO:54:

GGACCAGGAC CCCAAGCATT TTGACTGTGA ATCGA      35

( 2 ) INFORMATION FOR SEQ ID NO:55:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY: Peptide
        ( B ) LOCATION: 1..20
        ( D ) OTHER INFORMATION: /label=peptide
           / note="Amino terminal sequence of purified
           polypeptides obtained in Examples 8-(2), -(4) and
           - ( 5 )."

( x i ) SEQUENCE DESCRIPTION: SEQ ID NO:55:

Asp Pro Xaa Phe Arg Ala Asn Xaa Glu Tyr Gln Xaa Gln Pro Leu Xaa
1               5                   10                  15

Gln Thr Ser Tyr
            20

( 2 ) INFORMATION FOR SEQ ID NO:56:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (synthetic)

( i v ) ANTI-SENSE: YES ( i x ) FEATURE:

( A ) NAME/KEY: -
              ( B ) LOCATION: 1..25
              ( D ) OTHER INFORMATION: /label=oligonucleotide
                      / note="Lower strand of "deleter TMD9" in Figure
                      54"

( x i ) SEQUENCE DESCRIPTION: SEQ ID NO:56:

CGGAGGCCGC TCAGATGTCC GTGCA                                                                25

( 2 ) INFORMATION FOR SEQ ID NO:57:

( i ) SEQUENCE CHARACTERISTICS:
                ( A ) LENGTH: 36 base pairs
                ( B ) TYPE: nucleic acid
                ( C ) STRANDEDNESS: single
                ( D ) TOPOLOGY: linear ( i i ) MOLECULE TYPE: DNA (plasmid)

( i v ) ANTI-SENSE: NO ( i x ) FEATURE:
                ( A ) NAME/KEY: -
                ( B ) LOCATION: 1..36
                ( D ) OTHER INFORMATION: /label=oligonucleotide
                        / note="Upper strand of "deleter TMD9" in Figure
                        54."

( i x ) FEATURE:
                ( A ) NAME/KEY: CDS
                ( B ) LOCATION: 1..18
                ( D ) OTHER INFORMATION: /function="truncated wild type
                        M13TMD7 sequence"
                        / product="M13TMD7 amino acids"

( x i ) SEQUENCE DESCRIPTION: SEQ ID NO:57:

TTC ATC TGC ACG GAC ATC TGAGCGGCCT CCGTCCAG                                                36
Phe Ile Cys Thr Asp Ile
 1               5

( 2 ) INFORMATION FOR SEQ ID NO:58:

( i ) SEQUENCE CHARACTERISTICS:
                ( A ) LENGTH: 6 amino acids
                ( B ) TYPE: amino acid
                ( D ) TOPOLOGY: linear ( i i ) MOLECULE TYPE: protein ( x i ) SEQUENCE DESCRIPTION: SEQ ID NO:58:

Phe Ile Cys Thr Asp Ile
 1               5

( 2 ) INFORMATION FOR SEQ ID NO:59:

( i ) SEQUENCE CHARACTERISTICS:
                ( A ) LENGTH: 575 amino acids
                ( B ) TYPE: amino acid
                ( D ) TOPOLOGY: linear ( i i ) MOLECULE TYPE: protein ( v ) FRAGMENT TYPE: internal ( v i ) ORIGINAL SOURCE:
                ( A ) ORGANISM: Homo sapiens ( i x ) FEATURE:
                ( A ) NAME/KEY: Protein
                ( B ) LOCATION: 1..575
                ( D ) OTHER INFORMATION: /label=protein
                        / note="human thrombomodulin"

( x i ) SEQUENCE DESCRIPTION: SEQ ID NO:59:

| | | | | | | | | | | | | | | | |
|---|---|---|---|---|---|---|---|---|---|---|---|---|---|---|---|
| Met 1 | Leu | Gly | Val 5 | Leu | Val | Leu | Gly | Ala 10 | Leu | Ala | Leu | Ala | Gly 15 | Leu | Gly |
| Phe | Pro | Ala | Pro 20 | Ala | Glu | Pro | Gln | Pro 25 | Gly | Gly | Ser | Gln | Cys 30 | Val | Glu |
| His | Asp | Cys 35 | Phe | Ala | Leu | Tyr | Pro 40 | Gly | Pro | Ala | Thr | Phe 45 | Leu | Asn | Ala |
| Ser | Gln 50 | Ile | Cys | Asp | Gly | Leu 55 | Arg | Gly | His | Leu | Met 60 | Thr | Val | Arg | Ser |
| Ser 65 | Val | Ala | Ala | Asp | Val 70 | Ile | Ser | Leu | Leu | Leu 75 | Asn | Gly | Asp | Gly | Gly 80 |
| Val | Gly | Arg | Arg | Arg 85 | Leu | Trp | Ile | Gly | Leu 90 | Gln | Leu | Pro | Pro | Gly 95 | Cys |
| Gly | Asp | Pro | Lys 100 | Arg | Leu | Gly | Pro | Leu 105 | Arg | Gly | Phe | Gln | Trp 110 | Val | Thr |
| Gly | Asp | Asn 115 | Asn | Thr | Ser | Tyr | Ser 120 | Arg | Trp | Ala | Arg | Leu 125 | Asp | Leu | Asn |
| Gly | Ala | Pro 130 | Leu | Cys | Gly | Pro 135 | Leu | Cys | Val | Ala | Val 140 | Ser | Ala | Ala | Glu |
| Ala 145 | Thr | Val | Pro | Ser | Glu 150 | Pro | Ile | Trp | Glu | Glu 155 | Gln | Gln | Cys | Glu | Val 160 |
| Lys | Ala | Asp | Gly | Phe 165 | Leu | Cys | Glu | Phe | His 170 | Phe | Pro | Ala | Thr | Cys 175 | Arg |
| Pro | Leu | Ala | Val 180 | Glu | Pro | Gly | Ala | Ala 185 | Ala | Ala | Val | Ser 190 | Ile | Thr | |
| Tyr | Gly | Thr 195 | Pro | Phe | Ala | Ala | Arg 200 | Gly | Ala | Asp | Phe | Gln 205 | Ala | Leu | Pro |
| Val | Gly 210 | Ser | Ser | Ala | Ala | Val 215 | Ala | Pro | Leu | Gly | Leu 220 | Gln | Leu | Met | Cys |
| Thr 225 | Ala | Pro | Pro | Gly | Ala 230 | Val | Gln | Gly | His | Trp 235 | Ala | Arg | Glu | Ala | Pro 240 |
| Gly | Ala | Trp | Asp | Cys 245 | Ser | Val | Glu | Asn | Gly 250 | Gly | Cys | Glu | His | Ala 255 | Cys |
| Asn | Ala | Ile | Pro 260 | Gly | Ala | Pro | Arg | Cys 265 | Gln | Cys | Pro | Ala | Gly 270 | Ala | Ala |
| Leu | Gln | Ala 275 | Asp | Gly | Arg | Ser | Cys 280 | Thr | Ala | Ser | Ala | Thr 285 | Gln | Ser | Cys |
| Asn | Asp 290 | Leu | Cys | Glu | His | Phe 295 | Cys | Val | Pro | Asn | Pro 300 | Asp | Gln | Pro | Gly |
| Ser 305 | Tyr | Ser | Cys | Met | Cys 310 | Glu | Thr | Gly | Tyr | Arg 315 | Leu | Ala | Ala | Asp | Gln 320 |
| His | Arg | Cys | Glu | Asp 325 | Val | Asp | Asp | Cys | Ile 330 | Leu | Glu | Pro | Ser | Pro 335 | Cys |
| Pro | Gln | Arg | Cys 340 | Val | Asn | Thr | Gln | Gly 345 | Gly | Phe | Glu | Cys | His 350 | Cys | Tyr |
| Pro | Asn | Tyr 355 | Asp | Leu | Val | Asp | Gly 360 | Glu | Cys | Val | Glu | Pro 365 | Val | Asp | Pro |
| Cys | Phe 370 | Arg | Ala | Asn | Cys | Glu 375 | Tyr | Gln | Cys | Gln | Pro 380 | Leu | Asn | Gln | Thr |
| Ser 385 | Tyr | Leu | Cys | Val | Cys 390 | Ala | Glu | Gly | Phe | Ala 395 | Pro | Ile | Pro | His | Glu 400 |
| Pro | His | Arg | Cys | Gln 405 | Met | Phe | Cys | Asn | Gln 410 | Thr | Ala | Cys | Pro | Ala 415 | Asp |

| | | | | | | | | | | | | | | |
|---|---|---|---|---|---|---|---|---|---|---|---|---|---|---|
| Cys | Asp | Pro | Asn 420 | Thr | Gln | Ala | Ser | Cys 425 | Glu | Cys | Pro | Glu 430 | Gly | Tyr | Ile |
| Leu | Asp | Asp 435 | Gly | Phe | Ile | Cys | Thr 440 | Asp | Ile | Asp | Glu | Cys 445 | Glu | Asn | Gly |
| Gly | Phe 450 | Cys | Ser | Gly | Val | Cys 455 | His | Asn | Leu | Pro | Gly 460 | Thr | Phe | Glu | Cys |
| Ile 465 | Cys | Gly | Pro | Asp | Ser 470 | Ala | Leu | Val | Arg | His 475 | Ile | Gly | Thr | Asp | Cys 480 |
| Asp | Ser | Gly | Lys | Val 485 | Asp | Gly | Asp | Ser 490 | Gly | Ser | Gly | Glu | Pro 495 | Pro |
| Pro | Ser | Pro | Thr 500 | Pro | Gly | Ser | Thr | Leu 505 | Thr | Pro | Pro | Ala | Val 510 | Gly | Leu |
| Val | His | Ser 515 | Gly | Leu | Leu | Ile | Gly 520 | Ile | Ser | Ile | Ala | Ser 525 | Leu | Cys | Leu |
| Val | Val 530 | Ala | Leu | Leu | Ala | Leu 535 | Leu | Cys | His | Leu | Arg 540 | Lys | Lys | Gln | Gly |
| Ala 545 | Ala | Arg | Ala | Lys | Met 550 | Glu | Tyr | Lys | Cys | Ala 555 | Ala | Pro | Ser | Lys | Glu 560 |
| Val | Val | Leu | Gln | His 565 | Val | Arg | Thr | Glu | Arg 570 | Thr | Pro | Gln | Arg | Leu 575 |

( 2 ) INFORMATION FOR SEQ ID NO:60:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (synthetic)

( i v ) ANTI-SENSE: NO ( i x ) FEATURE:
        ( A ) NAME/KEY: -
        ( B ) LOCATION: 1..28
        ( D ) OTHER INFORMATION: /label=oligonucleotide
            / note="5'portion of upper strand of ACY linker, Figure 56."

( x i ) SEQUENCE DESCRIPTION: SEQ ID NO:60:

CGCGTCGATT CACAGTCAAA ATGACGAT                     28

( 2 ) INFORMATION FOR SEQ ID NO:61:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (synthetic)

( i v ) ANTI-SENSE: NO ( i x ) FEATURE:
        ( A ) NAME/KEY: -
        ( B ) LOCATION: 1..30
        ( D ) OTHER INFORMATION: /label=oligonucleotide
            / note="3'portion of upper strand of ACY linker, Figure 56."

( x i ) SEQUENCE DESCRIPTION: SEQ ID NO:61:

GGCGGCCAAG ACCGATCGCG AGGCCCTGCA                    30

( 2 ) INFORMATION FOR SEQ ID NO:62:

(i) SEQUENCE CHARACTERISTICS:
    (A) LENGTH: 30 base pairs
    (B) TYPE: nucleic acid
    (C) STRANDEDNESS: single
    (D) TOPOLOGY: linear (ii) MOLECULE TYPE: DNA (synthetic)

(iv) ANTI-SENSE: YES (ix) FEATURE:
    (A) NAME/KEY: -
    (B) LOCATION: 1..30
    (D) OTHER INFORMATION: /label=oligonucleotide
        / note="3'portion of lower strand of ACY linker,
        Figure 56."

(xi) SEQUENCE DESCRIPTION: SEQ ID NO:62:

GCCGCCATCG TCATTTTGAC TGTGAATCGA        30

(2) INFORMATION FOR SEQ ID NO:63:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: DNA (synthetic)

(iv) ANTI-SENSE: YES (ix) FEATURE:
    (A) NAME/KEY: -
    (B) LOCATION: 1..20
    (D) OTHER INFORMATION: /label=oligonucleotide
        / note="5'portion of lower strand of ACY linker,
        Figure 56."

(xi) SEQUENCE DESCRIPTION: SEQ ID NO:63:

GGGCCTCGCG ATCGGTCTTG        20

(2) INFORMATION FOR SEQ ID NO:64:

(i) SEQUENCE CHARACTERISTICS:
    (A) LENGTH: 58 base pairs
    (B) TYPE: nucleic acid
    (C) STRANDEDNESS: single
    (D) TOPOLOGY: linear (ii) MOLECULE TYPE: DNA (synthetic)

(iv) ANTI-SENSE: NO (ix) FEATURE:
    (A) NAME/KEY: -
    (B) LOCATION: 1..58
    (D) OTHER INFORMATION: /label=oligonucleotide
        / note="complete upper strand of ACY linker,
        Figure 56."

(ix) FEATURE:
    (A) NAME/KEY: CDS
    (B) LOCATION: 21..56
    (D) OTHER INFORMATION: /function="leader peptide"
        / product="cephalosporin C acylase amino terminus"

(xi) SEQUENCE DESCRIPTION: SEQ ID NO:64:

CGCGTCGATT CACAGTCAAA ATG ACG ATG GCG GCC AAG ACC GAT CGC GAG        50
                     Met Thr Met Ala Ala Lys Thr Asp Arg Glu
                      1               5                   10
GCC CTG CA        58
Ala Leu ( 2 ) INFORMATION FOR SEQ ID NO:65:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: protein ( x i ) SEQUENCE DESCRIPTION: SEQ ID NO:65:

```
Met  Thr  Met  Ala  Ala  Lys  Thr  Asp  Arg  Glu  Ala  Leu
 1                    5                      10
```

( 2 ) INFORMATION FOR SEQ ID NO:66:

( i ) SEQUENCE CHARACTERISTICS:
        ( A ) LENGTH: 60 base pairs
        ( B ) TYPE: nucleic acid
        ( C ) STRANDEDNESS: double
        ( D ) TOPOLOGY: linear ( i i ) MOLECULE TYPE: DNA (synthetic)

( i x ) FEATURE:
        ( A ) NAME/KEY: -
        ( B ) LOCATION: 1..60
        ( D ) OTHER INFORMATION: /label=oligonucleotide
            / note="polylinker from pUC18."

( x i ) SEQUENCE DESCRIPTION: SEQ ID NO:66:

```
GAATTCGAGC  TCGGTACCCG  GGGATCCTCT  AGAGTCGACC  TGCAGGCATG  CAAGCTTGGC        60
```

( 2 ) INFORMATION FOR SEQ ID NO:67:

( i ) SEQUENCE CHARACTERISTICS:
        ( A ) LENGTH: 26 base pairs
        ( B ) TYPE: nucleic acid
        ( C ) STRANDEDNESS: double
        ( D ) TOPOLOGY: linear ( i i ) MOLECULE TYPE: DNA (synthetic)

( i v ) ANTI-SENSE: NO ( i x ) FEATURE:
        ( A ) NAME/KEY: -
        ( B ) LOCATION: 1..26
        ( D ) OTHER INFORMATION: /label=oligonucleotide
            / note="'SF linker', Figure 57."

( x i ) SEQUENCE DESCRIPTION: SEQ ID NO:67:

```
TGGCCGAGGC  GGCCAGATCT  CCATGG                                              26
```

( 2 ) INFORMATION FOR SEQ ID NO:68:

( i ) SEQUENCE CHARACTERISTICS:
        ( A ) LENGTH: 90 base pairs
        ( B ) TYPE: nucleic acid
        ( C ) STRANDEDNESS: double
        ( D ) TOPOLOGY: linear ( i i ) MOLECULE TYPE: DNA (synthetic)

( i x ) FEATURE:
        ( A ) NAME/KEY: -
        ( B ) LOCATION: 1..90
        ( D ) OTHER INFORMATION: /label=oligonucleotide
            / note="SF linker inserted into EcoRI site of
              pUC18 polylinker to give pSFI-1, an intermediate
              in construction of pSFI-2, Figure 57."

( x i ) SEQUENCE DESCRIPTION: SEQ ID NO:68:

5,574,007

103                                                                                                   104
-continued

GAATTTGGCC GAGGCGGCCA GATCTCCATG GAATTCGAGC TCGGTACCCG GGGATCCTCT        60

AGAGTCGACC TGCAGGCATG CAAGCTTGGC                                        90

( 2 ) INFORMATION FOR SEQ ID NO:69:

( i ) SEQUENCE CHARACTERISTICS:
        ( A ) LENGTH: 116 base pairs
        ( B ) TYPE: nucleic acid
        ( C ) STRANDEDNESS: double
        ( D ) TOPOLOGY: linear ( i i ) MOLECULE TYPE: DNA (synthetic)

( i x ) FEATURE:
        ( A ) NAME/KEY: -
        ( B ) LOCATION: 1..116
        ( D ) OTHER INFORMATION: /label=oligonucleotide
          / note="SF linker inserted into the HincII site of
          plasmid pSFI-1 to give plasmid pSFI-2; Figure 57."

( x i ) SEQUENCE DESCRIPTION: SEQ ID NO:69:

GAATTTGGCC GAGGCGGCCA GATCTCCATG GAATTCGAGC TCGGTACCCG GGGATCCTCT        60

AGAGTCTGGC CGAGGCGCCC AGATCTCCAT GGGACCTGCA GGCATGCAAG CTTGGC          116

( 2 ) INFORMATION FOR SEQ ID NO:70:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (synthetic)

( i v ) ANTI-SENSE: NO ( i x ) FEATURE:
        ( A ) NAME/KEY: -
        ( B ) LOCATION: 1..24
        ( D ) OTHER INFORMATION: /label=oligonucleotide
          / note="synthetic oligonucleotide derived from S.
          cerevisiae PGK gene sequence. Used to screen
          library to isolate pYPGK1."

( x i ) SEQUENCE DESCRIPTION: SEQ ID NO:70:

CAGATCATCA AGAAGTAATT ATCT                                              24

( 2 ) INFORMATION FOR SEQ ID NO:71:

( i ) SEQUENCE CHARACTERISTICS:
        ( A ) LENGTH: 3306 base pairs
        ( B ) TYPE: nucleic acid
        ( C ) STRANDEDNESS: double
        ( D ) TOPOLOGY: linear ( i i ) MOLECULE TYPE: cDNA ( v i ) ORIGINAL SOURCE:
        ( A ) ORGANISM: Acremonium chrysogenum ( i x ) FEATURE:
        ( A ) NAME/KEY: -
        ( B ) LOCATION: 1..3306
        ( D ) OTHER INFORMATION: /label=PGK_gene
          / note="Nucleotide sequence of region A in Figure
          59. The sequence is presented as Figure 61."

( i x ) FEATURE:
        ( A ) NAME/KEY: exon
        ( B ) LOCATION: 1252..1317

( i x ) FEATURE:
        ( A ) NAME/KEY: exon (B) LOCATION: 1463..1883

(ix) FEATURE:
    (A) NAME/KEY: exon
    (B) LOCATION: 1948..2715

(ix) FEATURE:
    (A) NAME/KEY: CDS
    (B) LOCATION: join(1252..1317, 1463..1883, 1948..2714)

(xi) SEQUENCE DESCRIPTION: SEQ ID NO:71:

| | | | | | | |
|---|---|---|---|---|---|---|
| AGATCTTTCA | GGATGGTGCT | GATGGGGGCG | AGGGGCAAAA | CACCACCGGG | TGATCCTCGA | 60 |
| CGTGGAGGTT | GTGATAGAAG | GAGAGCAAGG | GGACGATGAT | GATGTGGACC | TTGTGATTGA | 120 |
| GGAGGATCAT | GGCGATGAGG | ATGAGGAAGA | GGATTTACCC | GATCTGATCG | ATCCTCCCCC | 180 |
| GAACGACGGG | GACCAGGAGC | GGGAGGGAGC | AGCCGGGCAC | GAGGCGATCA | GGCGCGAGGG | 240 |
| TCAAGAACCA | GACCGACAAG | GCCAGCACCA | AGAACAGGAA | CCGGCAGCAC | CGGAGGCACC | 300 |
| CGCAGCGGAC | GAGCAGCTCC | CGCCACAGAA | CAACCACGAA | GTACCGCCCG | CCCCGCCGGC | 360 |
| CAACCGCGTC | GGTCTGGGCA | CCGTCCTGTC | CAACTTCTCA | AACCAGCTCG | TCAGCGCCCT | 420 |
| CATCCTGCCG | GGAATCTCCT | TCGCCATGGG | CGAAGCTCTA | CGGGTGGCGC | TCCCCGCCAG | 480 |
| GTGGACACAG | TCGTCTCTGT | GCCCCTTTAG | GAACGCCCTC | CGGGCCTACT | CCAGCAGCAG | 540 |
| TGGGGTCGCA | GCCTCGTGGG | TGGGTGCCTG | TACGTGTGAT | CAAGGACGTG | ATCCGGGTCT | 600 |
| ACGCCAAGCA | CCGCAAGGTG | GCGGCTATGG | GCAACCGGCG | GGTCAGAAAC | GTGGACCGGC | 660 |
| CAAGGAGGAA | CGCGGGCTCG | TCGAGATGAA | ATCCAGTGAT | ACAACGCAGC | ATGGGAACGG | 720 |
| AGTTTGGGCT | GGCCAGGGTA | GATGACGGTA | TCCAAGGATT | ATACTATTAA | TATAGCGACT | 780 |
| ACTAGTAATT | ACTACTGGGC | AGAGTCTACC | GCCCAACGTT | GGTATGGGTT | ATTTGTAAAC | 840 |
| GTTCCACGCC | AATCTTTTCC | ACCGTCAGAA | TCGGCGTATC | ATTGCAATTG | ACGGCACCAG | 900 |
| AATGATGCGT | TGGTACTAAT | AGTAGGTACG | AGGTAACAAC | AGTAAAGATA | CTGCCATTAT | 960 |
| AGAAAGAGGA | AGTCGCTCCC | TCGGCAATGC | CGCGCCACAA | GCGCCTTTGG | CCGAGGACGC | 1020 |
| CGGAACCCAA | ACGCAGATCA | GATCGGGGGC | AACGGGAAGC | TTAGGGACGG | AAATGGGGTA | 1080 |
| ATACGAGTAA | TAATCCCCCA | CCACCACCAA | GAAGCTCCCA | ACCCAAAAGC | TTCCTGCGTC | 1140 |
| CTTTTCACCC | CGCCATCTTC | TCCCGACAGA | AAGACAAAAC | AACCCACCAT | ACCACTCCAC | 1200 |
| AGAGCATTGT | TCTTCTCCTT | CAGGACTACC | ACGCGTCGAT | TCACAGTCAA | A ATG TCT | 1257 |

Met Ser
                                                                                                                                              1

| CTC | TCT | AAC | AAG | CTG | TCC | ATT | ACT | GAT | GTC | GAC | CTC | AAG | GGC | AAG | AGG | 1305 |
|---|---|---|---|---|---|---|---|---|---|---|---|---|---|---|---|---|
| Leu | Ser | Asn | Lys | Leu | Ser | Ile | Thr | Asp | Val | Asp | Leu | Lys | Gly | Lys | Arg | |
| | | 5 | | | | 10 | | | | | 15 | | | | | |

| GTC | CTG | ATT | CGG | GTACGTCTTC | CTCTCCCCAA | TTGTCCTACC | GTCGTCATTG | 1357 |
|---|---|---|---|---|---|---|---|---|
| Val | Leu | Ile | Arg | | | | | |
| | 20 | | | | | | | |

TTGCCCCTCC ATTGAGGCGA CACCGGGATG GATGGGCTAC CCAAAAAAAA AACACAACCA   1417

CAGCAATGCA TTGAGAAAAG CTAATCGAAC CCCGCCATCA CGCAG GTC GAC TTC   1471
                                                                                                         Val Asp Phe
                                                                                                         25

| AAC | GTG | CCC | CTC | GAC | GAG | AAC | AAG | AAG | ATC | ACC | AAC | AAC | CAG | CGC | ATC | 1519 |
|---|---|---|---|---|---|---|---|---|---|---|---|---|---|---|---|---|
| Asn | Val | Pro | Leu | Asp | Glu | Asn | Lys | Lys | Ile | Thr | Asn | Asn | Gln | Arg | Ile | |
| | | | 30 | | | | 35 | | | | | 40 | | | | |

| GTC | GGT | GCC | CTC | CCC | ACC | ATC | AAG | TAC | GCC | GTC | GAG | CAT | GGC | GCC | AAG | 1567 |
|---|---|---|---|---|---|---|---|---|---|---|---|---|---|---|---|---|
| Val | Gly | Ala | Leu | Pro | Thr | Ile | Lys | Tyr | Ala | Val | Glu | His | Gly | Ala | Lys | |
| | | | 45 | | | | 50 | | | | | 55 | | | | |

| GCC | GTC | ATC | CTC | ATG | TCC | CAC | CTT | GGC | CGC | CCC | AAC | GGC | ACC | CCC | AAC | 1615 |
|---|---|---|---|---|---|---|---|---|---|---|---|---|---|---|---|---|

|     |     |     |     |     |     |     |     |     |     |     |     |     |     |     |      |
| --- | --- | --- | --- | --- | --- | --- | --- | --- | --- | --- | --- | --- | --- | --- | ---- |
| Ala | Val | Ile | Leu | Met | Ser | His | Leu | Gly | Arg | Pro | Asn | Gly | Thr | Pro | Asn  |
|     |     | 60  |     |     |     |     | 65  |     |     |     |     | 70  |     |     |      |
| CCC | AAG | TAC | TCG | CTG | CAG | CCC | GTC | GTC | CCC | GAG | CTC | GAG | AAG | CTG | CTC  | 1663 |
| Pro | Lys | Tyr | Ser | Leu | Gln | Pro | Val | Val | Pro | Glu | Leu | Glu | Lys | Leu | Leu  |
|     | 75  |     |     |     |     | 80  |     |     |     |     | 85  |     |     |     |      |
| GGC | AAG | AGC | GTC | ACT | TTC | GCC | CCC | GAC | TGC | GTC | GGC | GCC | GAG | GTC | GAG  | 1711 |
| Gly | Lys | Ser | Val | Thr | Phe | Ala | Pro | Asp | Cys | Val | Gly | Ala | Glu | Val | Glu  |
| 90  |     |     |     |     | 95  |     |     |     |     | 100 |     |     |     |     | 105  |
| GGC | ATC | GTC | GCC | AAA | GCC | GAC | GGC | GGC | GCC | GTT | GTC | CTG | CTC | GAG | AAC  | 1759 |
| Gly | Ile | Val | Ala | Lys | Ala | Asp | Gly | Gly | Ala | Val | Val | Leu | Leu | Glu | Asn  |
|     |     |     | 110 |     |     |     |     | 115 |     |     |     |     | 120 |     |      |
| CTC | CGC | TTC | CAC | ATC | GAG | GAG | GAG | GGC | AGC | GCC | AAG | GAT | AAG | GAT | GGA  | 1807 |
| Leu | Arg | Phe | His | Ile | Glu | Glu | Glu | Gly | Ser | Ala | Lys | Asp | Lys | Asp | Gly  |
|     |     |     | 125 |     |     |     |     | 130 |     |     |     |     | 135 |     |      |
| AAC | AAG | ACC | AAG | GCT | GAC | AAG | GCC | AAA | GTT | GAC | GAG | TTC | CGC | AAG | GGG  | 1855 |
| Asn | Lys | Thr | Lys | Ala | Asp | Lys | Ala | Lys | Val | Asp | Glu | Phe | Arg | Lys | Gly  |
|     |     | 140 |     |     |     |     | 145 |     |     |     |     | 150 |     |     |      |

CTG ACC GCC CTG GGC GAC GTC TAC ATC   A GTATGGCTCT TCCCCGCAAG        1903
Leu Thr Ala Leu Gly Asp Val Tyr Ile
    155                 160

GTCTGGGCGT GTGCGCGTGA GGGAATATGG CTAATGACGA GCAG   AT GAC GCC TTC    1958
                                                   Asn Asp Ala Phe
                                                           165

|     |     |     |     |     |     |     |     |     |     |     |     |     |     |     |      |      |
| --- | --- | --- | --- | --- | --- | --- | --- | --- | --- | --- | --- | --- | --- | --- | ---- | ---- |
| GGC | ACC | GCC | CAC | CGC | GCC | CAC | TCC | TCC | ATG | GTC | GGT | GTC | GAC | CTC | CCC  | 2006 |
| Gly | Thr | Ala | His | Arg | Ala | His | Ser | Ser | Met | Val | Gly | Val | Asp | Leu | Pro  |
|     |     |     | 170 |     |     |     |     | 175 |     |     |     |     | 180 |     |      |
| CAG | AAG | GCC | GCC | GGC | TTC | CTC | ATG | AAG | AAG | GAG | CTC | GAC | TAC | TTC | GCG  | 2054 |
| Gln | Lys | Ala | Ala | Gly | Phe | Leu | Met | Lys | Lys | Glu | Leu | Asp | Tyr | Phe | Ala  |
|     |     | 185 |     |     |     |     | 190 |     |     |     |     | 195 |     |     |      |
| CAG | GCC | CTC | GAG | GCG | CCC | CAG | CGT | CCC | TTC | CTC | GCC | ATC | CTG | GGC | GGC  | 2102 |
| Gln | Ala | Leu | Glu | Ala | Pro | Gln | Arg | Pro | Phe | Leu | Ala | Ile | Leu | Gly | Gly  |
|     | 200 |     |     |     |     | 205 |     |     |     |     | 210 |     |     |     |      |
| GCC | AAG | GTC | TCG | GAC | AAG | ATC | CAG | CTC | ATC | GAC | AAC | CTG | CTG | GAC | AAG  | 2150 |
| Ala | Lys | Val | Ser | Asp | Lys | Ile | Gln | Leu | Ile | Asp | Asn | Leu | Leu | Asp | Lys  |
| 215 |     |     |     | 220 |     |     |     |     | 225 |     |     |     |     | 230 |      |
| GTC | AAC | ACG | CTA | ATC | ATC | TGC | GGC | GGC | ATG | GCC | TTC | ACC | TTC | AAG | AAG  | 2198 |
| Val | Asn | Thr | Leu | Ile | Ile | Cys | Gly | Gly | Met | Ala | Phe | Thr | Phe | Lys | Lys  |
|     |     |     |     | 235 |     |     |     |     | 240 |     |     |     |     | 245 |      |
| ACG | CTG | GAC | GGC | ATG | TCC | ATC | GGC | AAC | TCG | CTC | TTT | GAC | GAG | GCC | GGC  | 2246 |
| Thr | Leu | Asp | Gly | Met | Ser | Ile | Gly | Asn | Ser | Leu | Phe | Asp | Glu | Ala | Gly  |
|     |     |     | 250 |     |     |     |     | 255 |     |     |     |     | 260 |     |      |
| GCC | AAG | ACG | GTC | GCC | TCC | CTC | ATG | GAC | AAG | GCC | AAG | CAG | AAG | GGT | GTC  | 2294 |
| Ala | Lys | Thr | Val | Ala | Ser | Leu | Met | Asp | Lys | Ala | Lys | Gln | Lys | Gly | Val  |
|     |     | 265 |     |     |     |     | 270 |     |     |     |     | 275 |     |     |      |
| AAG | GTC | GTC | GTC | CCC | GTC | GAC | TAC | ATC | ACC | GCC | GAC | AAG | TTC | GAC | AAG  | 2342 |
| Lys | Val | Val | Val | Pro | Val | Asp | Tyr | Ile | Thr | Ala | Asp | Lys | Phe | Asp | Lys  |
|     | 280 |     |     |     |     | 285 |     |     |     |     | 290 |     |     |     |      |
| GAC | GCC | AAC | ACG | GGC | AAG | GCC | TCG | GAC | GCC | CAG | GGC | ATC | CCC | GAC | GGC  | 2390 |
| Asp | Ala | Asn | Thr | Gly | Lys | Ala | Ser | Asp | Ala | Gln | Gly | Ile | Pro | Asp | Gly  |
| 295 |     |     |     | 300 |     |     |     |     | 305 |     |     |     |     | 310 |      |
| TGG | ATG | GGC | CTC | GAC | TGC | GGC | GAG | GAG | TCC | ATC | AAG | CTC | TAC | CGC | GAG  | 2438 |
| Trp | Met | Gly | Leu | Asp | Cys | Gly | Glu | Glu | Ser | Ile | Lys | Leu | Tyr | Arg | Glu  |
|     |     |     | 315 |     |     |     |     | 320 |     |     |     |     | 325 |     |      |
| GCC | ATC | GAC | AAC | GCC | AAG | ACC | ATC | CTC | TGG | AAC | TGC | CCC | GCC | GGC | GTC  | 2486 |
| Ala | Ile | Asp | Asn | Ala | Lys | Thr | Ile | Leu | Trp | Asn | Cys | Pro | Ala | Gly | Val  |
|     |     |     | 330 |     |     |     |     | 335 |     |     |     |     | 340 |     |      |
| TTC | GAG | TTC | GAG | AAG | TTC | GCC | TCG | GGA | ACC | AAG | GCC | ACC | CTC | GAC | GCC  | 2534 |
| Phe | Glu | Phe | Glu | Lys | Phe | Ala | Ser | Gly | Thr | Lys | Ala | Thr | Leu | Asp | Ala  |
|     |     | 345 |     |     |     |     | 350 |     |     |     |     | 355 |     |     |      |

| GTC | GTC | GAC | GGC | GCC | CAG | AAC | GCC | GGC | AAG | ATT | GTC | ATC | ATC | GGC | GGC | 2582 |
| Val | Val | Asp | Gly | Ala | Gln | Asn | Ala | Gly | Lys | Ile | Val | Ile | Ile | Gly | Gly | |
| | 360 | | | | | 365 | | | | | 370 | | | | | |

| GGC | GAC | ACC | GCT | ACC | GTC | GCT | GCC | AAG | TAC | GGC | GTC | GAG | GAC | AAG | CTC | 2630 |
| Gly | Asp | Thr | Ala | Thr | Val | Ala | Ala | Lys | Tyr | Gly | Val | Glu | Asp | Lys | Leu | |
| 375 | | | | | 380 | | | | | 385 | | | | | 390 | |

| AGC | CAC | GTA | TCT | ACC | GGT | GGC | GGC | GCC | AGC | CTG | GAG | CTG | CTC | GAG | GGC | 2678 |
| Ser | His | Val | Ser | Thr | Gly | Gly | Gly | Ala | Ser | Leu | Glu | Leu | Leu | Glu | Gly | |
| | | | | 395 | | | | | 400 | | | | | 405 | | |

| AAG | GAG | CTA | CCC | GGC | GTG | ACG | GCC | CTC | TCG | AGT | AAG | TAAGCCTCCA | | | | 2724 |
| Lys | Glu | Leu | Pro | Gly | Val | Thr | Ala | Leu | Ser | Ser | Lys | | | | | |
| | | | 410 | | | | | 415 | | | | | | | | |

| TATCGAGCGA | GGGAGTCGGC | GATGAATGGC | AGGCATGGTT | GATGATGGTT | GTTGTTTTTG | 2784 |
| CCCAGGTCGA | AGGGTGGCGA | GCCTGTAGGG | GTTGAGAATA | GAACTGCCTA | GTTTAGCAGT | 2844 |
| AACAATGTCG | GTGTAAAATT | GAGAAAAAAA | AAAAAAAAAC | CTTTGTTTGC | CATCCAAGTC | 2904 |
| GTTGGTCGTA | TCTCGTGTGA | GTCTGAGCTG | TGTAACGAGT | GACCCCATTG | ATCCCATGTA | 2964 |
| GTGGTGCTGG | CTCCATGTAG | CTGTCACCGC | AACACGCAAG | GCCGCCAACC | CCACGTAATA | 3024 |
| CCCACCTTGG | CCCAGAATAT | TCTAGTCTCA | GGCGCCACCA | AAATCAATCC | AAAGTTCCAA | 3084 |
| CCCGCCACGC | TTTCCACGCG | GGGCATATCA | TCACCACTCA | TCTACAATAG | ACCATCAGCC | 3144 |
| CAACCTCCCC | CAACAATATC | ACACATCCCC | TCTCACCGAC | AAACGGAAAT | CCCCAGCGCC | 3204 |
| CGCGCGCTTA | GCTCTGCCTG | ACATGGTAAT | TACCTCTCCC | AAAGTACCCC | CTCACTCCCT | 3264 |
| CTACCCGCAT | TCGCGCTCTA | GCGTCCCAAG | ATACTAGGTA | CC | | 3306 |

( 2 ) INFORMATION FOR SEQ ID NO:72:

( i ) SEQUENCE CHARACTERISTICS:
        ( A ) LENGTH: 418 amino acids
        ( B ) TYPE: amino acid
        ( D ) TOPOLOGY: linear ( i i ) MOLECULE TYPE: protein ( x i ) SEQUENCE DESCRIPTION: SEQ ID NO:72:

| Met | Ser | Leu | Ser | Asn | Lys | Leu | Ser | Ile | Thr | Asp | Val | Asp | Leu | Lys | Gly |
| 1 | | | | 5 | | | | | 10 | | | | | 15 | |
| Lys | Arg | Val | Leu | Ile | Arg | Val | Asp | Phe | Asn | Val | Pro | Leu | Asp | Glu | Asn |
| | | | 20 | | | | | 25 | | | | | 30 | | |
| Lys | Lys | Ile | Thr | Asn | Asn | Gln | Arg | Ile | Val | Gly | Ala | Leu | Pro | Thr | Ile |
| | | | 35 | | | | | 40 | | | | | 45 | | |
| Lys | Tyr | Ala | Val | Glu | His | Gly | Ala | Lys | Ala | Val | Ile | Leu | Met | Ser | His |
| | | 50 | | | | | 55 | | | | | 60 | | | |
| Leu | Gly | Arg | Pro | Asn | Gly | Thr | Pro | Asn | Pro | Lys | Tyr | Ser | Leu | Gln | Pro |
| 65 | | | | | 70 | | | | | 75 | | | | | 80 |
| Val | Val | Pro | Glu | Leu | Glu | Lys | Leu | Leu | Gly | Lys | Ser | Val | Thr | Phe | Ala |
| | | | | 85 | | | | | 90 | | | | | 95 | |
| Pro | Asp | Cys | Val | Gly | Ala | Glu | Val | Glu | Gly | Ile | Val | Ala | Lys | Ala | Asp |
| | | | 100 | | | | | 105 | | | | | 110 | | |
| Gly | Gly | Ala | Val | Val | Leu | Leu | Glu | Asn | Leu | Arg | Phe | His | Ile | Glu | Glu |
| | | | 115 | | | | | 120 | | | | | 125 | | |
| Glu | Gly | Ser | Ala | Lys | Asp | Lys | Asp | Gly | Asn | Lys | Thr | Lys | Ala | Asp | Lys |
| | | 130 | | | | | 135 | | | | | 140 | | | |
| Ala | Lys | Val | Asp | Glu | Phe | Arg | Lys | Gly | Leu | Thr | Ala | Leu | Gly | Asp | Val |
| 145 | | | | | 150 | | | | | 155 | | | | | 160 |
| Tyr | Ile | Asn | Asp | Ala | Phe | Gly | Thr | Ala | His | Arg | Ala | His | Ser | Ser | Met |
| | | | | 165 | | | | | 170 | | | | | 175 | |

| | | | | | | | | | | | | | |
|---|---|---|---|---|---|---|---|---|---|---|---|---|---|
|Val|Gly|Val|Asp<br>180|Leu|Pro|Gln|Lys|Ala<br>185|Ala|Gly|Phe|Leu|Met<br>190|Lys|Lys|
|Glu|Leu|Asp<br>195|Tyr|Phe|Ala|Gln|Ala<br>200|Leu|Glu|Ala|Pro|Gln<br>205|Arg|Pro|Phe|
|Leu|Ala<br>210|Ile|Leu|Gly|Gly|Ala<br>215|Lys|Val|Ser|Asp|Lys<br>220|Ile|Gln|Leu|Ile|
|Asp<br>225|Asn|Leu|Leu|Asp|Lys<br>230|Val|Asn|Thr|Leu|Ile<br>235|Ile|Cys|Gly|Gly|Met<br>240|
|Ala|Phe|Thr|Phe|Lys<br>245|Lys|Thr|Leu|Asp|Gly<br>250|Met|Ser|Ile|Gly|Asn<br>255|Ser|
|Leu|Phe|Asp|Glu<br>260|Ala|Gly|Ala|Lys|Thr<br>265|Val|Ala|Ser|Leu|Met<br>270|Asp|Lys|
|Ala|Lys|Gln<br>275|Lys|Gly|Val|Lys|Val<br>280|Val|Val|Pro|Val|Asp<br>285|Tyr|Ile|Thr|
|Ala|Asp|Lys<br>290|Phe|Asp|Lys|Asp<br>295|Ala|Asn|Thr|Gly|Lys<br>300|Ala|Ser|Asp|Ala|
|Gln|Gly<br>305|Ile|Pro|Asp|Gly<br>310|Trp|Met|Gly|Leu|Asp<br>315|Cys|Gly|Glu|Glu|Ser<br>320|
|Ile|Lys|Leu|Tyr|Arg<br>325|Glu|Ala|Ile|Asp|Asn<br>330|Ala|Lys|Thr|Ile|Leu<br>335|Trp|
|Asn|Cys|Pro|Ala<br>340|Gly|Val|Phe|Glu|Phe<br>345|Glu|Lys|Phe|Ala|Ser<br>350|Gly|Thr|
|Lys|Ala|Thr<br>355|Leu|Asp|Ala|Val|Val<br>360|Asp|Gly|Ala|Gln|Asn<br>365|Ala|Gly|Lys|
|Ile|Val<br>370|Ile|Ile|Gly|Gly|Gly<br>375|Asp|Thr|Ala|Thr|Val<br>380|Ala|Ala|Lys|Tyr|
|Gly<br>385|Val|Glu|Asp|Lys|Leu<br>390|Ser|His|Val|Ser|Thr<br>395|Gly|Gly|Gly|Ala|Ser<br>400|
|Leu|Glu|Leu|Leu|Glu<br>405|Gly|Lys|Glu|Leu|Pro<br>410|Gly|Val|Thr|Ala|Leu<br>415|Ser|
|Ser|Lys|

( 2 ) INFORMATION FOR SEQ ID NO:73:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (synthetic)

( i v ) ANTI-SENSE: NO ( i x ) FEATURE:
        ( A ) NAME/KEY: -
        ( B ) LOCATION: 1..25
        ( D ) OTHER INFORMATION: /label=oligonucleotide
          / note="upper strand of linker intermediate
          ligated to pGKBL to make pGKCS; Figure 63."

( x i ) SEQUENCE DESCRIPTION: SEQ ID NO:73:

CGCGTCGATT CACAGTCAAA AGATC        25

( 2 ) INFORMATION FOR SEQ ID NO:74:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (synthetic)

( i v ) ANTI-SENSE: YES ( i x ) FEATURE:
    ( A ) NAME/KEY: -
    ( B ) LOCATION: 1..25
    ( D ) OTHER INFORMATION: /label=oligonucleotide
        / note="lower strand of linker intermediate
        ligated to pGKBL to make pGKCS; Figure 63."

( x i ) SEQUENCE DESCRIPTION: SEQ ID NO:74:

| | | | |
|---|---|---|---|
| TCGAGATCTT TTGACTGTGA ATCGA | | | 25 |

( 2 ) INFORMATION FOR SEQ ID NO:75:

( i ) SEQUENCE CHARACTERISTICS:
        ( A ) LENGTH: 1251 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Acremonium chrysogenum ( i x ) FEATURE:
        ( A ) NAME/KEY: -
        ( B ) LOCATION: 1..1251
        ( D ) OTHER INFORMATION: /label=gene_sequence
            / note="5'untranslated region of PGK gene from A.
            chrysogenum."

( x i ) SEQUENCE DESCRIPTION: SEQ ID NO:75:

| | | | | | | |
|---|---|---|---|---|---|---|
| AGATCTTTCA | GGATGGTGCT | GATGGGGGCG | AGGGGCAAAA | CACCACCGGG | TGATCCTCGA | 60 |
| CGTGGAGGTT | GTGATAGAAG | GAGAGCAAGG | GGACGATGAT | GATGTGGACC | TTGTGATTGA | 120 |
| GGAGGATCAT | GGCGATGAGG | ATGAGGAAGA | GGATTTACCC | GATCTGATCG | ATCCTCCCCC | 180 |
| GAACGACGGG | GACCAGGAGC | GGGAGGGAGC | AGCCGGGCAC | GAGGCGATCA | GGCGCGAGGG | 240 |
| TCAAGAACCA | GACCGACAAG | GCCAGCACCA | AGAACAGGAA | CCGGCAGCAC | CGGAGGCACC | 300 |
| CGCAGCGGAC | GAGCAGCTCC | CGCCACAGAA | CAACCACGAA | GTACCGCCCG | CCCCGCCGGC | 360 |
| CAACCGCGTC | GGTCTGGGCA | CCGTCCTGTC | CAACTTCTCA | AACCAGCTCG | TCAGCGCCCT | 420 |
| CATCCTGCCG | GGAATCTCCT | TCGCCATGGG | CGAAGCTCTA | CGGGTGGCGC | TCCCCGCCAG | 480 |
| GTGGACACAG | TCGTCTCTGT | GCCCCTTTAG | GAACGCCCTC | CGGGCCTACT | CCAGCAGCAG | 540 |
| TGGGGTCGCA | GCCTCGTGGG | TGGGTGCCTG | TACGTGTGAT | CAAGGACGTG | ATCCGGGTCT | 600 |
| ACGCCAAGCA | CCGCAAGGTG | GCGGCTATGG | GCAACCGGCG | GGTCAGAAAC | GTGGACCGGC | 660 |
| CAAGGAGGAA | CGCGGGCTCG | TCGAGATGAA | ATCCAGTGAT | ACAACGCAGC | ATGGGAACGG | 720 |
| AGTTTGGGCT | GGCCAGGGTA | GATGACGGTA | TCCAAGGATT | ATACTATTAA | TATAGCGACT | 780 |
| ACTAGTAATT | ACTACTGGGC | AGAGTCTACC | GCCCAACGTT | GGTATGGGTT | ATTTGTAAAC | 840 |
| GTTCCACGCC | AATCTTTTCC | ACCGTCAGAA | TCGGCGTATC | ATTGCAATTG | ACGGCACCAG | 900 |
| AATGATGCGT | TGGTACTAAT | AGTAGGTACG | AGGTAACAAC | AGTAAAGATA | CTGCCATTAT | 960 |
| AGAAAGAGGA | AGTCGCTCCC | TCGGCAATGC | CGCGCCACAA | GCGCCTTTGG | CCGAGGACGC | 1020 |
| CGGAACCCAA | ACGCAGATCA | GATCGGGGGC | AACGGGAAGC | TTAGGGACGG | AAATGGGGTA | 1080 |
| ATACGAGTAA | TAATCCCCCA | CCACCACCAA | GAAGCTCCCA | ACCCAAAAGC | TTCCTGCGTC | 1140 |
| CTTTTCACCC | CGCCATCTTC | TCCCGACAGA | AAGACAAAAC | AACCCACCAT | ACCACTCCAC | 1200 |
| AGAGCATTGT | TCTTCTCCTT | CAGGACTACC | ACGCGTCGAT | TCACAGTCAA | A | 1251 |

( 2 ) INFORMATION FOR SEQ ID NO:76:

( i ) SEQUENCE CHARACTERISTICS:
        ( A ) LENGTH: 3748 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Acremonium chrysogenum ( i x ) FEATURE:
        ( A ) NAME/KEY: -
        ( B ) LOCATION: 1..3748
        ( D ) OTHER INFORMATION: /label=actin_gene
            / note="Nucleotide sequence of region B in Figure
            60. Sequence corresponds to Figure 62."

( i x ) FEATURE:
        ( A ) NAME/KEY: exon
        ( B ) LOCATION: 1294..1300

( i x ) FEATURE:
        ( A ) NAME/KEY: exon
        ( B ) LOCATION: 1428..1458

( i x ) FEATURE:
        ( A ) NAME/KEY: exon
        ( B ) LOCATION: 1631..1686

( i x ) FEATURE:
        ( A ) NAME/KEY: exon
        ( B ) LOCATION: 1797..1827

( i x ) FEATURE:
        ( A ) NAME/KEY: exon
        ( B ) LOCATION: 1918..2689

( i x ) FEATURE:
        ( A ) NAME/KEY: exon
        ( B ) LOCATION: 2757..2984

( i x ) FEATURE:
        ( A ) NAME/KEY: CDS
        ( B ) LOCATION: join(1294..1300, 1428..1458, 1631..1686, 1797
            . . 1827, 1918..2689, 2757..2984)

( x i ) SEQUENCE DESCRIPTION: SEQ ID NO:76:

```
ATGCATACTA  CGGATACTAG  TAGGGTAATT  AGCGGGTTTC  CACTCGCACA  TACGTACACG     60

TAAGTCGGTG  GCTCAGGTTC  GGACGAGGGG  GCGGTACAGC  AGGAGAGAGA  GAGGCTCTTC    120

GTAGCCTTGC  CTCTGCATCC  GCCGACCCCA  GCCGCGGGCG  CCAGAGATAG  CACAAGCCTG    180

CACGATTCGT  GGCACCCAGG  ACGCGGGATG  CGGAGTTGCG  TAATCGGCTG  CTTCTATTTC    240

AGATGGTGCG  AGGGAGTACT  CCTACTCACG  ATCTTGAATC  ACAGGAGGTC  CCCATCAAAG    300

CCACATGCCG  ACGTCGTTTA  CGAGACACGG  TACATGGTAC  ATCCGAAGAC  GGGACAGCAG    360

GAAGCACCTA  AAGACGCTTC  CCTCCGACAT  GGAAACACCC  CATTGGGCCA  GGCGGCAAGG    420

AGCAGGAGCA  GGAGCAGGCA  GTTGCTTTCG  ATGATGCTCG  ATCTCGCGCC  GAACCGTGAT    480

TAGGTACTGA  TGCCATCGGT  GCCGGCCAGG  CTGGCACCGG  CCTGCCTTGA  TGCGAGATGC    540

CTACTCGTAC  TATGCCTACA  GGTATGGGCT  TTCCGCGTGT  CGTCAGCTTG  CGACCGCGCG    600

GCTGCTGACG  ACCCAAGGCA  AGCTGGTAAC  ATGGCGGCAC  GAAATTTCTC  TCTGCCTGCT    660

CGTCCTCTTG  GTGTGGAGGG  GTACGAGTGC  AGGTATGATG  GGACGGCAGA  GGAGTGACGG    720

AGGCTGTGCG  GTTGGCACGA  GTACTGTACG  AGTACTCGTA  CTGTAGGTGC  AGCGACTGTG    780

GTGGTACTGC  TAGGTGGAAT  TGGGTCCAGC  AGGCATGCAG  CTCCCAGCCA  CCGTCGTTAA    840

CCAATCAGTT  AAAGCAGCAA  CGCAACCCGC  CCCCGTTTTT  CTGCCAGAAA  TTTGGGCGGT    900
```

-continued

```
GTCGTGCCCC CAGTCGTTGT TGCCCGCCCT TGTCTGGTCG CCTACAAGGC TGCACCACAG      960

GTAACAACAG CCCGCCCCAG GTCCTTGTAG GTGCCCAGTG AGTGCCCGGT GCCCACAAGT     1020

TTCTCGTAGG CATCCACTAG GCGGACTTGG AAGCCCATCA GTGATGCTTC CCTCCTTTCC     1080

CCCTCCACAT CTCACTCACG TCACGCAAGC CAACCCTCTC TCCCCCGTC  TCCATTCCAT     1140

CTTCTTCTCT CCACGACCCT TAAGAGTCCC TCCTGCTCAC GTCGACCATC CTTCGCTCCC     1200

AGCCCCACGA CATCTGCATC GTCTGGGCTT CTTGACACTC TGTCATTTCT TCCTTATAAA     1260

ACCTCTTTAC CGCTCTTCCC GTAATCCGAC GCC ATG GAG   G GTACGTGTCG            1310
                                    Met Glu
                                     1

CCGCAACGCA CTCCCGCTTC CCCTACTACC CCTATCGCGC ATCCATACGG CGCCGCGATG     1370

CCTAGCCATC GCGAGGGTGC ATCGCAACGA CTTGGCTAAC TGTTCTTCGC TTCACAG  AG    1429
                                                                Glu
```

```
GAG GTC GCC GCC CTC GTT ATC GAC AAT    GG  GTAAGCTCGC CCGCTGTCTC      1478
Glu Val Ala Ala Leu Val Ile Asp Asn     Gly
     5                        10
```

```
ACCGACATCC ATCGTCCCCC TGGCCTCTGT CGAGATGGGA GCCTCCAGGG GTCCCTTCGA     1538

CGAGCGCGTC GATTGCCAAA ATCCAACGAG ATCGGGCCAT ACTGAGCCGA CACTCGTGTG     1598

TTTTCTGGAC ATTAGGACTG ACTTGATTCT AG T TCG GGT ATG TGC AAG GCC         1649
                                      Ser Gly Met Cys Lys Ala
                                                    15
```

```
GGT TTC GCC GGT GAT GAT GCT CCC CGA GCT GTT TTC   C GTAAGTACCC        1696
Gly Phe Ala Gly Asp Asp Ala Pro Arg Ala Val Phe
 20                      25                   30
```

```
CACTTCCACC CGTCGAGCTC CCCAATTGTC CACCGCCAGG GCGAGAAGGG GGCAGAACGG     1756

GGCAAACTGC ATCGCAAACA TGGCTAATTC GATGCGACAG   CG TCC ATT GTC GGT      1810
                                                 Pro Ser Ile Val Gly
                                                                 35
```

```
CGT CCC CGC CAC CAT   GG  GTAAGTTTCC GGCCGCAGCC GACACCTCTC            1857
Arg Pro Arg His His   Gly
             40
```

```
ACCCCCCCCC GGGGGGCTCC TAAGCGAGTC AGCGCTGGTT CTGACCGCTG GATACTATAG     1917

C ATC ATG ATC GGC ATG GGC CAG AAG GAC TCG TAC GTC GGT GAC GAG         1963
  Ile Met Ile Gly Met Gly Gln Lys Asp Ser Tyr Val Gly Asp Glu
       45                  50                      55
```

```
GCT CAG TCC AAG CGT GGT ATC CTC ACC CTG CGC TAC CCC ATT GAG CAC       2011
Ala Gln Ser Lys Arg Gly Ile Leu Thr Leu Arg Tyr Pro Ile Glu His
             60                  65                      70
```

```
GTT GTT GTC ACC AAC TGG GAC GAC ATG GAG AAG ATC TGG CAC CAC ACC       2059
Val Val Val Thr Asn Trp Asp Asp Met Glu Lys Ile Trp His His Thr
 75                  80                  85
```

```
TTC TAC AAC GAG CTG CGT GTT GCC CCC GAG GAG CAC CCG GTC CTG CTC       2107
Phe Tyr Asn Glu Leu Arg Val Ala Pro Glu Glu His Pro Val Leu Leu
 90              95                  100                     105
```

```
ACC GAG GCG CCC ATC AAC CCC AAG TCC AAC CGT GAG AAG ATG ACC CAG       2155
Thr Glu Ala Pro Ile Asn Pro Lys Ser Asn Arg Glu Lys Met Thr Gln
                110                 115                 120
```

```
TTC GTC TTC GAG ACC TTC AAC GCC CCT GCC TTC TAC GTC TCC ATC CAG       2203
Phe Val Phe Glu Thr Phe Asn Ala Pro Ala Phe Tyr Val Ser Ile Gln
                125                 130                 135
```

```
GCC GTC CTG TCA CTG TAC GCC TCC GGC CGT ACG ACC GGT ATC GTC CTG       2251
Ala Val Leu Ser Leu Tyr Ala Ser Gly Arg Thr Thr Gly Ile Val Leu
            140                 145                 150
```

```
GAC TCT GGT GAT GGT GTC ACC CAC GTT GTC CCC ATC TAC GAG GGT TTC       2299
Asp Ser Gly Asp Gly Val Thr His Val Val Pro Ile Tyr Glu Gly Phe
            155                 160                 165
```

| | | | | | | | | | | | | | | | | |
|---|---|---|---|---|---|---|---|---|---|---|---|---|---|---|---|---|
| GCC | CTG | CCC | CAC | GCC | ATT | GCC | CGT | GTC | GAC | ATG | GTC | GGT | CGT | GAT | CTC | 2347 |
| Ala | Leu | Pro | His | Ala | Ile | Ala | Arg | Val | Asp | Met | Val | Gly | Arg | Asp | Leu | |
| 170 | | | | 175 | | | | | 180 | | | | | | 185 | |
| ACC | GAC | TAC | CTC | ATG | AAG | ATC | CTG | GCC | GAG | CGC | GGC | TAC | ACC | TTC | TTC | 2395 |
| Thr | Asp | Tyr | Leu | Met | Lys | Ile | Leu | Ala | Glu | Arg | Gly | Tyr | Thr | Phe | Phe | |
| | | | | 190 | | | | | 195 | | | | | 200 | | |
| ACC | ACG | GCC | GAG | CGT | GAG | ATT | GTC | CGT | GAC | ATC | AAG | GAG | GAG | CTC | TGC | 2443 |
| Thr | Thr | Ala | Glu | Arg | Glu | Ile | Val | Arg | Asp | Ile | Lys | Glu | Glu | Leu | Cys | |
| | | | 205 | | | | | 210 | | | | | 215 | | | |
| TAC | GTC | GCC | CTC | GAC | TTC | GAG | CAG | GAG | ATC | CAG | ACT | GCC | GCC | CAG | AGC | 2491 |
| Tyr | Val | Ala | Leu | Asp | Phe | Glu | Gln | Glu | Ile | Gln | Thr | Ala | Ala | Gln | Ser | |
| | | 220 | | | | | 225 | | | | | 230 | | | | |
| TCC | AGC | CTG | GAG | AAG | TCC | TAC | GAG | CTT | CCC | GAC | GGC | CAG | GTC | ATC | ACC | 2539 |
| Ser | Ser | Leu | Glu | Lys | Ser | Tyr | Glu | Leu | Pro | Asp | Gly | Gln | Val | Ile | Thr | |
| | 235 | | | | | 240 | | | | | 245 | | | | | |
| ATT | GGC | AAT | GAG | CGC | TTC | CGT | GCT | CCC | GAG | GCT | CTC | TTC | CAG | CCC | TCC | 2587 |
| Ile | Gly | Asn | Glu | Arg | Phe | Arg | Ala | Pro | Glu | Ala | Leu | Phe | Gln | Pro | Ser | |
| 250 | | | | | 255 | | | | | 260 | | | | | 265 | |
| GTC | CTG | GGT | CTC | GAG | AGC | GGC | GGC | ATC | CAC | GTC | ACC | ACC | TTC | AAC | TCC | 2635 |
| Val | Leu | Gly | Leu | Glu | Ser | Gly | Gly | Ile | His | Val | Thr | Thr | Phe | Asn | Ser | |
| | | | | 270 | | | | | 275 | | | | | 280 | | |
| ATC | ATG | AAG | TGC | GAC | GTC | GAT | GTC | CGT | AAG | GAT | CTG | TAC | GGC | AAC | ATT | 2683 |
| Ile | Met | Lys | Cys | Asp | Val | Asp | Val | Arg | Lys | Asp | Leu | Tyr | Gly | Asn | Ile | |
| | | | 285 | | | | | 290 | | | | | 295 | | | |
| GTC | ATG | GTAAGTCAGA | TGCCGGGCCT | GGAAGACACC | TCATTTAGGA | TCTTGCTAAC | | | | | | | | | | 2739 |
| Val | Met | | | | | | | | | | | | | | | |

| | | | | | | | | | | | |
|---|---|---|---|---|---|---|---|---|---|---|---|
| ACCAATTTTT | TTTTTAG | TCT | GGT | GGT | ACC | ACC | ATG | TAC | CCT | GGC CTC TCT | 2789 |
| | | Ser | Gly | Gly | Thr | Thr | Met | Tyr | Pro | Gly Leu Ser | |
| | | | 300 | | | | 305 | | | 310 | |

| | | | | | | | | | | | | | | | | |
|---|---|---|---|---|---|---|---|---|---|---|---|---|---|---|---|---|
| GAC | CGT | ATG | CAG | AAG | GAG | ATC | ACT | GCT | CTT | GCT | CCT | TCT | TCC | ATG | AAG | 2837 |
| Asp | Arg | Met | Gln | Lys | Glu | Ile | Thr | Ala | Leu | Ala | Pro | Ser | Ser | Met | Lys | |
| | | | | 315 | | | | | 320 | | | | | 325 | | |
| GTC | AAG | ATC | ATT | GCT | CCC | CCG | GAG | CGC | AAG | TAC | TCC | GTC | TGG | ATC | GGT | 2885 |
| Val | Lys | Ile | Ile | Ala | Pro | Pro | Glu | Arg | Lys | Tyr | Ser | Val | Trp | Ile | Gly | |
| | | | 330 | | | | | 335 | | | | | 340 | | | |
| GGT | TCC | ATT | CTG | GCG | TCT | CTG | TCC | ACC | TTC | CAG | CAG | ATG | TGG | ATC | TCG | 2933 |
| Gly | Ser | Ile | Leu | Ala | Ser | Leu | Ser | Thr | Phe | Gln | Gln | Met | Trp | Ile | Ser | |
| | | | 345 | | | | | 350 | | | | | 355 | | | |
| AAG | CAG | GAG | TAC | GAC | GAG | AGC | GGC | CCC | TCC | ATC | GTC | CAC | CGC | AAG | TGC | 2981 |
| Lys | Gln | Glu | Tyr | Asp | Glu | Ser | Gly | Pro | Ser | Ile | Val | His | Arg | Lys | Cys | |
| | | 360 | | | | | 365 | | | | | 370 | | | | |
| TTC | TAAGGTATGT | TGTCGCTGGG | AAGCCGGATA | CCCGAATGTA | AGGTTGACAG | | | | | | 3034 |
| Phe | | | | | | | | | | | |
| 375 | | | | | | | | | | | |

| | | | | | |
|---|---|---|---|---|---|
| GTTCGAAAAG | ACAAGGCAAC | CGGCCAGAAC | CAAATCCTTC | CACCCTCCGC | AAAAGAACGC | 3094 |
| CAAGATGTCG | GAGTCGGTGG | CGACCGATGC | AACGTCTACT | CAGCTGCGCG | CGTATCCCAC | 3154 |
| TCAAGTCTCA | TATTTACGAA | AAGTTATTTC | ACATGGTCAG | GCGGTGGTGG | GCGTTGCCTT | 3214 |
| TTCTCGGAAC | AGACATGACG | GCGGCCACTT | TTGTAGTCGG | ATGCGTTTAG | GGATGCGAGC | 3274 |
| CTAGGGGTGT | AGGAAGCTGA | GGTTGATATA | CAATAACTTT | TTTTGCTTTC | CGTTCTAGAC | 3334 |
| TCGTTCAATG | GGAAGACGTG | ACGGAATCGC | TTGGCTGTCT | AATAGCCCAG | CTTGATCAGG | 3394 |
| CGAGTCGGGT | TGTTGTGTTT | CGATGTTGAG | AGGTGCACCA | GCGTATTTGT | ATGGCCGAGG | 3454 |
| TAGGTATTAT | GGTCTCGTAT | TTGCAACACT | AGAGCTCGCT | TGCTCGTTTT | TACCAGCAGT | 3514 |
| GTCCTCTGCC | ATGCCGCGGC | TCCGACTCTC | GTCTGGCTTC | TCAGACCGTG | CCTCGTCAAT | 3574 |
| AGTATTATCC | CCCGTAGTAA | CCTCCGCACT | AGCCGGTTCT | TTGTCGTCTT | CCTGCTCGCC | 3634 |

```
GATGAGCTTC CTGTACTTGC GCCTCTTCTT CTTGTCGGCG CTGGCAGCCC TCTTCTGCTT     3694

GATGCGCCCG ACCATGGCGG ACCGGCTCTG CTCCCCGTTG AGCAGCTCGT CGAC           3748
```

( 2 ) INFORMATION FOR SEQ ID NO:77:

( i ) SEQUENCE CHARACTERISTICS:
        ( A ) LENGTH: 371 amino acids
        ( B ) TYPE: amino acid
        ( D ) TOPOLOGY: linear ( i i ) MOLECULE TYPE: protein ( x i ) SEQUENCE DESCRIPTION: SEQ ID NO:77:

```
Met Glu Glu Glu Val Ala Ala Leu Val Ile Asp Asn Arg Val Cys Ala
  1               5                  10                  15

Arg Pro Val Ser Pro Val Met Met Leu Pro Glu Leu Phe Ser Val His
             20                  25                  30

Cys Arg Ser Ser Pro Pro Pro Trp Ile Met Ile Gly Met Gly Gln Lys
         35                  40                  45

Asp Ser Tyr Val Gly Asp Glu Ala Gln Ser Lys Arg Gly Ile Leu Thr
     50                  55                  60

Leu Arg Tyr Pro Ile Glu His Val Val Val Thr Asn Trp Asp Asp Met
 65                  70                  75                  80

Glu Lys Ile Trp His His Thr Phe Tyr Asn Glu Leu Arg Val Ala Pro
                 85                  90                  95

Glu Glu His Pro Val Leu Leu Thr Glu Ala Pro Ile Asn Pro Lys Ser
            100                 105                 110

Asn Arg Glu Lys Met Thr Gln Phe Val Phe Glu Thr Phe Asn Ala Pro
        115                 120                 125

Ala Phe Tyr Val Ser Ile Gln Ala Val Leu Ser Leu Tyr Ala Ser Gly
    130                 135                 140

Arg Thr Thr Gly Ile Val Leu Asp Ser Gly Asp Gly Val Thr His Val
145                 150                 155                 160

Val Pro Ile Tyr Glu Gly Phe Ala Leu Pro His Ala Ile Ala Arg Val
                165                 170                 175

Asp Met Val Gly Arg Asp Leu Thr Asp Tyr Leu Met Lys Ile Leu Ala
            180                 185                 190

Glu Arg Gly Tyr Thr Phe Phe Thr Thr Ala Glu Arg Glu Ile Val Arg
        195                 200                 205

Asp Ile Lys Glu Glu Leu Cys Tyr Val Ala Leu Asp Phe Glu Gln Glu
    210                 215                 220

Ile Gln Thr Ala Ala Gln Ser Ser Ser Leu Glu Lys Ser Tyr Glu Leu
225                 230                 235                 240

Pro Asp Gly Gln Val Ile Thr Ile Gly Asn Glu Arg Phe Arg Ala Pro
                245                 250                 255

Glu Ala Leu Phe Gln Pro Ser Val Leu Gly Leu Glu Ser Gly Gly Ile
            260                 265                 270

His Val Thr Thr Phe Asn Ser Ile Met Lys Cys Asp Val Asp Val Arg
        275                 280                 285

Lys Asp Leu Tyr Gly Asn Ile Val Met Leu Val Val Pro Pro Cys Thr
    290                 295                 300

Leu Ala Ser Leu Thr Val Cys Arg Arg Arg Ser Leu Leu Leu Leu Leu
305                 310                 315                 320

Leu Pro Arg Ser Arg Ser Leu Leu Pro Arg Ser Ala Ser Thr Pro Ser
                325                 330                 335
```

```
Gly Ser Val Val Pro Phe Trp Arg Leu Cys Pro Pro Ser Ser Arg Cys
            340                 345                 350

Gly Ser Arg Ser Arg Ser Thr Thr Arg Ala Ala Pro Pro Ser Ser Thr
        355                 360             365

Ala Ser Ala
    370
```

( 2 ) INFORMATION FOR SEQ ID NO:78:

( i ) SEQUENCE CHARACTERISTICS:
        ( A ) LENGTH: 12 base pairs
        ( B ) TYPE: nucleic acid
        ( C ) STRANDEDNESS: double
        ( D ) TOPOLOGY: linear ( i i ) MOLECULE TYPE: DNA (synthetic)

( i v ) ANTI-SENSE: NO ( i x ) FEATURE:
        ( A ) NAME/KEY: -
        ( B ) LOCATION: 1..12
        ( D ) OTHER INFORMATION: /label=oligonucleotide
            / note="BamHI linker ligated to pACT-delta-NP to
            obtain pACTB1; Figure 64."

( x i ) SEQUENCE DESCRIPTION: SEQ ID NO:78:

CCCGGATCCG GG                                                    12

( 2 ) INFORMATION FOR SEQ ID NO:79:

( i ) SEQUENCE CHARACTERISTICS:
        ( A ) LENGTH: 10 base pairs
        ( B ) TYPE: nucleic acid
        ( C ) STRANDEDNESS: double
        ( D ) TOPOLOGY: linear ( i i ) MOLECULE TYPE: DNA (synthetic)

( i x ) FEATURE:
        ( A ) NAME/KEY: -
        ( B ) LOCATION: 1..10
        ( D ) OTHER INFORMATION: /label=oligonucleotide
            / note="BamHI linker ligated to pACT-delta-NP to
            obtain pACTB2."

( x i ) SEQUENCE DESCRIPTION: SEQ ID NO:79:

CCGGATCCGG                                                      10

( 2 ) INFORMATION FOR SEQ ID NO:80:

( i ) SEQUENCE CHARACTERISTICS:
        ( A ) LENGTH: 8 base pairs
        ( B ) TYPE: nucleic acid
        ( C ) STRANDEDNESS: double
        ( D ) TOPOLOGY: linear ( i i ) MOLECULE TYPE: DNA (synthetic)

( i x ) FEATURE:
        ( A ) NAME/KEY: -
        ( B ) LOCATION: 1..8
        ( D ) OTHER INFORMATION: /label=oligonucleotide
            / note="BamHI linker ligated to pACT-delta-NP to
            obtain pACTB3."

( x i ) SEQUENCE DESCRIPTION: SEQ ID NO:80:

CGGATCCG                                                        8